US011298408B2

(12) United States Patent
Hanes et al.

(10) Patent No.: US 11,298,408 B2
(45) Date of Patent: Apr. 12, 2022

(54) METHODS OF TREATING HYPERTENSION

(71) Applicant: THE FEINSTEIN INSTITUTES FOR MEDICAL RESEARCH, Manhasset, NY (US)

(72) Inventors: William Hanes, East Setauket, NY (US); Kevin J. Tracey, Old Greenwich, CT (US); Peder Olofsson, Lidingö (SE)

(73) Assignee: THE FEINSTEIN INSTITUTES FOR MEDICAL RESEARCH, Manhasset, NY (US)

( * ) Notice: Subject to any disclaimer, the term of this patent is extended or adjusted under 35 U.S.C. 154(b) by 288 days.

(21) Appl. No.: 16/331,306

(22) PCT Filed: Sep. 8, 2017

(86) PCT No.: PCT/US2017/050589

§ 371 (c)(1), (2) Date: Mar. 7, 2019

(87) PCT Pub. No.: WO2018/049095

PCT Pub. Date: Mar. 15, 2018

(65) Prior Publication Data

US 2019/0201499 A1 Jul. 4, 2019

Related U.S. Application Data

(60) Provisional application No. 62/385,335, filed on Sep. 9, 2016.

(51) Int. Cl.

| | |
|---|---|
| ***A61K 38/45*** | (2006.01) |
| ***A61K 35/17*** | (2015.01) |
| ***C12N 9/10*** | (2006.01) |

(52) U.S. Cl.

CPC .............. *A61K 38/45* (2013.01); *A61K 35/17* (2013.01); *C12N 9/1029* (2013.01); *C12Y 203/01006* (2013.01)

(58) Field of Classification Search

None

See application file for complete search history.

(56) References Cited

U.S. PATENT DOCUMENTS

| | | | |
|---|---|---|---|
| 6,656,743 | B2 | 12/2003 | Huson et al. |
| 2007/0054278 | A1 | 3/2007 | Cargill |
| 2009/0247934 | A1 | 10/2009 | Tracey et al. |
| 2010/0223695 | A1 | 9/2010 | Sivasankar et al. |
| 2012/0302466 | A1 | 11/2012 | Sentman |
| 2013/0224162 | A1 | 8/2013 | Kim et al. |
| 2013/0344039 | A1 | 12/2013 | Okada et al. |

FOREIGN PATENT DOCUMENTS

| | | | |
|---|---|---|---|
| WO | 2016033318 | A1 | 3/2016 |
| WO | 2018049095 | A1 | 3/2018 |

OTHER PUBLICATIONS

Olofsson et al., J. Immunol. 194(1 Suppl): 65.22 (May 1, 2015).*

Moore et al., Cancer Immunol. Immunother. 58: 719-728 (2009).*

(Continued)

*Primary Examiner* — Erin M. Bowers

(74) *Attorney, Agent, or Firm* — Amster, Rothestein & Ebenstein LLP

(57) ABSTRACT

Provided are CD4+ T-cell-based compositions and methods for treating hypertension.

14 Claims, 2 Drawing Sheets

Specification includes a Sequence Listing.

a

No. of observations 15
10
5
0

% ChAT-eGFP⁺ b

ChAT-deficient

ChAT-expressing control

MAP (mmHg)

120
100
80
0

0 12 24 36 48

Time (h)

P = 0.01

(56) References Cited

OTHER PUBLICATIONS

PCT International Search Report and Written Opinion dated Jan. 9, 2018 in connection with PCT International Patent Application No. PCT/US2017/050589.

Olofsson et al., Choline Acetyltransferase+ Lymphocytes Regulate Endolthelial Nitric Oxide Synthase (MUC2P.939), J Immunol, May 1, 2015, 194 (1 Supplement) 65.22.

International Search Report and Written Opinion dated Feb. 27, 2020 from PCT International Appln. PCT/US2019/065653.

Diaferia et al., "Structural Characaterization of PEGylated Hexaphenylalanine Nanostructures Exhibiting Green Photoluminescence Emission," Chem. Eur. J., vol. 23, 2017, pp. 14039-14048.

* cited by examiner

METHODS OF TREATING HYPERTENSION

CROSS-REFERENCE TO RELATED APPLICATIONS

This application is a U.S. national stage entry under 35 U.S.C. § 371 of PCT International Patent Application No. PCT/US2017/050589, filed Sep. 8, 2017, which claims benefit of U.S. Provisional Application No. 62/385,335, filed Sep. 9, 2016, the contents of each of which are incorporated herein by reference into the subject application.

STATEMENT OF GOVERNMENT SUPPORT

This invention was made with government support under grant numbers GM057226 and GM089807 awarded by the National Institutes of Health. The government has certain rights in the invention.

BACKGROUND OF THE INVENTION

Throughout this application various publications are referred to, including by number in parentheses. Full citations for these references may be found at the end of the specification. The disclosures of all publications cited herein, and all patents and patent applications mentioned herein, are hereby incorporated by reference in their entirety into the subject application to more fully describe the art to which the subject invention pertains.

Hypertension, or high blood pressure, is a long term condition wherein the blood pressure in the arteries is persistently elevated. While high blood pressure usually does not cause symptoms, persistent high blood pressure is a major risk factor for coronary artery disease, stroke, heart failure, peripheral vascular disease, vision loss, and chronic kidney disease. About 90-95% of cases are primary, defined as high blood pressure due to nonspecific lifestyle and genetic factors, such as obesity, high salt intake, and alcohol use. The remaining 5-10% of cases are categorized as secondary high blood pressure, defined as high blood pressure due to an identifiable cause, such as chronic kidney disease, narrowing of the kidney arteries, an endocrine disorder, or the use of birth control pills. Medical consensus generally defines high blood pressure as resting blood pressure persistently at or above 140/90 (systolic/diastolic) mmHg for most adults, although lower pressures can be treated depending on comorbidities.

According to data from the National Health Examination Surveys (NHANES), the age-adjusted prevalence of hypertension varies from 18-32%. A 2005 NHANES report in the United States found that in the population aged 20 years or older, an estimated 41.9 million men and 27.8 million women had prehypertension (SBP, 120-139 mm Hg; DBP, 80-99 mm Hg), 12.8 million men and 12.2 million women had stage 1 hypertension (SBP, 140-159 mm Hg; DBP, 90-99 mm Hg), and 4.1 million men and 6.9 million women had stage 2 hypertension (SBP≥160 mm Hg; DBP≥100 mm Hg). High blood pressure affects between 16 and 37% of the population globally. In 2010 hypertension was believed to have been a factor in 18% (9.4 million) deaths. The treatment of moderately high arterial blood pressure (defined as >160/100 mmHg) with medications is associated with an improved life expectancy. According to one review published in 2003, reduction of the blood pressure by 5 mmHg can decrease the risk of stroke by 34%, of ischemic heart disease by 21%, and reduce the likelihood of dementia, heart failure, and mortality from cardiovascular disease.

Several classes of medications, collectively referred to as antihypertensive medications, are available for treating hypertension. First line medications for hypertension include thiazide-diuretics, calcium channel blockers, angiotensin converting enzyme inhibitors, beta blockers, and angiotensin receptor blockers. These medications may be used alone or in combination; the latter option may serve to minimize counter-regulatory mechanisms that act to revert blood pressure values to pre-treatment levels. The majority of people require more than one medication to control their hypertension.

Resistant hypertension is defined as blood pressure that remains above goal despite concurrent use of three antihypertensive agents of different classes, one of which should be a diuretic. Resistant hypertension may also represent the result of chronic high activity of the autonomic nervous system; this concept is known as "neurogenic hypertension." Patients with resistant hypertension are at high risk for adverse cardiovascular events and are more likely than those with controlled hypertension to have a secondary cause, which is usually at least in partly reversible.

The prevalence of resistant hypertension is estimated at 9-16 percent globally. In addition, many of the current therapies carry unwanted side effects. Therefore, new techniques for control of hypertension are necessary. The present invention provides methods of treating hypertension that are expected to reduce unwanted side effects of systemic therapeutic drugs and should treat resistant hypertension.

SUMMARY OF THE INVENTION

A method is provided for treating hypertension in a subject or reducing development of hypertension in a subject, comprising administering to the subject an amount of CD4+ T-cells engineered to express increased levels of choline acetyltransferase relative to non-engineered CD4+ T-cells of the same type.

Also provided is an isolated, modified primary human T cell, wherein the cell is modified to express increased levels of choline acetyltransferase relative to an unmodified primary human T cell.

A composition is also provided comprising a therapeutically effective amount of the isolated, modified primary human T cells as described herein, and at least one pharmaceutically acceptable carrier.

Also provided is an isolated recombinant polynucleotide encoding a DNA-targeting region and a transcriptional activator, wherein said transcriptional activator induces transcription of a human ChAT gene when present in a human cell.

Also provided is an isolated T cell in which an agent has been introduced into the T cell to increase acetylcholine release from the T cell.

DETAILED DESCRIPTION OF THE INVENTION

Figures 1A, 1B, 1C, 1D:
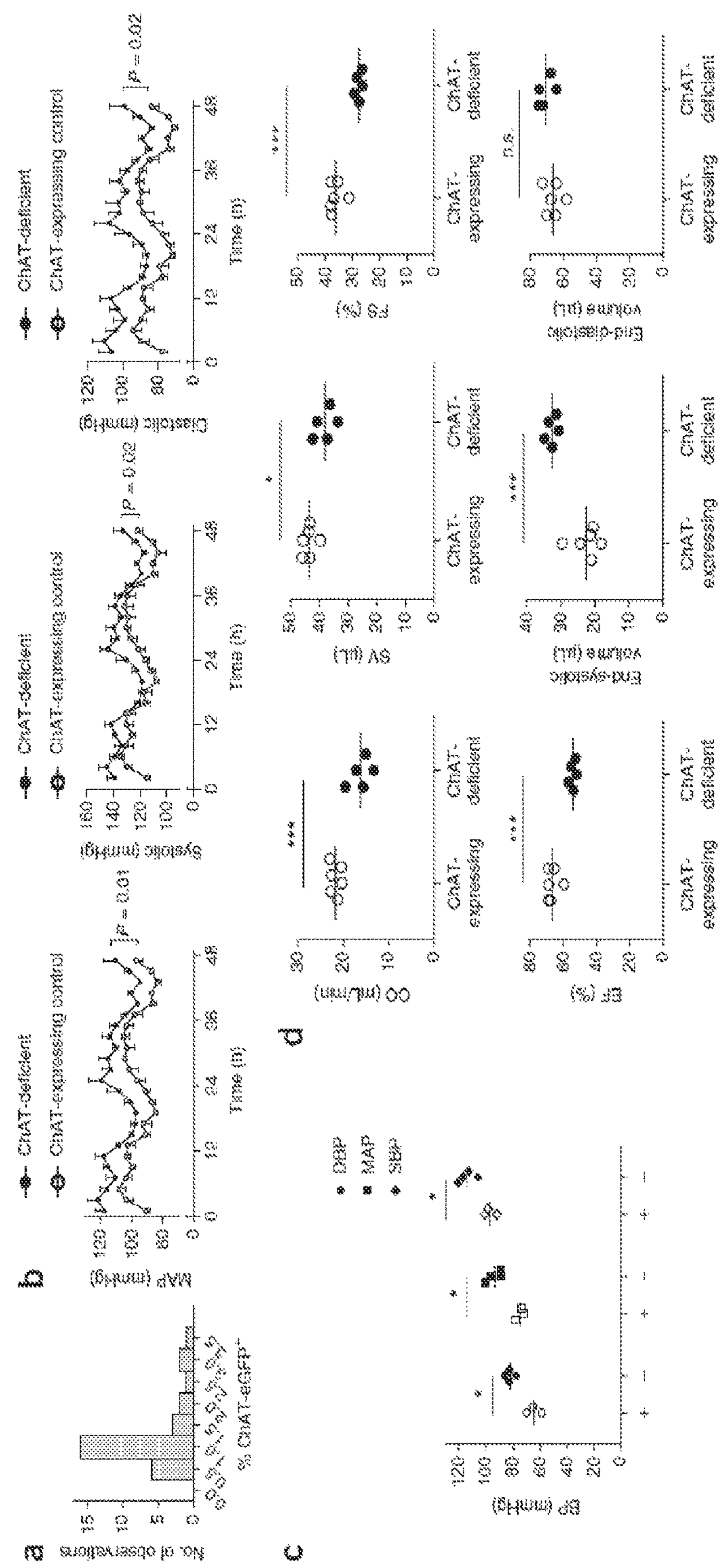
FIG. 1*a*-1*d*: Increased blood pressure in mice with genetic ablation of choline acetyltransferase+ CD4+ cells. (a) Histogram of the fraction of ChAT-eGFP+ cells in CD3+ cells in each mouse. Blood from male and female ChAT-eGFP reporter mice 6-12 weeks of age obtained by tail bleed was analyzed by flow cytometry. (b) Graphs of blood pressure measured by telemetry over 48 h in awake 12-week-old ChAT-deficient mice (n=6) and their ChAT-expressing (n=4) littermate controls. Data were analyzed using repeated measures ANOVA. Open circles, littermate controls, filled circles, ChAT deficient. (c) Blood pressure (BP) as measured by an indwelling catheter in the left carotid artery in anesthetized ChAT-expressing (+; n=3) and ChAT-deficient (−; n=4) mice. D, diastolic; M, mean arterial; S, systolic. *P<0.05 (two-tailed Student's t test). Open symbols, littermate controls, filled symbols, ChAT deficient. (d) Echocardiographic measurements in male 10- to 11-week-old ChAT-expressing (n=6) and ChAT-deficient (n=5) mice. CO, cardiac output; SV, stroke volume; FS, fractional shortening; EF, ejection fraction. *P<0.05 (two-tailed Student's t-test).

High blood pressure (hypertension) occurs when smaller arteries become abnormally narrow, which causes the blood to exert excessive pressure against the vessel walls. As a consequence, the heart must work harder to maintain the blood flow against this increased resistance. Over an extended period of time, this may lead to enlargement and damage of the heart (cardiac hypertrophy). Although the body can tolerate an increase in blood pressure for months or even years, eventually, damage to blood vessels of the kidneys, the brain, and/or the eyes can occur. Hypertension may also lead to congestive heart failure.

In most hypertensives, both the systolic and diastolic pressures are raised. However, in some older people, "isolated" systolic hypertension may occur. A rise in diastolic pressure used to be considered more serious than a rise in systolic pressure, but now it is accepted that this isolated form of systolic hypertension puts affected people at considerable risk of brain damage due to stroke.

It is estimated that approximately 50 million people in the US have high blood pressure. About half of these people never know it because of the lack of specific symptoms. High blood pressure is therefore sometimes called the "silent killer." It is further estimated that about 50 percent of all hypertensive people are women. Of the roughly 50 million adult Americans with high blood pressure, only about 27% have their hypertension under control. Of those who have been diagnosed, about 27% are being treated with medications, but are failing to control the condition, and nearly 15% are not participating in any treatment at all.

In most cases of hypertension, the cause is unknown. This is called primary hypertension. In about 5 to 10 percent of people, high blood pressure is a secondary symptom of some other medical condition. For example, there might be an organic cause such as kidney disease, tumor of the adrenal glands, heart defects, or disorders of the nervous system.

Aggressive drug treatment of long-term high blood pressure can significantly reduce the incidence of death from heart disease and other causes in both men and women. In people with diabetes, controlling both blood pressure and blood glucose levels prevents serious complications of that disease. If patients have mild hypertension and no heart problems, then lifestyle changes may suffice to control the condition, if carried out with determination. For more severe hypertension or for mild cases that do not respond to changes in diet and lifestyle within a year, drug treatment is usually necessary. A single-drug regimen can often control mild to moderate hypertension. More severe hypertension often requires a combination of two or more drugs. Prolonged-release drugs are being developed so that they are most effective during early morning periods, when patients are at highest risk for heart attack or stroke.

A number of oral and parenteral medications are available for the treatment of hypertension, listed as follows:

Beta-Blockers: Beta-blockers (beta-adrenergic blockers) work by reducing sympathetic nerve input to the heart. Thus, the heart beats less often per minute and with less force. Subsequently, the heart reduces its work, and blood pressure drops. Beta-blockers include propranolol, metoprolol, atenolol, and many others.

Diuretics: Diuretics cause the body to excrete water and salt. This leads to a reduction in plasma volume, which subsequently lowers systemic blood pressure. Diuretics include furosemide, hydrochlorothiazide, and spironolactone.

Angiotensin Converting Enzyme (ACE) Inhibitors: Angiotensin Converting Enzyme (ACE) inhibitors work by preventing the body's production of angiotensin II, a hormone that normally causes blood vessels to narrow. Consequently, the vessels remain wider, which lowers blood pressure. Angiotensin II also normally stimulates the release of another hormone, called aldosterone, which is responsible for the body's retention of sodium. Hence, in addition to creating wider vessels, ACE inhibitors mimic the effect of diuretics to a certain extent. As a result, blood vessels are subject to less pressure, and the heart performs less work. Examples of ACE inhibitors include enalapril, captopril, and lisinopril.

Angiotensin II Antagonists: Relatively new to the world of blood pressure treatment, angiotensin II antagonists are primarily used for patients who develop a cough as a side effect of taking ACE inhibitors. This medication antagonizes angiotensin II, thus inhibiting its effects. Examples include losartan and valsartan.

Calcium Channel Blockers: Calcium channel blockers keep calcium from entering the muscle cells of the heart and blood vessels. The heart and vessels relax, allowing blood pressure to go down. Some calcium channel blockers are nifedipine, verapamil, and diltiazem.

Alpha-Blockers: Alpha-blockers (alpha-adrenergic blockers) target the nervous system to relax blood vessels, allowing blood to pass more easily. Examples of alpha blockers are doxazosin, prazosin, and terazosin.

Alpha-Beta-Blockers: Alpha-beta-blockers (alpha- and beta-adrenergic blockers) basically have the same effect as a combined alpha-blocker and beta-blocker. They target the nervous system to relax the blood vessels, as well as work to slow the heartbeat. As a result, less blood is pumped through wider vessels, decreasing the overall blood pressure. Alpha-beta-blockers include labetalol and carvedilol.

Vasodilators: This category of medication works by relaxing the muscle in the blood vessel wall. Hydralazine and minoxidil are both generic forms of vasodilators.

Research now indicates that beta-blockers, diuretics, and ACE inhibitors all reduce the risk for fatal and nonfatal cardiovascular events. As first-line treatment for most people with hypertension but no comorbid conditions, experts generally recommend beta-blockers or diuretics, which are inexpensive, safe, and effective. Some individuals, however, may have special requirements that call for specific drugs or combinations. Diuretics continue to be the best choice for older adults and for many African-Americans, who are more likely to be salt-sensitive and so respond well to these drugs. Isolated high systolic pressure is usually treated with a diuretic; adding a beta-blocker may improve outcome. For diabetics, the best drugs are beta-blockers or angiotensin-converting enzyme (ACE) inhibitors. ACE inhibitors have been shown to delay the onset and progression of kidney disease by 30% to 60% and to limit progression of other complications. Beta-blockers are less expensive and one study found that they were as effective as ACE inhibitors in reducing diabetic complications, although more studies are needed. Myocardial infarction (MI) survivors are usually given beta-blockers and sometimes ACE inhibitors to prevent a second MI. People with heart failure should be given ACE inhibitors and diuretics; specific drugs in these classes may be particularly beneficial for these patients because they reduce left ventricle hypertrophy.

It is very important to rigorously maintain a drug regimen. According to a recent study, patients who discontinue anti-hypertensive therapy, particularly smokers and younger adults, are at a significantly increased risk for stroke. On an encouraging note, one major study found that people taking blood pressure drugs did not experience any greater decline in the general quality of life or daily functioning over five years than did people who were not on blood pressure medication. In all cases, healthy lifestyle changes must accompany any drug treatment.

Hypertensive Medication Side Effects: All drugs used for hypertension have side effects. Common side effects include fatigue, coughing, skin rash, sexual dysfunction, depression, cardiac dysfunction, or electrolyte abnormalities. Some of these are distressing, and ongoing patient compliance may be difficult. Some clinicians have been concerned about the long-term effects of anti-hypertensive drugs on mental processes. A recent study found that brain scans of people who took calcium channel blockers or "loop" diuretics (e.g., furosemide, so called due to diuretic activity on a specific structure in the kidney known as the loop of Henle) detected changes in brain tissue; those who took beta-blockers had no such changes. This is an isolated study and more research is needed to confirm the findings. In spite of worrisome reports of serious side effects associated with some calcium channel blockers, and despite recommendations by a major expert group for wider use of beta-blockers and diuretics, prescriptions for calcium-channel blockers have increased and beta-blockers have decreased over recent years.

A method is provided for treating hypertension in a subject or reducing development of hypertension in a subject, comprising administering to the subject an amount of CD4+ T-cells engineered to express increased levels of choline acetyltransferase relative to non-engineered CD4+ T-cells of the same type.

In an embodiment, the method is to treat hypertension in a subject. In an embodiment, the method is to reduce development of hypertension in a subject. In an embodiment, the hypertension is resistant hypertension. In an embodiment, the hypertension is essential hypertension.

In an embodiment, the CD4+ T-cells have been transformed with a nucleic acid having the sequence set forth in SEQ ID NO:1 (hChAT-TAL-VP64). In an embodiment, the CD4+ T-cells have been modified to functionally impair, or to reduce expression of, an endogenous T-cell receptor (TCR) of the T-cell. In an embodiment, the amount of CD4+ T-cells administered is sufficient to effect a reduction in a hypertension symptom in said subject. In an embodiment, the reduction in a hypertension symptom is a reduction in mean arterial pressure (MAP) in a subject or a stabilization of MAP of a subject. In an embodiment, the reduction in a hypertension symptom is a reduction in systolic blood pressure (SBP) in a subject or a stabilization of SBP of a subject. In an embodiment, the reduction in a hypertension symptom is a reduction in diastolic blood pressure (DBP) in a subject or a stabilization of DBP of a subject. In an embodiment, the CD4+ T-cells are allogenic to said subject. In an embodiment, the CD4+ T-cells are autologous to said subject.

In an embodiment, the method further comprises obtaining the CD4+ T-cells from the subject prior to engineering the cells to express increased levels of choline acetyltransferase.

In an embodiment, the CD4+ T-cells are also engineered to further comprise a suicide gene, wherein said suicide gene induces expression of the protein HSV-TK.

Also provided is an isolated, modified primary human T cell, modified to express increased levels of choline acetyltransferase relative to an unmodified primary human T cell. In an embodiment, the cell also is modified to functionally impair or to reduce expression of the endogenous T cell receptor (TCR). In an embodiment, the cell elicits no graft-versus-host disease (GVHD) response or a reduced GVHD response in a histo-incompatible human recipient of the cell as compared to a GVHD response elicited by a primary human T cell isolated from the same human donor that is not modified.

In an embodiment, the primary cell which is subsequently modified is an allogeneic T cell or a primary human PBMC isolated from a human subject. In an embodiment, the T cell expresses CD4. In an embodiment, the cell is capable of differentiating into a T regulatory cell. In an embodiment, the cell the reduced GVHD response is evidenced by the isolated, modified primary human T cell eliciting reduced expression of gamma interferon as compared to a primary human T cell isolated from the same human donor. In an embodiment, the reduced GVHD response is evidenced by the isolated, modified primary human T cell not eliciting an increase in expression of gamma interferon as compared to a primary human T cell isolated from the same human donor. In an embodiment, the isolated, modified primary human T cell does not elicit a GVHD response when administered to a human recipient. In an embodiment, cells are screened for histocompatibility. In an embodiment, the donor is screened for histocompatibility prior to donation.

In an embodiment, the cell further comprises a polynucleotide chosen from the group consisting of CMV-hChAT (SEQ ID NO:57), EF1a-hChAT (comprising SEQ ID NO:4), NLS-TAL-G4S-VP64 (SEQ ID NO:53) and NLS-TAL-VP64 (SEQ ID NO:55). In an embodiment, the cell further comprises a polynucleotide encoding a suicide gene, and/or wherein said cell further comprises a polynucleotide capable of downregulating the TCR.

A composition is also provided comprising a therapeutically effective amount of the isolated, modified primary human T cells as described herein, and at least one pharmaceutically acceptable carrier.

Also provided is an isolated recombinant polynucleotide encoding a DNA-targeting region and a transcriptional activator, wherein said transcriptional activator induces transcription of a human ChAT gene when present in a human cell.

In an embodiment, the polynucleotide comprises NLS-TAL-G4S-VP64 (SEQ ID NO:53). In an embodiment, the polynucleotide encodes for a polypeptide comprising the amino acids of NLS-TAL-G4S-VP64 (SEQ ID NO:54).

Also provided is an isolated T cell in which an agent has been introduced into the T cell to increase acetylcholine release from the T cell. In an embodiment, the agent increases expression of choline acetyltransferase (ChAT). In an embodiment, the agent comprises a CMV promoter. In an embodiment, the agent targets a native, genomic ChAT promoter. In an embodiment, the agent comprises a transcriptional activator. In an embodiment, the T cell is a CD4+ T cell. In an embodiment, the agent does not naturally occur in the T cell.

Vectors—The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids encoding hChAT or DNA-targeting elements and transcriptional activators is typically achieved by operably linking a nucleic acid encoding the polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Green & Sambrook (2014, Molecular Cloning: A Laboratory Manual (Fourth Edition), Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. A UBC, EF1A, PGK or CAGG promoter may be used also. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Sources of T Cells—Prior to expansion and engineering by genetic modification of the T cells of the invention, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca2+-free, Mg2+-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD28+, CD4+, CD8+, CD45RA+, and CD45RO+ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express CD4+, CD25+, CD62Lhi, GITR+, and FoxP3+. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rittman.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells—Whether prior to or after engineering by genetic modification of the T cells to express a increased choline-acetyltransferase, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; 8,906,682; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For costimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol. Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for CD4+ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle:cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of Tc cells. Accordingly, depending on the purpose of treatment, infusing a subject with a T cell population comprising predominately of TH cells may be advantageous. Similarly, if an antigen-specific subset of Tc cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application—when an "amount effective to" or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the engineered T cells or T cell compositions of the present invention are administered to a patient by intradermal or subcutaneous injection. In another embodiment, the engineered T cells or T cell compositions of the present invention are preferably administered by i.v. injection.

Methods of Producing TCR-Deficient T-Cells—T cells stably lacking expression of a functional TCR according to the invention may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

In one embodiment of the invention, TCR expression is eliminated using small-hairpin RNAs (shRNAs) that target nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR. Even though some TCR complexes can be recycled to the cell surface, the shRNA will prevent new production of TCR proteins resulting in degradation and removal of the entire TCR complex, resulting in the production of a T cell having a stable deficiency in functional TCR expression.

Expression of shRNAs in primary T cells can be achieved using any conventional expression system, e.g., a lentiviral expression system. Although lentiviruses are useful for targeting resting primary T cells, not all T cells will express the shRNAs. Some of these T cells may not express sufficient amounts of the shRNAs to allow enough inhibition of TCR expression to alter the functional activity of the T cell. Thus, T cells that retain moderate to high TCR expression after viral transduction can be removed, e.g., by cell sorting or separation techniques, so that the remaining T cells are deficient in cell surface TCR or CD3, enabling the expansion of an isolated population of T cells deficient in expression of functional TCR or CD3.

While not necessary for most therapeutic usages of the subject TCR-deficient T cells, in some instances it may be desirable to remove some or all of the donor T cells from the host shortly after they have mediated their anti-hypertensive effect. This may be facilitated by engineering the T cells to express additional receptors or markers that facilitate their removal and/or identification in the host such as GFP and the like. While the present invention should substantially eliminate any possibility of GVHD or other adverse immune reaction in the recipient this may be desired in some individuals. This should not compromise efficacy as it has already been shown that donor T cells do not need to remain long in the host for a long-term anti-tumor effect to be initiated (Zhang, T., et al. 2007. Cancer Res. 67:11029-11036; Barber, A. et al. 2008. J. Immunol. 180:72-78).

In one embodiment of the invention, nucleic acid constructs introduced into engineered T cells further contains a suicide gene such as thymidine kinase (TK) of the HSV virus (herpesvirus) type I (Bonini, et al. (1997) Science 276:1719-1724), a Fas-based "artificial suicide gene" (Thomis, et al. (2001) Blood 97:1249-1257), or *E. coli* cytosine deaminase gene which are activated by gancyclovir, AP1903, or 5-fluorocytosine, respectively. The suicide gene is advantageously included in the nucleic acid construct of the present invention to provide for the opportunity to ablate the transduced T cells in case of toxicity and to destroy the chimeric construct once a tumor has been reduced or eliminated. The use of suicide genes for eliminating transformed or transduced cells is well-known in the art. For example, Bonini, et al. ((1997) Science 276:1719-1724) teach that donor lymphocytes transduced with the HSV-TK suicide gene provide antitumor activity in patients for up to one year and elimination of the transduced cells is achieved using ganciclovir. Further, Gonzalez, et al. ((2004) J. Gene Med. 6:704-711) describe the targeting of neuroblastoma with cytotoxic T lymphocyte clones genetically modified to express a chimeric scFvFc:zeta immunoreceptor specific for an epitope on L1-CAM, wherein the construct further expresses the hygromycin thymidine kinase (HyTK) suicide gene to eliminate the transgenic clones.

It is contemplated that the suicide gene can be expressed from the same promoter as the shRNA, minigene, or non-TCR receptor, or from a different promoter. Generally, however, nucleic acid sequences encoding the suicide protein and shRNA, minigene, or non-TCR receptor reside on the same construct or vector. Expression of the suicide gene from the same promoter as the shRNA, minigene, or non-TCR receptor can be accomplished using any well-known internal ribosome entry site (IRES). Suitable IRES sequences which can be used in the nucleic acid construct of the present invention include, but are not limited to, IRES from EMCV, c-myc, FGF-2, poliovirus and HTLV-1. By way of illustration only, a nucleic acid construct for expressing a chimeric receptor can have the following structure: promoter→chimeric receptor→IRES→suicidal gene. Alternatively, the suicide gene can be expressed from a different promoter than that of the chimeric receptor (e.g., promoter 1→chimeric receptor→promoter 2→suicidal gene).

The expression of acetylcholine transferase is controlled by numerous intracellular factors acting on its promoter, as described in Toliver-Kinsky, et al, and Bausero, P., et al. Inhibition of factors that inhibit expression of hChAT would allow for increased expression of ChAT. The present invention contemplates the use of inhibitors of hChAT inhibition.

The present invention also contemplates the use of pharmaceutical compound to increase ChAT production.

"Activation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

"ChAT" as used herein refers to choline acetyltransferase, a transferase enzyme responsible for the synthesis of the neurotransmitter acetylcholine. ChAT catalyzes the transfer of an acetyl group from the coenzyme, acetyl-CoA, to choline yielding acetylcholine (ACh). There exist two isoforms of ChAT, both encoded by the same sequence. The common type ChAT (cChAT) is present in both the CNS and PNS. Peripheral type ChAT (pChAT) is preferentially expressed in the PNS in humans, and arises from exon skipping (exons 6-9) during post-transcriptional modification.

"Zinc finger protein" as used herein is a small protein structural motif that is characterized by the coordination of one or more zinc ions in order to stabilize the fold. Tandem repeats of engineered zinc fingers can be used to target desired genomic DNA sequences.

The term "TCR" or "T cell Receptor" refers to the complex of molecules found on the surface of T lymphocytes (or T cells) that is responsible for recognizing fragments of antigen as peptides bound to major histocompatibility complex (MHC) molecules. The binding between TCR and antigen peptides is of relatively low affinity and is degenerate: that is, many TCRs recognize the same antigen peptide and many antigen peptides are recognized by the same TCR. The TCR is composed of two different protein chains (that is, it is a heterodimer). In humans, in 95% of T cells the TCR consists of an alpha (α) and beta (β) chain, whereas in 5% of T cells the TCR consists of gamma and delta (γ/δ) chains. This ratio changes during ontogeny and in diseased states as well as in different species. When the TCR engages with antigenic peptide and MHC (peptide/MHC), the T lymphocyte is activated through signal transduction, that is, a series of biochemical events mediated by associated enzymes, co-receptors, specialized adaptor molecules, and activated or released transcription factors. Also part of the complex are the CD3 and zeta-chain molecules that initiate intracellular signaling pathways.

Transcription activator domains can be fused with a targeting domain, such as zinc-fingers, TAL, or CAS9 to target the activation of specific genes. Examples known in the art include VP16, VP64, NF-κB p65 transcriptional activation domain As used herein, "VP16" and "VP64" refer to transcriptional activators derived from viral trans-acting agents. VP16 is a trans-acting protein with amino acids DALDDFDLDML (SEQ ID NO:134) that forms a complex with the host transcription factors Oct-1 and HCF to induce immediate gene transcription. VP64 is a transcriptional activator composed of four tandem copies of VP16 connected with glycine-serine linkers and acts as a stony transcriptional activator.

A "TCR-deficient T cell", or a similar phrase is an isolated T cell(s) that lacks expression of a functional TCR, is internally capable of inhibiting its own TCR production, and further wherein progeny of said T cell(s) may also be reasonably expected to be internally capable of inhibiting their own TCR production. Methods of creating TCR-deficient T cells are known by those skilled in the art, and are described, for example, in U.S. Pat. No. 9,181,527, which is hereby incorporated by reference. Internal capability is important in the context of therapy where TCR turnover timescales (hours) are much faster than demonstrable efficacy timescales (days-months), i.e., internal capability is required to maintain the desired phenotype during the therapeutic period. This may e.g., be accomplished by different means as described infra, e.g., by engineering a T cell such that it does not express any functional TCR on its cell surface, or by engineering the T cell such that it does not express one or more of the subunits that comprise a functional TCR and therefore does not produce a functional TCR or by engineering a T cell such that it produces very little functional TCR on its surface, or which expresses a substantially impaired TCR, e.g by engineering the T cell to express mutated or truncated forms of one or more of the subunits that comprise the TCR, thereby rendering the T cell incapable of expressing a functional TCR or resulting in a cell that expresses a substantially impaired TCR. The different subunits that comprise a functional TCR are described infra. Whether a cell expresses a functional TCR may be determined using known assay methods such as are known in the art described herein. By a "substantially impaired TCR" applicants mean that this TCR will not substantially elicit an adverse immune reaction in a host, e.g., a GVHD reaction. Optionally these TCR-deficient cells may be engineered to comprise other mutations or transgenes that e.g., mutations or transgenes that affect T cell growth or proliferation, result in expression or absence of expression of a desired gene or gene construct, e.g., another receptor or a cytokine or other immunomodulatory or therapeutic polypeptide or a selectable marker such as a dominant selectable marker gene, e.g., DHFR or neomycin transferase. According to the present invention, modified allogeneic T cells are produced that do not express functional T cell receptors (TCRs). It is to be understood that some, or even all, of the TCR subunits/dimers may be expressed on the cell surface, but that the T cell does not express enough functional TCR to induce an undesirable reaction in the host. Without functional TCRs on their surface, the allogeneic T cells fail to mount an undesired immune response to host cells. As a result, these TCR-deficient T cells fail to cause GVHD, for example, as they cannot recognize the host MHC molecules. Additionally, these TCR-deficient T cells can be engineered to simultaneously express functional, non-TCR, disease-specific receptors. As is well known to one of skill in the art, various methods are readily available for isolating allogeneic T cells from a subject. For example, using cell surface marker expression or using commercially available kits (e.g., ISOCELL™ from Pierce, Rockford, Ill.).

A "pharmaceutical excipient" or a "pharmaceutically acceptable excipient" is a carrier, usually a liquid, in which an active therapeutic agent is formulated. In one embodiment of the invention, the active therapeutic agent is a population of TCR-deficient T cells. In one embodiment of the invention, the active therapeutic agent is a population of TCR-deficient T cells expressing a functional, non-TCR receptor. The excipient generally does not provide any pharmacological activity to the formulation, though it may provide chemical and/or biological stability. Exemplary formulations can be found, for example, in Remington's Pharmaceutical Sciences, 19$^{th}$ Ed., Grennaro, A., Ed., 1995 which is incorporated by reference.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, or sublingual administration. Pharmaceutically acceptable carriers include sterile aqueous solutions or dispersions for the extemporaneous preparation of sterile injectable solutions or dispersions. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

In a particularly preferred embodiment of the invention, appropriate carriers include, but are not limited to, Hank's Balanced Salt Solution (HBSS), Phosphate Buffered Saline (PBS), or any freezing medium having for example 10% DMSO and 90% human serum. Pharmaceutical compositions typically must be sterile and stable under the conditions of manufacture and storage. The composition can be formulated as a solution. The carrier can be a dispersion medium containing, for example, water.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "overexpressed" tumor antigen or "overexpression" of the tumor antigen is intended to indicate an abnormal level of expression of the tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

An "adenovirus" refers to members of the family Adenoviridae, and are medium-sized (90-100 nm), nonenveloped (without an outer lipid bilayer) viruses with an icosahedral nucleocapsid containing a double stranded DNA genome. Adenoviruses are used as a vehicle to administer targeted therapy in the form of recombinant DNA or protein, due to their ability to affect both replicating and non-replicating cells, accommodate large transgenes, and code for proteins without integrating into the host cell genome.

An "adeno-associated virus" or "AAV" refers to members of the family Parvoviridae. It causes a very mild immune response, contributing to its apparent lack of pathogenicity. Gene therapy vectors using AAV can infect both dividing and quiescent cells and persist in an extrachromosomal state without integrating into the genome of the host cell, although in the native virus some integration of virally carried genes into the host genome does occur. By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class 1 molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). Examples of subjects include humans, dogs, cats, mice, rats, and transgenic species thereof.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

The invention as described, including the cells and polynucleotides, can be used alone or with other therapies This invention will be better understood from the Experimental Details, which follow. However, one skilled in the art will readily appreciate that the specific methods and results discussed are merely illustrative of the invention as described more fully in the claims that follow thereafter.

Experimental Details

Introduction

A major physiological mechanism of blood pressure regulation is through modulation of blood flow by alterations in vessel diameter. Acetylcholine, a signaling molecule produced by neurons and lymphocytes, is a vasorelaxant that decreases blood vessel resistance and reduces blood pressure (2). Binding to cognate cholinergic receptors on endothelial cells, acetylcholine stimulates phosphorylation of endothelial nitric oxide synthase (eNOS), the rate-limiting enzyme in the biosynthesis of nitric oxide (NO). Endothelium-derived NO diffuses into smooth muscle cells in the vascular wall, where it interacts with the heme-containing protein guanylate cyclase to induce synthesis of cGMP. This secondary messenger down-modulates availability of intracellular calcium required for myosin phosphorylation, leading to relaxation of vascular smooth muscle cells, and decreased blood pressure. Paradoxically, most arteries are innervated by adrenergic nerves, and endothelial cells do not receive major direct input from acetylcholine-secreting neurons (3-5).

While studying the neural regulation of immunity, a specific role for lymphocyte-derived acetylcholine was previously identified in relaying neural signals in the inflammatory reflex (1). A subset of T cells in spleen and other tissues expresses choline acetyltransferase (ChAT), the rate-limiting enzyme for the biosynthesis of acetylcholine (1,6,7). The present study characterizes these cells further and determines whether ChAT-expressing lymphocytes provide an endogenous cellular mechanism for vasorelaxation in the regulation of blood pressure.

Materials and Methods

Mice.

All animal experiments were performed under protocols approved by the Institutional Animal Care and Use Committee of the Feinstein Institute for Medical Research, North Shore-LIJ Health System, the Karolinska Institutet or the University Health Network Animal Care Committee.

Choline acetyltransferase (ChAT)-GFP (B6.Cg-Tg(RP23-268L19-EGFP)2Mik/J), ChAT-floxed (B6.129-Chattm1Jrs/J), and mice expressing Cre recombinase under the control of the endogenous CD4 promoter (CD4-Cre) were purchased from Jackson Laboratories (Bar Harbor, Me., USA). ChAT-floxed and CD4-Cre mice were crossed to generate mice genetically devoid of ChAT in the CD4+ population. ChAT-flox mice were crossed with animals expressing Cre recombinase under the control of the CD4 promoter (CD4-$Cre^+$ $ChAT^{flox/flow}$). In these animals, Cre recombinase is expressed in the double positive stage of the thymus, resulting in recombination in the T cell lineage (29). Littermate controls were $Cre^-$ $ChAT^{flox/flox}$. Animals were housed at 25° C. on a 12-h light/dark cycle, and acclimatized for at least 1 week before conducting experiments. Water and regular rodent chow were available ad libitum. BALB/c nude (nu/nu) mice 8 to 12 weeks old were obtained from Taconic. Male eNOS-deficient mice (16) were provided by J. Lundberg and E. Weitzberg, Karolinska Institutet, Stockholm, Sweden. Cells pooled from ChAT(BAC)-eGFP male and female mice were used for functional and phenotypic characterization. Animals were euthanized using $CO_2$ asphyxiation.

Flow Cytometry and Cell Sorting.

ChAT-eGFP$^+$ and ChAT-eGFP$^-$ cells were isolated from spleens of B6.Cg-Tg(RP23-268L19-eGFP)2Mik/J reporter mice by negative selection for CD4$^+$ T cells followed by cell sorting by flow cytometry of the $CD4^+CD44^{hi}CD62L^{lo}$ population into eGFP$^+$ and eGFP$^-$ subsets (1). For cell sorting experiments, an enriched CD4$^+$ T-cell suspension was obtained by negative selection (CD4$^+$ T-cell isolation kit II, Miltenyi) of spleen cells harvested from male ChAT (BAC)-eGFP mice. The resulting enriched $CD4^+$ cell suspension with >90% purity was then stained with anti-CD44 PE (eBioscience, 12-0441-81), anti-CD4 Pacific Orange (Invitrogen, MCD0430), anti-CD62L PE-Cy7 (eBioscience, 25-0621-82), and anti-CD19 APC (BD Biosciences, BDB550992) antibodies and 7-AAD solution. After gating out $CD19^+$ and gating for $CD62L^{lo}$ $CD44^{hi}$ cells, a ChAT-$eGFP^-$ and a ChAT-$eGFP^+$ fraction were collected using a FACSAria cell sorter (Becton Dickinson). The resulting fractions were $CD4^+CD44^{hi}CD62L^{lo}$ChAT-$eGFP^-$ and $CD4^+CD44^{hi}CD62L^{lo}$ChAT-$eGFP^+$. 100-150,000 cells were sorted into FCS-containing cell culture medium. To improve purity, the freshly sorted cells were immediately sorted again using the same gating strategy, now directly into Trizol solution (Ambion) according to a modified ImmGen protocol (world wide web.immgen.org/Protocols) and subsequently frozen at −80° C. Subsequent RNA isolation and Affymetrix Mouse ST 1.0 gene array hybridization experiments were performed by ImmGen (13). Gene expression of $CD4^+$ChAT-eGFP+ and CD4+ ChAT-$eGFP^+$ cells were analyzed separately and in the context of subsets of the publicly available ImmGen data set (13) using the R programming language (see below).

Cell Culture. Stable Transfection of Jurkat Cells.

Jurkat cells (originally obtained from ATCC) were a generous gift from C. Chu, The Feinstein Institute for Medical Research, Manhasset, N.Y., USA. pCMV6-mChAT (mChAT ORF in a pCMV6-kan/neo plasmid (ORIGene, Rockville, Md. (MC220061)) was nucleofected into Jurkat cells with a mouse T-cell kit (Lonza, Allendale, N.J. VPA-1006) and a Nucleofector 2b (Lonza). Transformed cells were selected over 2 weeks with G418 (400 mg/mL) in RPMI containing 10% FBS. Isolated cells were individually selected by pipet and serial dilution for monoclonal populations, then grown for an additional month to ensure stable chromosomal integration. Monoclonal lines were analyzed for ChAT expression by western blotting. Jurkat cell lines tested negative for *Mycoplasma* sp., EBV, HAdV, Hantaan, HCMV, Hepatitis A, Hepatitis B, Hepatitis C, HHV 6, HHV 8, HIV1, HIV2, HSV 1, HSV 2, HTLV 1, HTLV 2, LCMV, Seoul, Sin Nombre, VZV.

Co-Incubation Experiments.

Primary $ChAT^+$ lymphocytes or Jurkat T lymphocytes or pCMV6-mChAT-transfected Jurkat T cells (JTChAT) were co-incubated with either human endothelial cells derived from pulmonary microcirculation or murine endothelial cells (30,31). Human PEC1.6ST cells were seeded in 6-well plates in Endothelial Cell Growth Medium MV with supplement mix C-39225 (PromoCell) and experiments were performed at confluency. $2\times10^6$ ChAT+ Jurkat T cells, $2\times10^6$ Jurkat T cells, $10^6$ primary ChAT+ lymphocytes or acetylcholine to a concentration of 100 μM in fresh medium was added to the endothelial cell culture, and cells incubated for 1 h. During co-culture experiments, cells were kept in a modular incubator chamber (Billups-Rothenberg, Del Mar, Calif., USA) in a microenvironment within the chamber of 37° C., 1% $O_2$, 5% $CO_2$, and 100% humidity (32). Culture wells were subsequently washed twice with cold PBS and removal of non-adherent cells verified by microscopy. Protein was extracted using T-PER solution (Thermo Scientific) in the presence of HALT protease and phosphatase inhibitors (Thermo Scientific) according to manufacturer's instructions, and lysates stored at −80° C. until analysis using western blot. Membranes were probed with anti-peNOS (Cell Signaling) and anti-beta actin (GeneScript) and developed with standard reagents (Pierce). Images were acquired on a GS-800 calibrated densitometer (Bio-Rad) and images analyzed using Image Studio software (Licor). Nitrite and nitrate in supernatants was measured using the Nitrate/Nitrite Colorimetric Assay Kit (Cayman Chemical, Ann Arbor, Mich.) according to manufacturer's instructions.

Murine lung microvascular endothelial cells were isolated and cultured as previously described (31). In brief, fresh mouse lungs were rinsed, minced aseptically into small pieces, and digested in collagenase A (1 mg/mL, Worthington, N.J.) at 37° C. for 60 min with occasional agitation. The single-cell suspension was filtered through sterile 40 μm cell strainer, washed in DMEM medium containing 10% FCS (10% FCS-DMEM), and incubated with magnetic beads conjugated with anti-mouse CD31 antibody (Invitrogen, Carlsbad, Calif.) at 4° C. for 30 min. The bead-bound cells were recovered by placing the tube in a magnetic separation rack, washed with 10% FCS-DMEM, collected, and cultured in DMEM medium containing 10% FCS, 2 mM L-glutamine, 2 mM sodium pyruvate, 20 mM HEPES, 1% nonessential amino acids, 100 μg/mL streptomycin, 100 U/mL penicillin, 100 μg/mL heparin, and 100 μg/mL endothelial cell growth supplement. Endothelial cell phenotype was confirmed by positive staining of multiple endothelial-specific markers.

Calcium Measurements.

Endothelial cells derived from pulmonary microvasculature (31) were seeded onto glass coverslips 16-24 h before use in calcium imaging experiments. The coverslips were placed in a stainless steel imaging cell chamber (Attofluor Cell Chamber, Life Technologies, Grand Island, N.Y., USA). Within this chamber, the cells were washed with DMEM and loaded with the calcium-sensitive Fluo-4 NW in DMEM with probenecid (Fluo-4 NW Calcium Assay Kit, Molecular Probes, Eugene Oreg., USA) for 45-60 min at 37° C. under 5% $CO_2$. The imaging chamber was placed in a temperature-controlled Leiden chamber holder mounted on the stage of an Axiovert 200 M inverted fluorescence microscope (Carl Zeiss Microscopy, Thornwood, N.Y., USA) equipped with a 40×, 0.60 numerical aperture objective. Data were recorded every 10 s by illuminating the sample with light from a mercury lamp passing through an excitation filter (470 nm±40) before being directed at the cells by a 495-nm dichroic mirror. A single field was visualized in each experiment. Emitted light was captured by a cooled CCD camera (AxioCam monochromatic, Carl Zeiss Microscopy, Thornwood, N.Y., USA) following passage through a 525-nm±50 emission filter. The image acquisition setup was controlled by Axiovision 4.7 software (Carl Zeiss Microscopy, Thornwood, N.Y., USA).

After being placed on the microscope stage, cells were washed once with HEPES-buffered and indicator-free DMEM-containing acetylcholine esterase inhibitor. Baseline fluorescence was recorded for 2 min at which time cells were treated with 0.1 mM acetylcholine or co-culture with $10^6$/mL of Jurkat T lymphocytes, pCMV6-mChAT vector-transfected Jurkat T lymphocytes, primary $ChAT^+$ lymphocytes, or primary $ChAT^-$ lymphocytes. Intracellular fluorescence was monitored for an additional 5 min before concluding the experiment by treatment with 10 μM ionomycin (Sigma-Aldrich, St-Louis, Mo., USA).

The acquired images were exported to ImageJ software for analysis. The mean fluorescence intensity values of 6-31 cells per experiment were extracted for each time point and normalized to the average baseline intensity. Individual cell data were then averaged for each experiment. To quantify the treatment response, the average fluorescence in the 1-min intervals immediately before and after treatment was calculated.

Blood Pressure Measurement. Arterial Catheterization.

Adult C57Bl/6 male mice (23-30 g) were anesthetized using isoflurane and maintained on a heating pad at rectal temperature 37.5-38° C. throughout the experiment. An incision on the left side of the neck followed by blunt dissection was performed to gain access to the carotid artery. The artery was tied off toward the head before cannulation. A PE 10 catheter (0.28 mm inner diameter and 0.61 mm outer diameter) was inserted in the artery and secured with USP 6.0 silk suture. Arterial blood pressure was then monitored through the saline-filled catheter with recording system (AD-instruments). Cells for infusion were spun down and resuspended in NaCl before experiments. The suspensions (200 μL) were pre-warmed and administered via a T-branch on the catheter. In all experiments, the animals were allowed to stabilize for 5 min after catheter insertion and after that an initial record of blood pressure with saline injection was recorded followed by an initial 10-s to 3-min baseline recording. Animals with hypotension were excluded. The infusion was administered subsequently during approximately 10 s, and blood pressure recorded every 10 s for ≥9 min. Blood pressure change over time was assessed by calculating the area under the curve for the baseline normalized MAP tracing of cells and then calculating the area under the curve between the $240^{th}$ and the $780^{th}$ second and/or analyzed using 2-way ANOVA followed by Bonferroni post hoc test using GraphPad Prism. The baseline was calculated as the mean MAP over 3 min before injection. Jurkat T or JTChAT lymphocytes ($50\times10^7$ cells in 200 μL saline or the number of cells indicated in the figures) were administered, with or without pretreatment with atropine (0.05 mg/kg) or L-NAME (10 mg/kg). The cells were injected 30 and 10 min after atropine and L-NAME, respectively. In experiments with eNOS-deficient mice, ~1 year of age, saline, Jurkat T cells, or JTChAT cells were infused sequentially after a ≈10-s base line and blood pressure monitored for ~4 min after each infusion. Animals with recordings interrupted before 4 min were excluded. In anesthetized CD4-Cre$^{+/0}$×ChAT$^{flox/flox}$ mice and their littermate controls, a 1.2 F pressure catheter (Transonic, US) in the right carotid artery was used for measurements and data acquired using Biopack 3.8 software.

Telemetry Hemodynamic Recording.

12-week-old mice were anesthetized using 2% isoflurane oxygen mixture and placed on a heating pad. A midline incision was made on the neck and the right common carotid was isolated. The flexible tip of a hemodynamic telemetry unit (Data Sciences International, PA-C10) was introduced into the carotid after puncturing the carotid with a 26-gauge needle. The catheter was secured in place using a 6-0 silk suture. The body of the telemetry unit was placed subdermally close to the abdomen. After 5 days of recovery, arterial pressures were recorded for 10 s every 1 min over a 48 h period. Data analysis and acquisition were performed using DataQuest A.R.T software (Data Sciences International). The investigator was blinded for animal group at time of unit implantation and for the analysis.

Echocardiography.

Mice were anesthetized using 1.5% isoflurane oxygen mixture. Mice were placed on a heating pad and body temperature was maintained between 37.3 and 37.6° C. for the duration of the measurements. The investigator was fully blinded for animal group for examination and analysis. Transthoracic M-mode echocardiographic examination was performed from the long axis view of the heart at the level of the posteromedial papillary muscle using a Vevo 7700 system (VisualSonics) with a 30-MHz ultrasonic linear transducer scanning head. The papillary muscles were not included in the measurements. Measurements of left ventricle diastolic diameter (LVDd) and left ventricle systolic diameter (LVDs) were done under Time Motion-mode (TM-Mode) and were averaged from at least three cardiac cycles. End Systolic volume (ESV) and end diastolic volumes (EDV) were calculated using Vevo770 heart analysis package (volume estimate based on Teichholz's formula). SV was calculated as EDV−ESV; cardiac output (CO) as SV×heart rate (HR); ejection fraction (EF) as (EDV−ESV)/EDV×100; and fraction shortening (FS) was calculated as (LVDd−LVDs)/LVDd×100.

Non-Invasive Blood Pressure Measurement.

Non-invasive blood pressure measurements were conducted in male CD4-Cre+/0×ChATflox/flox mice and their littermate controls at 7 weeks of age using the CODA NIBP tail-cuff device (Kent Scientific Corp., Torrington, Conn., USA) as per the manufacturer's instructions. Mice were anesthetized using isoflurane (4-5% induction, 1.5% maintenance) and the NIBP and heart rate recorded every 45 s for 10-12 min. The serial measurements were then averaged. All measurements were conducted during the animals' light cycle.

Statistical Analysis. Gene Expression.

RNA isolation and Affymetrix Mouse ST 1.0 gene array hybridization was performed by ImmGen (world wide web.immgen.org/Protocols). Samples with high and comparable array expression levels of CD3, CD4, and CD44 were included in the analysis.

Data analysis was performed using the R programming language. The raw data sets from ImmGen (13) (Release September 2012) were downloaded from NCB's GEO data repository (GSE15907). After removal of control, test, and certain variant subsets, this data set comprises 2-7 replicates of 198 different immune cell subsets.

The R/Bioconductor package "oligo" was used for data import and normalization (through 'rma') and the packages "pd.mogene.1.0.st.v1", "mogene10sttranscriptcluster.db", and the getNetAffx function from the "oligo" package for annotation of transcripts. This annotation process created a set of 476 transcripts that were identical to the $9^{th}$ decimal, which were removed. See also Ericson J et al. "ImmGen microarray gene expression data: Data Generation and Quality Control pipeline", available at world wide web.immgen.org/Protocols/ImmGen%20QC%20Documentation_ALL-DataGeneration_0612.pdf. Transcripts without any annotated gene symbol available were removed, and the remaining data set of 24,925 unique transcripts IDs were analyzed.

Expression data from ChAT-eGFP$^{+}$ and ChAT-eGFP$^{-}$ subsets were merged with the ImmGen data using a ratio-based method for batch effect removal (33). To accomplish this, overlapping groups between batches were used as reference samples. The ImmGen data set contains CD4$^{+}$CD44$^{hi}$CD62L$^{lo}$ memory T cells from the spleen, labeled T.4Mem44h62l.Sp. According to available data on ChAT-eGFP$^{+}$ and ChAT-eGFP$^{-}$ T-cell populations (1), >90% of this subset consists of CD4$^{+}$CD44$^{hi}$CD62L$^{lo}$ ChAT-eGFP$^{-}$ lymphocytes; therefore, the T.4Mem44h62l.Sp and CD4$^{+}$CD44$^{hi}$CD62L$^{lo}$ ChAT-eGFP$^{-}$ T-cell subsets were used to normalize expression data between ImmGen and ChAT_eGFP reporter samples. Each batch was first normalized separately using 'rma'. Then, each sample was divided by the mean of the T.4Mem44h62l.Sp or $CD4^+CD44^{hi}CD62L^{lo}$ ChAT-eGFP⁻ subsets, respectively. Data were subsequently merged into a ratio matrix for transcript IDs.

Hierarchical clustering analysis was performed using complete linkage clustering with a Euclidean distance measure. Differential analysis in group comparisons was performed using the R/Bioconductor package "limma" (34). The David Bioinformatics Annotation Tool (david.abcc.ncifcrf.gov/) (10,11) was used for Gene Ontology (GO) and KEGG pathway enrichment analysis. The Gene Ontology enrichment analysis and visualization tool (GOrilla) (9,35) was used for further analysis and visualization of GO terms.

In the analysis of transcription factor expression across the data set, the absolute value of the log-transformed expression values of each transcription factor in 14 splenic T-cell samples was calculated. Since expression data are in ratio format this presents a symmetry for high and low expression values. The absolute values of the log-transformed expression ratios were then ranked for each transcription factor across the 14 samples. For transcription factors that were ranked highest in the $ChAT\_eGFP^+$ T-cell sample, pairwise comparisons for differential expression between the $ChAT\_eGFP^+$ T-cell sample and each of the other 13 splenic T-cell subsets were performed. Transcription factors for which $ChAT\_eGFP^+$ samples were ranked highest and significantly different in each pairwise comparison were plotted in a heat map (FDR-adjusted $P<0.05$ in any pairwise comparison between ChAT_eGFP+ T and the other T cells samples).

Sample size was chosen depending on available data (Immgen) and for experiments according to prior experience with similar experiments in the involved research laboratories. Differences between experimental groups were analyzed using one-way ANOVA followed by Dunnett's or Bonferroni post hoc analysis or Student's t test as indicated. Blood pressure data obtained using telemetry were analyzed using repeated measures ANOVA. $P<0.05$ was considered significant.

Results and Discussion

To characterize these ChAT-expressing T cells, we used fluorescence-activated cell sorting (FACS) to isolate splenic $ChAT\text{-}eGFP^+CD4^+CD44^{hi}CD62L^{lo}$ T lymphocytes from transgenic mice expressing enhanced green fluorescence protein (eGFP) under the control of regulatory elements for expression of ChAT (1, 8). These acetylcholine-producing memory T cells have been shown to control innate immune responses and constitute <10% of the $CD4^+CD44^{hi}CD62L^{lo}$ population in spleen (1). Comparison to $ChAT\text{-}eGFP^-CD^{4+}CD44^{hi}CD62L^{lo}$ T lymphocytes by microarray analysis using Affymetrix Gene 1.0 ST arrays and unsupervised hierarchical clustering of the complete transcriptome showed that ChAT-eGFP⁻ and ChAT-eGFP⁺ cells formed distinct clusters. Transcript expression in ChAT-eGFP⁺ subsets differed considerably as compared to ChAT-eGFP⁻ subsets. Analysis of the significant differences using the Gene Ontology enrichment analysis and visualization tool (GOrilla) (9) revealed that genes modulating immune process regulation and negative regulation of leukocyte activation were highly overrepresented; and genes modulating G-protein-coupled signaling were downregulated. Analysis using the Kyoto Encyclopedia of Genes and Genomes (KEGG) database by the DAVID Bioinformatics tools (10-12) showed over-representation of genes implicated in cytokine-cytokine receptor interaction. ChAT expression in ChAT-eGFP⁺ T lymphocytes was compared against that in 198 different immune cell subsets in the ImmGen data set (13). The ChAT-eGFP⁺ T-cell subset expressed ChAT at significantly higher levels as compared to the other subsets. Microarray analysis using unsupervised hierarchical clustering demonstrated that ChAT-eGFP⁺ T lymphocytes clustered with CD4⁺ memory and regulatory T lymphocytes.

ChAT-eGFP⁺ T cells within the $CD4^+CD44^{hi}CD62L^{lo}$ T helper cell population defined a unique branch, significantly distinct from other splenic T lymphocyte subsets in hierarchical clustering. Pairwise Euclidean distance plots of complete gene expression revealed that ChAT-eGFP⁺ T lymphocytes were highly segregated. Principal component analysis showed that ChAT-eGFP⁺ T lymphocytes harbored a T-cell gene signature, but differed significantly as compared to other T lymphocyte subsets by the first principal component. Gene ontology classification demonstrated that genes implicated in regulation of leukocyte activation, cytokine receptor activity, and G-protein-coupled receptor activity were highly over-represented. Pairwise comparison against 13 other T lymphocyte subsets in the ImmGen database showed that from the cohort of transcription factors implicated in T-cell differentiation (14), 41 were highly over- or under-represented in the ChAT-eGFP⁺ T lymphocyte subset. These $ChAT^+CD4^+$ T cells are referred to as CD4 $T_{ChAT}$ cells.

Figures 2A, 2B, 2C:
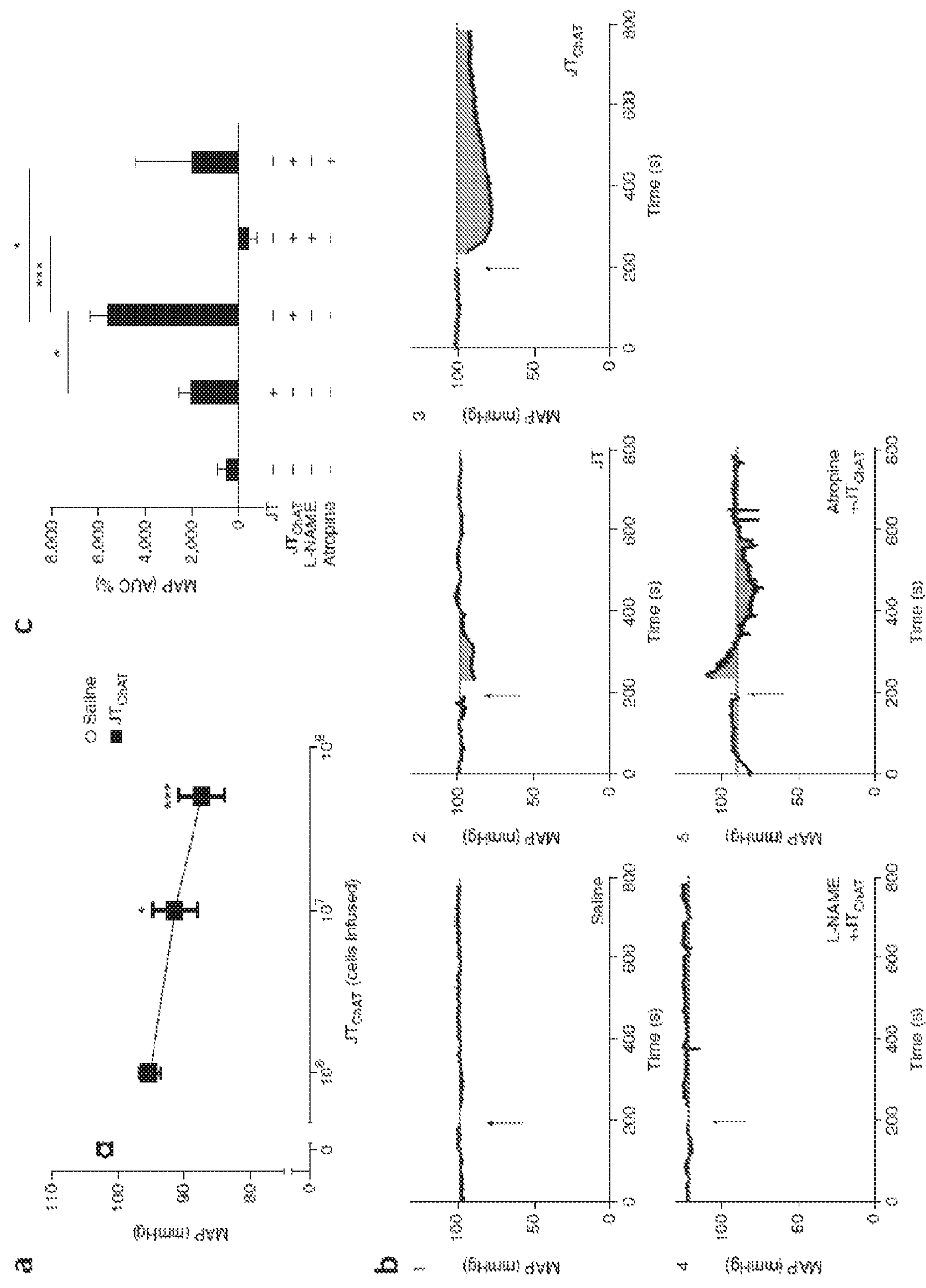
FIG. 2*a*-2*c*: Mean arterial blood pressure (MAP) after infusion of JTChAT lymphocytes in wild-type C57Bl/6 mice. (a) Mean arterial blood pressure (MAP) over ~9 min after infusion of JTChAT lymphocytes or saline. Saline (n=14); JTChAT cells (n=7-13). *P<0.05, ***P<0.001, JTChAT cells vs. saline by ANOVA followed by Bonferroni post hoc test. (b) Tracings of MAP over time in mice infused with (1) saline, (2) Jurkat T cells lymphocytes, or (3) JTChAT lymphocytes, or infusion of JTChAT lymphocytes after with (4) L-NAME or (5) atropine. Arrows indicate the time for infusion start. The cut in the tracings indicates the period of infusion-related measurement artifacts. (c) MAP change from baseline×time expressed as area under the curve±s.e.m. for mice injected with saline (n=19), Jurkat T lymphocytes (n=13), or JTChAT lymphocytes (n=9). Mice were pre-treated with L-NAME (n=7) or atropine (n=8) as indicated. *P<0.05, ***P<0.001 (ANOVA with Bonferroni post hoc analysis). AUC, area under the curve.

Tail vein blood was collected from ChAT-eGFP mice and it was found that ChAT-eGFP⁺ T lymphocytes represented 1.1% of total circulating T lymphocytes (median 95% confidence interval: 0.5-2%) (FIG. 1*a*). To study whether this relatively small number of lymphocytes modulates blood pressure, Cre-loxP recombination was used in mice to selectively ablate ChAT in CD4⁺ cells. Mice expressing Cre recombinase under the control of the endogenous CD4 promoter (CD4-Cre) were crossed with mice having loxP-flanked ChAT (ChAT-floxed) to generate CD4⁺ ChAT-deficient offspring (CD4 $ChAT^{-/-}$). Continuous recordings of carotid blood pressure were obtained in awake, freely moving CD4 $ChAT^{-/-}$ and littermate CD4 $ChAT^{+/+}$ mice using telemetry. Both strains displayed normal and similar diurnal blood pressure variation. Systolic, diastolic, and mean arterial pressures were significantly higher in CD4 $ChAT^{-/-}$ as compared to littermate CD4 $ChAT^{+/+}$ mice (FIG. 1*b*). Blood pressure recordings as mean arterial tail cuff blood pressure in another cohort of CD4 $ChAT^{-/-}$ and CD4 $ChAT^{+/+}$ mice were also significantly higher in CD4 $ChAT^{-/-}$ mice as compared to littermate CD4 ChAT controls$^{+/+}$ (113±3 mm Hg, n=23 vs. 103±4 mm Hg, n=17, P=0.028). Finally, blood pressure measured through an indwelling left carotid artery catheter during anesthesia was also significantly higher in CD4 $ChAT^{-/-}$ as compared to littermate CD4 $ChAT^{+/+}$ mice (FIG. 2*c*). Heart rate was unchanged or decreased in CD4 $ChAT^{-/-}$ mice as compared to CD4 $ChAT^{+/+}$ mice. Moreover, echocardiographic assessment of cardiovascular function in these animals revealed that cardiac output, ejection fraction, stroke volume, and fractional shortening of the left ventricle were all significantly decreased in CD4 $ChAT^{-/-}$ as compared to the CD4 $ChAT^{+/+}$ mice (FIG. 2*d*). Together, these data indicate that deletion of CD4 $T_{ChAT}$ cells increases vascular resistance and blood pressure in mice.

To study the mechanism of lymphocyte-derived acetylcholine in blood pressure regulation, we stably transfected Jurkat T lymphocytes with the pCMV6-mChAT vector engineered to express ChAT. These $JT_{ChAT}$ cells constitutively produced acetylcholine, whereas non-transfected Jurkat T cells did not produce detectable levels of acetylcholine (data not shown). It has been previously established that acetylcholine mediates vasodilation and hypotension by increasing intracellular $Ca^{2+}$ levels, and by activating Ser1177 phosphorylation of endothelial nitric oxide synthase (eNOS) to catalyze biosynthesis of NO from L-arginine (15). To investigate whether $JT_{ChAT}$ cells stimulate these mechanisms of NO-production here, vascular endothelial cells were pre-loaded with the calcium-responsive Fluo-4 dye and incubated with $JT_{ChAT}$ cells. It was observed that incubation of $JT_{ChAT}$ cells with endothelial cells triggered a transient increase in endothelial $Ca^{2+}$ levels as measured by time-lapse fluorescent microscopy, whereas incubation of Jurkat T cells with endothelial cells failed to increase endothelial intracellular $Ca^{2+}$ levels. Incubation of primary ChAT-eGFP$^{+}$ lymphocytes derived from ChAT-eGFP reporter mice or $JT_{ChAT}$ cells with endothelial cells stimulated Ser1177 phosphorylation; this eNOS phosphorylation was attenuated by atropine. Addition of $JT_{ChAT}$ cells to endothelial cultures also increased production of nitrate and nitrite in the medium, the stable end products of enhanced NO production, mediated by exposure of endothelial cells to $JT_{ChAT}$ cells in vitro.

To determine whether $JT_{ChAT}$ cells mediate vasorelaxation in vivo, we measured blood pressure in anesthetized mice following insertion of a catheter into the left carotid artery. Infusion of $JT_{ChAT}$ cells significantly reduced mean arterial pressure within minutes, transiently producing up to a 10% decrease (FIG. 2*a*). In contrast, administration of saline or Jurkat T cells failed to significantly decrease mean arterial pressure from baseline (FIG. 2*b,c*). Administration of the muscarinic receptor blocker atropine, or the NOS inhibitor L-N$^{G}$-nitroarginine methyl ester (L-NAME) attenuated $JT_{ChAT}$ cell-mediated decreases in blood pressure (FIG. 2*b,c*). Administration of $JT_{ChAT}$ cells failed to significantly reduce mean arterial pressure from baseline in a group of mice with a genetic disruption of eNOS (16), as expected from the prior experiments indicating that $JT_{ChAT}$ cells enhance endothelial NO production. Together, these results indicate that lymphocyte-derived acetylcholine can decrease blood pressure through a mechanism of endothelium-dependent vasorelaxation.

The identification here of lymphocytes that contribute to blood pressure regulation reveals a previously unknown mechanism in cardiovascular homeostasis. The observation that genetic ablation of ChAT in CD4$^{+}$ cells results in increased blood pressure in mice indicates that CD4 $T_{ChAT}$ cells have a homeostatic role in vasorelaxation and regulation of blood pressure. T cells have previously been linked to development of chronic vascular inflammation, atherosclerosis, and chronic increase in blood pressure (17-19). Putative pathogenic mechanisms of T cells in hypertension, which are incompletely understood, include pro-inflammatory cytokine production, T-cell infiltration into vascular walls, and structural changes and stiffening of arterial walls secondary to inflammation (19-20). It has also been argued that specific T-cell subtypes may play distinct roles in hypertension. For example, regulatory T cells may attenuate hypertension by differentially modulating vascular inflammation (21). Furthermore, it has been suggested that neural signaling originating in the brain stem and circumventricular organs may modulate the role of T lymphocytes in the development of experimental hypertension, and that T cells may play a role in the cerebral regulation of blood pressure (22). The present findings offer an additional possibility, that a deficiency of CD4 $T_{ChAT}$ cells could contribute to an increase in blood pressure.

This laboratory and others have previously implicated CD4 $T_{ChAT}$ cells in neural control of inflammation (1, 23, 24). Blood-borne CD4 $T_{ChAT}$ cells may deliver acetylcholine to cells devoid of direct cholinergic innervation, including vascular endothelial cells, which respond with NO-dependent vasodilation. Because of the physical constraints within 20- to 40-μm sized arterioles (25), blood-borne CD4 $T_{ChAT}$ (which are on the order of ~10 μm in diameter) are likely capable of interacting directly with arteriolar endothelial cells, providing a cellular mechanism of acetylcholine-mediated arteriolar relaxation. Prior unexplained evidence of decreased ChAT expression in lymphocytes of hypertensive rats as compared to normotensive rats (26) support a role of blood-borne acetylcholine-producing lymphocytes in vasorelaxation. Our findings that CD4 ChAT$^{-/-}$ mice have an increase in blood pressure render plausible consideration of whether dysregulation of CD4 $T_{ChAT}$ cells and acetylcholine contributes to the pathogenesis of essential hypertension, and whether this mechanism may underlie hypertension in some cases. This improved understanding of lymphocyte-derived acetylcholine to mediate endothelial-dependent arterial relaxation suggests that it may be possible to enhance cellular acetylcholine release in the vasculature to therapeutically regulate local flow and blood pressure, insights that may have implications for developing a novel therapy for hypertension.

Moreover, CD4 $T_{ChAT}$ cells are regulated by neural signals traveling in the vagus and splenic nerves (1). Ongoing studies of these mechanisms using implanted electrical nerve stimulators (28,29) may offer another strategy to control the activity of blood pressure-regulating ChAT$^{+}$ lymphocytes and prevent or reverse hypertension.

Methods

Mice. All animal experiments were performed under protocols approved by the Institutional Animal Care and Use Committee of the Feinstein Institute for Medical Research, North Shore-LIJ Health System, the Karolinska Institutet or the University Health Network Animal Care Committee.

Choline acetyltransferase (ChAT)-GFP (B6.Cg-Tg(RP23-268L19-EGFP)2Mik/J), ChAT-floxed (B6.129-Chattm1Jrs/J), and mice expressing Cre recombinase under the control of the endogenous CD4 promoter (CD4-Cre) were purchased from Jackson Laboratories (Bar Harbor, Me., USA). ChATfloxed and CD4-Cre mice were crossed to generate mice genetically devoid of ChAT in the CD4+ population. ChAT-flox mice were crossed with animals expressing Cre recombinase under the control of the CD4 promoter (CD4-Cre+ ChAT flox/flox). In these animals, Cre recombinase is expressed in the double positive stage of the thymus, resulting in recombination in the T cell lineage (29). Littermate controls were Cre− ChATflox/flox Animals were housed at 25° C. on a 12-h light/dark cycle, and acclimatized for at least 1 week before conducting experiments. Water and regular rodent chow were available ad libitum. BALB/c nude (nu/nu) mice 8 to 12 weeks old were obtained from Taconic. Male eNOS-deficient mice16 were provided by J. Lundberg and E. Weitzberg, Karolinska Institutet, Stockholm, Sweden. Cells pooled from ChAT(BAC)-eGFP male and female mice were used for functional and phenotypic characterization. Animals were euthanized using $CO_2$ asphyxiation or cervical dislocation.

Flow cytometry and cell sorting. ChAT-eGFP+ and ChAT-eGFP− cells were isolated from spleens of B6.Cg-Tg(RP23-268L19-eGFP)2Mik/J reporter mice by negative selection for CD4+ T cells followed by cell sorting by flow cytometry of the CD4+CD44hiCD62Llo population into eGFP+ and eGFP− subsets (1). For cell sorting experiments, an enriched CD4+ T-cell suspension was obtained by negative selection (CD4+ T-cell isolation kit II, Miltenyi) of spleen cells harvested from male ChAT(BAC)-eGFP mice. The resulting enriched CD4+ cell suspension with >90% purity was then stained with anti-CD44 PE (eBioscience, 12-0441-81), anti-CD4 Pacific Orange (Invitrogen, MCD0430), anti-CD62L PE-Cy7 (eBioscience, 25-0621-82), and anti-CD19APC (BD Biosciences, BDB550992) antibodies and 7-AAD solution. After gating out CD19+ and gating for CD62Llo CD44hi cells, a ChAT-eGFP− and a ChAT-eGFP+ fraction were collected using a FACSAria cell sorter (Becton Dickinson). The resulting fractions were CD4+ CD44hiCD62LloChAT-eGFP− and CD4+ CD44hiCD62LloChAT-eGFP+. 100-150,000 cells were sorted into FCS-containing cell culture medium. To improve purity, the freshly sorted cells were immediately sorted again using the same gating strategy, now directly into Trizol solution (Ambion) according to a modified ImmGen protocol (immgen.org/Protocols/ImmGen%2Cell%20prep%20and%20sorting%20SOP.pdf) and subsequently frozen at −80° C. Subsequent RNA isolation and Affymetrix Mouse ST 1.0 gene array hybridization experiments were performed by ImmGen (13). Gene expression of CD4+ChAT-eGFP+ and CD4+ ChAT-eGFP+ cells were analyzed separately and in the context of subsets of the publicly available ImmGen data set (13) using the R programming language (see below).

Cell culture. Stable transfection of Jurkat cells. Jurkat cells (originally obtained from ATCC) were a generous gift from C. Chu, The Feinstein Institute for Medical Research, Manhasset, N.Y., USA. pCMV6-mChAT (mChAT ORF in a pCMV6-kan/neo plasmid (ORIGene, Rockville, Md. (MC220061)) was nucleofected into Jurkat cells with a mouse T-cell kit (Lonza, Allendale, N.J. VPA-1006) and a Nucleofector 2b (Lonza). Transformed cells were selected over 2 weeks with G418 (400 mg/mL) in RPMI containing 10% FBS. Isolated cells were individually selected by pipet and serial dilution for monoclonal populations, then grown for an additional month to ensure stable chromosomal integration. Monoclonal lines were analyzed for ChAT expression by western blotting. Jurkat cell lines tested negative for *Mycoplasma* sp., EBV, HAdV, Hantaan, HCMV, Hepatitis A, Hepatitis B, Hepatitis C, HHV 6, HHV 8, HIV1, HIV2, HSV 1, HSV 2, HTLV 1, HTLV 2, LCMV, Seoul, Sin Nombre, VZV.

Co-incubation experiments. Primary ChAT+ lymphocytes or Jurkat T lymphocytes or pCMV6-mChAT-transfected Jurkat T cells (JTChAT) were co-incubated with either human endothelial cells derived from pulmonary microcirculation or murine endothelial cells (30,31). Human PEC1.6ST cells were seeded in 6-well plates in Endothelial Cell Growth Medium MV with supplement mix C-39225 (PromoCell) and experiments were performed at confluency. $2\times10^6$ ChAT+ Jurkat T cells, $2\times10^6$ Jurkat T cells, 106 primary ChAT+ lymphocytes or acetylcholine to a concentration of 100 μM in fresh medium was added to the endothelial cell culture, and cells incubated for 1 h.

During co-culture experiments, cells were kept in a modular incubator chamber (Billups-Rothenberg, Del Mar, Calif., USA) in a microenvironment within the chamber of 37° C., 1% $O_2$, 5% $CO_2$, and 100% humidity (32). Culture wells were subsequently washed twice with cold PBS and removal of non-adherent cells verified by microscopy. Protein was extracted using T-PER solution (Thermo Scientific) in the presence of HALT protease and phosphatase inhibitors (Thermo Scientific) according to manufacturer's instructions, and lysates stored at −80° C. until analysis using western blot. Membranes were probed with anti-peNOS (Cell Signaling) and anti-beta actin (GeneScript) and developed with standard reagents (Pierce). Images were acquired on a GS-800 calibrated densitometer (Bio-Rad) and images analyzed using Image Studio software (Licor). Nitrite and nitrate in supernatants was measured using the Nitrate/Nitrite Colorimetric Assay Kit (Cayman Chemical, Ann Arbor, Mich.) according to manufacturer's instructions.

Murine lung microvascular endothelial cells were isolated and cultured as previously described31. In brief, fresh mouse lungs were rinsed, minced aseptically into small pieces, and digested in collagenase A (1 mg/mL, Worthington, N.J.) at 37° C. for 60 min with occasional agitation. The single-cell suspension was filtered through sterile 40 μm cell strainer, washed in DMEM medium containing 10% FCS (10% FCS-DMEM), and incubated with magnetic beads conjugated with anti-mouse CD31 antibody (Invitrogen, Carlsbad, Calif.) at 4° C. for 30 min. The bead-bound cells were recovered by placing the tube in a magnetic separation rack, washed with 10% FCS-DMEM, collected, and cultured in DMEM medium containing 10% FCS, 2 mM 1-glutamine, 2 mM sodium pyruvate, 20 mM HEPES, 1% nonessential amino acids, 100 μg/mL streptomycin, 100 U/mL penicillin, 100 μg/mL heparin, and 100 μg/mL endothelial cell growth supplement. Endothelial cell phenotype was confirmed by positive staining of multiple endothelial-specific markers.

Calcium measurements. Endothelial cells derived from pulmonary microvasculature (31) were seeded onto glass coverslips 16-24 h before use in calcium imaging experiments. The coverslips were placed in a stainless steel imaging cell chamber (Attofluor Cell Chamber, Life Technologies, Grand Island, N.Y., USA). Within this chamber, the cells were washed with DMEM and loaded with the calcium-sensitive Fluo-4 NW in DMEM with probenecid (Fluo-4 NW Calcium Assay Kit, Molecular Probes, Eugene Oreg., USA) for 45-60 min at 37° C. under 5% $CO_2$. The imaging chamber was placed in a temperature-controlled Leiden chamber holder mounted on the stage of an Axiovert 200 M inverted fluorescence microscope (Carl Zeiss Microscopy, Thornwood, N.Y., USA) equipped with a 40×, 0.60 numerical aperture objective. Data were recorded every 10 s by illuminating the sample with light from a mercury lamp passing through an excitation filter (470 nm±40) before being directed at the cells by a 495-nm dichroic mirror. A single field was visualized in each experiment. Emitted light was captured by a cooled CCD camera (AxioCam monochromatic, Carl Zeiss Microscopy, Thornwood, N.Y., USA) following passage through a 525-nm±50 emission filter.

The image acquisition setup was controlled by Axiovision 4.7 software (Carl Zeiss Microscopy, Thornwood, N.Y., USA). After being placed on the microscope stage, cells were washed once with HEPES-buffered and indicator-free DMEM-containing acetylcholine esterase inhibitor. Baseline fluorescence was recorded for 2 min at which time cells were treated with 0.1 mM acetylcholine or co-culture with 106/mL of Jurkat T lymphocytes, pCMV6-mChAT vector-transfected Jurkat T lymphocytes, primary ChAT+ lymphocytes, or primary ChAT− lymphocytes. Intracellular fluorescence was monitored for an additional 5 min before concluding the experiment by treatment with 10 μM ionomycin (Sigma-Aldrich, St. Louis, Mo., USA).

The acquired images were exported to ImageJ software for analysis. The mean fluorescence intensity values of 6-31 cells per experiment were extracted for each time point and normalized to the average baseline intensity. Individual cell data were then averaged for each experiment. To quantify the treatment response, the average fluorescence in the 1-min intervals immediately before and after treatment was calculated.

Sequences hChAT promoter region (SEQ ID NO: 1)

```
GGAGGCTGAGGCTGGGCCCCACTGAGGGGCTGTGACTTGCCCAAGGTCATCCAGGGCC
AGGCCTGTGCCCACATTGGGACTCTTTTCCTCCCTCAGACAGAGGGCACTTCAGTCACT
GCAGAGCAGGTGGCAGCAGCCCTTCAGTGGATGAGTTTCTCCTTTCCCAGGGTGACTGG
GTGGGTGAAGGAATTGAGCAACAGGTGGCCAGGCTGCCGCCTCTCACCCTGACACATT
GGTCCCCATCCCCTCATCCTACAGCCATCTCAGGGACAGATGGAGACATTCCAATGCCC
TCCGGGTCCTCCACCAACCCAGACAGAGCCTGGAGTCACAATGCCCACCTAGCCAGAG
GGATCAGCCAGCTAGCCAAGTGCCCCCTGTGTCTTTCATCTGTTCTTCACAAGACCCAC
AAGTGAAAAATGAGGATAAACCGCACATTCTACACACGATAACAACATAGCAAGTCCT
TATACTGCTCTTACTGTGTGCCCGGCCCCCTTAGCAGTAGGTACTATTATTATTCAATTT
TACAAAGAAACTAACTGAGGGACAGAGAGGCAAAGTAATTCCCTGCAGGTACTCTAAT
GAGTACGTGGCAGAGCTGGGAGCCATCCTGGTTGTCTGCCTCGAAAGACCACACTCTTT
GCACTGCATCGCGGCACTTCCTGCGGGGTGGGGGGCACAATGGGAGAAGCATCTGCGT
CTAATGCTGCTTTACTTTTGAGGCCAGAAAAATGGGAAGGCTCCCCTCTGACTCTGGAA
GAGAGACGCAAACCGTAATCTCAACAACACAATCCCCACCTCCAACCTCAGCCGCCCT
GGAGCCTCTCTCCCGCCAGTCCGCCCACTGGAACACGGGTTCCATGTGCCATCCAGGGT
CAACGCCGCTCTGGGGACGCGTCAGGCCCAGCGCACAGCCTGGGCAGCTCAGCCTGTC
AGCT
```

hChAT cDNA

NM_020549.2

(SEQ ID NO: 2)

```
   1 TGGGGTTGGG GAAGTGCGGT GACTGGGAAA TGCTGAGCTA GGGGCAGGAG GCATGGGCGG
  61 GACAGTGTTC TGTGCCCCCT TCTAGAGCCT AAATTTGTTG CCCGAGTTCC TCCGGGAAGC
 121 GCTCCGGGTA GATTCTCGGG GCCGGGAGCT GAGATCCCTG GGCGGGGAGC GGGGGAAGGG
 181 ATGGGGCTGA GGACAGCGAA GAAGAGGGGG CTTGGGGGAG GGGGGAAATG GAAGAGAGAG
 241 GAGGGAGGAG GTACAAGAGG AAGGAGAGAA GTGCGGCCAG CTTGCTTTCT CCAGTCGGGT
 301 GGCCGCGGGG ACCCGGGCGA CGTCGGAGGC CCTGCCGGGA ACCCAGGCTG CAGCCCCCAC
 361 CCCCGCGCTG CGACACGCCC CCCACCCCTT CCGGCTCACA CCCCCGCCCA CACTCCTGAG
 421 TGGTGCGGTG CAGCGTCGGC CGAGGCAGCA GAGCCGAGGA GAGCAGGTCC ACACCTCTGC
 481 ATCCCTGCAC CAGGACTCAC CAAGACGCCC ATCCTGGAAA AGGTCCCCCG TAAGATGGCA
 541 GCAAAAACTC CCAGCAGTGA GGAGTCTGGG CTGCCCAAAC TGCCCGTGCC CCCGCTGCAG
 601 CAGACCCTGG CCACGTACCT GCAGTGCATG CGACACTTGG TGTCTGAGGA GCAGTTCAGG
 661 AAGAGCCAGG CCATTGTGCA GCAGTTTGGG GCCCCTGGTG GCCTCGGCGA GACCCTGCAG
 721 CAGAAACTCC TGGAGCGGCA GGAGAAGACA GCCAACTGGG TGTCTGAGTA CTGGCTGAAT
 781 GACATGTATC TCAACAACCG CCTGGCCCTG CCTGTCAACT CCAGCCCTGC CGTGATCTTT
 841 GCTCGGCAGC ACTTCCCTGG CACCGATGAC CAGCTGAGGT TTGCAGCCAG CCTCATCTCT
 901 GGTGTACTCA GCTACAAGGC CCTGCTGGAC AGCCACTCCA TTCCCACTGA CTGTGCCAAA
 961 CCGGAGCTGT CAGGGCAGCC CCTTTGCATG AAGCAATACT ATGGGCTCTT CTCCTCCTAC
1021 CGGCTCCCCG GCCATACCCA GGACACGCTG GTGGCTCAGA ACAGCAGCAT CATGCCGGAG
1081 CCTGAGCACG TCATCGTAGC CTGCTGCAAT CAGTTCTTTG TCTTGGATGT TGTCATTAAT
1141 TTCCGCCGTC TCAGTGAGGG GGATCTGTTC ACTCAGTTGA GAAAGATAGT CAAAATGGCT
1201 TCCAACGAGG ACGAGCGTTT GCCTCCAATT GGCCTGCTGA CGTCTGACGG GAGGAGCGAG
```

-continued

```
1261    TGGGCCGAGG CCAGGACGGT CCTCGTGAAA GACTCCACCA ACCGGGACTC GCTGGACATG
1321    ATTGAGCGCT GCATCTGCCT TGTATGCCTG GACGGCCCAG GAGGCGTGGA GCTCAGCGAC
1381    ACCCACAGGG CACTCCAGCT CCTTCACGGC GGAGGCTACA GCAAGAACGG GGCCAATCGC
1441    TGGTACGACA AGTCCCTGCA GTTTGTGGTG GGCCGAGACG CGACCTGCGG TGTGGTGTGC
1501    GAACACTCCC CATTCGATGG CATCGTCCTG GTGCAGTGCA CTGAGCATCT GCTCAAGCAC
1561    ATGACGCAGA GCAGCAGGAA GCTGATCCGA GCAGACTCCG TCAGCGAGCT CCCCGCCCCC
1621    CGGAGGCTGC GGTGGAAATG CTCCCCGGAA ATTCAAGGCC ACTTAGCCTC CTCGGCAGAA
1681    AAACTTCAAC GAATAGTAAA GAACCTTGAC TTCATTGTCT ATAAGTTTGA CAACTATGGG
1741    AAAACATTCA TTAAGAAGCA GAAATGCAGC CCTGATGCCT TCATCCAGGT GGCCCTCCAG
1801    CTGGCCTTCT ACAGGCTCCA CCGAAGACTG GTGCCCACCT ACGAGAGCGC GTCCATCCGC
1861    CGATTCCAGG AGGGACGCGT GGACAACATC AGATCGGCCA CTCCAGAGGC ACTGGCTTTT
1921    GTGAGAGCCG TGACTGACCA CAAGGCTGCT GTGCCAGCTT CTGAGAAGCT TCTGCTCCTG
1981    AAGGATGCCA TCCGTGCCCA GACTGCATAC ACAGTCATGG CCATAACAGG GATGGCCATT
2041    GACAACCACC TGCTGGCACT GCGGGAGCTG GCCCGGGCCA TGTGCAAGGA GCTGCCCGAG
2101    ATGTTCATGG ATGAAACCTA CCTGATGAGC AACCGGTTTG TCCTCTCCAC TAGCCAGGTG
2161    CCCACAACCA CGGAGATGTT CTGCTGCTAT GGTCCTGTGG TCCCAAATGG GTATGGTGCC
2221    TGCTACAACC CCCAGCCAGA GACCATCCTT TTCTGCATCT CTAGCTTTCA CAGCTGCAAA
2281    GAGACTTCTT CTAGCAAGTT TGCAAAAGCT GTGGAAGAAA GCCTCATTGA CATGAGAGAC
2341    CTCTGCAGTC TGCTGCCGCC TACTGAGAGC AAGCCATTGG CAACAAAGGA AAAAGCCACG
2401    AGGCCCAGCC AGGGACACCA ACCTTGACTC CTGCCACTAG GTTTCACCTC CCAAACCCAG
2461    CCTCTAGAAC AGCCAGACCC TGCAG
```

mChAT cDNA
NM_009891.2

(SEQ ID NO: 3)

```
   1    GTGTGCAGCC CTCCCGGAAG GAAGGTGAGC CTTCCTAAGC CTCTACTGAC AGCAAAGCTG
  61    CAGAGGCCCT GCTGCGTGAG ACCCAGAAGC TTCCACGCCA CTTTCAGTCA GTCGGGGCGG
 121    CTGCTGGGAT CTGGCAACTT CGTCGGAGGC TCTGCTACAG AACCTAGGTG GCGGGCCCAA
 181    CCTCTGGTAC TGCTGCCACC CCCTCCCTGG CCCTTCTGGC TCACGCAGCC GCCTCCAGCC
 241    CTGCTTGGTG TGGAACAGTG CCGGTTCGGT GCGTAACAGC CCAGGAGAGC AGGTCGGCAG
 301    CTCTGCTACT CTGGATTAAG AATCGCTAGG ATGCCTATCC TGGAAAAGGT CCCCCCAAAG
 361    ATGCCTGTAC AAGCTTCTAG CTGTGAGGAG GTGCTGGACT TACCTAAGTT GCCAGTGCCC
 421    CCACTGCAGC AAACCCTGGC CACCTACCTT CAGTGCATGC AACACCTGGT ACCTGAAGAG
 481    CAGTTCAGGA AGAGCCAGGC CATTGTGAAG CGGTTTGGGG CCCCTGGTGG CCTGGGTGAG
 541    ACCCTGCAGG AAAAGCTCTT GGAGAGACAG GAGAAGACAG CCAATTGGGT CTCTGAATAC
 601    TGGCTGAATG ACATGTATCT AAACAACCGC CTGGCCCTGC CAGTCAACTC TAGCCCTGCT
 661    GTGATCTTTG CTCGGCAGCA CTTCCAAGAC ACCAATGACC AGCTAAGGTT TGCAGCCAGC
 721    CTCATCTCTG GTGTGCTTAG CTACAAGGCT CTGCTGGACA GCCAATCCAT TCCCACTGAC
 781    TGGGCCAAGG GGCAGCTCTC AGGGCAGCCT CTCTGTATGA AGCAGTACTA CAGACTCTTC
 841    TCATCATACC GGCTTCCTGG CCATACCCAG GACACACTGG TGGCCCAGAA GAGCAGTATC
 901    ATGCCTGAGC CCGAGCATGT CATCGTGGCC TGCTGCAACC AGTTCTTTGT CTTGGATGTT
 961    GTCATTAATT TCCGCCGTCT CAGTGAGGGT GATCTGTTCA CTCAGTTGAG AAAGATAGTC
1021    AAAATGGCGT CCAACGAGGA TGAACGCCTG CCTCCAATCG GCCTGCTGAC GTCAGACGGG
```

-continued

1081 AGGAGCGAGT GGGCCAAGGC CAGGACGGTC CTCTTAAAAG ACTCCACCAA CCGGGACTCC

1141 CTGGACATGA TCGAGCGCTG CATCTGCCTG GTATGCCTGG ATGGTCCAGG CACTGGAGAC

1201 CTCAGTGACA CACACAGGGC CCTCCAGCTC CTTCATGGTG GAGGCTGCAG CTTGAATGGA

1261 GCGAATCGTT GGTATGACAA GTCCCTGCAG TTTGTGGTGG GCCGAGATGG CACCTGCGGT

1321 GTGGTGTGTG AGCACTCCCC TTTTGATGGC ATCGTCCTGG TGCAGTGCAC GGAGCACCTG

1381 CTGAAACATA TGATGACAGG CAACAAGAAG CTCGTCCGAG CTGACTCAGT GAGTGAACTC

1441 CCTGCTCCCA GAAGGCTGAG GTGGAAATGT TCCCCAGAAA CTCAAGGCCA TCTCGCCTCC

1501 TCGGCAGAGA AACTTCAAAG AATCGTAAAG AATCTGGATT TCATTGTTTA TAAGTTTGAC

1561 AACTATGGGA AAACATTTAT TAAGAAGCAG AAATGCAGTC CTGATGGCTT CATCCAGGTG

1621 GCCCTCCAGC TGGCTTACTA CAGGCTTTAC CAGAGGCTGG TGCCCACCTA TGAGAGTGCA

1681 TCCATCCGCC GCTTCCAGGA AGGTCGGGTG GACAACATCA GATCGGCCAC TCCTGAGGCT

1741 CTGGCTTTTG TGCAAGCCAT GACTGACCAC AAGGCTGCCG TGCTGGCTTC TGAGAAACTG

1801 CAGCTGCTGC AGAGGGCCAT CCAGGCCCAA ACTGAGTACA CAGTCATGGC CATAACCGGC

1861 ATGGCCATTG ACAACCATCT TCTGGCACTG AGGGAGCTGG CCCGAGACCT GTGCAAAGAG

1921 CCACCTGAGA TGTTCATGGA TGAAACATAC CTGATGAGCA ACCGGTTTAT TCTCTCCACC

1981 AGCCAGGTGC CCACGACCAT GGAGATGTTC TGCTGTTATG GCCCTGTGGT ACCCAATGGG

2041 TATGGAGCCT GTTATAACCC CCAGCCTGAG GCCATCACCT TCTGCATCTC CAGCTTTCAC

2101 GGCTGCAAAG AGACCTCATC TGTGGAGTTT GCAGAAGCGG TGGGAGCGAG CCTTGTTGAC

2161 ATGAGAGACC TCTGTAGTTC GAGGCAGCCT GCTGAAGGCA AGCCACCAAC AGCAAAGGAA

2221 AGAGCTAGAG GCCCAACCAA GCCAAGCAAT CTTGACTACT CCCACTAGCC AATGTCCTAC

2281 AGGAGTCAGC CCCTACTAAC CCTGCTCCCA TCCCCCACCC CAGCTTGTTG CTGCTCCCCT

2341 ATCCTTGGGG GCTCACATGA AGCTGGCATG TTAAGAGAGA GAGAGCCCCT CATTATCTAT

2401 CTAAGTGGCC TGTGGCCTTT ACAACTGGAA ATGAGACCCA GCCTGGCTTG GAAGCAGCCT

2461 GGGTGGGCTG GGAGCTCCCT CTGAGGTCTT TAGAAACTTA ACCTTTCTGC TTCTTTCCCA

2521 GCAACACCCA GTGGTGCACA TGGTAGCTCT GCCAGTGGAA GAATCGTCAT CTCATCACAT

2581 GCTATGGGCC CAAATAAGTC ATAAAGGCAG AGGCTAGCTC CCTCCACACA CTCACATGCA

2641 CAAAGACAGC CCAAGTTCAT TTAGAATACA GTGGCCCACA TCCACAAAGA CATTTCTTCC

2701 TTTATCTTCC ATAGCACAGT CTTCCTTGAG TTCAGATTAT CTCATCCAGC TATTCAGAAA

2761 GAAAGAAAGA AAGAAAGAAA GAAAGAAAGA AAGAAAGAAA GAAAGGAAGG

EF1a promoter (SEQ ID NO: 4)

CGTGAGGCTCCGGTGCCCGTCAGTGGGCAGAGCGCACATCGCCCACAGTCCCCGAGAA

GTTGGGGGGAGGGGTCGGCAATTGAACCGGTGCCTAGAGAAGGTGGCGCGGGGTAAA

CTGGGAAAGTGATGTCGTGTACTGGCTCCGCCTTTTTCCCGAGGGTGGGGGAGAACCGT

ATATAAGTGCAGTAGTCGCCGTGAACGTTCTTTTTCGCAACGGGTTTGCCGCCAGAACA

CAGGTAAGTGCCGTGTGTGGTTCCCGCGGGCCTGGCCTCTTTACGGGTTATGGCCCTTG

CGTGCCTTGAATTACTTCCACCTGGCTGCAGTACGTGATTCTTGATCCCGAGCTTCGGGT

TGGAAGTGGGTGGGAGAGTTCGAGGCCTTGCGCTTAAGGAGCCCCTTCGCCTCGTGCTT

GAGTTGAGGCCTGGCCTGGGCGCTGGGGCCGCCGCGTGCGAATCTGGTGGCACCTTCG

CGCCTGTCTCGCTGCTTTCGATAAGTCTCTAGCCATTTAAAATTTTTGATGACCTGCTGC

GACGCTTTTTTTCTGGCAAGATAGTCTTGTAAATGCGGGCCAAGATCTGCACACTGGTA

-continued

TTTCGGTTTTTGGGGCCGCGGGCGGCGACGGGGCCCGTGCGTCCCAGCGCACATGTTCG

GCGAGGCGGGGCCTGCGAGCGCGGCCACCGAGAATCGGACGGGGGTAGTCTCAAGCTG

GCCGGCCTGCTCTGGTGCCTGGCCTCGCGCCGCCGTGTATCGCCCCGCCCTGGGCGGCA

AGGCTGGCCCGGTCGGCACCAGTTGCGTGAGCGGAAAGATGGCCGCTTCCCGGCCCTG

CTGCAGGGAGCTCAAAATGGAGGACGCGGCGCTCGGGAGAGCGGGCGGGTGAGTCAC

CCACACAAAGGAAAAGGGCCTTTCCGTCCTCAGCCGTCGCTTCATGTGACTCCACGGAG

TACCGGGCGCCGTCCAGGCACCTCGATTAGTTCTCGAGCTTTTGGAGTACGTCGTCTTT

AGGTTGGGGGGAGGGGTTTTATGCGATGGAGTTTCCCCACACTGAGTGGGTGGAGACT

GAAGTTAGGCCAGCTTGGCACTTGATGTAATTCTCCTTGGAATTTGCCCTTTTTGAGTTT

GGATCTTGGTTCATTCTCAAGCCTCAGACAGTGGTTCAAAGTTTTTTTCTTCCATTTCAG

GTGTCGTGA

CMV promoter sequence (SEQ ID NO: 5)

TAGTAATCAATTACGGGGTCATTAGTTCATAGCCCATATATGGAGTTCCGCGTTACATAACTTACGGTAAAT

GGCCCGCCTGGCTGACCGCCCAACGACCCCCGCCCATTGACGTCAATAATGACGTATGTTCCCATAGTAACG

CCAATAGGGACTTTCCATTGACGTCAATGGGTGGAGTATTTACGGTAAACTGCCCACTTGGCAGTACATCAA

GTGTATCATATGCCAAGTACGCCCCCTATTGACGTCAATGACGGTAAATGGCCCGCCTGGCATTATGCCCAG

TACATGACCTTATGGGACTTTCCTACTTGGCAGTACATCTACGTATTAGTCATCGCTATTACCATGGTGATG

CGGTTTTGGCAGTACATCAATGGGCGTGGATAGCGGTTTGACTCACGGGGATTTCCAAGTCTCCACCCCATT

GACGTCAATGGGAGTTTGTTTTGGCACCAAAATCAACGGGACTTTCCAAAATGTCGTAACAACTCCGCCCCA

TTGACGCAAATGGGCGGTAGGCGTGTACGGTGGGAGGTCTATATAAGCAGAGCTGGTTTAGTGAACCGTCAG hChAT promoter TAL target binding sequences- (SEQ ID NOS:6-26, top to bottom, respectively)

1. TCCGCCCAAATCAATAAAC

2. TGCCGCCTCTCACCCTGAC

3. TCGCGGCACTTCCTGCGGG

4. TCCCGCCAGTCCGCCCACT

5. TCCGCCCACTGGAACACGG

6. TGGCCAGGCTGCCGCCTCT

7. TCCGGGTCCTCCACCAACC

8. TGCCCACCTAGCCAGAGGG

9. TGGGCAGCTCAGCCTGTCA

10. TGCCCAAGGTCATCCAGGG

11. TGCCCACATTGGGACTCTT

12. TGCCGCCTCTACCCTGACACATTG

13. TCCCGCCAGTCCGCCCACTGGAACA

14. TCCGCCCACTGGAACACGGGTTCCA

15. TGGCCAGGCTGCCGCCTCTCACCCT

16. TCCGGGTCCTCCACCAACCCAGACA

17. TGCCCACCTAGCCAGAGGGATCAGC

18. TGCCCAAGGTCATCCAGGGCCAGGC

-continued

19. TGGCAGCAGCCCTTCAGTGGATGAG

20. TCCCAGGGTGACTGGGTGGGTGAAG

21. TGGGTGGGTGAAGGAATTGAGCAAC

TAL nucleotide sequence for each target site
1

(SEQ ID NO: 27)

ATGGTGGACTTGAGGACACTCGGTTATTCGCAACAGCAACAGGAGAAAATCAAGCCTA

AGGTCAGGAGCACCGTCGCGCAACACCACGAGGCGCTTGTGGGGCATGGCTTCACTCA

TGCGCATATTGTCGCGCTTTCACAGCACCCTGCGGCGCTTGGGACGGTGGCTGTCAAAT

ACCAAGATATGATTGCGGCCCTGCCCGAAGCCACGCACGAGGCAATTGTAGGGGTCGG

TAAACAGTGGTCGGGAGCGCGAGCACTTGAGGCGCTGCTGACTGTGGCGGGTGAGCTT

AGGGGGCCTCCGCTCCAGCTCGACACCGGGCAGCTGCTGAAGATCGCGAAGAGAGGGG

GAGTAACAGCGGTAGAGGCAGTGCACGCCTGGCGCAATGCGCTCACCGGGGCCCCCTT

GAACCTGACCCCAGACCAGGTAGTCGCAATCGCGTCACATGACGGGGGAAAGCAAGCC

CTGGAAACCGTGCAAAGGTTGTTGCCGGTCCTTTGTCAAGACCACGGCCTTACACCGGA

GCAAGTCGTGGCCATTGCATCCCACGACGGTGGCAAACAGGCTCTTGAGACGGTTCAG

AGACTTCTCCCAGTTCTCTGTCAAGCCCACGGGCTGACTCCCGATCAAGTTGTAGCGAT

TGCGAATAACAATGGAGGGAAACAAGCATTGGAGACTGTCCAACGGCTCCTTCCCGTG

TTGTGTCAAGCCCACGGTTTGACGCCTGCACAAGTGGTCGCCATCGCCAGCCATGATGG

CGGTAAGCAGGCGCTGGAAACAGTACAGCGCCTGCTGCCTGTACTGTGCCAGGATCAT

GGACTGACCCCAGACCAGGTAGTCGCAATCGCGTCACATGACGGGGGAAAGCAAGCCC

TGGAAACCGTGCAAAGGTTGTTGCCGGTCCTTTGTCAAGACCACGGCCTTACACCGGAG

CAAGTCGTGGCCATTGCATCCCACGACGGTGGCAAACAGGCTCTTGAGACGGTTCAGA

GACTTCTCCCAGTTCTCTGTCAAGCCCACGGGCTGACTCCCGATCAAGTTGTAGCGATT

GCGTCGAACATTGGAGGGAAACAAGCATTGGAGACTGTCCAACGGCTCCTTCCCGTGTT

GTGTCAAGCCCACGGTTTGACGCCTGCACAAGTGGTCGCCATCGCCTCCAATATTGGCG

GTAAGCAGGCGCTGGAAACAGTACAGCGCCTGCTGCCTGTACTGTGCCAGGATCATGG

ACTGACCCCAGACCAGGTAGTCGCAATCGCGTCGAACATTGGGGGAAAGCAAGCCCTG

GAAACCGTGCAAAGGTTGTTGCCGGTCCTTTGTCAAGACCACGGCCTTACACCGGAGCA

AGTCGTGGCCATTGCAAGCAATGGGGGTGGCAAACAGGCTCTTGAGACGGTTCAGAGA

CTTCTCCCAGTTCTCTGTCAAGCCCACGGGCTGACTCCCGATCAAGTTGTAGCGATTGC

GTCGCATGACGGAGGGAAACAAGCATTGGAGACTGTCCAACGGCTCCTTCCCGTGTTGT

GTCAAGCCCACGGTTTGACGCCTGCACAAGTGGTCGCCATCGCCTCCAATATTGGCGGT

AAGCAGGCGCTGGAAACAGTACAGCGCCTGCTGCCTGTACTGTGCCAGGATCATGGAC

TGACCCCAGACCAGGTAGTCGCAATCGCGTCGAACATTGGGGGAAAGCAAGCCCTGGA

AACCGTGCAAAGGTTGTTGCCGGTCCTTTGTCAAGACCACGGCCTTACACCGGAGCAAG

TCGTGGCCATTGCAAGCAATGGGGGTGGCAAACAGGCTCTTGAGACGGTTCAGAGACT

TCTCCCAGTTCTCTGTCAAGCCCACGGGCTGACTCCCGATCAAGTTGTAGCGATTGCGT

CGAACATTGGAGGGAAACAAGCATTGGAGACTGTCCAACGGCTCCTTCCCGTGTTGTGT

CAAGCCCACGGTTTGACGCCTGCACAAGTGGTCGCCATCGCCTCCAATATTGGCGGTAA

GCAGGCGCTGGAAACAGTACAGCGCCTGCTGCCTGTACTGTGCCAGGATCATGGACTG

ACCCCAGACCAGGTAGTCGCAATCGCGTCGAACATTGGGGGAAAGCAAGCCCTGGAAA

-continued

CCGTGCAAAGGTTGTTGCCGGTCCTTTGTCAAGACCACGGCCTGACACCCGAACAGGTG

GTCGCCATTGCTTCCCACGACGGAGGACGGCCAGCCTTGGAG

2

(SEQ ID NO: 28)

ATGGTGGACTTGAGGACACTCGGTTATTCGCAACAGCAACAGGAGAAAATCAA

GCCTAAGGTCAGGAGCACCGTCGCGCAACACCACGAGGCGCTTGTGGGGCATGGCTTC

ACTCATGCGCATATTGTCGCGCTTTCACAGCACCCTGCGGCGCTTGGGACGGTGGCTGT

CAAATACCAAGATATGATTGCGGCCCTGCCCGAAGCCACGCACGAGGCAATTGTAGGG

GTCGGTAAACAGTGGTCGGGAGCGCGAGCACTTGAGGCGCTGCTGACTGTGGCGGGTG

AGCTTAGGGGGCCTCCGCTCCAGCTCGACACCGGGCAGCTGCTGAAGATCGCGAAGAG

AGGGGGAGTAACAGCGGTAGAGGCAGTGCACGCCTGGCGCAATGCGCTCACCGGGGCC

CCCTTGAACCTGACCCCAGACCAGGTAGTCGCAATCGCGAACAATAATGGGGGAAAGC

AAGCCCTGGAAACCGTGCAAAGGTTGTTGCCGGTCCTTTGTCAAGACCACGGCCTTACA

CCGGAGCAAGTCGTGGCCATTGCATCCCACGACGGTGGCAAACAGGCTCTTGAGACGG

TTCAGAGACTTCTCCCAGTTCTCTGTCAAGCCCACGGGCTGACTCCCGATCAAGTTGTA

GCGATTGCGTCGCATGACGGAGGGAAACAAGCATTGGAGACTGTCCAACGGCTCCTTC

CCGTGTTGTGTCAAGCCCACGGTTTGACGCCTGCACAAGTGGTCGCCATCGCCAACAAC

AACGGCGGTAAGCAGGCGCTGGAAACAGTACAGCGCCTGCTGCCTGTACTGTGCCAGG

ATCATGGACTGACCCCAGACCAGGTAGTCGCAATCGCGTCACATGACGGGGGAAAGCA

AGCCCTGGAAACCGTGCAAAGGTTGTTGCCGGTCCTTTGTCAAGACCACGGCCTTACAC

CGGAGCAAGTCGTGGCCATTGCATCCCACGACGGTGGCAAACAGGCTCTTGAGACGGT

TCAGAGACTTCTCCCAGTTCTCTGTCAAGCCCACGGGCTGACTCCCGATCAAGTTGTAG

CGATTGCGTCCAACGGTGGAGGGAAACAAGCATTGGAGACTGTCCAACGGCTCCTTCC

CGTGTTGTGTCAAGCCCACGGTTTGACGCCTGCACAAGTGGTCGCCATCGCCAGCCATG

ATGGCGGTAAGCAGGCGCTGGAAACAGTACAGCGCCTGCTGCCTGTACTGTGCCAGGA

TCATGGACTGACCCCAGACCAGGTAGTCGCAATCGCGTCAAACGGAGGGGGAAAGCAA

GCCCTGGAAACCGTGCAAAGGTTGTTGCCGGTCCTTTGTCAAGACCACGGCCTTACACC

GGAGCAAGTCGTGGCCATTGCATCCCACGACGGTGGCAAACAGGCTCTTGAGACGGTT

CAGAGACTTCTCCCAGTTCTCTGTCAAGCCCACGGGCTGACTCCCGATCAAGTTGTAGC

GATTGCGTCGAACATTGGAGGGAAACAAGCATTGGAGACTGTCCAACGGCTCCTTCCC

GTGTTGTGTCAAGCCCACGGTTTGACGCCTGCACAAGTGGTCGCCATCGCCAGCCATGA

TGGCGGTAAGCAGGCGCTGGAAACAGTACAGCGCCTGCTGCCTGTACTGTGCCAGGAT

CATGGACTGACCCCAGACCAGGTAGTCGCAATCGCGTCACATGACGGGGGAAAGCAAG

CCCTGGAAACCGTGCAAAGGTTGTTGCCGGTCCTTTGTCAAGACCACGGCCTTACACCG

GAGCAAGTCGTGGCCATTGCATCCCACGACGGTGGCAAACAGGCTCTTGAGACGGTTC

AGAGACTTCTCCCAGTTCTCTGTCAAGCCCACGGGCTGACTCCCGATCAAGTTGTAGCG

ATTGCGTCCAACGGTGGAGGGAAACAAGCATTGGAGACTGTCCAACGGCTCCTTCCCG

TGTTGTGTCAAGCCCACGGTTTGACGCCTGCACAAGTGGTCGCCATCGCCAACAACAAC

-continued

GGCGGTAAGCAGGCGCTGGAAACAGTACAGCGCCTGCTGCCTGTACTGTGCCAGGATC

ATGGACTGACCCCAGACCAGGTAGTCGCAATCGCGTCGAACATTGGGGGAAAGCAAGC

CCTGGAAACCGTGCAAAGGTTGTTGCCGGTCCTTTGTCAAGACCACGGCCTGACACCCG

AACAGGTGGTCGCCATTGCTTCCCACGACGGAGGACGGCCAGCCTTGGAG

3

(SEQ ID NO: 29)

ATGGTGGACTTGAGGACACTCGGTTATTCGCAACAGCAACAGGAGAAAATCAA

GCCTAAGGTCAGGAGCACCGTCGCGCAACACCACGAGGCGCTTGTGGGGCATGGCTTC

ACTCATGCGCATATTGTCGCGCTTTCACAGCACCCTGCGGCGCTTGGGACGGTGGCTGT

CAAATACCAAGATATGATTGCGGCCCTGCCCGAAGCCACGCACGAGGCAATTGTAGGG

GTCGGTAAACAGTGGTCGGGAGCGCGAGCACTTGAGGCGCTGCTGACTGTGGCGGGTG

AGCTTAGGGGGCCTCCGCTCCAGCTCGACACCGGGCAGCTGCTGAAGATCGCGAAGAG

AGGGGGAGTAACAGCGGTAGAGGCAGTGCACGCCTGGCGCAATGCGCTCACCGGGGCC

CCCTTGAACCTGACCCCAGACCAGGTAGTCGCAATCGCGTCACATGACGGGGGAAAGC

AAGCCCTGGAAACCGTGCAAAGGTTGTTGCCGGTCCTTTGTCAAGACCACGGCCTTACA

CCGGAGCAAGTCGTGGCCATTGCAAATAATAACGGTGGCAAACAGGCTCTTGAGACGG

TTCAGAGACTTCTCCCAGTTCTCTGTCAAGCCCACGGGCTGACTCCCGATCAAGTTGTA

GCGATTGCGTCGCATGACGGAGGGAAACAAGCATTGGAGACTGTCCAACGGCTCCTTC

CCGTGTTGTGTCAAGCCCACGGTTTGACGCCTGCACAAGTGGTCGCCATCGCCAACAAC

AACGGCGGTAAGCAGGCGCTGGAAACAGTACAGCGCCTGCTGCCTGTACTGTGCCAGG

ATCATGGACTGACCCCAGACCAGGTAGTCGCAATCGCGAACAATAATGGGGGAAAGCA

AGCCCTGGAAACCGTGCAAAGGTTGTTGCCGGTCCTTTGTCAAGACCACGGCCTTACAC

CGGAGCAAGTCGTGGCCATTGCATCCCACGACGGTGGCAAACAGGCTCTTGAGACGGT

TCAGAGACTTCTCCCAGTTCTCTGTCAAGCCCACGGGCTGACTCCCGATCAAGTTGTAG

CGATTGCGTCGAACATTGGAGGGAAACAAGCATTGGAGACTGTCCAACGGCTCCTTCC

CGTGTTGTGTCAAGCCCACGGTTTGACGCCTGCACAAGTGGTCGCCATCGCCAGCCATG

ATGGCGGTAAGCAGGCGCTGGAAACAGTACAGCGCCTGCTGCCTGTACTGTGCCAGGA

TCATGGACTGACCCCAGACCAGGTAGTCGCAATCGCGTCAAACGGAGGGGGAAAGCAA

GCCCTGGAAACCGTGCAAAGGTTGTTGCCGGTCCTTTGTCAAGACCACGGCCTTACACC

GGAGCAAGTCGTGGCCATTGCAAGCAATGGGGGTGGCAAACAGGCTCTTGAGACGGTT

CAGAGACTTCTCCCAGTTCTCTGTCAAGCCCACGGGCTGACTCCCGATCAAGTTGTAGC

GATTGCGTCGCATGACGGAGGGAAACAAGCATTGGAGACTGTCCAACGGCTCCTTCCC

GTGTTGTGTCAAGCCCACGGTTTGACGCCTGCACAAGTGGTCGCCATCGCCAGCCATGA

TGGCGGTAAGCAGGCGCTGGAAACAGTACAGCGCCTGCTGCCTGTACTGTGCCAGGAT

CATGGACTGACCCCAGACCAGGTAGTCGCAATCGCGTCAAACGGAGGGGGAAAGCAA

GCCCTGGAAACCGTGCAAAGGTTGTTGCCGGTCCTTTGTCAAGACCACGGCCTTACACC

GGAGCAAGTCGTGGCCATTGCAAATAATAACGGTGGCAAACAGGCTCTTGAGACGGTT

CAGAGACTTCTCCCAGTTCTCTGTCAAGCCCACGGGCTGACTCCCGATCAAGTTGTAGC

GATTGCGTCGCATGACGGAGGGAAACAAGCATTGGAGACTGTCCAACGGCTCCTTCCC

GTGTTGTGTCAAGCCCACGGTTTGACGCCTGCACAAGTGGTCGCCATCGCCAACAACAA

CGGCGGTAAGCAGGCGCTGGAAACAGTACAGCGCCTGCTGCCTGTACTGTGCCAGGAT

-continued

CATGGACTGACCCCAGACCAGGTAGTCGCAATCGCGAACAATAATGGGGGAAAGCAAG

CCCTGGAAACCGTGCAAAGGTTGTTGCCGGTCCTTTGTCAAGACCACGGCCTGACACCC

GAACAGGTGGTCGCCATTGCTAATAATAACGGAGGACGGCCAGCCTTGGAG

4

(SEQ ID NO: 30)

ATGGTGGACTTGAGGACACTCGGTTATTCGCAACAGCAACAGGAGAAAATCAA

GCCTAAGGTCAGGAGCACCGTCGCGCAACACCACGAGGCGCTTGTGGGGCATGGCTTC

ACTCATGCGCATATTGTCGCGCTTTCACAGCACCCTGCGGCGCTTGGGACGGTGGCTGT

CAAATACCAAGATATGATTGCGGCCCTGCCCGAAGCCACGCACGAGGCAATTGTAGGG

GTCGGTAAACAGTGGTCGGGAGCGCGAGCACTTGAGGCGCTGCTGACTGTGGCGGGTG

AGCTTAGGGGGCCTCCGCTCCAGCTCGACACCGGGCAGCTGCTGAAGATCGCGAAGAG

AGGGGGAGTAACAGCGGTAGAGGCAGTGCACGCCTGGCGCAATGCGCTCACCGGGGCC

CCCTTGAACCTGACCCCAGACCAGGTAGTCGCAATCGCGTCACATGACGGGGGAAAGC

AAGCCCTGGAAACCGTGCAAAGGTTGTTGCCGGTCCTTTGTCAAGACCACGGCCTTACA

CCGGAGCAAGTCGTGGCCATTGCATCCCACGACGGTGGCAAACAGGCTCTTGAGACGG

TTCAGAGACTTCTCCCAGTTCTCTGTCAAGCCCACGGGCTGACTCCCGATCAAGTTGTA

GCGATTGCGTCGCATGACGGAGGGAAACAAGCATTGGAGACTGTCCAACGGCTCCTTC

CCGTGTTGTGTCAAGCCCACGGTTTGACGCCTGCACAAGTGGTCGCCATCGCCAACAAC

AACGGCGGTAAGCAGGCGCTGGAAACAGTACAGCGCCTGCTGCCTGTACTGTGCCAGG

ATCATGGACTGACCCCAGACCAGGTAGTCGCAATCGCGTCACATGACGGGGGAAAGCA

AGCCCTGGAAACCGTGCAAAGGTTGTTGCCGGTCCTTTGTCAAGACCACGGCCTTACAC

CGGAGCAAGTCGTGGCCATTGCATCCCACGACGGTGGCAAACAGGCTCTTGAGACGGT

TCAGAGACTTCTCCCAGTTCTCTGTCAAGCCCACGGGCTGACTCCCGATCAAGTTGTAG

CGATTGCGTCGAACATTGGAGGGAAACAAGCATTGGAGACTGTCCAACGGCTCCTTCC

CGTGTTGTGTCAAGCCCACGGTTTGACGCCTGCACAAGTGGTCGCCATCGCCAACAACA

ACGGCGGTAAGCAGGCGCTGGAAACAGTACAGCGCCTGCTGCCTGTACTGTGCCAGGA

TCATGGACTGACCCCAGACCAGGTAGTCGCAATCGCGTCAAACGGAGGGGGAAAGCAA

GCCCTGGAAACCGTGCAAAGGTTGTTGCCGGTCCTTTGTCAAGACCACGGCCTTACACC

GGAGCAAGTCGTGGCCATTGCATCCCACGACGGTGGCAAACAGGCTCTTGAGACGGTT

CAGAGACTTCTCCCAGTTCTCTGTCAAGCCCACGGGCTGACTCCCGATCAAGTTGTAGC

GATTGCGTCGCATGACGGAGGGAAACAAGCATTGGAGACTGTCCAACGGCTCCTTCCC

GTGTTGTGTCAAGCCCACGGTTTGACGCCTGCACAAGTGGTCGCCATCGCCAACAACAA

CGGCGGTAAGCAGGCGCTGGAAACAGTACAGCGCCTGCTGCCTGTACTGTGCCAGGAT

CATGGACTGACCCCAGACCAGGTAGTCGCAATCGCGTCACATGACGGGGGAAAGCAAG

CCCTGGAAACCGTGCAAAGGTTGTTGCCGGTCCTTTGTCAAGACCACGGCCTTACACCG

GAGCAAGTCGTGGCCATTGCATCCCACGACGGTGGCAAACAGGCTCTTGAGACGGTTC

AGAGACTTCTCCCAGTTCTCTGTCAAGCCCACGGGCTGACTCCCGATCAAGTTGTAGCG

ATTGCGTCGCATGACGGAGGGAAACAAGCATTGGAGACTGTCCAACGGCTCCTTCCCG

TGTTGTGTCAAGCCCACGGTTTGACGCCTGCACAAGTGGTCGCCATCGCCTCCAATATT

GGCGGTAAGCAGGCGCTGGAAACAGTACAGCGCCTGCTGCCTGTACTGTGCCAGGATC

ATGGACTGACCCCAGACCAGGTAGTCGCAATCGCGTCACATGACGGGGGAAAGCAAGC

-continued

CCTGGAAACCGTGCAAAGGTTGTTGCCGGTCCTTTGTCAAGACCACGGCCTGACACCCG

AACAGGTGGTCGCCATTGCTTCTAATGGGGGAGGACGGCCAGCCTTGGAG

5

(SEQ ID NO: 31)

ATGGTGGACTTGAGGACACTCGGTTATTCGCAACAGCAACAGGAGAAAATCAA

GCCTAAGGTCAGGAGCACCGTCGCGCAACACCACGAGGCGCTTGTGGGGCATGGCTTC

ACTCATGCGCATATTGTCGCGCTTTCACAGCACCCTGCGGCGCTTGGGACGGTGGCTGT

CAAATACCAAGATATGATTGCGGCCCTGCCCGAAGCCACGCACGAGGCAATTGTAGGG

GTCGGTAAACAGTGGTCGGGAGCGCGAGCACTTGAGGCGCTGCTGACTGTGGCGGGTG

AGCTTAGGGGGCCTCCGCTCCAGCTCGACACCGGGCAGCTGCTGAAGATCGCGAAGAG

AGGGGGAGTAACAGCGGTAGAGGCAGTGCACGCCTGGCGCAATGCGCTCACCGGGGCC

CCCTTGAACCTGACCCCAGACCAGGTAGTCGCAATCGCGTCACATGACGGGGGAAAGC

AAGCCCTGGAAACCGTGCAAAGGTTGTTGCCGGTCCTTTGTCAAGACCACGGCCTTACA

CCGGAGCAAGTCGTGGCCATTGCATCCCACGACGGTGGCAAACAGGCTCTTGAGACGG

TTCAGAGACTTCTCCCAGTTCTCTGTCAAGCCCACGGGCTGACTCCCGATCAAGTTGTA

GCGATTGCGAATAACAATGGAGGGAAACAAGCATTGGAGACTGTCCAACGGCTCCTTC

CCGTGTTGTGTCAAGCCCACGGTTTGACGCCTGCACAAGTGGTCGCCATCGCCAGCCAT

GATGGCGGTAAGCAGGCGCTGGAAACAGTACAGCGCCTGCTGCCTGTACTGTGCCAGG

ATCATGGACTGACCCCAGACCAGGTAGTCGCAATCGCGTCACATGACGGGGGAAAGCA

AGCCCTGGAAACCGTGCAAAGGTTGTTGCCGGTCCTTTGTCAAGACCACGGCCTTACAC

CGGAGCAAGTCGTGGCCATTGCATCCCACGACGGTGGCAAACAGGCTCTTGAGACGGT

TCAGAGACTTCTCCCAGTTCTCTGTCAAGCCCACGGGCTGACTCCCGATCAAGTTGTAG

CGATTGCGTCGAACATTGGAGGGAAACAAGCATTGGAGACTGTCCAACGGCTCCTTCC

CGTGTTGTGTCAAGCCCACGGTTTGACGCCTGCACAAGTGGTCGCCATCGCCAGCCATG

ATGGCGGTAAGCAGGCGCTGGAAACAGTACAGCGCCTGCTGCCTGTACTGTGCCAGGA

TCATGGACTGACCCCAGACCAGGTAGTCGCAATCGCGTCAAACGGAGGGGGAAAGCAA

GCCCTGGAAACCGTGCAAAGGTTGTTGCCGGTCCTTTGTCAAGACCACGGCCTTACACC

GGAGCAAGTCGTGGCCATTGCAAATAATAACGGTGGCAAACAGGCTCTTGAGACGGTT

CAGAGACTTCTCCCAGTTCTCTGTCAAGCCCACGGGCTGACTCCCGATCAAGTTGTAGC

GATTGCGAATAACAATGGAGGGAAACAAGCATTGGAGACTGTCCAACGGCTCCTTCCC

GTGTTGTGTCAAGCCCACGGTTTGACGCCTGCACAAGTGGTCGCCATCGCCTCCAATAT

TGGCGGTAAGCAGGCGCTGGAAACAGTACAGCGCCTGCTGCCTGTACTGTGCCAGGAT

CATGGACTGACCCCAGACCAGGTAGTCGCAATCGCGTCGAACATTGGGGGAAAGCAAG

CCCTGGAAACCGTGCAAAGGTTGTTGCCGGTCCTTTGTCAAGACCACGGCCTTACACCG

GAGCAAGTCGTGGCCATTGCATCCCACGACGGTGGCAAACAGGCTCTTGAGACGGTTC

AGAGACTTCTCCCAGTTCTCTGTCAAGCCCACGGGCTGACTCCCGATCAAGTTGTAGCG

ATTGCGTCGAACATTGGAGGGAAACAAGCATTGGAGACTGTCCAACGGCTCCTTCCCGT

GTTGTGTCAAGCCCACGGTTTGACGCCTGCACAAGTGGTCGCCATCGCCAGCCATGATG

GCGGTAAGCAGGCGCTGGAAACAGTACAGCGCCTGCTGCCTGTACTGTGCCAGGATCA

TGGACTGACCCCAGACCAGGTAGTCGCAATCGCGAACAATAATGGGGGAAAGCAAGCC

CTGGAAACCGTGCAAAGGTTGTTGCCGGTCCTTTGTCAAGACCACGGCCTGACACCCGA

ACAGGTGGTCGCCATTGCTAATAATAACGGAGGACGGCCAGCCTTGGAG

-continued

6

(SEQ ID NO: 32)

ATGGTGGACTTGAGGACACTCGGTTATTCGCAACAGCAACAGGAGAAAATCAA
GCCTAAGGTCAGGAGCACCGTCGCGCAACACCACGAGGCGCTTGTGGGGCATGGCTTC
ACTCATGCGCATATTGTCGCGCTTTCACAGCACCCTGCGGCGCTTGGGACGGTGGCTGT
CAAATACCAAGATATGATTGCGGCCCTGCCCGAAGCCACGCACGAGGCAATTGTAGGG
GTCGGTAAACAGTGGTCGGGAGCGCGAGCACTTGAGGCGCTGCTGACTGTGGCGGGTG
AGCTTAGGGGGCCTCCGCTCCAGCTCGACACCGGGCAGCTGCTGAAGATCGCGAAGAG
AGGGGGAGTAACAGCGGTAGAGGCAGTGCACGCCTGGCGCAATGCGCTCACCGGGGCC
CCCTTGAACCTGACCCCAGACCAGGTAGTCGCAATCGCGAACAATAATGGGGGAAAGC
AAGCCCTGGAAACCGTGCAAAGGTTGTTGCCGGTCCTTTGTCAAGACCACGGCCTTACA
CCGGAGCAAGTCGTGGCCATTGCAAATAATAACGGTGGCAAACAGGCTCTTGAGACGG
TTCAGAGACTTCTCCCAGTTCTCTGTCAAGCCCACGGGCTGACTCCCGATCAAGTTGTA
GCGATTGCGTCGCATGACGGAGGGAAACAAGCATTGGAGACTGTCCAACGGCTCCTTC
CCGTGTTGTGTCAAGCCCACGGTTTGACGCCTGCACAAGTGGTCGCCATCGCCAGCCAT
GATGGCGGTAAGCAGGCGCTGGAAACAGTACAGCGCCTGCTGCCTGTACTGTGCCAGG
ATCATGGACTGACCCCAGACCAGGTAGTCGCAATCGCGTCGAACATTGGGGGAAAGCA
AGCCCTGGAAACCGTGCAAAGGTTGTTGCCGGTCCTTTGTCAAGACCACGGCCTTACAC
CGGAGCAAGTCGTGGCCATTGCAAATAATAACGGTGGCAAACAGGCTCTTGAGACGGT
TCAGAGACTTCTCCCAGTTCTCTGTCAAGCCCACGGGCTGACTCCCGATCAAGTTGTAG
CGATTGCGAATAACAATGGAGGGAAACAAGCATTGGAGACTGTCCAACGGCTCCTTCC
CGTGTTGTGTCAAGCCCACGGTTTGACGCCTGCACAAGTGGTCGCCATCGCCAGCCATG
ATGGCGGTAAGCAGGCGCTGGAAACAGTACAGCGCCTGCTGCCTGTACTGTGCCAGGA
TCATGGACTGACCCCAGACCAGGTAGTCGCAATCGCGTCAAACGGAGGGGGAAAGCAA
GCCCTGGAAACCGTGCAAAGGTTGTTGCCGGTCCTTTGTCAAGACCACGGCCTTACACC
GGAGCAAGTCGTGGCCATTGCAAATAATAACGGTGGCAAACAGGCTCTTGAGACGGTT
CAGAGACTTCTCCCAGTTCTCTGTCAAGCCCACGGGCTGACTCCCGATCAAGTTGTAGC
GATTGCGTCGCATGACGGAGGGAAACAAGCATTGGAGACTGTCCAACGGCTCCTTCCC
GTGTTGTGTCAAGCCCACGGTTTGACGCCTGCACAAGTGGTCGCCATCGCCAGCCATGA
TGGCGGTAAGCAGGCGCTGGAAACAGTACAGCGCCTGCTGCCTGTACTGTGCCAGGAT
CATGGACTGACCCCAGACCAGGTAGTCGCAATCGCGAACAATAATGGGGGAAAGCAAG
CCCTGGAAACCGTGCAAAGGTTGTTGCCGGTCCTTTGTCAAGACCACGGCCTTACACCG
GAGCAAGTCGTGGCCATTGCATCCCACGACGGTGGCAAACAGGCTCTTGAGACGGTTC
AGAGACTTCTCCCAGTTCTCTGTCAAGCCCACGGGCTGACTCCCGATCAAGTTGTAGCG
ATTGCGTCGCATGACGGAGGGAAACAAGCATTGGAGACTGTCCAACGGCTCCTTCCCG
TGTTGTGTCAAGCCCACGGTTTGACGCCTGCACAAGTGGTCGCCATCGCCTCGAATGGC
GGCGGTAAGCAGGCGCTGGAAACAGTACAGCGCCTGCTGCCTGTACTGTGCCAGGATC
ATGGACTGACCCCAGACCAGGTAGTCGCAATCGCGTCACATGACGGGGGAAAGCAAGC
CCTGGAAACCGTGCAAAGGTTGTTGCCGGTCCTTTGTCAAGACCACGGCCTGACACCCG
AACAGGTGGTCGCCATTGCTTCTAATGGGGGAGGACGGCCAGCCTTGGAG

-continued

7

(SEQ ID NO: 33)

ATGGTGGACTTGAGGACACTCGGTTATTCGCAACAGCAACAGGAGAAAATCAA

GCCTAAGGTCAGGAGCACCGTCGCGCAACACCACGAGGCGCTTGTGGGGCATGGCTTC

ACTCATGCGCATATTGTCGCGCTTTCACAGCACCCTGCGGCGCTTGGGACGGTGGCTGT

CAAATACCAAGATATGATTGCGGCCCTGCCCGAAGCCACGCACGAGGCAATTGTAGGG

GTCGGTAAACAGTGGTCGGGAGCGCGAGCACTTGAGGCGCTGCTGACTGTGGCGGGTG

AGCTTAGGGGGCCTCCGCTCCAGCTCGACACCGGGCAGCTGCTGAAGATCGCGAAGAG

AGGGGGAGTAACAGCGGTAGAGGCAGTGCACGCCTGGCGCAATGCGCTCACCGGGGCC

CCCTTGAACCTGACCCCAGACCAGGTAGTCGCAATCGCGTCACATGACGGGGGAAAGC

AAGCCCTGGAAACCGTGCAAAGGTTGTTGCCGGTCCTTTGTCAAGACCACGGCCTTACA

CCGGAGCAAGTCGTGGCCATTGCATCCCACGACGGTGGCAAACAGGCTCTTGAGACGG

TTCAGAGACTTCTCCCAGTTCTCTGTCAAGCCCACGGGCTGACTCCCGATCAAGTTGTA

GCGATTGCGAATAACAATGGAGGGAAACAAGCATTGGAGACTGTCCAACGGCTCCTTC

CCGTGTTGTGTCAAGCCCACGGTTTGACGCCTGCACAAGTGGTCGCCATCGCCAACAAC

AACGGCGGTAAGCAGGCGCTGGAAACAGTACAGCGCCTGCTGCCTGTACTGTGCCAGG

ATCATGGACTGACCCCAGACCAGGTAGTCGCAATCGCGAACAATAATGGGGGAAAGCA

AGCCCTGGAAACCGTGCAAAGGTTGTTGCCGGTCCTTTGTCAAGACCACGGCCTTACAC

CGGAGCAAGTCGTGGCCATTGCAAGCAATGGGGGTGGCAAACAGGCTCTTGAGACGGT

TCAGAGACTTCTCCCAGTTCTCTGTCAAGCCCACGGGCTGACTCCCGATCAAGTTGTAG

CGATTGCGTCGCATGACGGAGGGAAACAAGCATTGGAGACTGTCCAACGGCTCCTTCC

CGTGTTGTGTCAAGCCCACGGTTTGACGCCTGCACAAGTGGTCGCCATCGCCAGCCATG

ATGGCGGTAAGCAGGCGCTGGAAACAGTACAGCGCCTGCTGCCTGTACTGTGCCAGGA

TCATGGACTGACCCCAGACCAGGTAGTCGCAATCGCGTCAAACGGAGGGGGAAAGCAA

GCCCTGGAAACCGTGCAAAGGTTGTTGCCGGTCCTTTGTCAAGACCACGGCCTTACACC

GGAGCAAGTCGTGGCCATTGCATCCCACGACGGTGGCAAACAGGCTCTTGAGACGGTT

CAGAGACTTCTCCCAGTTCTCTGTCAAGCCCACGGGCTGACTCCCGATCAAGTTGTAGC

GATTGCGTCGCATGACGGAGGGAAACAAGCATTGGAGACTGTCCAACGGCTCCTTCCC

GTGTTGTGTCAAGCCCACGGTTTGACGCCTGCACAAGTGGTCGCCATCGCCTCCAATAT

TGGCGGTAAGCAGGCGCTGGAAACAGTACAGCGCCTGCTGCCTGTACTGTGCCAGGAT

CATGGACTGACCCCAGACCAGGTAGTCGCAATCGCGTCACATGACGGGGGAAAGCAAG

CCCTGGAAACCGTGCAAAGGTTGTTGCCGGTCCTTTGTCAAGACCACGGCCTTACACCG

GAGCAAGTCGTGGCCATTGCATCCCACGACGGTGGCAAACAGGCTCTTGAGACGGTTC

AGAGACTTCTCCCAGTTCTCTGTCAAGCCCACGGGCTGACTCCCGATCAAGTTGTAGCG

ATTGCGTCGAACATTGGAGGGAAACAAGCATTGGAGACTGTCCAACGGCTCCTTCCCGT

GTTGTGTCAAGCCCACGGTTTGACGCCTGCACAAGTGGTCGCCATCGCCTCCAATATTG

GCGGTAAGCAGGCGCTGGAAACAGTACAGCGCCTGCTGCCTGTACTGTGCCAGGATCA

TGGACTGACCCCAGACCAGGTAGTCGCAATCGCGTCACATGACGGGGGAAAGCAAGCC

CTGGAAACCGTGCAAAGGTTGTTGCCGGTCCTTTGTCAAGACCACGGCCTGACACCCGA

ACAGGTGGTCGCCATTGCTTCCCACGACGGAGGACGGCCAGCCTTGGAG

-continued

8

(SEQ ID NO: 34)

ATGGTGGACTTGAGGACACTCGGTTATTCGCAACAGCAACAGGAGAAAATCAA

GCCTAAGGTCAGGAGCACCGTCGCGCAACACCACGAGGCGCTTGTGGGGCATGGCTTC

ACTCATGCGCATATTGTCGCGCTTTCACAGCACCCTGCGGCGCTTGGGACGGTGGCTGT

CAAATACCAAGATATGATTGCGGCCCTGCCCGAAGCCACGCACGAGGCAATTGTAGGG

GTCGGTAAACAGTGGTCGGGAGCGCGAGCACTTGAGGCGCTGCTGACTGTGGCGGGTG

AGCTTAGGGGGCCTCCGCTCCAGCTCGACACCGGGCAGCTGCTGAAGATCGCGAAGAG

AGGGGGAGTAACAGCGGTAGAGGCAGTGCACGCCTGGCGCAATGCGCTCACCGGGGCC

CCCTTGAACCTGACCCCAGACCAGGTAGTCGCAATCGCGAACAATAATGGGGGAAAGC

AAGCCCTGGAAACCGTGCAAAGGTTGTTGCCGGTCCTTTGTCAAGACCACGGCCTTACA

CCGGAGCAAGTCGTGGCCATTGCATCCCACGACGGTGGCAAACAGGCTCTTGAGACGG

TTCAGAGACTTCTCCCAGTTCTCTGTCAAGCCCACGGGCTGACTCCCGATCAAGTTGTA

GCGATTGCGTCGCATGACGGAGGGAAACAAGCATTGGAGACTGTCCAACGGCTCCTTC

CCGTGTTGTGTCAAGCCCACGGTTTGACGCCTGCACAAGTGGTCGCCATCGCCAGCCAT

GATGGCGGTAAGCAGGCGCTGGAAACAGTACAGCGCCTGCTGCCTGTACTGTGCCAGG

ATCATGGACTGACCCCAGACCAGGTAGTCGCAATCGCGTCGAACATTGGGGGAAAGCA

AGCCCTGGAAACCGTGCAAAGGTTGTTGCCGGTCCTTTGTCAAGACCACGGCCTTACAC

CGGAGCAAGTCGTGGCCATTGCATCCCACGACGGTGGCAAACAGGCTCTTGAGACGGT

TCAGAGACTTCTCCCAGTTCTCTGTCAAGCCCACGGGCTGACTCCCGATCAAGTTGTAG

CGATTGCGTCGCATGACGGAGGGAAACAAGCATTGGAGACTGTCCAACGGCTCCTTCC

CGTGTTGTGTCAAGCCCACGGTTTGACGCCTGCACAAGTGGTCGCCATCGCCTCGAATG

GCGGCGGTAAGCAGGCGCTGGAAACAGTACAGCGCCTGCTGCCTGTACTGTGCCAGGA

TCATGGACTGACCCCAGACCAGGTAGTCGCAATCGCGTCGAACATTGGGGGAAAGCAA

GCCCTGGAAACCGTGCAAAGGTTGTTGCCGGTCCTTTGTCAAGACCACGGCCTTACACC

GGAGCAAGTCGTGGCCATTGCAAATAATAACGGTGGCAAACAGGCTCTTGAGACGGTT

CAGAGACTTCTCCCAGTTCTCTGTCAAGCCCACGGGCTGACTCCCGATCAAGTTGTAGC

GATTGCGTCGCATGACGGAGGGAAACAAGCATTGGAGACTGTCCAACGGCTCCTTCCC

GTGTTGTGTCAAGCCCACGGTTTGACGCCTGCACAAGTGGTCGCCATCGCCAGCCATGA

TGGCGGTAAGCAGGCGCTGGAAACAGTACAGCGCCTGCTGCCTGTACTGTGCCAGGAT

CATGGACTGACCCCAGACCAGGTAGTCGCAATCGCGTCGAACATTGGGGGAAAGCAAG

CCCTGGAAACCGTGCAAAGGTTGTTGCCGGTCCTTTGTCAAGACCACGGCCTTACACCG

GAGCAAGTCGTGGCCATTGCAAATAATAACGGTGGCAAACAGGCTCTTGAGACGGTTC

AGAGACTTCTCCCAGTTCTCTGTCAAGCCCACGGGCTGACTCCCGATCAAGTTGTAGCG

ATTGCGTCGAACATTGGAGGGAAACAAGCATTGGAGACTGTCCAACGGCTCCTTCCCGT

GTTGTGTCAAGCCCACGGTTTGACGCCTGCACAAGTGGTCGCCATCGCCAACAACAACG

GCGGTAAGCAGGCGCTGGAAACAGTACAGCGCCTGCTGCCTGTACTGTGCCAGGATCA

TGGACTGACCCCAGACCAGGTAGTCGCAATCGCGAACAATAATGGGGGAAAGCAAGCC

CTGGAAACCGTGCAAAGGTTGTTGCCGGTCCTTTGTCAAGACCACGGCCTGACACCCGA

ACAGGTGGTCGCCATTGCTAATAATAACGGAGGACGGCCAGCCTTGGAG

9

(SEQ ID NO: 35)

ATGGTGGACTTGAGGACACTCGGTTATTCGCAACAGCAACAGGAGAAAATCAA

GCCTAAGGTCAGGAGCACCGTCGCGCAACACCACGAGGCGCTTGTGGGGCATGGCTTC

ACTCATGCGCATATTGTCGCGCTTTCACAGCACCCTGCGGCGCTTGGGACGGTGGCTGT

CAAATACCAAGATATGATTGCGGCCCTGCCCGAAGCCACGCACGAGGCAATTGTAGGG

GTCGGTAAACAGTGGTCGGGAGCGCGAGCACTTGAGGCGCTGCTGACTGTGGCGGGTG

AGCTTAGGGGGCCTCCGCTCCAGCTCGACACCGGGCAGCTGCTGAAGATCGCGAAGAG

AGGGGGAGTAACAGCGGTAGAGGCAGTGCACGCCTGGCGCAATGCGCTCACCGGGGCC

CCCTTGAACCTGACCCCAGACCAGGTAGTCGCAATCGCGAACAATAATGGGGGAAAGC

AAGCCCTGGAAACCGTGCAAAGGTTGTTGCCGGTCCTTTGTCAAGACCACGGCCTTACA

CCGGAGCAAGTCGTGGCCATTGCAAATAATAACGGTGGCAAACAGGCTCTTGAGACGG

TTCAGAGACTTCTCCCAGTTCTCTGTCAAGCCCACGGGCTGACTCCCGATCAAGTTGTA

GCGATTGCGAATAACAATGGAGGGAAACAAGCATTGGAGACTGTCCAACGGCTCCTTC

CCGTGTTGTGTCAAGCCCACGGTTTGACGCCTGCACAAGTGGTCGCCATCGCCAGCCAT

GATGGCGGTAAGCAGGCGCTGGAAACAGTACAGCGCCTGCTGCCTGTACTGTGCCAGG

ATCATGGACTGACCCCAGACCAGGTAGTCGCAATCGCGTCGAACATTGGGGGAAAGCA

AGCCCTGGAAACCGTGCAAAGGTTGTTGCCGGTCCTTTGTCAAGACCACGGCCTTACAC

CGGAGCAAGTCGTGGCCATTGCAAATAATAACGGTGGCAAACAGGCTCTTGAGACGGT

TCAGAGACTTCTCCCAGTTCTCTGTCAAGCCCACGGGCTGACTCCCGATCAAGTTGTAG

CGATTGCGTCGCATGACGGAGGGAAACAAGCATTGGAGACTGTCCAACGGCTCCTTCC

CGTGTTGTGTCAAGCCCACGGTTTGACGCCTGCACAAGTGGTCGCCATCGCCTCGAATG

GCGGCGGTAAGCAGGCGCTGGAAACAGTACAGCGCCTGCTGCCTGTACTGTGCCAGGA

TCATGGACTGACCCCAGACCAGGTAGTCGCAATCGCGTCACATGACGGGGGAAAGCAA

GCCCTGGAAACCGTGCAAAGGTTGTTGCCGGTCCTTTGTCAAGACCACGGCCTTACACC

GGAGCAAGTCGTGGCCATTGCAAGCAACATCGGTGGCAAACAGGCTCTTGAGACGGTT

CAGAGACTTCTCCCAGTTCTCTGTCAAGCCCACGGGCTGACTCCCGATCAAGTTGTAGC

GATTGCGAATAACAATGGAGGGAAACAAGCATTGGAGACTGTCCAACGGCTCCTTCCC

GTGTTGTGTCAAGCCCACGGTTTGACGCCTGCACAAGTGGTCGCCATCGCCAGCCATGA

TGGCGGTAAGCAGGCGCTGGAAACAGTACAGCGCCTGCTGCCTGTACTGTGCCAGGAT

CATGGACTGACCCCAGACCAGGTAGTCGCAATCGCGTCACATGACGGGGGAAAGCAAG

CCCTGGAAACCGTGCAAAGGTTGTTGCCGGTCCTTTGTCAAGACCACGGCCTTACACCG

GAGCAAGTCGTGGCCATTGCAAGCAATGGGGGTGGCAAACAGGCTCTTGAGACGGTTC

AGAGACTTCTCCCAGTTCTCTGTCAAGCCCACGGGCTGACTCCCGATCAAGTTGTAGCG

ATTGCGAATAACAATGGAGGGAAACAAGCATTGGAGACTGTCCAACGGCTCCTTCCCG

TGTTGTGTCAAGCCCACGGTTTGACGCCTGCACAAGTGGTCGCCATCGCCTCGAATGGC

GGCGGTAAGCAGGCGCTGGAAACAGTACAGCGCCTGCTGCCTGTACTGTGCCAGGATC

ATGGACTGACCCCAGACCAGGTAGTCGCAATCGCGTCACATGACGGGGGAAAGCAAGC

-continued

CCTGGAAACCGTGCAAAGGTTGTTGCCGGTCCTTTGTCAAGACCACGGCCTGACACCCG

AACAGGTGGTCGCCATTGCTTCTAACATCGGAGGACGGCCAGCCTTGGAG

10

(SEQ ID NO: 36)

ATGGTGGACTTGAGGACACTCGGTTATTCGCAACAGCAACAGGAGAAAATCAA

GCCTAAGGTCAGGAGCACCGTCGCGCAACACCACGAGGCGCTTGTGGGGCATGGCTTC

ACTCATGCGCATATTGTCGCGCTTTCACAGCACCCTGCGGCGCTTGGGACGGTGGCTGT

CAAATACCAAGATATGATTGCGGCCCTGCCCGAAGCCACGCACGAGGCAATTGTAGGG

GTCGGTAAACAGTGGTCGGGAGCGCGAGCACTTGAGGCGCTGCTGACTGTGGCGGGTG

AGCTTAGGGGGCCTCCGCTCCAGCTCGACACCGGGCAGCTGCTGAAGATCGCGAAGAG

AGGGGGAGTAACAGCGGTAGAGGCAGTGCACGCCTGGCGCAATGCGCTCACCGGGGCC

CCCTTGAACCTGACCCCAGACCAGGTAGTCGCAATCGCGAACAATAATGGGGGAAAGC

AAGCCCTGGAAACCGTGCAAAGGTTGTTGCCGGTCCTTTGTCAAGACCACGGCCTTACA

CCGGAGCAAGTCGTGGCCATTGCATCCCACGACGGTGGCAAACAGGCTCTTGAGACGG

TTCAGAGACTTCTCCCAGTTCTCTGTCAAGCCCACGGGCTGACTCCCGATCAAGTTGTA

GCGATTGCGTCGCATGACGGAGGGAAACAAGCATTGGAGACTGTCCAACGGCTCCTTC

CCGTGTTGTGTCAAGCCCACGGTTTGACGCCTGCACAAGTGGTCGCCATCGCCAGCCAT

GATGGCGGTAAGCAGGCGCTGGAAACAGTACAGCGCCTGCTGCCTGTACTGTGCCAGG

ATCATGGACTGACCCCAGACCAGGTAGTCGCAATCGCGTCGAACATTGGGGGAAAGCA

AGCCCTGGAAACCGTGCAAAGGTTGTTGCCGGTCCTTTGTCAAGACCACGGCCTTACAC

CGGAGCAAGTCGTGGCCATTGCAAGCAACATCGGTGGCAAACAGGCTCTTGAGACGGT

TCAGAGACTTCTCCCAGTTCTCTGTCAAGCCCACGGGCTGACTCCCGATCAAGTTGTAG

CGATTGCGAATAACAATGGAGGGAAACAAGCATTGGAGACTGTCCAACGGCTCCTTCC

CGTGTTGTGTCAAGCCCACGGTTTGACGCCTGCACAAGTGGTCGCCATCGCCAACAACA

ACGGCGGTAAGCAGGCGCTGGAAACAGTACAGCGCCTGCTGCCTGTACTGTGCCAGGA

TCATGGACTGACCCCAGACCAGGTAGTCGCAATCGCGTCAAACGGAGGGGGAAAGCAA

GCCCTGGAAACCGTGCAAAGGTTGTTGCCGGTCCTTTGTCAAGACCACGGCCTTACACC

GGAGCAAGTCGTGGCCATTGCATCCCACGACGGTGGCAAACAGGCTCTTGAGACGGTT

CAGAGACTTCTCCCAGTTCTCTGTCAAGCCCACGGGCTGACTCCCGATCAAGTTGTAGC

GATTGCGTCGAACATTGGAGGGAAACAAGCATTGGAGACTGTCCAACGGCTCCTTCCC

GTGTTGTGTCAAGCCCACGGTTTGACGCCTGCACAAGTGGTCGCCATCGCCTCGAATGG

CGGCGGTAAGCAGGCGCTGGAAACAGTACAGCGCCTGCTGCCTGTACTGTGCCAGGAT

CATGGACTGACCCCAGACCAGGTAGTCGCAATCGCGTCACATGACGGGGGAAAGCAAG

CCCTGGAAACCGTGCAAAGGTTGTTGCCGGTCCTTTGTCAAGACCACGGCCTTACACCG

GAGCAAGTCGTGGCCATTGCATCCCACGACGGTGGCAAACAGGCTCTTGAGACGGTTC

AGAGACTTCTCCCAGTTCTCTGTCAAGCCCACGGGCTGACTCCCGATCAAGTTGTAGCG

ATTGCGTCGAACATTGGAGGGAAACAAGCATTGGAGACTGTCCAACGGCTCCTTCCCGT

GTTGTGTCAAGCCCACGGTTTGACGCCTGCACAAGTGGTCGCCATCGCCAACAACAACG

GCGGTAAGCAGGCGCTGGAAACAGTACAGCGCCTGCTGCCTGTACTGTGCCAGGATCA

-continued

TGGACTGACCCCAGACCAGGTAGTCGCAATCGCGAACAATAATGGGGGAAAGCAAGCC

CTGGAAACCGTGCAAAGGTTGTTGCCGGTCCTTTGTCAAGACCACGGCCTGACACCCGA

ACAGGTGGTCGCCATTGCTAATAATAACGGAGGACGGCCAGCCTTGGAG

11

(SEQ ID NO: 37)

ATGGTGGACTTGAGGACACTCGGTTATTCGCAACAGCAACAGGAGAAAATCAA

GCCTAAGGTCAGGAGCACCGTCGCGCAACACCACGAGGCGCTTGTGGGGCATGGCTTC

ACTCATGCGCATATTGTCGCGCTTTCACAGCACCCTGCGGCGCTTGGGACGGTGGCTGT

CAAATACCAAGATATGATTGCGGCCCTGCCCGAAGCCACGCACGAGGCAATTGTAGGG

GTCGGTAAACAGTGGTCGGGAGCGCGAGCACTTGAGGCGCTGCTGACTGTGGCGGGTG

AGCTTAGGGGGCCTCCGCTCCAGCTCGACACCGGGCAGCTGCTGAAGATCGCGAAGAG

AGGGGGAGTAACAGCGGTAGAGGCAGTGCACGCCTGGCGCAATGCGCTCACCGGGGCC

CCCTTGAACCTGACCCCAGACCAGGTAGTCGCAATCGCGAACAATAATGGGGGAAAGC

AAGCCCTGGAAACCGTGCAAAGGTTGTTGCCGGTCCTTTGTCAAGACCACGGCCTTACA

CCGGAGCAAGTCGTGGCCATTGCATCCCACGACGGTGGCAAACAGGCTCTTGAGACGG

TTCAGAGACTTCTCCCAGTTCTCTGTCAAGCCCACGGGCTGACTCCCGATCAAGTTGTA

GCGATTGCGTCGCATGACGGAGGGAAACAAGCATTGGAGACTGTCCAACGGCTCCTTC

CCGTGTTGTGTCAAGCCCACGGTTTGACGCCTGCACAAGTGGTCGCCATCGCCAGCCAT

GATGGCGGTAAGCAGGCGCTGGAAACAGTACAGCGCCTGCTGCCTGTACTGTGCCAGG

ATCATGGACTGACCCCAGACCAGGTAGTCGCAATCGCGTCGAACATTGGGGGAAAGCA

AGCCCTGGAAACCGTGCAAAGGTTGTTGCCGGTCCTTTGTCAAGACCACGGCCTTACAC

CGGAGCAAGTCGTGGCCATTGCATCCCACGACGGTGGCAAACAGGCTCTTGAGACGGT

TCAGAGACTTCTCCCAGTTCTCTGTCAAGCCCACGGGCTGACTCCCGATCAAGTTGTAG

CGATTGCGTCGAACATTGGAGGGAAACAAGCATTGGAGACTGTCCAACGGCTCCTTCC

CGTGTTGTGTCAAGCCCACGGTTTGACGCCTGCACAAGTGGTCGCCATCGCCTCGAATG

GCGGCGGTAAGCAGGCGCTGGAAACAGTACAGCGCCTGCTGCCTGTACTGTGCCAGGA

TCATGGACTGACCCCAGACCAGGTAGTCGCAATCGCGTCAAACGGAGGGGGAAAGCAA

GCCCTGGAAACCGTGCAAAGGTTGTTGCCGGTCCTTTGTCAAGACCACGGCCTTACACC

GGAGCAAGTCGTGGCCATTGCAAATAATAACGGTGGCAAACAGGCTCTTGAGACGGTT

CAGAGACTTCTCCCAGTTCTCTGTCAAGCCCACGGGCTGACTCCCGATCAAGTTGTAGC

GATTGCGAATAACAATGGAGGGAAACAAGCATTGGAGACTGTCCAACGGCTCCTTCCC

GTGTTGTGTCAAGCCCACGGTTTGACGCCTGCACAAGTGGTCGCCATCGCCAACAACAA

CGGCGGTAAGCAGGCGCTGGAAACAGTACAGCGCCTGCTGCCTGTACTGTGCCAGGAT

CATGGACTGACCCCAGACCAGGTAGTCGCAATCGCGTCGAACATTGGGGGAAAGCAAG

CCCTGGAAACCGTGCAAAGGTTGTTGCCGGTCCTTTGTCAAGACCACGGCCTTACACCG

GAGCAAGTCGTGGCCATTGCATCCCACGACGGTGGCAAACAGGCTCTTGAGACGGTTC

AGAGACTTCTCCCAGTTCTCTGTCAAGCCCACGGGCTGACTCCCGATCAAGTTGTAGCG

ATTGCGTCCAACGGTGGAGGGAAACAAGCATTGGAGACTGTCCAACGGCTCCTTCCCG

TGTTGTGTCAAGCCCACGGTTTGACGCCTGCACAAGTGGTCGCCATCGCCAGCCATGAT

GGCGGTAAGCAGGCGCTGGAAACAGTACAGCGCCTGCTGCCTGTACTGTGCCAGGATC

ATGGACTGACCCCAGACCAGGTAGTCGCAATCGCGTCAAACGGAGGGGGAAAGCAAG

-continued

CCCTGGAAACCGTGCAAAGGTTGTTGCCGGTCCTTTGTCAAGACCACGGCCTGACACCC

GAACAGGTGGTCGCCATTGCTTCTAATGGGGGAGGACGGCCAGCCTTGGAG

12

(SEQ ID NO: 38)

ATGGTGGACTTGAGGACACTCGGTTATTCGCAACAGCAACAGGAGAAAATCAA

GCCTAAGGTCAGGAGCACCGTCGCGCAACACCACGAGGCGCTTGTGGGGCATGGCTTC

ACTCATGCGCATATTGTCGCGCTTTCACAGCACCCTGCGGCGCTTGGGACGGTGGCTGT

CAAATACCAAGATATGATTGCGGCCCTGCCCGAAGCCACGCACGAGGCAATTGTAGGG

GTCGGTAAACAGTGGTCGGGAGCGCGAGCACTTGAGGCGCTGCTGACTGTGGCGGGTG

AGCTTAGGGGGCCTCCGCTCCAGCTCGACACCGGGCAGCTGCTGAAGATCGCGAAGAG

AGGGGGAGTAACAGCGGTAGAGGCAGTGCACGCCTGGCGCAATGCGCTCACCGGGGCC

CCCTTGAACCTGACCCCAGACCAGGTAGTCGCAATCGCGAACAATAATGGGGGAAAGC

AAGCCCTGGAAACCGTGCAAAGGTTGTTGCCGGTCCTTTGTCAAGACCACGGCCTTACA

CCGGAGCAAGTCGTGGCCATTGCATCCCACGACGGTGGCAAACAGGCTCTTGAGACGG

TTCAGAGACTTCTCCCAGTTCTCTGTCAAGCCCACGGGCTGACTCCCGATCAAGTTGTA

GCGATTGCGTCGCATGACGGAGGGAAACAAGCATTGGAGACTGTCCAACGGCTCCTTC

CCGTGTTGTGTCAAGCCCACGGTTTGACGCCTGCACAAGTGGTCGCCATCGCCAACAAC

AACGGCGGTAAGCAGGCGCTGGAAACAGTACAGCGCCTGCTGCCTGTACTGTGCCAGG

ATCATGGACTGACCCCAGACCAGGTAGTCGCAATCGCGTCACATGACGGGGGAAAGCA

AGCCCTGGAAACCGTGCAAAGGTTGTTGCCGGTCCTTTGTCAAGACCACGGCCTTACAC

CGGAGCAAGTCGTGGCCATTGCATCCCACGACGGTGGCAAACAGGCTCTTGAGACGGT

TCAGAGACTTCTCCCAGTTCTCTGTCAAGCCCACGGGCTGACTCCCGATCAAGTTGTAG

CGATTGCGTCCAACGGTGGAGGGAAACAAGCATTGGAGACTGTCCAACGGCTCCTTCC

CGTGTTGTGTCAAGCCCACGGTTTGACGCCTGCACAAGTGGTCGCCATCGCCAGCCATG

ATGGCGGTAAGCAGGCGCTGGAAACAGTACAGCGCCTGCTGCCTGTACTGTGCCAGGA

TCATGGACTGACCCCAGACCAGGTAGTCGCAATCGCGTCAAACGGAGGGGGAAAGCAA

GCCCTGGAAACCGTGCAAAGGTTGTTGCCGGTCCTTTGTCAAGACCACGGCCTTACACC

GGAGCAAGTCGTGGCCATTGCAAGCAACATCGGTGGCAAACAGGCTCTTGAGACGGTT

CAGAGACTTCTCCCAGTTCTCTGTCAAGCCCACGGGCTGACTCCCGATCAAGTTGTAGC

GATTGCGTCGCATGACGGAGGGAAACAAGCATTGGAGACTGTCCAACGGCTCCTTCCC

GTGTTGTGTCAAGCCCACGGTTTGACGCCTGCACAAGTGGTCGCCATCGCCAGCCATGA

TGGCGGTAAGCAGGCGCTGGAAACAGTACAGCGCCTGCTGCCTGTACTGTGCCAGGAT

CATGGACTGACCCCAGACCAGGTAGTCGCAATCGCGTCACATGACGGGGGAAAGCAAG

CCCTGGAAACCGTGCAAAGGTTGTTGCCGGTCCTTTGTCAAGACCACGGCCTTACACCG

GAGCAAGTCGTGGCCATTGCAAGCAATGGGGGTGGCAAACAGGCTCTTGAGACGGTTC

AGAGACTTCTCCCAGTTCTCTGTCAAGCCCACGGGCTGACTCCCGATCAAGTTGTAGCG

ATTGCGAATAACAATGGAGGGAAACAAGCATTGGAGACTGTCCAACGGCTCCTTCCCG

TGTTGTGTCAAGCCCACGGTTTGACGCCTGCACAAGTGGTCGCCATCGCCTCCAATATT

GGCGGTAAGCAGGCGCTGGAAACAGTACAGCGCCTGCTGCCTGTACTGTGCCAGGATC

ATGGACTGACCCCAGACCAGGTAGTCGCAATCGCGTCACATGACGGGGGAAAGCAAGC

CCTGGAAACCGTGCAAAGGTTGTTGCCGGTCCTTTGTCAAGACCACGGCCTTACACCGG

AGCAAGTCGTGGCCATTGCAAGCAACATCGGTGGCAAACAGGCTCTTGAGACGGTTCA

-continued

GAGACTTCTCCCAGTTCTCTGTCAAGCCCACGGGCTGACTCCCGATCAAGTTGTAGCGA

TTGCGTCGCATGACGGAGGGAAACAAGCATTGGAGACTGTCCAACGGCTCCTTCCCGT

GTTGTGTCAAGCCCACGGTTTGACGCCTGCACAAGTGGTCGCCATCGCCTCCAATATTG

GCGGTAAGCAGGCGCTGGAAACAGTACAGCGCCTGCTGCCTGTACTGTGCCAGGATCA

TGGACTGACCCCAGACCAGGTAGTCGCAATCGCGTCAAACGGAGGGGGAAAGCAAGCC

CTGGAAACCGTGCAAAGGTTGTTGCCGGTCCTTTGTCAAGACCACGGCCTTACACCGGA

GCAAGTCGTGGCCATTGCAAGCAATGGGGGTGGCAAACAGGCTCTTGAGACGGTTCAG

AGACTTCTCCCAGTTCTCTGTCAAGCCCACGGGCTGACACCCGAACAGGTGGTCGCCAT

TGCTAATAATAACGGAGGACGGCCAGCCTTGGAG

13

(SEQ ID NO: 39)

ATGGTGGACTTGAGGACACTCGGTTATTCGCAACAGCAACAGGAGAAAATCAA

GCCTAAGGTCAGGAGCACCGTCGCGCAACACCACGAGGCGCTTGTGGGGCATGGCTTC

ACTCATGCGCATATTGTCGCGCTTTCACAGCACCCTGCGGCGCTTGGGACGGTGGCTGT

CAAATACCAAGATATGATTGCGGCCCTGCCCGAAGCCACGCACGAGGCAATTGTAGGG

GTCGGTAAACAGTGGTCGGGAGCGCGAGCACTTGAGGCGCTGCTGACTGTGGCGGGTG

AGCTTAGGGGGCCTCCGCTCCAGCTCGACACCGGGCAGCTGCTGAAGATCGCGAAGAG

AGGGGGAGTAACAGCGGTAGAGGCAGTGCACGCCTGGCGCAATGCGCTCACCGGGGCC

CCCTTGAACCTGACCCCAGACCAGGTAGTCGCAATCGCGTCACATGACGGGGGAAAGC

AAGCCCTGGAAACCGTGCAAAGGTTGTTGCCGGTCCTTTGTCAAGACCACGGCCTTACA

CCGGAGCAAGTCGTGGCCATTGCATCCCACGACGGTGGCAAACAGGCTCTTGAGACGG

TTCAGAGACTTCTCCCAGTTCTCTGTCAAGCCCACGGGCTGACTCCCGATCAAGTTGTA

GCGATTGCGTCGCATGACGGAGGGAAACAAGCATTGGAGACTGTCCAACGGCTCCTTC

CCGTGTTGTGTCAAGCCCACGGTTTGACGCCTGCACAAGTGGTCGCCATCGCCAACAAC

AACGGCGGTAAGCAGGCGCTGGAAACAGTACAGCGCCTGCTGCCTGTACTGTGCCAGG

ATCATGGACTGACCCCAGACCAGGTAGTCGCAATCGCGTCACATGACGGGGGAAAGCA

AGCCCTGGAAACCGTGCAAAGGTTGTTGCCGGTCCTTTGTCAAGACCACGGCCTTACAC

CGGAGCAAGTCGTGGCCATTGCATCCCACGACGGTGGCAAACAGGCTCTTGAGACGGT

TCAGAGACTTCTCCCAGTTCTCTGTCAAGCCCACGGGCTGACTCCCGATCAAGTTGTAG

CGATTGCGTCGAACATTGGAGGGAAACAAGCATTGGAGACTGTCCAACGGCTCCTTCC

CGTGTTGTGTCAAGCCCACGGTTTGACGCCTGCACAAGTGGTCGCCATCGCCAACAACA

ACGGCGGTAAGCAGGCGCTGGAAACAGTACAGCGCCTGCTGCCTGTACTGTGCCAGGA

TCATGGACTGACCCCAGACCAGGTAGTCGCAATCGCGTCAAACGGAGGGGGAAAGCAA

GCCCTGGAAACCGTGCAAAGGTTGTTGCCGGTCCTTTGTCAAGACCACGGCCTTACACC

GGAGCAAGTCGTGGCCATTGCATCCCACGACGGTGGCAAACAGGCTCTTGAGACGGTT

CAGAGACTTCTCCCAGTTCTCTGTCAAGCCCACGGGCTGACTCCCGATCAAGTTGTAGC

GATTGCGTCGCATGACGGAGGGAAACAAGCATTGGAGACTGTCCAACGGCTCCTTCCC

GTGTTGTGTCAAGCCCACGGTTTGACGCCTGCACAAGTGGTCGCCATCGCCAACAACAA

CGGCGGTAAGCAGGCGCTGGAAACAGTACAGCGCCTGCTGCCTGTACTGTGCCAGGAT

CATGGACTGACCCCAGACCAGGTAGTCGCAATCGCGTCACATGACGGGGGAAAGCAAG

CCCTGGAAACCGTGCAAAGGTTGTTGCCGGTCCTTTGTCAAGACCACGGCCTTACACCG

-continued

GAGCAAGTCGTGGCCATTGCATCCCACGACGGTGGCAAACAGGCTCTTGAGACGGTTC

AGAGACTTCTCCCAGTTCTCTGTCAAGCCCACGGGCTGACTCCCGATCAAGTTGTAGCG

ATTGCGTCGCATGACGGAGGGAAACAAGCATTGGAGACTGTCCAACGGCTCCTTCCCG

TGTTGTGTCAAGCCCACGGTTTGACGCCTGCACAAGTGGTCGCCATCGCCTCCAATATT

GGCGGTAAGCAGGCGCTGGAAACAGTACAGCGCCTGCTGCCTGTACTGTGCCAGGATC

ATGGACTGACCCCAGACCAGGTAGTCGCAATCGCGTCACATGACGGGGGAAAGCAAGC

CCTGGAAACCGTGCAAAGGTTGTTGCCGGTCCTTTGTCAAGACCACGGCCTTACACCGG

AGCAAGTCGTGGCCATTGCAAGCAATGGGGGTGGCAAACAGGCTCTTGAGACGGTTCA

GAGACTTCTCCCAGTTCTCTGTCAAGCCCACGGGCTGACTCCCGATCAAGTTGTAGCGA

TTGCGAATAACAATGGAGGGAAACAAGCATTGGAGACTGTCCAACGGCTCCTTCCCGT

GTTGTGTCAAGCCCACGGTTTGACGCCTGCACAAGTGGTCGCCATCGCCAACAACAACG

GCGGTAAGCAGGCGCTGGAAACAGTACAGCGCCTGCTGCCTGTACTGTGCCAGGATCA

TGGACTGACCCCAGACCAGGTAGTCGCAATCGCGTCGAACATTGGGGGAAAGCAAGCC

CTGGAAACCGTGCAAAGGTTGTTGCCGGTCCTTTGTCAAGACCACGGCCTTACACCGGA

GCAAGTCGTGGCCATTGCAAGCAACATCGGTGGCAAACAGGCTCTTGAGACGGTTCAG

AGACTTCTCCCAGTTCTCTGTCAAGCCCACGGGCTGACTCCCGATCAAGTTGTAGCGAT

TGCGTCGCATGACGGAGGGAAACAAGCATTGGAGACTGTCCAACGGCTCCTTCCCGTG

TTGTGTCAAGCCCACGGTCTGACACCCGAACAGGTGGTCGCCATTGCTTCTAACATCGG

AGGACGGCCAGCCTTGGAG

14

(SEQ ID NO: 40)

ATGGTGGACTTGAGGACACTCGGTTATTCGCAACAGCAACAGGAGAAAATCAA

GCCTAAGGTCAGGAGCACCGTCGCGCAACACCACGAGGCGCTTGTGGGGCATGGCTTC

ACTCATGCGCATATTGTCGCGCTTTCACAGCACCCTGCGGCGCTTGGGACGGTGGCTGT

CAAATACCAAGATATGATTGCGGCCCTGCCCGAAGCCACGCACGAGGCAATTGTAGGG

GTCGGTAAACAGTGGTCGGGAGCGCGAGCACTTGAGGCGCTGCTGACTGTGGCGGGTG

AGCTTAGGGGGCCTCCGCTCCAGCTCGACACCGGGCAGCTGCTGAAGATCGCGAAGAG

AGGGGGAGTAACAGCGGTAGAGGCAGTGCACGCCTGGCGCAATGCGCTCACCGGGGCC

CCCTTGAACCTGACCCCAGACCAGGTAGTCGCAATCGCGTCACATGACGGGGGAAAGC

AAGCCCTGGAAACCGTGCAAAGGTTGTTGCCGGTCCTTTGTCAAGACCACGGCCTTACA

CCGGAGCAAGTCGTGGCCATTGCATCCCACGACGGTGGCAAACAGGCTCTTGAGACGG

TTCAGAGACTTCTCCCAGTTCTCTGTCAAGCCCACGGGCTGACTCCCGATCAAGTTGTA

GCGATTGCGAATAACAATGGAGGGAAACAAGCATTGGAGACTGTCCAACGGCTCCTTC

CCGTGTTGTGTCAAGCCCACGGTTTGACGCCTGCACAAGTGGTCGCCATCGCCAGCCAT

GATGGCGGTAAGCAGGCGCTGGAAACAGTACAGCGCCTGCTGCCTGTACTGTGCCAGG

ATCATGGACTGACCCCAGACCAGGTAGTCGCAATCGCGTCACATGACGGGGGAAAGCA

AGCCCTGGAAACCGTGCAAAGGTTGTTGCCGGTCCTTTGTCAAGACCACGGCCTTACAC

CGGAGCAAGTCGTGGCCATTGCATCCCACGACGGTGGCAAACAGGCTCTTGAGACGGT

TCAGAGACTTCTCCCAGTTCTCTGTCAAGCCCACGGGCTGACTCCCGATCAAGTTGTAG

CGATTGCGTCGAACATTGGAGGGAAACAAGCATTGGAGACTGTCCAACGGCTCCTTCC

CGTGTTGTGTCAAGCCCACGGTTTGACGCCTGCACAAGTGGTCGCCATCGCCAGCCATG

ATGGCGGTAAGCAGGCGCTGGAAACAGTACAGCGCCTGCTGCCTGTACTGTGCCAGGA

-continued

TCATGGACTGACCCCAGACCAGGTAGTCGCAATCGCGTCAAACGGAGGGGGAAAGCAA

GCCCTGGAAACCGTGCAAAGGTTGTTGCCGGTCCTTTGTCAAGACCACGGCCTTACACC

GGAGCAAGTCGTGGCCATTGCAAATAATAACGGTGGCAAACAGGCTCTTGAGACGGTT

CAGAGACTTCTCCCAGTTCTCTGTCAAGCCCACGGGCTGACTCCCGATCAAGTTGTAGC

GATTGCGAATAACAATGGAGGGAAACAAGCATTGGAGACTGTCCAACGGCTCCTTCCC

GTGTTGTGTCAAGCCCACGGTTTGACGCCTGCACAAGTGGTCGCCATCGCCTCCAATAT

TGGCGGTAAGCAGGCGCTGGAAACAGTACAGCGCCTGCTGCCTGTACTGTGCCAGGAT

CATGGACTGACCCCAGACCAGGTAGTCGCAATCGCGTCGAACATTGGGGGAAAGCAAG

CCCTGGAAACCGTGCAAAGGTTGTTGCCGGTCCTTTGTCAAGACCACGGCCTTACACCG

GAGCAAGTCGTGGCCATTGCATCCCACGACGGTGGCAAACAGGCTCTTGAGACGGTTC

AGAGACTTCTCCCAGTTCTCTGTCAAGCCCACGGGCTGACTCCCGATCAAGTTGTAGCG

ATTGCGTCGAACATTGGAGGGAAACAAGCATTGGAGACTGTCCAACGGCTCCTTCCCGT

GTTGTGTCAAGCCCACGGTTTGACGCCTGCACAAGTGGTCGCCATCGCCAGCCATGATG

GCGGTAAGCAGGCGCTGGAAACAGTACAGCGCCTGCTGCCTGTACTGTGCCAGGATCA

TGGACTGACCCCAGACCAGGTAGTCGCAATCGCGAACAATAATGGGGGAAAGCAAGCC

CTGGAAACCGTGCAAAGGTTGTTGCCGGTCCTTTGTCAAGACCACGGCCTTACACCGGA

GCAAGTCGTGGCCATTGCAAATAATAACGGTGGCAAACAGGCTCTTGAGACGGTTCAG

AGACTTCTCCCAGTTCTCTGTCAAGCCCACGGGCTGACTCCCGATCAAGTTGTAGCGAT

TGCGAATAACAATGGAGGGAAACAAGCATTGGAGACTGTCCAACGGCTCCTTCCCGTG

TTGTGTCAAGCCCACGGTTTGACGCCTGCACAAGTGGTCGCCATCGCCTCGAATGGCGG

CGGTAAGCAGGCGCTGGAAACAGTACAGCGCCTGCTGCCTGTACTGTGCCAGGATCAT

GGACTGACCCCAGACCAGGTAGTCGCAATCGCGTCAAACGGAGGGGGAAAGCAAGCC

CTGGAAACCGTGCAAAGGTTGTTGCCGGTCCTTTGTCAAGACCACGGCCTTACACCGGA

GCAAGTCGTGGCCATTGCATCCCACGACGGTGGCAAACAGGCTCTTGAGACGGTTCAG

AGACTTCTCCCAGTTCTCTGTCAAGCCCACGGGCTGACTCCCGATCAAGTTGTAGCGAT

TGCGTCGCATGACGGAGGGAAACAAGCATTGGAGACTGTCCAACGGCTCCTTCCCGTG

TTGTGTCAAGCCCACGGTCTGACACCCGAACAGGTGGTCGCCATTGCTTCTAACATCGG

AGGACGGCCAGCCTTGGAG

15

(SEQ ID NO: 41)

ATGGTGGACTTGAGGACACTCGGTTATTCGCAACAGCAACAGGAGAAAATCAA

GCCTAAGGTCAGGAGCACCGTCGCGCAACACCACGAGGCGCTTGTGGGGCATGGCTTC

ACTCATGCGCATATTGTCGCGCTTTCACAGCACCCTGCGGCGCTTGGGACGGTGGCTGT

CAAATACCAAGATATGATTGCGGCCCTGCCCGAAGCCACGCACGAGGCAATTGTAGGG

GTCGGTAAACAGTGGTCGGGAGCGCGAGCACTTGAGGCGCTGCTGACTGTGGCGGGTG

AGCTTAGGGGGCCTCCGCTCCAGCTCGACACCGGGCAGCTGCTGAAGATCGCGAAGAG

AGGGGGAGTAACAGCGGTAGAGGCAGTGCACGCCTGGCGCAATGCGCTCACCGGGGCC

CCCTTGAACCTGACCCCAGACCAGGTAGTCGCAATCGCGAACAATAATGGGGGAAAGC

AAGCCCTGGAAACCGTGCAAAGGTTGTTGCCGGTCCTTTGTCAAGACCACGGCCTTACA

CCGGAGCAAGTCGTGGCCATTGCAAATAATAACGGTGGCAAACAGGCTCTTGAGACGG

TTCAGAGACTTCTCCCAGTTCTCTGTCAAGCCCACGGGCTGACTCCCGATCAAGTTGTA

-continued

GCGATTGCGTCGCATGACGGAGGGAAACAAGCATTGGAGACTGTCCAACGGCTCCTTC

CCGTGTTGTGTCAAGCCCACGGTTTGACGCCTGCACAAGTGGTCGCCATCGCCAGCCAT

GATGGCGGTAAGCAGGCGCTGGAAACAGTACAGCGCCTGCTGCCTGTACTGTGCCAGG

ATCATGGACTGACCCCAGACCAGGTAGTCGCAATCGCGTCGAACATTGGGGGAAAGCA

AGCCCTGGAAACCGTGCAAAGGTTGTTGCCGGTCCTTTGTCAAGACCACGGCCTTACAC

CGGAGCAAGTCGTGGCCATTGCAAATAATAACGGTGGCAAACAGGCTCTTGAGACGGT

TCAGAGACTTCTCCCAGTTCTCTGTCAAGCCCACGGGCTGACTCCCGATCAAGTTGTAG

CGATTGCGAATAACAATGGAGGGAAACAAGCATTGGAGACTGTCCAACGGCTCCTTCC

CGTGTTGTGTCAAGCCCACGGTTTGACGCCTGCACAAGTGGTCGCCATCGCCAGCCATG

ATGGCGGTAAGCAGGCGCTGGAAACAGTACAGCGCCTGCTGCCTGTACTGTGCCAGGA

TCATGGACTGACCCCAGACCAGGTAGTCGCAATCGCGTCAAACGGAGGGGGAAAGCAA

GCCCTGGAAACCGTGCAAAGGTTGTTGCCGGTCCTTTGTCAAGACCACGGCCTTACACC

GGAGCAAGTCGTGGCCATTGCAAATAATAACGGTGGCAAACAGGCTCTTGAGACGGTT

CAGAGACTTCTCCCAGTTCTCTGTCAAGCCCACGGGCTGACTCCCGATCAAGTTGTAGC

GATTGCGTCGCATGACGGAGGGAAACAAGCATTGGAGACTGTCCAACGGCTCCTTCCC

GTGTTGTGTCAAGCCCACGGTTTGACGCCTGCACAAGTGGTCGCCATCGCCAGCCATGA

TGGCGGTAAGCAGGCGCTGGAAACAGTACAGCGCCTGCTGCCTGTACTGTGCCAGGAT

CATGGACTGACCCCAGACCAGGTAGTCGCAATCGCGAACAATAATGGGGGAAAGCAAG

CCCTGGAAACCGTGCAAAGGTTGTTGCCGGTCCTTTGTCAAGACCACGGCCTTACACCG

GAGCAAGTCGTGGCCATTGCATCCCACGACGGTGGCAAACAGGCTCTTGAGACGGTTC

AGAGACTTCTCCCAGTTCTCTGTCAAGCCCACGGGCTGACTCCCGATCAAGTTGTAGCG

ATTGCGTCGCATGACGGAGGGAAACAAGCATTGGAGACTGTCCAACGGCTCCTTCCCG

TGTTGTGTCAAGCCCACGGTTTGACGCCTGCACAAGTGGTCGCCATCGCCTCGAATGGC

GGCGGTAAGCAGGCGCTGGAAACAGTACAGCGCCTGCTGCCTGTACTGTGCCAGGATC

ATGGACTGACCCCAGACCAGGTAGTCGCAATCGCGTCACATGACGGGGGAAAGCAAGC

CCTGGAAACCGTGCAAAGGTTGTTGCCGGTCCTTTGTCAAGACCACGGCCTTACACCGG

AGCAAGTCGTGGCCATTGCAAGCAATGGGGGTGGCAAACAGGCTCTTGAGACGGTTCA

GAGACTTCTCCCAGTTCTCTGTCAAGCCCACGGGCTGACTCCCGATCAAGTTGTAGCGA

TTGCGTCGCATGACGGAGGGAAACAAGCATTGGAGACTGTCCAACGGCTCCTTCCCGT

GTTGTGTCAAGCCCACGGTTTGACGCCTGCACAAGTGGTCGCCATCGCCTCCAATATTG

GCGGTAAGCAGGCGCTGGAAACAGTACAGCGCCTGCTGCCTGTACTGTGCCAGGATCA

TGGACTGACCCCAGACCAGGTAGTCGCAATCGCGTCACATGACGGGGGAAAGCAAGCC

CTGGAAACCGTGCAAAGGTTGTTGCCGGTCCTTTGTCAAGACCACGGCCTTACACCGGA

GCAAGTCGTGGCCATTGCATCCCACGACGGTGGCAAACAGGCTCTTGAGACGGTTCAG

AGACTTCTCCCAGTTCTCTGTCAAGCCCACGGGCTGACTCCCGATCAAGTTGTAGCGAT

TGCGTCGCATGACGGAGGGAAACAAGCATTGGAGACTGTCCAACGGCTCCTTCCCGTG

TTGTGTCAAGCCCACGGTCTGACACCCGAACAGGTGGTCGCCATTGCTTCTAATGGGGG

AGGACGGCCAGCCTTGGAG

16

(SEQ ID NO: 42)

ATGGTGGACTTGAGGACACTCGGTTATTCGCAACAGCAACAGGAGAAAATCAA

GCCTAAGGTCAGGAGCACCGTCGCGCAACACCACGAGGCGCTTGTGGGGCATGGCTTC

-continued

ACTCATGCGCATATTGTCGCGCTTTCACAGCACCCTGCGGCGCTTGGGACGGTGGCTGT

CAAATACCAAGATATGATTGCGGCCCTGCCCGAAGCCACGCACGAGGCAATTGTAGGG

GTCGGTAAACAGTGGTCGGGAGCGCGAGCACTTGAGGCGCTGCTGACTGTGGCGGGTG

AGCTTAGGGGGCCTCCGCTCCAGCTCGACACCGGGCAGCTGCTGAAGATCGCGAAGAG

AGGGGGAGTAACAGCGGTAGAGGCAGTGCACGCCTGGCGCAATGCGCTCACCGGGGCC

CCCTTGAACCTGACCCCAGACCAGGTAGTCGCAATCGCGTCACATGACGGGGGAAAGC

AAGCCCTGGAAACCGTGCAAAGGTTGTTGCCGGTCCTTTGTCAAGACCACGGCCTTACA

CCGGAGCAAGTCGTGGCCATTGCATCCCACGACGGTGGCAAACAGGCTCTTGAGACGG

TTCAGAGACTTCTCCCAGTTCTCTGTCAAGCCCACGGGCTGACTCCCGATCAAGTTGTA

GCGATTGCGAATAACAATGGAGGGAAACAAGCATTGGAGACTGTCCAACGGCTCCTTC

CCGTGTTGTGTCAAGCCCACGGTTTGACGCCTGCACAAGTGGTCGCCATCGCCAACAAC

AACGGCGGTAAGCAGGCGCTGGAAACAGTACAGCGCCTGCTGCCTGTACTGTGCCAGG

ATCATGGACTGACCCCAGACCAGGTAGTCGCAATCGCGAACAATAATGGGGGAAAGCA

AGCCCTGGAAACCGTGCAAAGGTTGTTGCCGGTCCTTTGTCAAGACCACGGCCTTACAC

CGGAGCAAGTCGTGGCCATTGCAAGCAATGGGGGTGGCAAACAGGCTCTTGAGACGGT

TCAGAGACTTCTCCCAGTTCTCTGTCAAGCCCACGGGCTGACTCCCGATCAAGTTGTAG

CGATTGCGTCGCATGACGGAGGGAAACAAGCATTGGAGACTGTCCAACGGCTCCTTCC

CGTGTTGTGTCAAGCCCACGGTTTGACGCCTGCACAAGTGGTCGCCATCGCCAGCCATG

ATGGCGGTAAGCAGGCGCTGGAAACAGTACAGCGCCTGCTGCCTGTACTGTGCCAGGA

TCATGGACTGACCCCAGACCAGGTAGTCGCAATCGCGTCAAACGGAGGGGGAAAGCAA

GCCCTGGAAACCGTGCAAAGGTTGTTGCCGGTCCTTTGTCAAGACCACGGCCTTACACC

GGAGCAAGTCGTGGCCATTGCATCCCACGACGGTGGCAAACAGGCTCTTGAGACGGTT

CAGAGACTTCTCCCAGTTCTCTGTCAAGCCCACGGGCTGACTCCCGATCAAGTTGTAGC

GATTGCGTCGCATGACGGAGGGAAACAAGCATTGGAGACTGTCCAACGGCTCCTTCCC

GTGTTGTGTCAAGCCCACGGTTTGACGCCTGCACAAGTGGTCGCCATCGCCTCCAATAT

TGGCGGTAAGCAGGCGCTGGAAACAGTACAGCGCCTGCTGCCTGTACTGTGCCAGGAT

CATGGACTGACCCCAGACCAGGTAGTCGCAATCGCGTCACATGACGGGGGAAAGCAAG

CCCTGGAAACCGTGCAAAGGTTGTTGCCGGTCCTTTGTCAAGACCACGGCCTTACACCG

GAGCAAGTCGTGGCCATTGCATCCCACGACGGTGGCAAACAGGCTCTTGAGACGGTTC

AGAGACTTCTCCCAGTTCTCTGTCAAGCCCACGGGCTGACTCCCGATCAAGTTGTAGCG

ATTGCGTCGAACATTGGAGGGAAACAAGCATTGGAGACTGTCCAACGGCTCCTTCCCGT

GTTGTGTCAAGCCCACGGTTTGACGCCTGCACAAGTGGTCGCCATCGCCTCCAATATTG

GCGGTAAGCAGGCGCTGGAAACAGTACAGCGCCTGCTGCCTGTACTGTGCCAGGATCA

TGGACTGACCCCAGACCAGGTAGTCGCAATCGCGTCACATGACGGGGGAAAGCAAGCC

CTGGAAACCGTGCAAAGGTTGTTGCCGGTCCTTTGTCAAGACCACGGCCTTACACCGGA

GCAAGTCGTGGCCATTGCATCCCACGACGGTGGCAAACAGGCTCTTGAGACGGTTCAG

AGACTTCTCCCAGTTCTCTGTCAAGCCCACGGGCTGACTCCCGATCAAGTTGTAGCGAT

TGCGTCGCATGACGGAGGGAAACAAGCATTGGAGACTGTCCAACGGCTCCTTCCCGTG

TTGTGTCAAGCCCACGGTTTGACGCCTGCACAAGTGGTCGCCATCGCCTCCAATATTGG

CGGTAAGCAGGCGCTGGAAACAGTACAGCGCCTGCTGCCTGTACTGTGCCAGGATCAT

-continued

GGACTGACCCCAGACCAGGTAGTCGCAATCGCGAACAATAATGGGGGAAAGCAAGCCC
TGGAAACCGTGCAAAGGTTGTTGCCGGTCCTTTGTCAAGACCACGGCCTTACACCGGAG
CAAGTCGTGGCCATTGCAAGCAACATCGGTGGCAAACAGGCTCTTGAGACGGTTCAGA
GACTTCTCCCAGTTCTCTGTCAAGCCCACGGGCTGACTCCCGATCAAGTTGTAGCGATT
GCGTCGCATGACGGAGGGAAACAAGCATTGGAGACTGTCCAACGGCTCCTTCCCGTGT
TGTGTCAAGCCCACGGTCTGACACCCGAACAGGTGGTCGCCATTGCTTCTAACATCGGA
GGACGGCCAGCCTTGGAG

17

(SEQ ID NO: 43)

ATGGTGGACTTGAGGACACTCGGTTATTCGCAACAGCAACAGGAGAAAATCAA
GCCTAAGGTCAGGAGCACCGTCGCGCAACACCACGAGGCGCTTGTGGGGCATGGCTTC
ACTCATGCGCATATTGTCGCGCTTTCACAGCACCCTGCGGCGCTTGGGACGGTGGCTGT
CAAATACCAAGATATGATTGCGGCCCTGCCCGAAGCCACGCACGAGGCAATTGTAGGG
GTCGGTAAACAGTGGTCGGGAGCGCGAGCACTTGAGGCGCTGCTGACTGTGGCGGGTG
AGCTTAGGGGGCCTCCGCTCCAGCTCGACACCGGGCAGCTGCTGAAGATCGCGAAGAG
AGGGGGAGTAACAGCGGTAGAGGCAGTGCACGCCTGGCGCAATGCGCTCACCGGGGCC
CCCTTGAACCTGACCCCAGACCAGGTAGTCGCAATCGCGAACAATAATGGGGGAAAGC
AAGCCCTGGAAACCGTGCAAAGGTTGTTGCCGGTCCTTTGTCAAGACCACGGCCTTACA
CCGGAGCAAGTCGTGGCCATTGCATCCCACGACGGTGGCAAACAGGCTCTTGAGACGG
TTCAGAGACTTCTCCCAGTTCTCTGTCAAGCCCACGGGCTGACTCCCGATCAAGTTGTA
GCGATTGCGTCGCATGACGGAGGGAAACAAGCATTGGAGACTGTCCAACGGCTCCTTC
CCGTGTTGTGTCAAGCCCACGGTTTGACGCCTGCACAAGTGGTCGCCATCGCCAGCCAT
GATGGCGGTAAGCAGGCGCTGGAAACAGTACAGCGCCTGCTGCCTGTACTGTGCCAGG
ATCATGGACTGACCCCAGACCAGGTAGTCGCAATCGCGTCGAACATTGGGGGAAAGCA
AGCCCTGGAAACCGTGCAAAGGTTGTTGCCGGTCCTTTGTCAAGACCACGGCCTTACAC
CGGAGCAAGTCGTGGCCATTGCATCCCACGACGGTGGCAAACAGGCTCTTGAGACGGT
TCAGAGACTTCTCCCAGTTCTCTGTCAAGCCCACGGGCTGACTCCCGATCAAGTTGTAG
CGATTGCGTCGCATGACGGAGGGAAACAAGCATTGGAGACTGTCCAACGGCTCCTTCC
CGTGTTGTGTCAAGCCCACGGTTTGACGCCTGCACAAGTGGTCGCCATCGCCTCGAATG
GCGGCGGTAAGCAGGCGCTGGAAACAGTACAGCGCCTGCTGCCTGTACTGTGCCAGGA
TCATGGACTGACCCCAGACCAGGTAGTCGCAATCGCGTCGAACATTGGGGGAAAGCAA
GCCCTGGAAACCGTGCAAAGGTTGTTGCCGGTCCTTTGTCAAGACCACGGCCTTACACC
GGAGCAAGTCGTGGCCATTGCAAATAATAACGGTGGCAAACAGGCTCTTGAGACGGTT
CAGAGACTTCTCCCAGTTCTCTGTCAAGCCCACGGGCTGACTCCCGATCAAGTTGTAGC
GATTGCGTCGCATGACGGAGGGAAACAAGCATTGGAGACTGTCCAACGGCTCCTTCCC
GTGTTGTGTCAAGCCCACGGTTTGACGCCTGCACAAGTGGTCGCCATCGCCAGCCATGA
TGGCGGTAAGCAGGCGCTGGAAACAGTACAGCGCCTGCTGCCTGTACTGTGCCAGGAT
CATGGACTGACCCCAGACCAGGTAGTCGCAATCGCGTCGAACATTGGGGGAAAGCAAG
CCCTGGAAACCGTGCAAAGGTTGTTGCCGGTCCTTTGTCAAGACCACGGCCTTACACCG
GAGCAAGTCGTGGCCATTGCAAATAATAACGGTGGCAAACAGGCTCTTGAGACGGTTC
AGAGACTTCTCCCAGTTCTCTGTCAAGCCCACGGGCTGACTCCCGATCAAGTTGTAGCG
ATTGCGTCGAACATTGGAGGGAAACAAGCATTGGAGACTGTCCAACGGCTCCTTCCCGT

-continued

GTTGTGTCAAGCCCACGGTTTGACGCCTGCACAAGTGGTCGCCATCGCCAACAACAACG

GCGGTAAGCAGGCGCTGGAAACAGTACAGCGCCTGCTGCCTGTACTGTGCCAGGATCA

TGGACTGACCCCAGACCAGGTAGTCGCAATCGCGAACAATAATGGGGGAAAGCAAGCC

CTGGAAACCGTGCAAAGGTTGTTGCCGGTCCTTTGTCAAGACCACGGCCTTACACCGGA

GCAAGTCGTGGCCATTGCAAATAATAACGGTGGCAAACAGGCTCTTGAGACGGTTCAG

AGACTTCTCCCAGTTCTCTGTCAAGCCCACGGGCTGACTCCCGATCAAGTTGTAGCGAT

TGCGTCGAACATTGGAGGGAAACAAGCATTGGAGACTGTCCAACGGCTCCTTCCCGTGT

TGTGTCAAGCCCACGGTTTGACGCCTGCACAAGTGGTCGCCATCGCCTCGAATGGCGGC

GGTAAGCAGGCGCTGGAAACAGTACAGCGCCTGCTGCCTGTACTGTGCCAGGATCATG

GACTGACCCCAGACCAGGTAGTCGCAATCGCGTCACATGACGGGGGAAAGCAAGCCCT

GGAAACCGTGCAAAGGTTGTTGCCGGTCCTTTGTCAAGACCACGGCCTTACACCGGAGC

AAGTCGTGGCCATTGCAAGCAACATCGGTGGCAAACAGGCTCTTGAGACGGTTCAGAG

ACTTCTCCCAGTTCTCTGTCAAGCCCACGGGCTGACTCCCGATCAAGTTGTAGCGATTG

CGAATAACAATGGAGGGAAACAAGCATTGGAGACTGTCCAACGGCTCCTTCCCGTGTT

GTGTCAAGCCCACGGTCTGACACCCGAACAGGTGGTCGCCATTGCTTCCCACGACGGA

GGACGGCCAGCCTTGGAG

18

(SEQ ID NO: 44)

ATGGTGGACTTGAGGACACTCGGTTATTCGCAACAGCAACAGGAGAAAATCAA

GCCTAAGGTCAGGAGCACCGTCGCGCAACACCACGAGGCGCTTGTGGGGCATGGCTTC

ACTCATGCGCATATTGTCGCGCTTTCACAGCACCCTGCGGCGCTTGGGACGGTGGCTGT

CAAATACCAAGATATGATTGCGGCCCTGCCCGAAGCCACGCACGAGGCAATTGTAGGG

GTCGGTAAACAGTGGTCGGGAGCGCGAGCACTTGAGGCGCTGCTGACTGTGGCGGGTG

AGCTTAGGGGGCCTCCGCTCCAGCTCGACACCGGGCAGCTGCTGAAGATCGCGAAGAG

AGGGGGAGTAACAGCGGTAGAGGCAGTGCACGCCTGGCGCAATGCGCTCACCGGGGCC

CCCTTGAACCTGACCCCAGACCAGGTAGTCGCAATCGCGAACAATAATGGGGGAAAGC

AAGCCCTGGAAACCGTGCAAAGGTTGTTGCCGGTCCTTTGTCAAGACCACGGCCTTACA

CCGGAGCAAGTCGTGGCCATTGCATCCCACGACGGTGGCAAACAGGCTCTTGAGACGG

TTCAGAGACTTCTCCCAGTTCTCTGTCAAGCCCACGGGCTGACTCCCGATCAAGTTGTA

GCGATTGCGTCGCATGACGGAGGGAAACAAGCATTGGAGACTGTCCAACGGCTCCTTC

CCGTGTTGTGTCAAGCCCACGGTTTGACGCCTGCACAAGTGGTCGCCATCGCCAGCCAT

GATGGCGGTAAGCAGGCGCTGGAAACAGTACAGCGCCTGCTGCCTGTACTGTGCCAGG

ATCATGGACTGACCCCAGACCAGGTAGTCGCAATCGCGTCGAACATTGGGGGAAAGCA

AGCCCTGGAAACCGTGCAAAGGTTGTTGCCGGTCCTTTGTCAAGACCACGGCCTTACAC

CGGAGCAAGTCGTGGCCATTGCAAGCAACATCGGTGGCAAACAGGCTCTTGAGACGGT

TCAGAGACTTCTCCCAGTTCTCTGTCAAGCCCACGGGCTGACTCCCGATCAAGTTGTAG

CGATTGCGAATAACAATGGAGGGAAACAAGCATTGGAGACTGTCCAACGGCTCCTTCC

CGTGTTGTGTCAAGCCCACGGTTTGACGCCTGCACAAGTGGTCGCCATCGCCAACAACA

ACGGCGGTAAGCAGGCGCTGGAAACAGTACAGCGCCTGCTGCCTGTACTGTGCCAGGA

TCATGGACTGACCCCAGACCAGGTAGTCGCAATCGCGTCAAACGGAGGGGGAAAGCAA

GCCCTGGAAACCGTGCAAAGGTTGTTGCCGGTCCTTTGTCAAGACCACGGCCTTACACC

-continued

GGAGCAAGTCGTGGCCATTGCATCCCACGACGGTGGCAAACAGGCTCTTGAGACGGTT

CAGAGACTTCTCCCAGTTCTCTGTCAAGCCCACGGGCTGACTCCCGATCAAGTTGTAGC

GATTGCGTCGAACATTGGAGGGAAACAAGCATTGGAGACTGTCCAACGGCTCCTTCCC

GTGTTGTGTCAAGCCCACGGTTTGACGCCTGCACAAGTGGTCGCCATCGCCTCGAATGG

CGGCGGTAAGCAGGCGCTGGAAACAGTACAGCGCCTGCTGCCTGTACTGTGCCAGGAT

CATGGACTGACCCCAGACCAGGTAGTCGCAATCGCGTCACATGACGGGGGAAAGCAAG

CCCTGGAAACCGTGCAAAGGTTGTTGCCGGTCCTTTGTCAAGACCACGGCCTTACACCG

GAGCAAGTCGTGGCCATTGCATCCCACGACGGTGGCAAACAGGCTCTTGAGACGGTTC

AGAGACTTCTCCCAGTTCTCTGTCAAGCCCACGGGCTGACTCCCGATCAAGTTGTAGCG

ATTGCGTCGAACATTGGAGGGAAACAAGCATTGGAGACTGTCCAACGGCTCCTTCCCGT

GTTGTGTCAAGCCCACGGTTTGACGCCTGCACAAGTGGTCGCCATCGCCAACAACAACG

GCGGTAAGCAGGCGCTGGAAACAGTACAGCGCCTGCTGCCTGTACTGTGCCAGGATCA

TGGACTGACCCCAGACCAGGTAGTCGCAATCGCGAACAATAATGGGGGAAAGCAAGCC

CTGGAAACCGTGCAAAGGTTGTTGCCGGTCCTTTGTCAAGACCACGGCCTTACACCGGA

GCAAGTCGTGGCCATTGCAAATAATAACGGTGGCAAACAGGCTCTTGAGACGGTTCAG

AGACTTCTCCCAGTTCTCTGTCAAGCCCACGGGCTGACTCCCGATCAAGTTGTAGCGAT

TGCGTCGCATGACGGAGGGAAACAAGCATTGGAGACTGTCCAACGGCTCCTTCCCGTG

TTGTGTCAAGCCCACGGTTTGACGCCTGCACAAGTGGTCGCCATCGCCAGCCATGATGG

CGGTAAGCAGGCGCTGGAAACAGTACAGCGCCTGCTGCCTGTACTGTGCCAGGATCAT

GGACTGACCCCAGACCAGGTAGTCGCAATCGCGTCGAACATTGGGGGAAAGCAAGCCC

TGGAAACCGTGCAAAGGTTGTTGCCGGTCCTTTGTCAAGACCACGGCCTTACACCGGAG

CAAGTCGTGGCCATTGCAAATAATAACGGTGGCAAACAGGCTCTTGAGACGGTTCAGA

GACTTCTCCCAGTTCTCTGTCAAGCCCACGGGCTGACTCCCGATCAAGTTGTAGCGATT

GCGAATAACAATGGAGGGAAACAAGCATTGGAGACTGTCCAACGGCTCCTTCCCGTGT

TGTGTCAAGCCCACGGTCTGACACCCGAACAGGTGGTCGCCATTGCTTCCCACGACGGA

GGACGGCCAGCCTTGGAG

19

(SEQ ID NO: 45)

ATGGTGGACTTGAGGACACTCGGTTATTCGCAACAGCAACAGGAGAAAATCAA

GCCTAAGGTCAGGAGCACCGTCGCGCAACACCACGAGGCGCTTGTGGGGCATGGCTTC

ACTCATGCGCATATTGTCGCGCTTTCACAGCACCCTGCGGCGCTTGGGACGGTGGCTGT

CAAATACCAAGATATGATTGCGGCCCTGCCCGAAGCCACGCACGAGGCAATTGTAGGG

GTCGGTAAACAGTGGTCGGGAGCGCGAGCACTTGAGGCGCTGCTGACTGTGGCGGGTG

AGCTTAGGGGGCCTCCGCTCCAGCTCGACACCGGGCAGCTGCTGAAGATCGCGAAGAG

AGGGGGAGTAACAGCGGTAGAGGCAGTGCACGCCTGGCGCAATGCGCTCACCGGGGCC

CCCTTGAACCTGACCCCAGACCAGGTAGTCGCAATCGCGAACAATAATGGGGGAAAGC

AAGCCCTGGAAACCGTGCAAAGGTTGTTGCCGGTCCTTTGTCAAGACCACGGCCTTACA

CCGGAGCAAGTCGTGGCCATTGCAAATAATAACGGTGGCAAACAGGCTCTTGAGACGG

TTCAGAGACTTCTCCCAGTTCTCTGTCAAGCCCACGGGCTGACTCCCGATCAAGTTGTA

GCGATTGCGTCGCATGACGGAGGGAAACAAGCATTGGAGACTGTCCAACGGCTCCTTC

CCGTGTTGTGTCAAGCCCACGGTTTGACGCCTGCACAAGTGGTCGCCATCGCCTCCAAT

ATTGGCGGTAAGCAGGCGCTGGAAACAGTACAGCGCCTGCTGCCTGTACTGTGCCAGG

-continued

ATCATGGACTGACCCCAGACCAGGTAGTCGCAATCGCGAACAATAATGGGGGAAAGCA

AGCCCTGGAAACCGTGCAAAGGTTGTTGCCGGTCCTTTGTCAAGACCACGGCCTTACAC

CGGAGCAAGTCGTGGCCATTGCATCCCACGACGGTGGCAAACAGGCTCTTGAGACGGT

TCAGAGACTTCTCCCAGTTCTCTGTCAAGCCCACGGGCTGACTCCCGATCAAGTTGTAG

CGATTGCGTCGAACATTGGAGGGAAACAAGCATTGGAGACTGTCCAACGGCTCCTTCC

CGTGTTGTGTCAAGCCCACGGTTTGACGCCTGCACAAGTGGTCGCCATCGCCAACAACA

ACGGCGGTAAGCAGGCGCTGGAAACAGTACAGCGCCTGCTGCCTGTACTGTGCCAGGA

TCATGGACTGACCCCAGACCAGGTAGTCGCAATCGCGTCACATGACGGGGGAAAGCAA

GCCCTGGAAACCGTGCAAAGGTTGTTGCCGGTCCTTTGTCAAGACCACGGCCTTACACC

GGAGCAAGTCGTGGCCATTGCATCCCACGACGGTGGCAAACAGGCTCTTGAGACGGTT

CAGAGACTTCTCCCAGTTCTCTGTCAAGCCCACGGGCTGACTCCCGATCAAGTTGTAGC

GATTGCGTCGCATGACGGAGGGAAACAAGCATTGGAGACTGTCCAACGGCTCCTTCCC

GTGTTGTGTCAAGCCCACGGTTTGACGCCTGCACAAGTGGTCGCCATCGCCTCGAATGG

CGGCGGTAAGCAGGCGCTGGAAACAGTACAGCGCCTGCTGCCTGTACTGTGCCAGGAT

CATGGACTGACCCCAGACCAGGTAGTCGCAATCGCGTCAAACGGAGGGGGAAAGCAA

GCCCTGGAAACCGTGCAAAGGTTGTTGCCGGTCCTTTGTCAAGACCACGGCCTTACACC

GGAGCAAGTCGTGGCCATTGCATCCCACGACGGTGGCAAACAGGCTCTTGAGACGGTT

CAGAGACTTCTCCCAGTTCTCTGTCAAGCCCACGGGCTGACTCCCGATCAAGTTGTAGC

GATTGCGTCGAACATTGGAGGGAAACAAGCATTGGAGACTGTCCAACGGCTCCTTCCC

GTGTTGTGTCAAGCCCACGGTTTGACGCCTGCACAAGTGGTCGCCATCGCCAACAACAA

CGGCGGTAAGCAGGCGCTGGAAACAGTACAGCGCCTGCTGCCTGTACTGTGCCAGGAT

CATGGACTGACCCCAGACCAGGTAGTCGCAATCGCGTCAAACGGAGGGGGAAAGCAA

GCCCTGGAAACCGTGCAAAGGTTGTTGCCGGTCCTTTGTCAAGACCACGGCCTTACACC

GGAGCAAGTCGTGGCCATTGCAAATAATAACGGTGGCAAACAGGCTCTTGAGACGGTT

CAGAGACTTCTCCCAGTTCTCTGTCAAGCCCACGGGCTGACTCCCGATCAAGTTGTAGC

GATTGCGAATAACAATGGAGGGAAACAAGCATTGGAGACTGTCCAACGGCTCCTTCCC

GTGTTGTGTCAAGCCCACGGTTTGACGCCTGCACAAGTGGTCGCCATCGCCTCCAATAT

TGGCGGTAAGCAGGCGCTGGAAACAGTACAGCGCCTGCTGCCTGTACTGTGCCAGGAT

CATGGACTGACCCCAGACCAGGTAGTCGCAATCGCGTCAAACGGAGGGGGAAAGCAA

GCCCTGGAAACCGTGCAAAGGTTGTTGCCGGTCCTTTGTCAAGACCACGGCCTTACACC

GGAGCAAGTCGTGGCCATTGCAAATAATAACGGTGGCAAACAGGCTCTTGAGACGGTT

CAGAGACTTCTCCCAGTTCTCTGTCAAGCCCACGGGCTGACTCCCGATCAAGTTGTAGC

GATTGCGTCGAACATTGGAGGGAAACAAGCATTGGAGACTGTCCAACGGCTCCTTCCC

GTGTTGTGTCAAGCCCACGGTCTGACACCCGAACAGGTGGTCGCCATTGCTAATAATAA

CGGAGGACGGCCAGCCTTGGAG

20

(SEQ ID NO: 46)

ATGGTGGACTTGAGGACACTCGGTTATTCGCAACAGCAACAGGAGAAAATCAA

GCCTAAGGTCAGGAGCACCGTCGCGCAACACCACGAGGCGCTTGTGGGGCATGGCTTC

ACTCATGCGCATATTGTCGCGCTTTCACAGCACCCTGCGGCGCTTGGGACGGTGGCTGT

CAAATACCAAGATATGATTGCGGCCCTGCCCGAAGCCACGCACGAGGCAATTGTAGGG

-continued

GTCGGTAAACAGTGGTCGGGAGCGCGAGCACTTGAGGCGCTGCTGACTGTGGCGGGTG

AGCTTAGGGGGCCTCCGCTCCAGCTCGACACCGGGCAGCTGCTGAAGATCGCGAAGAG

AGGGGGAGTAACAGCGGTAGAGGCAGTGCACGCCTGGCGCAATGCGCTCACCGGGGCC

CCCTTGAACCTGACCCCAGACCAGGTAGTCGCAATCGCGTCACATGACGGGGGAAAGC

AAGCCCTGGAAACCGTGCAAAGGTTGTTGCCGGTCCTTTGTCAAGACCACGGCCTTACA

CCGGAGCAAGTCGTGGCCATTGCATCCCACGACGGTGGCAAACAGGCTCTTGAGACGG

TTCAGAGACTTCTCCCAGTTCTCTGTCAAGCCCACGGGCTGACTCCCGATCAAGTTGTA

GCGATTGCGTCGCATGACGGAGGGAAACAAGCATTGGAGACTGTCCAACGGCTCCTTC

CCGTGTTGTGTCAAGCCCACGGTTTGACGCCTGCACAAGTGGTCGCCATCGCCTCCAAT

ATTGGCGGTAAGCAGGCGCTGGAAACAGTACAGCGCCTGCTGCCTGTACTGTGCCAGG

ATCATGGACTGACCCCAGACCAGGTAGTCGCAATCGCGAACAATAATGGGGGAAAGCA

AGCCCTGGAAACCGTGCAAAGGTTGTTGCCGGTCCTTTGTCAAGACCACGGCCTTACAC

CGGAGCAAGTCGTGGCCATTGCAAATAATAACGGTGGCAAACAGGCTCTTGAGACGGT

TCAGAGACTTCTCCCAGTTCTCTGTCAAGCCCACGGGCTGACTCCCGATCAAGTTGTAG

CGATTGCGAATAACAATGGAGGGAAACAAGCATTGGAGACTGTCCAACGGCTCCTTCC

CGTGTTGTGTCAAGCCCACGGTTTGACGCCTGCACAAGTGGTCGCCATCGCCTCGAATG

GCGGCGGTAAGCAGGCGCTGGAAACAGTACAGCGCCTGCTGCCTGTACTGTGCCAGGA

TCATGGACTGACCCCAGACCAGGTAGTCGCAATCGCGAACAATAATGGGGGAAAGCAA

GCCCTGGAAACCGTGCAAAGGTTGTTGCCGGTCCTTTGTCAAGACCACGGCCTTACACC

GGAGCAAGTCGTGGCCATTGCAAGCAACATCGGTGGCAAACAGGCTCTTGAGACGGTT

CAGAGACTTCTCCCAGTTCTCTGTCAAGCCCACGGGCTGACTCCCGATCAAGTTGTAGC

GATTGCGTCGCATGACGGAGGGAAACAAGCATTGGAGACTGTCCAACGGCTCCTTCCC

GTGTTGTGTCAAGCCCACGGTTTGACGCCTGCACAAGTGGTCGCCATCGCCTCGAATGG

CGGCGGTAAGCAGGCGCTGGAAACAGTACAGCGCCTGCTGCCTGTACTGTGCCAGGAT

CATGGACTGACCCCAGACCAGGTAGTCGCAATCGCGAACAATAATGGGGGAAAGCAAG

CCCTGGAAACCGTGCAAAGGTTGTTGCCGGTCCTTTGTCAAGACCACGGCCTTACACCG

GAGCAAGTCGTGGCCATTGCAAATAATAACGGTGGCAAACAGGCTCTTGAGACGGTTC

AGAGACTTCTCCCAGTTCTCTGTCAAGCCCACGGGCTGACTCCCGATCAAGTTGTAGCG

ATTGCGAATAACAATGGAGGGAAACAAGCATTGGAGACTGTCCAACGGCTCCTTCCCG

TGTTGTGTCAAGCCCACGGTTTGACGCCTGCACAAGTGGTCGCCATCGCCTCGAATGGC

GGCGGTAAGCAGGCGCTGGAAACAGTACAGCGCCTGCTGCCTGTACTGTGCCAGGATC

ATGGACTGACCCCAGACCAGGTAGTCGCAATCGCGAACAATAATGGGGGAAAGCAAGC

CCTGGAAACCGTGCAAAGGTTGTTGCCGGTCCTTTGTCAAGACCACGGCCTTACACCGG

AGCAAGTCGTGGCCATTGCAAATAATAACGGTGGCAAACAGGCTCTTGAGACGGTTCA

GAGACTTCTCCCAGTTCTCTGTCAAGCCCACGGGCTGACTCCCGATCAAGTTGTAGCGA

TTGCGAATAACAATGGAGGGAAACAAGCATTGGAGACTGTCCAACGGCTCCTTCCCGT

GTTGTGTCAAGCCCACGGTTTGACGCCTGCACAAGTGGTCGCCATCGCCTCGAATGGCG

GCGGTAAGCAGGCGCTGGAAACAGTACAGCGCCTGCTGCCTGTACTGTGCCAGGATCA

TGGACTGACCCCAGACCAGGTAGTCGCAATCGCGAACAATAATGGGGGAAAGCAAGCC

CTGGAAACCGTGCAAAGGTTGTTGCCGGTCCTTTGTCAAGACCACGGCCTTACACCGGA

GCAAGTCGTGGCCATTGCAAGCAACATCGGTGGCAAACAGGCTCTTGAGACGGTTCAG

-continued

AGACTTCTCCCAGTTCTCTGTCAAGCCCACGGGCTGACTCCCGATCAAGTTGTAGCGAT

TGCGTCGAACATTGGAGGGAAACAAGCATTGGAGACTGTCCAACGGCTCCTTCCCGTGT

TGTGTCAAGCCCACGGTCTGACACCCGAACAGGTGGTCGCCATTGCTAATAATAACGG

AGGACGGCCAGCCTTGGAG

21

(SEQ ID NO: 47)

ATGGTGGACTTGAGGACACTCGGTTATTCGCAACAGCAACAGGAGAAAATCAA

GCCTAAGGTCAGGAGCACCGTCGCGCAACACCACGAGGCGCTTGTGGGGCATGGCTTC

ACTCATGCGCATATTGTCGCGCTTTCACAGCACCCTGCGGCGCTTGGGACGGTGGCTGT

CAAATACCAAGATATGATTGCGGCCCTGCCCGAAGCCACGCACGAGGCAATTGTAGGG

GTCGGTAAACAGTGGTCGGGAGCGCGAGCACTTGAGGCGCTGCTGACTGTGGCGGGTG

AGCTTAGGGGGCCTCCGCTCCAGCTCGACACCGGGCAGCTGCTGAAGATCGCGAAGAG

AGGGGGAGTAACAGCGGTAGAGGCAGTGCACGCCTGGCGCAATGCGCTCACCGGGGCC

CCCTTGAACCTGACCCCAGACCAGGTAGTCGCAATCGCGAACAATAATGGGGGAAAGC

AAGCCCTGGAAACCGTGCAAAGGTTGTTGCCGGTCCTTTGTCAAGACCACGGCCTTACA

CCGGAGCAAGTCGTGGCCATTGCAAATAATAACGGTGGCAAACAGGCTCTTGAGACGG

TTCAGAGACTTCTCCCAGTTCTCTGTCAAGCCCACGGGCTGACTCCCGATCAAGTTGTA

GCGATTGCGAATAACAATGGAGGGAAACAAGCATTGGAGACTGTCCAACGGCTCCTTC

CCGTGTTGTGTCAAGCCCACGGTTTGACGCCTGCACAAGTGGTCGCCATCGCCTCGAAT

GGCGGCGGTAAGCAGGCGCTGGAAACAGTACAGCGCCTGCTGCCTGTACTGTGCCAGG

ATCATGGACTGACCCCAGACCAGGTAGTCGCAATCGCGAACAATAATGGGGGAAAGCA

AGCCCTGGAAACCGTGCAAAGGTTGTTGCCGGTCCTTTGTCAAGACCACGGCCTTACAC

CGGAGCAAGTCGTGGCCATTGCAAATAATAACGGTGGCAAACAGGCTCTTGAGACGGT

TCAGAGACTTCTCCCAGTTCTCTGTCAAGCCCACGGGCTGACTCCCGATCAAGTTGTAG

CGATTGCGAATAACAATGGAGGGAAACAAGCATTGGAGACTGTCCAACGGCTCCTTCC

CGTGTTGTGTCAAGCCCACGGTTTGACGCCTGCACAAGTGGTCGCCATCGCCTCGAATG

GCGGCGGTAAGCAGGCGCTGGAAACAGTACAGCGCCTGCTGCCTGTACTGTGCCAGGA

TCATGGACTGACCCCAGACCAGGTAGTCGCAATCGCGAACAATAATGGGGGAAAGCAA

GCCCTGGAAACCGTGCAAAGGTTGTTGCCGGTCCTTTGTCAAGACCACGGCCTTACACC

GGAGCAAGTCGTGGCCATTGCAAGCAACATCGGTGGCAAACAGGCTCTTGAGACGGTT

CAGAGACTTCTCCCAGTTCTCTGTCAAGCCCACGGGCTGACTCCCGATCAAGTTGTAGC

GATTGCGTCGAACATTGGAGGGAAACAAGCATTGGAGACTGTCCAACGGCTCCTTCCC

GTGTTGTGTCAAGCCCACGGTTTGACGCCTGCACAAGTGGTCGCCATCGCCAACAACAA

CGGCGGTAAGCAGGCGCTGGAAACAGTACAGCGCCTGCTGCCTGTACTGTGCCAGGAT

CATGGACTGACCCCAGACCAGGTAGTCGCAATCGCGAACAATAATGGGGGAAAGCAAG

CCCTGGAAACCGTGCAAAGGTTGTTGCCGGTCCTTTGTCAAGACCACGGCCTTACACCG

GAGCAAGTCGTGGCCATTGCAAGCAACATCGGTGGCAAACAGGCTCTTGAGACGGTTC

AGAGACTTCTCCCAGTTCTCTGTCAAGCCCACGGGCTGACTCCCGATCAAGTTGTAGCG

ATTGCGTCGAACATTGGAGGGAAACAAGCATTGGAGACTGTCCAACGGCTCCTTCCCGT

GTTGTGTCAAGCCCACGGTTTGACGCCTGCACAAGTGGTCGCCATCGCCTCGAATGGCG

GCGGTAAGCAGGCGCTGGAAACAGTACAGCGCCTGCTGCCTGTACTGTGCCAGGATCA

-continued

TGGACTGACCCCAGACCAGGTAGTCGCAATCGCGTCAAACGGAGGGGGAAAGCAAGCC

CTGGAAACCGTGCAAAGGTTGTTGCCGGTCCTTTGTCAAGACCACGGCCTTACACCGGA

GCAAGTCGTGGCCATTGCAAATAATAACGGTGGCAAACAGGCTCTTGAGACGGTTCAG

AGACTTCTCCCAGTTCTCTGTCAAGCCCACGGGCTGACTCCCGATCAAGTTGTAGCGAT

TGCGTCGAACATTGGAGGGAAACAAGCATTGGAGACTGTCCAACGGCTCCTTCCCGTGT

TGTGTCAAGCCCACGGTTTGACGCCTGCACAAGTGGTCGCCATCGCCAACAACAACGG

CGGTAAGCAGGCGCTGGAAACAGTACAGCGCCTGCTGCCTGTACTGTGCCAGGATCAT

GGACTGACCCCAGACCAGGTAGTCGCAATCGCGTCACATGACGGGGGAAAGCAAGCCC

TGGAAACCGTGCAAAGGTTGTTGCCGGTCCTTTGTCAAGACCACGGCCTTACACCGGAG

CAAGTCGTGGCCATTGCAAGCAACATCGGTGGCAAACAGGCTCTTGAGACGGTTCAGA

GACTTCTCCCAGTTCTCTGTCAAGCCCACGGGCTGACTCCCGATCAAGTTGTAGCGATT

GCGTCGAACATTGGAGGGAAACAAGCATTGGAGACTGTCCAACGGCTCCTTCCCGTGTT

GTGTCAAGCCCACGGTCTGACACCCGAACAGGTGGTCGCCATTGCTTCCCACGACGGA

GGACGGCCAGCCTTGGAG

Gly4-Ser linker (SEQ ID NO: 48)

GGTGGTGGTGGTTCTGGGGS

VP16 Activation Domain (SEQ ID NO: 49)

GACGCTTTGGACGACTTCGACTTGGACATGTTGDALDDFDLDML

VP64 Activation Domain (SEQ ID NO: 50)

GACGCTTTGGACGACTTCGACTTGGACATGTTGGGTTCTGACGCTTTGGACGACTTCGA

CTTGGACATGTTGGGTTCTGACGCTTTGGACGACTTCGACTTGGACATGTTGGGTTCTGA

CGCTTTGGACGACTTCGACTTGGACATGTTGDALDDFDLDMLGSDALDDFDLDMLGSDA

LDDFDLDMLGSDALDDFDLDML

Nuclear localization Sequence (SEQ ID NO: 51)

CCCAAAAGAAGAGGAAGGTG

Start and NLS (SEQ ID NO: 52)

ATGGCCCCCAAGAAGAAGAGGAAGGTGGGCATTCACCGCGGGGTACCTATG

Example full sequence NLS-TAL-G4S-VP64

(SEQ ID NO: 53)

ATGGCCCCCAAGAAGAAGAGGAAGGTGGGCATTCACCGCGGGGTACCTATGGTGGACT

TGAGGACACTCGGTTATTCGCAACAGCAACAGGAGAAAATCAAGCCTAAGGTCAGGAG

CACCGTCGCGCAACACCACGAGGCGCTTGTGGGGCATGGCTTCACTCATGCGCATATTG

TCGCGCTTTCACAGCACCCTGCGGCGCTTGGGACGGTGGCTGTCAAATACCAAGATATG

ATTGCGGCCCTGCCCGAAGCCACGCACGAGGCAATTGTAGGGGTCGGTAAACAGTGGT

CGGGAGCGCGAGCACTTGAGGCGCTGCTGACTGTGGCGGGTGAGCTTAGGGGGCCTCC

GCTCCAGCTCGACACCGGGCAGCTGCTGAAGATCGCGAAGAGAGGGGGAGTAACAGC

GGTAGAGGCAGTGCACGCCTGGCGCAATGCGCTCACCGGGGCCCCCTTGAACCTGACC

CCAGACCAGGTAGTCGCAATCGCGTCACATGACGGGGGAAAGCAAGCCCTGGAAACCG

TGCAAAGGTTGTTGCCGGTCCTTTGTCAAGACCACGGCCTTACACCGGAGCAAGTCGTG

GCCATTGCATCCCACGACGGTGGCAAACAGGCTCTTGAGACGGTTCAGAGACTTCTCCC

AGTTCTCTGTCAAGCCCACGGGCTGACTCCCGATCAAGTTGTAGCGATTGCGTCGCATG

ACGGAGGGAAACAAGCATTGGAGACTGTCCAACGGCTCCTTCCCGTGTTGTGTCAAGC

-continued

CCACGGTTTGACGCCTGCACAAGTGGTCGCCATCGCCAACAACAACGGCGGTAAGCAG

GCGCTGGAAACAGTACAGCGCCTGCTGCCTGTACTGTGCCAGGATCATGGACTGACCCC

AGACCAGGTAGTCGCAATCGCGTCACATGACGGGGGAAAGCAAGCCCTGGAAACCGTG

CAAAGGTTGTTGCCGGTCCTTTGTCAAGACCACGGCCTTACACCGGAGCAAGTCGTGGC

CATTGCATCCCACGACGGTGGCAAACAGGCTCTTGAGACGGTTCAGAGACTTCTCCCAG

TTCTCTGTCAAGCCCACGGGCTGACTCCCGATCAAGTTGTAGCGATTGCGTCGAACATT

GGAGGGAAACAAGCATTGGAGACTGTCCAACGGCTCCTTCCCGTGTTGTGTCAAGCCC

ACGGTTTGACGCCTGCACAAGTGGTCGCCATCGCCAACAACAACGGCGGTAAGCAGGC

GCTGGAAACAGTACAGCGCCTGCTGCCTGTACTGTGCCAGGATCATGGACTGACCCCA

GACCAGGTAGTCGCAATCGCGTCAAACGGAGGGGGAAAGCAAGCCCTGGAAACCGTG

CAAAGGTTGTTGCCGGTCCTTTGTCAAGACCACGGCCTTACACCGGAGCAAGTCGTGGC

CATTGCATCCCACGACGGTGGCAAACAGGCTCTTGAGACGGTTCAGAGACTTCTCCCAG

TTCTCTGTCAAGCCCACGGGCTGACTCCCGATCAAGTTGTAGCGATTGCGTCGCATGAC

GGAGGGAAACAAGCATTGGAGACTGTCCAACGGCTCCTTCCCGTGTTGTGTCAAGCCC

ACGGTTTGACGCCTGCACAAGTGGTCGCCATCGCCAACAACAACGGCGGTAAGCAGGC

GCTGGAAACAGTACAGCGCCTGCTGCCTGTACTGTGCCAGGATCATGGACTGACCCCA

GACCAGGTAGTCGCAATCGCGTCACATGACGGGGGAAAGCAAGCCCTGGAAACCGTGC

AAAGGTTGTTGCCGGTCCTTTGTCAAGACCACGGCCTTACACCGGAGCAAGTCGTGGCC

ATTGCATCCCACGACGGTGGCAAACAGGCTCTTGAGACGGTTCAGAGACTTCTCCCAGT

TCTCTGTCAAGCCCACGGGCTGACTCCCGATCAAGTTGTAGCGATTGCGTCGCATGACG

GAGGGAAACAAGCATTGGAGACTGTCCAACGGCTCCTTCCCGTGTTGTGTCAAGCCCAC

GGTTTGACGCCTGCACAAGTGGTCGCCATCGCCTCCAATATTGGCGGTAAGCAGGCGCT

GGAAACAGTACAGCGCCTGCTGCCTGTACTGTGCCAGGATCATGGACTGACCCCAGAC

CAGGTAGTCGCAATCGCGTCACATGACGGGGGAAAGCAAGCCCTGGAAACCGTGCAAA

GGTTGTTGCCGGTCCTTTGTCAAGACCACGGCCTGACACCCGAACAGGTGGTCGCCATT

GCTTCTAATGGGGGAGGACGGCCAGCCTTGGAGGGTGGTGGTGGTTCTGACGCTTTGGA

CGACTTCGACTTGGACATGTTGGGTTCTGACGCTTTGGACGACTTCGACTTGGACATGTT

GGGTTCTGACGCTTTGGACGACTTCGACTTGGACATGTTGGGTTCTGACGCTTTGGACG

ACTTCGACTTGGACATGTTG

Example full polypeptide NLS-TAL-G4S-VP64 AA (SEQ ID NO: 54)

MAPKKKRKVGIHRGVPMVDLRTLGYSQQQQEKIKPKVRSTVAQHHEALVGHGFTHAHIV

ALSQHPAALGTVAVKYQDMIAALPEATHEAIVGVGKQWSGARALEALLTVAGELRGPPLQ

LDTGQLLKIAKRGGVTAVEAVHAWRNALTGAPLNLTPDQVVAIASHDGGKQALETVQRLL

PVLCQDHGLTPEQVVAIASHDGGKQALETVQRLLPVLCQAHGLTPDQVVAIASHDGGKQA

LETVQRLLPVLCQAHGLTPAQVVAIANNNGGKQALETVQRLLPVLCQDHGLTPDQVVAIA

SHDGGKQALETVQRLLPVLCQDHGLTPEQVVAIASHDGGKQALETVQRLLPVLCQAHGLT

PDQVVAIASNIGGKQALETVQRLLPVLCQAHGLTPAQVVAIANNNGGKQALETVQRLLPVL

CQDHGLTPDQVVAIASNGGGKQALETVQRLLPVLCQDHGLTPEQVVAIASHDGGKQALET

VQRLLPVLCQAHGLTPDQVVAIASHDGGKQALETVQRLLPVLCQAHGLTPAQVVAIANNN

GGKQALETVQRLLPVLCQDHGLTPDQVVAIASHDGGKQALETVQRLLPVLCQDHGLTPEQ

-continued

VVAIASHDGGKQALETVQRLLPVLCQAHGLTPDQVVAIASHDGGKQALETVQRLLPVLCQ

AHGLTPAQVVAIASNIGGKQALETVQRLLPVLCQDHGLTPDQVVAIASHDGGKQALETVQ

RLLPVLCQDHGLTPEQVVAIASNGGGRPALEGGGGSDALDDFDLDMLGSDALDDFDLDML

GSDALDDFDLDMLGSDALDDFDLDML

Example full sequence NLS-TAL-VP64

(SEQ ID NO: 55)

ATGGCCCCCAAGAAGAAGAGGAAGGTGGGCATTCACCGCGGGGTACCTATGGTGGACT

TGAGGACACTCGGTTATTCGCAACAGCAACAGGAGAAAATCAAGCCTAAGGTCAGGAG

CACCGTCGCGCAACACCACGAGGCGCTTGTGGGGCATGGCTTCACTCATGCGCATATTG

TCGCGCTTTCACAGCACCCTGCGGCGCTTGGGACGGTGGCTGTCAAATACCAAGATATG

ATTGCGGCCCTGCCCGAAGCCACGCACGAGGCAATTGTAGGGGTCGGTAAACAGTGGT

CGGGAGCGCGAGCACTTGAGGCGCTGCTGACTGTGGCGGGTGAGCTTAGGGGGCCTCC

GCTCCAGCTCGACACCGGGCAGCTGCTGAAGATCGCGAAGAGAGGGGGAGTAACAGC

GGTAGAGGCAGTGCACGCCTGGCGCAATGCGCTCACCGGGGCCCCCTTGAACCTGACC

CCAGACCAGGTAGTCGCAATCGCGTCACATGACGGGGGAAAGCAAGCCCTGGAAACCG

TGCAAAGGTTGTTGCCGGTCCTTTGTCAAGACCACGGCCTTACACCGGAGCAAGTCGTG

GCCATTGCATCCCACGACGGTGGCAAACAGGCTCTTGAGACGGTTCAGAGACTTCTCCC

AGTTCTCTGTCAAGCCCACGGGCTGACTCCCGATCAAGTTGTAGCGATTGCGTCGCATG

ACGGAGGGAAACAAGCATTGGAGACTGTCCAACGGCTCCTTCCCGTGTTGTGTCAAGC

CCACGGTTTGACGCCTGCACAAGTGGTCGCCATCGCCAACAACAACGGCGGTAAGCAG

GCGCTGGAAACAGTACAGCGCCTGCTGCCTGTACTGTGCCAGGATCATGGACTGACCCC

AGACCAGGTAGTCGCAATCGCGTCACATGACGGGGGAAAGCAAGCCCTGGAAACCGTG

CAAAGGTTGTTGCCGGTCCTTTGTCAAGACCACGGCCTTACACCGGAGCAAGTCGTGGC

CATTGCATCCCACGACGGTGGCAAACAGGCTCTTGAGACGGTTCAGAGACTTCTCCCAG

TTCTCTGTCAAGCCCACGGGCTGACTCCCGATCAAGTTGTAGCGATTGCGTCGAACATT

GGAGGGAAACAAGCATTGGAGACTGTCCAACGGCTCCTTCCCGTGTTGTGTCAAGCCC

ACGGTTTGACGCCTGCACAAGTGGTCGCCATCGCCAACAACAACGGCGGTAAGCAGGC

GCTGGAAACAGTACAGCGCCTGCTGCCTGTACTGTGCCAGGATCATGGACTGACCCCA

GACCAGGTAGTCGCAATCGCGTCAAACGGAGGGGGAAAGCAAGCCCTGGAAACCGTG

CAAAGGTTGTTGCCGGTCCTTTGTCAAGACCACGGCCTTACACCGGAGCAAGTCGTGGC

CATTGCATCCCACGACGGTGGCAAACAGGCTCTTGAGACGGTTCAGAGACTTCTCCCAG

TTCTCTGTCAAGCCCACGGGCTGACTCCCGATCAAGTTGTAGCGATTGCGTCGCATGAC

GGAGGGAAACAAGCATTGGAGACTGTCCAACGGCTCCTTCCCGTGTTGTGTCAAGCCC

ACGGTTTGACGCCTGCACAAGTGGTCGCCATCGCCAACAACAACGGCGGTAAGCAGGC

GCTGGAAACAGTACAGCGCCTGCTGCCTGTACTGTGCCAGGATCATGGACTGACCCCA

GACCAGGTAGTCGCAATCGCGTCACATGACGGGGGAAAGCAAGCCCTGGAAACCGTGC

AAAGGTTGTTGCCGGTCCTTTGTCAAGACCACGGCCTTACACCGGAGCAAGTCGTGGCC

ATTGCATCCCACGACGGTGGCAAACAGGCTCTTGAGACGGTTCAGAGACTTCTCCCAGT

TCTCTGTCAAGCCCACGGGCTGACTCCCGATCAAGTTGTAGCGATTGCGTCGCATGACG

GAGGGAAACAAGCATTGGAGACTGTCCAACGGCTCCTTCCCGTGTTGTGTCAAGCCCAC

GGTTTGACGCCTGCACAAGTGGTCGCCATCGCCTCCAATATTGGCGGTAAGCAGGCGCT

GGAAACAGTACAGCGCCTGCTGCCTGTACTGTGCCAGGATCATGGACTGACCCCAGAC

-continued

CAGGTAGTCGCAATCGCGTCACATGACGGGGGAAAGCAAGCCCTGGAAACCGTGCAAA
GGTTGTTGCCGGTCCTTTGTCAAGACCACGGCCTGACACCCGAACAGGTGGTCGCCATT
GCTTCTAATGGGGGAGGACGGCCAGCCTTGGAGGACGCTTTGGACGACTTCGACTTGG
ACATGTTGGGTTCTGACGCTTTGGACGACTTCGACTTGGACATGTTGGGTTCTGACGCTT
TGGACGACTTCGACTTGGACATGTTGGGTTCTGACGCTTTGGACGACTTCGACTTGGAC
ATGTTG

Example full polypeptide NLS-TAL-VP64 AA (SEQ ID NO: 56)

MAPKKKRKVGIHRGVPMVDLRTLGYSQQQQEKIKPKVRSTVAQHHEALVGHGFTHAHIV
ALSQHPAALGTVAVKYQDMIAALPEATHEAIVGVGKQWSGARALEALLTVAGELRGPPLQ
LDTGQLLKIAKRGGVTAVEAVHAWRNALTGAPLNLTPDQVVAIASHDGGKQALETVQRLL
PVLCQDHGLTPEQVVAIASHDGGKQALETVQRLLPVLCQAHGLTPDQVVAIASHDGGKQA
LETVQRLLPVLCQAHGLTPAQVVAIANNNGGKQALETVQRLLPVLCQDHGLTPDQVVAIA
SHDGGKQALETVQRLLPVLCQDHGLTPEQVVAIASHDGGKQALETVQRLLPVLCQAHGLT
PDQVVAIASNIGGKQALETVQRLLPVLCQAHGLTPAQVVAIANNNGGKQALETVQRLLPVL
CQDHGLTPDQVVAIASNGGGKQALETVQRLLPVLCQDHGLTPEQVVAIASHDGGKQALET
VQRLLPVLCQAHGLTPDQVVAIASHDGGKQALETVQRLLPVLCQAHGLTPAQVVAIANNN
GGKQALETVQRLLPVLCQDHGLTPDQVVAIASHDGGKQALETVQRLLPVLCQDHGLTPEQ
VVAIASHDGGKQALETVQRLLPVLCQAHGLTPDQVVAIASHDGGKQALETVQRLLPVLCQ
AHGLTPAQVVAIASNIGGKQALETVQRLLPVLCQDHGLTPDQVVAIASHDGGKQALETVQ
RLLPVLCQDHGLTPEQVVAIASNPALEGGGGSDALDDFDLDMLGSDALDDFDLDMLGSDA
LDDFDLDMLGSDALDDFDLDML

Example CMV-hChAT (SEQ ID NO: 57)

| | | |
|---|---|---|
| 1 | GCCGCGATCG CCATGGGGCT GAGGACAGCG AAGAAGAGGG GGCTTGGGGG | 50 |
| 51 | AGGGGGGAAA TGGAAGAGAG AGGAGGGAGG AGGTACAAGA GGAAGGAGAG | 100 |
| 101 | AAGTGCGGCC AGCTTGCTTT CTCCAGTCGG GTGGCCGCGG GGACCCGGGC | 150 |
| 151 | GACGTCGGAG GCCCTGCCGG GAACCCAGGC TGCAGCCCCC ACCCCCGCGC | 200 |
| 201 | TGCGACACGC CCCCCACCCC TTCCGGCTCA CACCCCCGCC CACACTCCTG | 250 |
| 251 | AGTGGTGCGG TGCAGCGTCG GCCGAGGCAG CAGAGCCGAG GAGAGCAGGT | 300 |
| 301 | CCACACCTCT GCATCCCTGC ACCAGGACTC ACCAAGACGC CCATCCTGGA | 350 |
| 351 | AAAGGTCCCC CGTAAGATGG CAGCAAAAAC TCCCAGCAGT GAGGAGTCTG | 400 |
| 401 | GGCTGCCCAA ACTGCCCGTG CCCCCGCTGC AGCAGACCCT GGCCACGTAC | 450 |
| 451 | CTGCAGTGCA TGCGACACTT GGTGTCTGAG GAGCAGTTCA GGAAGAGCCA | 500 |
| 501 | GGCCATTGTG CAGCAGTTTG GGGCCCCTGG TGGCCTCGGC GAGACCCTGC | 550 |
| 551 | AGCAGAAACT CCTGGAGCGG CAGGAGAAGA CAGCCAACTG GGTGTCTGAG | 600 |
| 601 | TACTGGCTGA ATGACATGTA TCTCAACAAC CGCCTGGCCC TGCCTGTCAA | 650 |
| 651 | CTCCAGCCCT GCCGTGATCT TTGCTCGGCA GCACTTCCCT GGCACCGATG | 700 |
| 701 | ACCAGCTGAG GTTTGCAGCC AGCCTCATCT CTGGTGTACT CAGCTACAAG | 750 |
| 751 | GCCCTGCTGG ACAGCCACTC CATTCCCACT GACTGTGCCA AAGGCCAGCT | 800 |
| 801 | GTCAGGGCAG CCCCTTTGCA TGAAGCAATA CTATGGGCTC TTCTCCTCCT | 850 |
| 851 | ACCGGCTCCC CGGCCATACC CAGGACACGC TGGTGGCTCA GAACAGCAGC | 900 |

-continued

901 ATCATGCCGG AGCCTGAGCA CGTCATCGTA GCCTGCTGCA ATCAGTTCTT 950

951 TGTCTTGGAT GTTGTCATTA ATTTCCGCCG TCTCAGTGAG GGGGATCTGT 1000

1001 TCACTCAGTT GAGAAAGATA GTCAAAATGG CTTCCAACGA GGACGAGCGT 1050

1051 TTGCCTCCAA TTGGCCTGCT GACGTCTGAC GGGAGGAGCG AGTGGGCCGA 1100

1101 GGCCAGGACG GTCCTCGTGA AAGACTCCAC CAACCGGGAC TCGCTGGACA 1150

1151 TGATTGAGCG CTGCATCTGC CTTGTATGCC TGGACGCGCC AGGAGGCGTG 1200

1201 GAGCTCAGCG ACACCCACAG GGCACTCCAG CTCCTTCACG GCGGAGGCTA 1250

1251 CAGCAAGAAC GGGGCCAATC GCTGGTACGA CAAGTCCCTG CAGTTTGTGG 1300

1301 TGGGCCGAGA CGGCACCTGC GGTGTGGTGT GCGAACACTC CCCATTCGAT 1350

1351 GGCATCGTCC TGGTGCAGTG CACTGAGCAT CTGCTCAAGC ACATGACGCA 1400

1401 GAGCAGCAGG AAGCTGATCC GAGCAGACTC CGTCAGCGAG CTCCCCGCCC 1450

1451 CCCGGAGGCT GCGGTGGAAA TGCTCCCCGG AAATTCAAGG CCACTTAGCC 1500

1501 TCCTCGGCAG AAAAACTTCA ACGAATAGTA AAGAACCTTG ACTTCATTGT 1550

1551 CTATAAGTTT GACAACTATG GGAAAACATT CATTAAGAAG CAGAAATGCA 1600

1601 GCCCTGATGC CTTCATCCAG GTGGCCCTCC AGCTGGCCTT CTACAGGCTC 1650

1651 CATCGAAGAC TGGTGCCCAC CTACGAGAGC GCGTCCATCC GCCGATTCCA 1700

1701 GGAGGGACGC GTGGACAACA TCAGATCGGC CACTCCAGAG GCACTGGCTT 1750

1751 TTGTGAGAGC CGTGACTGAC CACAAGGCTG CTGTGCCAGC TTCTGAGAAG 1800

1801 CTTCTGCTCCTGAAGGATGC CATCCGTGCC CAGACTGCAT ACACAGTCAT 1850

1851 GGCCATAACA GGGATGGCCA TTGACAACCA CCTGCTGGCA CTGCGGGAGC 1900

1901 TGGCCCGGGC CATGTGCAAG GAGCTGCCCG AGATGTTCAT GGATGAAACC 1950

1951 TACCTGATGA GCAACCGGTT TGTCCTCTCCACTAGCCAGG TGCCCACAAC 2000

2001 CACGGAGATG TTCTGCTGCTATGGTCCTGT GGTCCCAAAT GGGTATGGTG 2050

2051 CCTGCTACAA CCCCCAGCCA GAGACCATCC TTTTCTGCAT CTCTAGCTTT 2100

2101 CACAGCTGCA AAGAGACTTC TTCTAGCAAG TTTGCAAAAG CTGTGGAAGA 2150

2151 AAGCCTCATT GACATGAGAG ACCTCTGCAG TCTGCTGCCG CCTACTGAGA 2200

2201 GCAAGCCATT GGCAACAAAG GAAAAAGCCA CGAGGCCCAG CCAGGGACAC 2250

2251 CAACCTAGCG GACCGACGCG TACGCGGCCG CTCTAA dCas9-VP64 fusion protein (SEQ ID NO: 58)

MDKKYSIGLAIGTNSVGWAVITDEYKVPSKKFKVLGNTDRHSIKKNLIGALLFDSGETAEATRLKRTARRRYTRRKNRICY

LQEIFSNEMAKVDDSFFHRLEESFLVEEDKKHERHPIFGNIVDEVAYHEKYPTIYHLRKKLVDSTDKADLRLIYLALAHMIK

FRGHFLIEGDLNPDNSDVDKLFIQLVQTYNQLFEENPINASGVDAKAILSARLSKSRRLENLIAQLPGEKKNGLFGNLIALS

LGLTPNFKSNFDLAEDAKLQLSKDTYDDDLDNLLAQIGDQYADLFLAAKNLSDAILLSDILRVNTEITKAPLSASMIKRYDE

HHQDLTLLKALVRQQLPEKYKEIFFDQSKNGYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGNSRFAWMTRKSEETITPWNFEEVVDKGASAQ

SFIERMTNFDKNLPNEKVLPKHSLLYEYFTVYNELTKVKYVTEGMRKPAFLSGEQKKAIVDLLFKTNRKVTVKQLKEDYFK

KIECFDSVEISGVEDRFNASLGTYHDLLKIIKDKDFLDNEENEDILEDIVLTLTLFEDREMIEERLKTYAHLFDDKVMKQLKR

RRYTGWGRLSRKLINGIRDKQSGKTILDFLKSDGFANRNFMQLIHDDSLTFKEDIQKAQVSGQGDSLHEHIANLAGSPAI

KKGILQTVKVVDELVKVMGRHKPENIVIEMARENQTTQKGQKNSRERMKRIEEGIKELGSQILKEHPVENTQLQNEKLY

LYYLQNGRDMYVDQELDINRLSDYDVDAIVPQSFLKDDSIDNKVLTRSDKNRGKSDNVPSEEVVKKMKNYWRQLLNA

KLITQRKFDNLTKAERGGLSELDKAGFIKRQLVETRQITKHVAQILDSRMNTKYDENDKLIREVKVITLKSKLVSDFRKDFQ

-continued

FYKVREINNYHHAHDAYLNAVVGTALIKKYPKLESEFVYGDYKVYDVRKMIAKSEQEIGKATAKYFFYSNIMNFFKTEITL

ANGEIRKRPLIETNGETGEIVWDKGRDFATVRKVLSMPQVNIVKKTEVQTGGFSKESILPKRNSDKLIARKKDWDPKKY

GGFDSPTVAYSVLVVAKVEKGKSKKLKSVKELLGITIMERSSFEKNPIDFLEAKGYKEVKKDLIIKLPKYSLFELENGRKRML

ASAGELQKGNELALPSKYVNFLYLASHYEKLKGSPEDNEQKQLFVEQHKHYLDEIIEQISEFSKRVILADANLDKVLSAYNK

HRDKPIREQAENIIHLFTLTNLGAPAAFKYFDTTIDRKRYTSTKEVLDATLIHQSITGLYETRIDLSQLGGDGSPKKKRKVSS

DYKDHDGDYKDHDIDYKDDDDKAAGGGGSGRADALDDFDLDMLGSDALDDFDLDMLGSDALDDFDLDMLGSDALDDFDLDML

Additional target sites that can be used:

(SEQ ID NOS: 59-133 top to bottom, respectively)

TCTTTGCACTGCATCGCGGCACT

TCTTTGCACTGCATCGCGGCACTT

TCTTTGCACTGCATCGCGGCACTTCCT

TGCACTGCATCGCGGCACTTCCT

TGTTCTTCACAAGACCCACAAGTGAAAAAT

TCTTCACAAGACCCACAAGTGAAAAAT

TGCCCACATTGGGACTCTTTTCCTCCCT

TCCCCATCCCCTCATCCTACAGCCAT

TCCCCATCCCCTCATCCTACAGCCATCT

TGGAGACATTCCAATGCCCTCCGGGTCCT

TGCTGCTTTACTTTTGAGGCCAGAAAAAT

TGGCCAGGCTGCCGCCTCTCACCCT

TCCATGTGCCATCCAGGGTCAACGCCGCT

TCCATGTGCCATCCAGGGTCAACGCCGCTCT

TGCTCTTACTGTGTGCCCGGCCCCCT

TGCTCTTACTGTGTGCCCGGCCCCCTT

TCCAACCTCAGCCGCCCTGGAGCCT

TCCAACCTCAGCCGCCCTGGAGCCTCT

TCCAACCTCAGCCGCCCTGGAGCCTCTCT

TCCGGGTCCTCCACCAACCCAGACAGAGCCT

TGCCCGGCCCCCTTAGCAGTAGGTACTAT

TGCCCGGCCCCCTTAGCAGTAGGTACTATT

TGCCATCCAGGGTCAACGCCGCTCT

TCCTCCACCAACCCAGACAGAGCCT

TCCTCCACCAACCCAGACAGAGCCTGGAGT

TCCACCAACCCAGACAGAGCCTGGAGT

TGGAGCCTCTCTCCCGCCAGTCCGCCCACT

TCTACACACGATAACAACATAGCAAGT

TCTACACACGATAACAACATAGCAAGTCCT

TCTACACACGATAACAACATAGCAAGTCCTT

TCCCTGCAGGTACTCTAATGAGTACGT

TCTGCGTCTAATGCTGCTTTACT

TGTGCCCACATTGGGACTCTTTTCCT

-continued

TGTGCCCACATTGGGACTCTTTTCCTCCCT

TACTGCTCTTACTGTGTGCCCGGCCCCCT

TACTGCTCTTACTGTGTGCCCGGCCCCCTT

TGCTTTACTTTTGAGGCCAGAAAAAT

TCCGCCCACTGGAACACGGGTTCCAT

TAGCAAGTCCTTATACTGCTCTTACTGT

TAGCAAGTCCTTATACTGCTCTTACTGTGT

TCTCAACAACACAATCCCCACCTCCAACCT

TCTTTTCCTCCCTCAGACAGAGGGCACT

TCTTTTCCTCCCTCAGACAGAGGGCACTT

TGCCGCCTCTCACCCTGACACATT

TGCCGCCTCTCACCCTGACACATTGGT

TATACTGCTCTTACTGTGTGCCCGGCCCCCT

TCCTCCCTCAGACAGAGGGCACT

TCCTCCCTCAGACAGAGGGCACTT

TCCTCCCTCAGACAGAGGGCACTTCAGT

TACACACGATAACAACATAGCAAGT

TACACACGATAACAACATAGCAAGTCCT

TACACACGATAACAACATAGCAAGTCCTT

TACACACGATAACAACATAGCAAGTCCTTAT

TCCCTCAGACAGAGGGCACTTCAGT

TCCCTCAGACAGAGGGCACTTCAGTCACT

TCTCACCCTGACACATTGGTCCCCAT

TCTCACCCTGACACATTGGTCCCCATCCCCT

TCTTACTGTGTGCCCGGCCCCCTTAGCAGT

TCTCTCCCGCCAGTCCGCCCACT

TCCTGGTTGTCTGCCTCGAAAGACCACACT

TGGTTGTCTGCCTCGAAAGACCACACT

TGGTTGTCTGCCTCGAAAGACCACACTCT

TGGTTGTCTGCCTCGAAAGACCACACTCTT

TGGTTGTCTGCCTCGAAAGACCACACTCTTT

TGGTCCCCATCCCCTCATCCTACAGCCAT

TGGTCCCCATCCCCTCATCCTACAGCCATCT

TAGCCAAGTGCCCCCTGTGTCT

TAGCCAAGTGCCCCCTGTGTCTT

TAGCCAAGTGCCCCCTGTGTCTTT

TAGCCAAGTGCCCCCTGTGTCTTTCAT

TAGCCAAGTGCCCCCTGTGTCTTTCATCT

TAGCCAAGTGCCCCCTGTGTCTTTCATCTGT

TCTGCCTCGAAAGACCACACTCTTTGCACT

-continued

TGCCTCGAAAGACCACACTCTTTGCACT

TCCTACAGCCATCTCAGGGACAGAT.

REFERENCES

1. Rosas-Ballina, M. et al. Acetylcholine-synthesizing T cells relay neural signals in a vagus nerve circuit. Science 334, 98-101 (2011).
2. SEVENTY-FOURTH ANNUAL MEETING of the British Medical Association. BMJ (Clinical research ed) 2, 1760-1816 (1906).
3. Furchgott, R. F. & Zawadzki, J. V. The obligatory role of endothelial cells in the relaxation of arterial smooth muscle by acetylcholine. Nature 288, 373-376 (1980).
4. Fleming, I. & Busse, R. NO: the primary EDRF. J. Mol. Cell. Cardiol. 31, 5-14 (1999).
5. Mulvany, M. J. & Aalkjaer, C. Structure and function of small arteries. Physiol. Rev. 70, 921-961 (1990).
6. Andersson, U. & Tracey, K. J. Reflex principles of immunological homeostasis. Annu. Rev. Immunol. 30, 313-335 (2012).
7. Olofsson, P. S. et al. α7 nicotinic acetylcholine receptor (α7nAChR) expression in bone marrow-derived non-T cells is required for the inflammatory reflex. Mol. Med. 18, 539-543 (2012).
8. Tallini, Y. N. et al. BAC transgenic mice express enhanced green fluorescent protein in central and peripheral cholinergic neurons. Physiol. Genomics 27, 391-397 (2006).
9. Eden, E., Navon, R., Steinfeld, I., Lipson, D. & Yakhini, Z. GOrilla: a tool for discovery and visualization of enriched GO terms in ranked gene lists. BMC Bioinformatics 10, 48 (2009).
10. Huang, W., Sherman, B. T. & Lempicki, R. A. Systematic and integrative analysis of large gene lists using DAVID bioinformatics resources. Nat. Protoc. 4, 44-57 (2009).
11. Huang, W., Sherman, B. T. & Lempicki, R. A. Bioinformatics enrichment tools: paths toward the comprehensive functional analysis of large gene lists. Nucleic Acids Res. 37, 1-13 (2009).
12. Kanehisa, M., Goto, S., Sato, Y., Furumichi, M. & Tanabe, M. KEGG for integration and interpretation of large-scale molecular data sets. Nucleic Acids Res. 40, D109-D114 (2012).
13. Heng, T. S. & Painter, M. W. The Immunological Genome Project: networks of gene expression in immune cells. Nat. Immunol. 9, 1091-1094 (2008).
14. Mingueneau, M. et al. The transcriptional landscape of αβ T cell differentiation. Nat. Immunol. 14, 619-632 (2013).
15. Dimmeler, S. et al. Activation of nitric oxide synthase in endothelial cells by Aktdependent phosphorylation. Nature 399, 601-605 (1999).
16. Huang, P. L. et al. Hypertension in mice lacking the gene for endothelial nitric oxide synthase. Nature 377, 239-242 (1995).
17. Laurat, E. et al. In vivo downregulation of T helper cell 1 immune responses reduces atherogenesis in apolipoprotein E-knockout mice. Circulation 104, 197-202 (2001).
18. Robertson, A. K. et al. Disruption of TGF-beta signaling in T cells accelerates atherosclerosis. J. Clin. Invest. 112, 1342-1350 (2003).
19. Guzik, T. J. et al. Role of the T cell in the genesis of angiotensin II induced hypertension and vascular dysfunction. J. Exp. Med. 204, 2449-2460 (2007).
20. Harrison, D. G. et al. Inflammation, immunity, and hypertension. Hypertension 57, 132-140 (2011).
21. Matrougui, K. et al. Natural regulatory T cells control coronary arteriolar endothelial dysfunction in hypertensive mice. Am. J. Pathol. 178, 434-441 (2011).
22. Marvar, P. J. & Harrison, D. G. Stress-dependent hypertension and the role of T lymphocytes. Exp. Physiol. 97, 1161-1167 (2012).
23. Olofsson, P. S., Rosas-Ballina, M., Levine, Y. A. & Tracey, K. J. Rethinking inflammation: neural circuits in the regulation of immunity. Immunol. Rev. 248, 188-204 (2012).
24. Kawashima, K., Fujii, T., Moriwaki, Y., Misawa, H. & Horiguchi, K. Reconciling neuronally and nonneuronally derived acetylcholine in the regulation of immune function. Ann. N Y Acad. Sci. 1261, 7-17 (2012).
25. Bearden, S. E., Payne, G. W., Chisty, A. & Segal, S. S. Arteriolar network architecture and vasomotor function with ageing in mouse gluteus maximus muscle. J. Physiol. (Lond.) 561, 535-545 (2004).
26. Fujimoto, K., Matsui, M., Fujii, T. & Kawashima, K. Decreased acetylcholine content and choline acetyltransferase mRNA expression in circulating mononuclear leukocytes and lymphoid organs of the spontaneously hypertensive rat. Life Sci. 69, 1629-1638 (2001).
27. Tracey, K. J. Shock medicine. Sci. Am. 312, 28-35 (2015).
28. Olofsson, P. S. A stimulating concept: bioelectronic medicine in inflammatory disease. Bioelectron. Med. 1, 30-3 (2015).
29. Lee, P. P. et al. A critical role for Dnmt1 and DNA methylation in T cell development, function, and survival. Immunity 15, 763-774 (2001).
30. Krump-Konvalinkova, V. et al. Generation of human pulmonary microvascular endothelial cell lines. Lab. Invest. 81, 1717-1727 (2001).
31. Ye, X., Ding, J., Zhou, X., Chen, G. & Liu, S. F. Divergent roles of endothelial NFkappaB in multiple organ injury and bacterial clearance in mouse models of sepsis. J. Exp. Med. 205, 1303-1315 (2008).
32. Ahmed, M. N. et al. Extracellular superoxide dismutase overexpression can reverse the course of hypoxia-induced pulmonary hypertension. Mol. Med. 18, 38-46 (2012).
33. Luo, J. et al. A comparison of batch effect removal methods for enhancement of prediction performance using MAQC-II microarray gene expression data. Pharmacogenomics J. 10, 278-291 (2010).
34. Smyth, G. K. in Bioinformatics and Computational Biology Solutions using R and Bioconductor (ed. Gentleman, R., Carey, V., Dudoit, S., Irizarry, R. & Huber, W.) 397-420 (Springer, New York, 2005).
35. Eden, E., Lipson, D., Yogev, S. & Yakhini, Z. Discovering motifs in ranked lists of DNA sequences. PLoS Comput. Biol. 3, e39 (2007).

What is claimed is:

1. A method for treating hypertension in a subject, or for reducing development of hypertension in a subject, comprising:

administering to a subject in need thereof an amount of CD4+ T-cells, engineered to express increased levels of choline acetyltransferase relative to non-engineered CD4+ T-cells of the same type, effective to treat or reduce development of hypertension;

wherein the CD4+ T-cells are engineered by having been transformed with a nucleic acid comprising the sequence set forth in SEQ ID NO:1 (hChAT-TAL-VP64);

wherein the CD4+ T-cells have been modified to functionally impair, or to reduce expression of, an endogenous T-cell receptor (TCR) of the T-cell, wherein the CD4+ T-cells are allogenic to the subject;

wherein the CD4+ T-cells are autologous to the subject;

and/or wherein the CD4+ T-cells are also engineered to further comprise a suicide gene, wherein said suicide gene induces expression of the protein HSV-TK.

2. The method of claim 1, wherein the method is to treat hypertension in a subject.

3. The method of claim 1, wherein the method is to reduce development of hypertension in a subject.

4. The method of claim 1, wherein the CD4+ T-cells are engineered by having been transformed with a nucleic acid comprising the sequence set forth in SEQ ID NO:1 (hChAT-TAL-VP64).

5. The method of claim 1, wherein the CD4+ T-cells have been modified to functionally impair, or to reduce expression of, an endogenous T-cell receptor (TCR) of the T-cell.

6. The method of claim 1, wherein the amount of CD4+ T-cells administered is sufficient to effect a reduction in a hypertension symptom in said subject.

7. The method of claim 6, wherein the reduction in a hypertension symptom is a reduction in mean arterial pressure (MAP) in a subject or a stabilization of MAP of a subject.

8. The method of claim 1, wherein the CD4+ T-cells are allogenic to the subject.

9. The method of claim 1, wherein the CD4+ T-cells are autologous to the subject.

10. The method of claim 9, further comprising obtaining the CD4+ T-cells from the subject prior to engineering the cells to express increased levels of choline acetyltransferase.

11. The method of claim 1, wherein the CD4+ T-cells are also engineered to further comprise a suicide gene, wherein said suicide gene induces expression of the protein HSV-TK.

12. A method comprising administering to a subject an amount of CD4+ T-cells engineered to express increased levels of choline acetyltransferase relative to non-engineered CD4+ T-cells of the same type, wherein the CD4+ T-cells are engineered by having been transformed with a nucleic acid comprising the sequence set forth in SEQ ID NO:1 (hChAT-TAL-VP64), wherein the CD4+ T-cells have been modified to functionally impair, or to reduce expression of, an endogenous T-cell receptor (TCR) of the T-cell, wherein the CD4+ T-cells are allogenic to the subject, wherein the CD4+ T-cells are autologous to the subject, and/or wherein the CD4+ T-cells are also engineered to further comprise a suicide gene, wherein said suicide gene induces expression of the protein HSV-TK.

13. The method of claim 12, wherein the CD4+ T-cells are allogenic to the subject.

14. The method of claim 12, wherein the CD4+ T-cells are autologous to the subject.

* * * * *

SEQUENCE LISTING

<160> NUMBER OF SEQ ID NOS: 134

<210> SEQ ID NO 1
<211> LENGTH: 941
<212> TYPE: DNA
<213> ORGANISM: Homo sapiens

<400> SEQUENCE: 1
ggaggctgag gctgggcccc actgaggggc tgtgacttgc ccaaggtcat ccagggccag 60
gcctgtgccc acattgggac tcttttcctc cctcagacag agggcacttc agtcactgca 120
gagcaggtgg cagcagccct tcagtggatg agtttctcct ttcccagggt gactgggtgg 180
gtgaaggaat tgagcaacag gtggccaggc tgccgcctct caccctgaca cattggtccc 240
catcccctca tcctacagcc atctcaggga cagatggaga cattccaatg ccctccgggt 300
cctccaccaa cccagacaga gcctggagtc acaatgccca cctagccaga gggatcagcc 360
agctagccaa gtgcccccctg tgtctttcat ctgttcttca caagacccac aagtgaaaaa 420
tgaggataaa ccgcacattc tacacacgat aacaacatag caagtcctta tactgctctt 480
actgtgtgcc cggcccccctt agcagtaggt actattatta ttcaatttta caaagaaact 540
aactgaggga cagagaggca aagtaattcc ctgcaggtac tctaatgagt acgtggcaga 600
gctgggagcc atcctggttg tctgcctcga aagaccacac tctttgcact gcatcgcggc 660
acttcctgcg ggtgggggg cacaatggga gaagcatctg cgtctaatgc tgctttactt 720
ttgaggccag aaaaatggga aggctcccct ctgactctgg aagagagacg caaaccgtaa 780
tctcaacaac acaatcccca cctccaacct cagccgccct ggagcctctc tcccgccagt 840
ccgcccactg gaacacgggt tccatgtgcc atccagggtc aacgccgctc tggggacgcg 900
tcaggcccag cgcacagcct gggcagctca gcctgtcagc t 941

<210> SEQ ID NO 2
<211> LENGTH: 2485
<212> TYPE: DNA
<213> ORGANISM: Homo sapiens

<400> SEQUENCE: 2
tggggttggg gaagtgcggt gactgggaaa tgctgagcta ggggcaggag gcatgggcgg 60
gacagtgttc tgtgcccccct tctagagcct aaatttgttg cccgagttcc tccgggaagc 120
gctccgggta gattctcggg gccgggagct gagatccctg ggcggggagc gggggaaggg 180
atggggctga ggacagcgaa gaagaggggg cttgggggag gggggaaatg gaagagagag 240
gagggaggag gtacaagagg aaggagagaa gtgcggccag cttgctttct ccagtcgggt 300
ggccgcgggg acccgggcga cgtcggaggc cctgccggga acccaggctg cagccccccac 360 ccccgcgctg cgacacgccc cccacccctt ccggctcaca cccccgccca cactcctgag 420
tggtgcggtg cagcgtcggc cgaggcagca gagccgagga gagcaggtcc acacctctgc 480
atccctgcac caggactcac caagacgccc atcctggaaa aggtcccccg taagatggca 540
gcaaaaactc ccagcagtga ggagtctggg ctgcccaaac tgcccgtgcc cccgctgcag 600
cagaccctgg ccacgtacct gcagtgcatg cgacacttgg tgtctgagga gcagttcagg 660
aagagccagg ccattgtgca gcagtttggg gcccctggtg gcctcggcga gaccctgcag 720
cagaaactcc tggagcggca ggagaagaca gccaactggg tgtctgagta ctggctgaat 780
gacatgtatc tcaacaaccg cctggccctg cctgtcaact ccagccctgc cgtgatcttt 840
gctcggcagc acttccctgg caccgatgac cagctgaggt ttgcagccag cctcatctct 900
ggtgtactca gctacaaggc cctgctggac agccactcca ttcccactga ctgtgccaaa 960
ccggagctgt cagggcagcc cctttgcatg aagcaatact atgggctctt ctcctcctac 1020
cggctccccg gccataccca ggacacgctg gtggctcaga acagcagcat catgccggag 1080
cctgagcacg tcatcgtagc ctgctgcaat cagttctttg tcttggatgt tgtcattaat 1140
ttccgccgtc tcagtgaggg ggatctgttc actcagttga gaaagatagt caaaatggct 1200
tccaacgagg acgagcgttt gcctccaatt ggcctgctga cgtctgacgg gaggagcgag 1260
tgggccgagg ccaggacggt cctcgtgaaa gactccacca accgggactc gctggacatg 1320
attgagcgct gcatctgcct tgtatgcctg gacggcccag gaggcgtgga gctcagcgac 1380
acccacaggg cactccagct ccttcacggc ggaggctaca gcaagaacgg ggccaatcgc 1440
tggtacgaca agtccctgca gtttgtggtg ggccgagacg cgacctgcgg tgtggtgtgc 1500
gaacactccc cattcgatgg catcgtcctg gtgcagtgca ctgagcatct gctcaagcac 1560
atgacgcaga gcagcaggaa gctgatccga gcagactccg tcagcgagct ccccgccccc 1620
cggaggctgc ggtggaaatg ctccccggaa attcaaggcc acttagcctc ctcggcagaa 1680
aaacttcaac gaatagtaaa gaaccttgac ttcattgtct ataagtttga caactatggg 1740
aaaacattca ttaagaagca gaaatgcagc cctgatgcct tcatccaggt ggccctccag 1800
ctggccttct acaggctcca ccgaagactg gtgcccacct acgagagcgc gtccatccgc 1860
cgattccagg agggacgcgt ggacaacatc agatcggcca ctccagaggc actggctttt 1920
gtgagagccg tgactgacca caaggctgct gtgccagctt ctgagaagct tctgctcctg 1980
aaggatgcca tccgtgccca gactgcatac acagtcatgg ccataacagg gatggccatt 2040
gacaaccacc tgctggcact gcgggagctg gcccgggcca tgtgcaagga gctgcccgag 2100
atgttcatgg atgaaaccta cctgatgagc aaccggtttg tcctctccac tagccaggtg 2160
cccacaacca cggagatgtt ctgctgctat ggtcctgtgg tcccaaatgg gtatggtgcc 2220
tgctacaacc cccagccaga gaccatcctt ttctgcatct ctagctttca cagctgcaaa 2280
gagacttctt ctagcaagtt tgcaaaagct gtggaagaaa gcctcattga catgagagac 2340
ctctgcagtc tgctgccgcc tactgagagc aagccattgg caacaaagga aaaagccacg 2400
aggcccagcc agggacacca accttgactc ctgccactag gtttcacctc ccaaacccag 2460
cctctagaac agccagaccc tgcag 2485

<210> SEQ ID NO 3
<211> LENGTH: 2810
<212> TYPE: DNA
<213> ORGANISM: Homo sapiens

<400> SEQUENCE: 3
gtgtgcagcc ctcccggaag gaaggtgagc cttcctaagc ctctactgac agcaaagctg 60
cagaggccct gctgcgtgag acccagaagc ttccacgcca ctttcagtca gtcggggcgg 120
ctgctgggat ctggcaactt cgtcggaggc tctgctacag aacctaggtg gcgggcccaa 180
cctctggtac tgctgccacc ccctccctgg ccccttctggc tcacgcagcc gcctccagcc 240
ctgcttggtg tggaacagtg ccggttcggt gcgtaacagc ccaggagagc aggtcggcag 300
ctctgctact ctggattaag aatcgctagg atgcctatcc tggaaaaggt ccccccaaag 360
atgcctgtac aagcttctag ctgtgaggag gtgctggact tacctaagtt gccagtgccc 420
ccactgcagc aaaccctggc cacctacctt cagtgcatgc aacacctggt acctgaagag 480

```
cagttcagga agagccaggc cattgtgaag cggtttgggg cccctggtgg cctgggtgag    540
accctgcagg aaaagctctt ggagagacag gagaagacag ccaattgggt ctctgaatac    600
tggctgaatg acatgtatct aaacaaccgc ctggccctgc cagtcaactc tagccctgct    660
gtgatctttg ctcggcagca cttccaagac accaatgacc agctaaggtt tgcagccagc    720
ctcatctctg gtgtgcttag ctacaaggct ctgctggaca gccaatccat tcccactgac    780
tgggccaagg ggcagctctc agggcagcct ctctgtatga agcagtacta cagactcttc    840
tcatcatacc ggcttcctgg ccatacccag gacacactgg tggcccagaa gagcagtatc    900
atgcctgagc ccgagcatgt catcgtggcc tgctgcaacc agttctttgt cttggatgtt    960
gtcattaatt tccgccgtct cagtgagggt gatctgttca ctcagttgag aaagatagtc   1020
aaaatggcgt ccaacgagga tgaacgcctg cctccaatcg gcctgctgac gtcagacggg   1080
aggagcgagt gggccaaggc caggacggtc ctcttaaaag actccaccaa ccgggactcc   1140
ctggacatga tcgagcgctg catctgcctg gtatgcctgg atggtccagg cactggagac   1200
ctcagtgaca cacacagggc cctccagctc cttcatggtg gaggctgcag cttgaatgga   1260
gcgaatcgtt ggtatgacaa gtccctgcag tttgtggtgg gccgagatgg cacctgcggt   1320
gtggtgtgtg agcactcccc ttttgatggc atcgtcctgg tgcagtgcac ggagcacctg   1380
ctgaaacata tgatgacagg caacaagaag ctcgtccgag ctgactcagt gagtgaactc   1440
cctgctccca gaaggctgag gtggaaatgt tccccagaaa ctcaaggcca tctcgcctcc   1500
tcggcagaga aacttcaaag aatcgtaaag aatctggatt tcattgttta taagtttgac   1560
aactatggga aaacatttat taagaagcag aaatgcagtc ctgatggctt catccaggtg   1620
gccctccagc tggcttacta caggctttac cagaggctgg tgcccaccta tgagagtgca   1680
tccatccgcc gcttccagga aggtcgggtg gacaacatca gatcggccac tcctgaggct   1740
ctggcttttg tgcaagccat gactgaccac aaggctgccg tgctggcttc tgagaaactg   1800
cagctgctgc agagggccat ccaggcccaa actgagtaca cagtcatggc cataaccggc   1860
atggccattg acaaccatct tctggcactg agggagctgg cccgagacct gtgcaaagag   1920
ccacctgaga tgttcatgga tgaaacatac ctgatgagca accggtttat tctctccacc   1980
agccaggtgc ccacgaccat ggagatgttc tgctgttatg gccctgtggt acccaatggg   2040
tatggagcct gttataaccc ccagcctgag gccatcacct tctgcatctc cagctttcac   2100
ggctgcaaag agacctcatc tgtggagttt gcagaagcgg tgggagcgag ccttgttgac   2160
atgagagacc tctgtagttc gaggcagcct gctgaaggca agccaccaac agcaaaggaa   2220
agagctagag gcccaaccaa gccaagcaat cttgactact cccactagcc aatgtcctac   2280
aggagtcagc ccctactaac cctgctccca tcccccaccc cagcttgttg ctgctcccct   2340
atccttgggg gctcacatga agctggcatg ttaagagaga gagagcccct cattatctat   2400
ctaagtggcc tgtggccttt acaactggaa atgagaccca gcctggcttg gaagcagcct   2460
gggtgggctg ggagctccct ctgaggtctt tagaaactta acctttctgc ttctttccca   2520
gcaacaccca gtggtgcaca tggtagctct gccagtggaa gaatcgtcat ctcatcacat   2580
gctatgggcc caaataagtc ataaaggcag aggctagctc cctccacaca ctcacatgca   2640
caaagacagc ccaagttcat ttagaataca gtggcccaca tccacaaaga catttcttcc   2700
tttatcttcc atagcacagt cttccttgag ttcagattat ctcatccagc tattcagaaa   2760
gaaagaaaga aagaaagaaa gaaagaaaga aagaaagaaa gaaaggaagg              2810
```

<210> SEQ ID NO 4
<211> LENGTH: 1184
<212> TYPE: DNA
<213> ORGANISM: Homo sapiens

<400> SEQUENCE: 4

```
cgtgaggctc cggtgcccgt cagtgggcag agcgcacatc gcccacagtc cccgagaagt     60
tggggggagg ggtcggcaat tgaaccggtg cctagagaag gtggcgcggg gtaaactggg    120
aaagtgatgt cgtgtactgg ctccgccttt ttcccgaggg tgggggagaa ccgtatataa    180
gtgcagtagt cgccgtgaac gttctttttc gcaacgggtt tgccgccaga acacaggtaa    240
gtgccgtgtg tggttcccgc gggcctggcc tctttacggg ttatggccct tgcgtgcctt    300
gaattacttc cacctggctg cagtacgtga ttcttgatcc cgagcttcgg gttggaagtg    360
ggtgggagag ttcgaggcct tgcgcttaag gagccccttc gcctcgtgct tgagttgagg    420
cctggcctgg gcgctggggc cgccgcgtgc gaatctggtg gcaccttcgc gcctgtctcg    480
ctgctttcga taagtctcta gccatttaaa atttttgatg acctgctgcg acgctttttt    540
tctggcaaga tagtcttgta aatgcgggcc aagatctgca cactggtatt tcggtttttg    600
gggccgcggg cggcgacggg gcccgtgcgt cccagcgcac atgttcggcg aggcggggcc    660
tgcgagcgcg gccaccgaga atcggacggg ggtagtctca agctggccgg cctgctctgg    720
tgcctggcct cgcgccgccg tgtatcgccc cgccctgggc ggcaaggctg gcccggtcgg    780
caccagttgc gtgagcggaa agatggccgc ttcccggccc tgctgcaggg agctcaaaat    840
ggaggacgcg gcgctcggga gagcgggcgg gtgagtcacc cacacaaagg aaaagggcct    900
ttccgtcctc agccgtcgct tcatgtgact ccacggagta ccgggcgccg tccaggcacc    960
tcgattagtt ctcgagcttt tggagtacgt cgtctttagg ttggggggag gggttttatg   1020
cgatggagtt tccccacact gagtgggtgg agactgaagt taggccagct tggcacttga   1080
tgtaattctc cttggaattt gccctttttg agtttggatc ttggttcatt ctcaagcctc   1140
agacagtggt tcaaagtttt tttcttccat ttcaggtgtc gtga                    1184
```

<210> SEQ ID NO 5
<211> LENGTH: 576
<212> TYPE: DNA
<213> ORGANISM: Homo sapiens

<400> SEQUENCE: 5

```
tagtaatcaa ttacggggtc attagttcat agcccatata tggagttccg cgttacataa     60
cttacggtaa atggcccgcc tggctgaccg cccaacgacc cccgcccatt gacgtcaata    120
atgacgtatg ttcccatagt aacgccaata gggactttcc attgacgtca atgggtggag    180
tatttacggt aaactgccca cttggcagta catcaagtgt atcatatgcc aagtacgccc    240
cctattgacg tcaatgacgg taaatggccc gcctggcatt atgcccagta catgacctta    300
tgggactttc ctacttggca gtacatctac gtattagtca tcgctattac catggtgatg    360
cggttttggc agtacatcaa tgggcgtgga tagcggtttg actcacgggg atttccaagt    420
ctccacccca ttgacgtcaa tgggagtttg ttttggcacc aaaatcaacg ggactttcca    480
aaatgtcgta acaactccgc cccattgacg caaatgggcg gtaggcgtgt acggtgggag    540
gtctatataa gcagagctgg tttagtgaac cgtcag                              576
```

<210> SEQ ID NO 6
<211> LENGTH: 19
<212> TYPE: DNA

<213> ORGANISM: Homo sapiens

<400> SEQUENCE: 6
tccgcccaaa tcaataaac 19

<210> SEQ ID NO 7
<211> LENGTH: 19
<212> TYPE: DNA
<213> ORGANISM: Homo sapiens

<400> SEQUENCE: 7
tgccgcctct caccctgac 19

<210> SEQ ID NO 8
<211> LENGTH: 19
<212> TYPE: DNA
<213> ORGANISM: Homo sapiens

<400> SEQUENCE: 8
tcgcggcact tcctgcggg 19

<210> SEQ ID NO 9
<211> LENGTH: 19
<212> TYPE: DNA
<213> ORGANISM: Homo sapiens

<400> SEQUENCE: 9
tcccgccagt ccgcccact 19

<210> SEQ ID NO 10
<211> LENGTH: 19
<212> TYPE: DNA
<213> ORGANISM: Homo sapiens

<400> SEQUENCE: 10
tccgcccact ggaacacgg 19

<210> SEQ ID NO 11
<211> LENGTH: 19
<212> TYPE: DNA
<213> ORGANISM: Homo sapiens

<400> SEQUENCE: 11
tggccaggct gccgcctct 19

<210> SEQ ID NO 12
<211> LENGTH: 19
<212> TYPE: DNA
<213> ORGANISM: Homo sapiens

<400> SEQUENCE: 12
tccgggtcct ccaccaacc 19

<210> SEQ ID NO 13
<211> LENGTH: 19
<212> TYPE: DNA
<213> ORGANISM: Homo sapiens

<400> SEQUENCE: 13
tgcccaccta gccagaggg 19

<210> SEQ ID NO 14
<211> LENGTH: 19

<212> TYPE: DNA
<213> ORGANISM: Homo sapiens

<400> SEQUENCE: 14
tgggcagctc agcctgtca 19

<210> SEQ ID NO 15
<211> LENGTH: 19
<212> TYPE: DNA
<213> ORGANISM: Homo sapiens

<400> SEQUENCE: 15
tgcccaaggt catccaggg 19

<210> SEQ ID NO 16
<211> LENGTH: 19
<212> TYPE: DNA
<213> ORGANISM: Homo sapiens

<400> SEQUENCE: 16
tgcccacatt gggactctt 19

<210> SEQ ID NO 17
<211> LENGTH: 24
<212> TYPE: DNA
<213> ORGANISM: Homo sapiens

<400> SEQUENCE: 17
tgccgcctct accctgacac attg 24

<210> SEQ ID NO 18
<211> LENGTH: 25
<212> TYPE: DNA
<213> ORGANISM: Homo sapiens

<400> SEQUENCE: 18
tcccgccagt ccgcccactg gaaca 25

<210> SEQ ID NO 19
<211> LENGTH: 25
<212> TYPE: DNA
<213> ORGANISM: Homo sapiens

<400> SEQUENCE: 19
tccgcccact ggaacacggg ttcca 25

<210> SEQ ID NO 20
<211> LENGTH: 25
<212> TYPE: DNA
<213> ORGANISM: Homo sapiens

<400> SEQUENCE: 20
tggccaggct gccgcctctc accct 25

<210> SEQ ID NO 21
<211> LENGTH: 25
<212> TYPE: DNA
<213> ORGANISM: Homo sapiens

<400> SEQUENCE: 21
tccgggtcct ccaccaaccc agaca 25

<210> SEQ ID NO 22

<211> LENGTH: 25
<212> TYPE: DNA
<213> ORGANISM: Homo sapiens

<400> SEQUENCE: 22
tgcccaccta gccagaggga tcagc 25

<210> SEQ ID NO 23
<211> LENGTH: 25
<212> TYPE: DNA
<213> ORGANISM: Homo sapiens

<400> SEQUENCE: 23
tgcccaaggt catccagggc caggc 25

<210> SEQ ID NO 24
<211> LENGTH: 25
<212> TYPE: DNA
<213> ORGANISM: Homo sapiens

<400> SEQUENCE: 24
tggcagcagc ccttcagtgg atgag 25

<210> SEQ ID NO 25
<211> LENGTH: 25
<212> TYPE: DNA
<213> ORGANISM: Homo sapiens

<400> SEQUENCE: 25
tcccagggtg actgggtggg tgaag 25

<210> SEQ ID NO 26
<211> LENGTH: 25
<212> TYPE: DNA
<213> ORGANISM: Homo sapiens

<400> SEQUENCE: 26
tgggtgggtg aaggaattga gcaac 25

<210> SEQ ID NO 27
<211> LENGTH: 2205
<212> TYPE: DNA
<213> ORGANISM: Homo sapiens

<400> SEQUENCE: 27
atggtggact tgaggacact cggttattcg caacagcaac aggagaaaat caagcctaag 60
gtcaggagca ccgtcgcgca acaccacgag gcgcttgtgg ggcatggctt cactcatgcg 120
catattgtcg cgctttcaca gcaccctgcg gcgcttggga cggtggctgt caaataccaa 180
gatatgattg cggccctgcc cgaagccacg cacgaggcaa ttgtaggggt cggtaaacag 240
tggtcgggag cgcgagcact tgaggcgctg ctgactgtgg cgggtgagct tagggggcct 300
ccgctccagc tcgacaccgg gcagctgctg aagatcgcga agagaggggg agtaacagcg 360
gtagaggcag tgcacgcctg gcgcaatgcg ctcaccgggg ccccccttgaa cctgacccca 420 gaccaggtag tcgcaatcgc gtcacatgac gggggaaagc aagccctgga aaccgtgcaa 480
aggttgttgc cggtcctttg tcaagaccac ggccttacac cggagcaagt cgtggccatt 540
gcatcccacg acggtggcaa acaggctctt gagacggttc agagacttct cccagttctc 600
tgtcaagccc acgggctgac tcccgatcaa gttgtagcga ttgcgaataa caatggaggg 660
aaacaagcat tggagactgt ccaacggctc cttcccgtgt tgtgtcaagc ccacggtttg 720

```
acgcctgcac aagtggtcgc catcgccagc catgatggcg gtaagcaggc gctggaaaca    780
gtacagcgcc tgctgcctgt actgtgccag gatcatggac tgaccccaga ccaggtagtc    840
gcaatcgcgt cacatgacgg gggaaagcaa gccctggaaa ccgtgcaaag gttgttgccg    900
gtcctttgtc aagaccacgg ccttacaccg gagcaagtcg tggccattgc atcccacgac    960
ggtggcaaac aggctcttga gacggttcag agacttctcc cagttctctg tcaagcccac   1020
gggctgactc ccgatcaagt tgtagcgatt gcgtcgaaca ttggagggaa acaagcattg   1080
gagactgtcc aacggctcct tcccgtgttg tgtcaagccc acggtttgac gcctgcacaa   1140
gtggtcgcca tcgcctccaa tattggcggt aagcaggcgc tggaaacagt acagcgcctg   1200
ctgcctgtac tgtgccagga tcatggactg accccagacc aggtagtcgc aatcgcgtcg   1260
aacattgggg gaaagcaagc cctggaaacc gtgcaaaggt tgttgccggt cctttgtcaa   1320
gaccacggcc ttacaccgga gcaagtcgtg gccattgcaa gcaatggggg tggcaaacag   1380
gctcttgaga cggttcagag acttctccca gttctctgtc aagcccacgg gctgactccc   1440
gatcaagttg tagcgattgc gtcgcatgac ggagggaaac aagcattgga gactgtccaa   1500
cggctccttc ccgtgttgtg tcaagcccac ggtttgacgc ctgcacaagt ggtcgccatc   1560
gcctccaata ttggcggtaa gcaggcgctg gaaacagtac agcgcctgct gcctgtactg   1620
tgccaggatc atggactgac cccagaccag gtagtcgcaa tcgcgtcgaa cattggggga   1680
aagcaagccc tggaaaccgt gcaaaggttg ttgccggtcc tttgtcaaga ccacggcctt   1740
acaccggagc aagtcgtggc cattgcaagc aatgggggtg gcaaacaggc tcttgagacg   1800
gttcagagac ttctcccagt tctctgtcaa gcccacgggc tgactcccga tcaagttgta   1860
gcgattgcgt cgaacattgg agggaaacaa gcattggaga ctgtccaacg gctccttccc   1920
gtgttgtgtc aagcccacgg tttgacgcct gcacaagtgg tcgccatcgc ctccaatatt   1980
ggcggtaagc aggcgctgga aacagtacag cgcctgctgc ctgtactgtg ccaggatcat   2040
ggactgaccc cagaccaggt agtcgcaatc gcgtcgaaca ttgggggaaa gcaagccctg   2100
gaaaccgtgc aaaggttgtt gccggtcctt tgtcaagacc acggcctgac acccgaacag   2160
gtggtcgcca ttgcttccca cgacggagga cggccagcct tggag                   2205
```

<210> SEQ ID NO 28
<211> LENGTH: 2205
<212> TYPE: DNA
<213> ORGANISM: Homo sapiens

<400> SEQUENCE: 28

```
atggtggact tgaggacact cggttattcg caacagcaac aggagaaaat caagcctaag     60
gtcaggagca ccgtcgcgca acaccacgag gcgcttgtgg ggcatggctt cactcatgcg    120
catattgtcg cgctttcaca gcaccctgcg gcgcttggga cggtggctgt caaataccaa    180
gatatgattg cggccctgcc cgaagccacg cacgaggcaa ttgtaggggt cggtaaacag    240
tggtcgggag cgcgagcact tgaggcgctg ctgactgtgg cgggtgagct tagggggcct    300
ccgctccagc tcgacaccgg gcagctgctg aagatcgcga agagaggggg agtaacagcg    360
gtagaggcag tgcacgcctg gcgcaatgcg ctcaccgggg ccccccttgaa cctgacccca    420
gaccaggtag tcgcaatcgc gaacaataat gggggaaagc aagccctgga aaccgtgcaa    480
aggttgttgc cggtcctttg tcaagaccac ggccttacac cggagcaagt cgtggccatt    540
gcatcccacg acggtggcaa acaggctctt gagacggttc agagacttct cccagttctc    600
```

```
tgtcaagccc acgggctgac tcccgatcaa gttgtagcga ttgcgtcgca tgacggaggg    660
aaacaagcat tggagactgt ccaacggctc cttcccgtgt tgtgtcaagc ccacggtttg    720
acgcctgcac aagtggtcgc catcgccaac aacaacggcg gtaagcaggc gctggaaaca    780
gtacagcgcc tgctgcctgt actgtgccag gatcatggac tgaccccaga ccaggtagtc    840
gcaatcgcgt cacatgacgg gggaaagcaa gccctggaaa ccgtgcaaag gttgttgccg    900
gtcctttgtc aagaccacgg ccttacaccg gagcaagtcg tggccattgc atcccacgac    960
ggtggcaaac aggctcttga gacggttcag agacttctcc cagttctctg tcaagcccac   1020
gggctgactc ccgatcaagt tgtagcgatt gcgtccaacg gtggagggaa acaagcattg   1080
gagactgtcc aacggctcct tcccgtgttg tgtcaagccc acggtttgac gcctgcacaa   1140
gtggtcgcca tcgccagcca tgatggcggt aagcaggcgc tggaaacagt acagcgcctg   1200
ctgcctgtac tgtgccagga tcatggactg accccagacc aggtagtcgc aatcgcgtca   1260
aacggagggg gaaagcaagc cctggaaacc gtgcaaaggt tgttgccggt cctttgtcaa   1320
gaccacggcc ttacaccgga gcaagtcgtg gccattgcat cccacgacgg tggcaaacag   1380
gctcttgaga cggttcagag acttctccca gttctctgtc aagcccacgg gctgactccc   1440
gatcaagttg tagcgattgc gtcgaacatt ggagggaaac aagcattgga gactgtccaa   1500
cggctccttc ccgtgttgtg tcaagcccac ggtttgacgc ctgcacaagt ggtcgccatc   1560
gccagccatg atggcggtaa gcaggcgctg gaaacagtac agcgcctgct gcctgtactg   1620
tgccaggatc atggactgac cccagaccag gtagtcgcaa tcgcgtcaca tgacggggga   1680
aagcaagccc tggaaaccgt gcaaaggttg ttgccggtcc tttgtcaaga ccacggcctt   1740
acaccggagc aagtcgtggc cattgcatcc cacgacggtg gcaaacaggc tcttgagacg   1800
gttcagagac ttctcccagt tctctgtcaa gcccacgggc tgactcccga tcaagttgta   1860
gcgattgcgt ccaacggtgg agggaaacaa gcattggaga ctgtccaacg gctccttccc   1920
gtgttgtgtc aagcccacgg tttgacgcct gcacaagtgg tcgccatcgc caacaacaac   1980
ggcggtaagc aggcgctgga aacagtacag cgcctgctgc ctgtactgtg ccaggatcat   2040
ggactgaccc cagaccaggt agtcgcaatc gcgtcgaaca ttgggggaaa gcaagccctg   2100
gaaaccgtgc aaaggttgtt gccggtcctt tgtcaagacc acggcctgac acccgaacag   2160
gtggtcgcca ttgcttccca cgacggagga cggccagcct tggag                   2205
```

<210> SEQ ID NO 29
<211> LENGTH: 2205
<212> TYPE: DNA
<213> ORGANISM: Homo sapiens

<400> SEQUENCE: 29

```
atggtggact tgaggacact cggttattcg caacagcaac aggagaaaat caagcctaag     60
gtcaggagca ccgtcgcgca acaccacgag gcgcttgtgg ggcatggctt cactcatgcg    120
catattgtcg cgctttcaca gcaccctgcg gcgcttggga cggtggctgt caaataccaa    180
gatatgattg cggccctgcc cgaagccacg cacgaggcaa ttgtaggggt cggtaaacag    240
tggtcgggag cgcgagcact tgaggcgctg ctgactgtgg cgggtgagct tagggggcct    300
ccgctccagc tcgacaccgg gcagctgctg aagatcgcga agagaggggg agtaacagcg    360
gtagaggcag tgcacgcctg gcgcaatgcg ctcaccgggg ccccccttgaa cctgacccca    420
gaccaggtag tcgcaatcgc gtcacatgac gggggaaagc aagccctgga aaccgtgcaa    480
aggttgttgc cggtcctttg tcaagaccac ggccttacac cggagcaagt cgtggccatt    540
```

```
gcaaataata acggtggcaa acaggctctt gagacggttc agagacttct cccagttctc    600

tgtcaagccc acgggctgac tcccgatcaa gttgtagcga ttgcgtcgca tgacggaggg    660

aaacaagcat tggagactgt ccaacggctc cttcccgtgt tgtgtcaagc ccacggtttg    720

acgcctgcac aagtggtcgc catcgccaac aacaacggcg gtaagcaggc gctggaaaca    780

gtacagcgcc tgctgcctgt actgtgccag gatcatggac tgaccccaga ccaggtagtc    840

gcaatcgcga acaataatgg gggaaagcaa gccctggaaa ccgtgcaaag gttgttgccg    900

gtcctttgtc aagaccacgg ccttacaccg gagcaagtcg tggccattgc atcccacgac    960

ggtggcaaac aggctcttga gacggttcag agacttctcc cagttctctg tcaagcccac   1020

gggctgactc ccgatcaagt tgtagcgatt gcgtcgaaca ttggagggaa acaagcattg   1080

gagactgtcc aacggctcct tcccgtgttg tgtcaagccc acggtttgac gcctgcacaa   1140

gtggtcgcca tcgccagcca tgatggcggt aagcaggcgc tggaaacagt acagcgcctg   1200

ctgcctgtac tgtgccagga tcatggactg accccagacc aggtagtcgc aatcgcgtca   1260

aacggagggg gaaagcaagc cctggaaacc gtgcaaaggt tgttgccggt cctttgtcaa   1320

gaccacggcc ttacaccgga gcaagtcgtg gccattgcaa gcaatggggg tggcaaacag   1380

gctcttgaga cggttcagag acttctccca gttctctgtc aagcccacgg gctgactccc   1440

gatcaagttg tagcgattgc gtcgcatgac ggagggaaac aagcattgga gactgtccaa   1500

cggctccttc ccgtgttgtg tcaagcccac ggtttgacgc ctgcacaagt ggtcgccatc   1560

gccagccatg atggcggtaa gcaggcgctg gaaacagtac agcgcctgct gcctgtactg   1620

tgccaggatc atggactgac cccagaccag gtagtcgcaa tcgcgtcaaa cggaggggga   1680

aagcaagccc tggaaaccgt gcaaaggttg ttgccggtcc tttgtcaaga ccacggcctt   1740

acaccggagc aagtcgtggc cattgcaaat aataacggtg gcaaacaggc tcttgagacg   1800

gttcagagac ttctcccagt tctctgtcaa gcccacgggc tgactcccga tcaagttgta   1860

gcgattgcgt cgcatgacgg agggaaacaa gcattggaga ctgtccaacg gctccttccc   1920

gtgttgtgtc aagcccacgg tttgacgcct gcacaagtgg tcgccatcgc caacaacaac   1980

ggcggtaagc aggcgctgga aacagtacag cgcctgctgc ctgtactgtg ccaggatcat   2040

ggactgaccc cagaccaggt agtcgcaatc gcgaacaata atgggggaaa gcaagccctg   2100

gaaaccgtgc aaaggttgtt gccggtcctt tgtcaagacc acggcctgac acccgaacag   2160

gtggtcgcca ttgctaataa taacggagga cggccagcct tggag                   2205
```

<210> SEQ ID NO 30
<211> LENGTH: 2205
<212> TYPE: DNA
<213> ORGANISM: Homo sapiens

<400> SEQUENCE: 30

```
atggtggact tgaggacact cggttattcg caacagcaac aggagaaaat caagcctaag     60

gtcaggagca ccgtcgcgca acaccacgag gcgcttgtgg ggcatggctt cactcatgcg    120

catattgtcg cgctttcaca gcaccctgcg gcgcttggga cggtggctgt caaataccaa    180

gatatgattg cggccctgcc cgaagccacg cacgaggcaa ttgtaggggt cggtaaacag    240

tggtcgggag cgcgagcact tgaggcgctg ctgactgtgg cgggtgagct tagggggcct    300

ccgctccagc tcgacaccgg gcagctgctg aagatcgcga agagaggggg agtaacagcg    360

gtagaggcag tgcacgcctg gcgcaatgcg ctcaccgggg ccccccttgaa cctgacccca    420
```

```
gaccaggtag tcgcaatcgc gtcacatgac gggggaaagc aagccctgga aaccgtgcaa    480

aggttgttgc cggtcctttg tcaagaccac ggccttacac cggagcaagt cgtggccatt    540

gcatcccacg acggtggcaa acaggctctt gagacggttc agagacttct cccagttctc    600

tgtcaagccc acgggctgac tcccgatcaa gttgtagcga ttgcgtcgca tgacggaggg    660

aaacaagcat tggagactgt ccaacggctc cttcccgtgt tgtgtcaagc ccacggtttg    720

acgcctgcac aagtggtcgc catcgccaac aacaacggcg gtaagcaggc gctggaaaca    780

gtacagcgcc tgctgcctgt actgtgccag gatcatggac tgaccccaga ccaggtagtc    840

gcaatcgcgt cacatgacgg gggaaagcaa gccctggaaa ccgtgcaaag gttgttgccg    900

gtcctttgtc aagaccacgg ccttacaccg gagcaagtcg tggccattgc atcccacgac    960

ggtggcaaac aggctcttga gacggttcag agacttctcc cagttctctg tcaagcccac   1020

gggctgactc ccgatcaagt tgtagcgatt gcgtcgaaca ttggagggaa acaagcattg   1080

gagactgtcc aacggctcct tcccgtgttg tgtcaagccc acggtttgac gcctgcacaa   1140

gtggtcgcca tcgccaacaa caacggcggt aagcaggcgc tggaaacagt acagcgcctg   1200

ctgcctgtac tgtgccagga tcatggactg accccagacc aggtagtcgc aatcgcgtca   1260

aacggagggg gaaagcaagc cctggaaacc gtgcaaaggt tgttgccggt cctttgtcaa   1320

gaccacggcc ttacaccgga gcaagtcgtg gccattgcat cccacgacgg tggcaaacag   1380

gctcttgaga cggttcagag acttctccca gttctctgtc aagcccacgg gctgactccc   1440

gatcaagttg tagcgattgc gtcgcatgac ggagggaaac aagcattgga gactgtccaa   1500

cggctccttc ccgtgttgtg tcaagcccac ggtttgacgc ctgcacaagt ggtcgccatc   1560

gccaacaaca acggcggtaa gcaggcgctg gaaacagtac agcgcctgct gcctgtactg   1620

tgccaggatc atggactgac cccagaccag gtagtcgcaa tcgcgtcaca tgacggggga   1680

aagcaagccc tggaaaccgt gcaaaggttg ttgccggtcc tttgtcaaga ccacggcctt   1740

acaccggagc aagtcgtggc cattgcatcc cacgacggtg gcaaacaggc tcttgagacg   1800

gttcagagac ttctcccagt tctctgtcaa gcccacgggc tgactcccga tcaagttgta   1860

gcgattgcgt cgcatgacgg agggaaacaa gcattggaga ctgtccaacg gctccttccc   1920

gtgttgtgtc aagcccacgg tttgacgcct gcacaagtgg tcgccatcgc ctccaatatt   1980

ggcggtaagc aggcgctgga aacagtacag cgcctgctgc ctgtactgtg ccaggatcat   2040

ggactgaccc cagaccaggt agtcgcaatc gcgtcacatg acgggggaaa gcaagccctg   2100

gaaaccgtgc aaaggttgtt gccggtcctt tgtcaagacc acggcctgac acccgaacag   2160

gtggtcgcca ttgcttctaa tgggggagga cggccagcct tggag                   2205
```

<210> SEQ ID NO 31
<211> LENGTH: 2205
<212> TYPE: DNA
<213> ORGANISM: Homo sapiens

<400> SEQUENCE: 31

```
atggtggact tgaggacact cggttattcg caacagcaac aggagaaaat caagcctaag     60

gtcaggagca ccgtcgcgca acaccacgag gcgcttgtgg ggcatggctt cactcatgcg    120

catattgtcg cgctttcaca gcaccctgcg gcgcttggga cggtggctgt caaataccaa    180

gatatgattg cggccctgcc cgaagccacg cacgaggcaa ttgtaggggt cggtaaacag    240

tggtcgggag cgcgagcact tgaggcgctg ctgactgtgg cgggtgagct tagggggcct    300

ccgctccagc tcgacaccgg gcagctgctg aagatcgcga agagaggggg agtaacagcg    360
```

```
gtagaggcag tgcacgcctg gcgcaatgcg ctcaccgggg ccccccttgaa cctgacccca    420

gaccaggtag tcgcaatcgc gtcacatgac gggggaaagc aagccctgga aaccgtgcaa    480

aggttgttgc cggtcctttg tcaagaccac ggccttacac cggagcaagt cgtggccatt    540

gcatcccacg acggtggcaa acaggctctt gagacggttc agagacttct cccagttctc    600

tgtcaagccc acgggctgac tcccgatcaa gttgtagcga ttgcgaataa caatggaggg    660

aaacaagcat tggagactgt ccaacggctc cttcccgtgt tgtgtcaagc ccacggtttg    720

acgcctgcac aagtggtcgc catcgccagc catgatggcg gtaagcaggc gctggaaaca    780

gtacagcgcc tgctgcctgt actgtgccag gatcatggac tgaccccaga ccaggtagtc    840

gcaatcgcgt cacatgacgg gggaaagcaa gccctggaaa ccgtgcaaag gttgttgccg    900

gtcctttgtc aagaccacgg ccttacaccg gagcaagtcg tggccattgc atcccacgac    960

ggtggcaaac aggctcttga gacggttcag agacttctcc cagttctctg tcaagcccac   1020

gggctgactc ccgatcaagt tgtagcgatt gcgtcgaaca ttggagggaa acaagcattg   1080

gagactgtcc aacggctcct tcccgtgttg tgtcaagccc acggtttgac gcctgcacaa   1140

gtggtcgcca tcgccagcca tgatggcggt aagcaggcgc tggaaacagt acagcgcctg   1200

ctgcctgtac tgtgccagga tcatggactg accccagacc aggtagtcgc aatcgcgtca   1260

aacggagggg gaaagcaagc cctggaaacc gtgcaaaggt tgttgccggt cctttgtcaa   1320

gaccacggcc ttacaccgga gcaagtcgtg gccattgcaa ataataacgg tggcaaacag   1380

gctcttgaga cggttcagag acttctccca gttctctgtc aagcccacgg gctgactccc   1440

gatcaagttg tagcgattgc gaataacaat ggagggaaac aagcattgga gactgtccaa   1500

cggctccttc ccgtgttgtg tcaagcccac ggtttgacgc ctgcacaagt ggtcgccatc   1560

gcctccaata ttggcggtaa gcaggcgctg gaaacagtac agcgcctgct gcctgtactg   1620

tgccaggatc atggactgac cccagaccag gtagtcgcaa tcgcgtcgaa cattggggga   1680

aagcaagccc tggaaaccgt gcaaaggttg ttgccggtcc tttgtcaaga ccacggcctt   1740

acaccggagc aagtcgtggc cattgcatcc cacgacggtg gcaaacaggc tcttgagacg   1800

gttcagagac ttctcccagt tctctgtcaa gcccacgggc tgactcccga tcaagttgta   1860

gcgattgcgt cgaacattgg agggaaacaa gcattggaga ctgtccaacg gctccttccc   1920

gtgttgtgtc aagcccacgg tttgacgcct gcacaagtgg tcgccatcgc cagccatgat   1980

ggcggtaagc aggcgctgga aacagtacag cgcctgctgc ctgtactgtg ccaggatcat   2040

ggactgaccc cagaccaggt agtcgcaatc gcgaacaata atgggggaaa gcaagccctg   2100

gaaaccgtgc aaaggttgtt gccggtcctt tgtcaagacc acggcctgac acccgaacag   2160

gtggtcgcca ttgctaataa taacggagga cggccagcct tggag                  2205
```

```
<210> SEQ ID NO 32
<211> LENGTH: 2205
<212> TYPE: DNA
<213> ORGANISM: Homo sapiens

<400> SEQUENCE: 32

atggtggact tgaggacact cggttattcg caacagcaac aggagaaaat caagcctaag     60

gtcaggagca ccgtcgcgca acaccacgag gcgcttgtgg ggcatggctt cactcatgcg    120

catattgtcg cgctttcaca gcaccctgcg gcgcttggga cggtggctgt caaataccaa    180

gatatgattg cggccctgcc cgaagccacg cacgaggcaa ttgtaggggt cggtaaacag    240
```

```
tggtcgggag cgcgagcact tgaggcgctg ctgactgtgg cgggtgagct taggggggcct   300
ccgctccagc tcgacaccgg gcagctgctg aagatcgcga agagaggggg agtaacagcg   360
gtagaggcag tgcacgcctg gcgcaatgcg ctcaccgggg ccccccttgaa cctgacccca   420
gaccaggtag tcgcaatcgc gaacaataat gggggaaagc aagccctgga aaccgtgcaa   480
aggttgttgc cggtcctttg tcaagaccac ggccttacac cggagcaagt cgtggccatt   540
gcaaataata acggtggcaa acaggctctt gagacggttc agagacttct cccagttctc   600
tgtcaagccc acgggctgac tcccgatcaa gttgtagcga ttgcgtcgca tgacggaggg   660
aaacaagcat tggagactgt ccaacggctc cttcccgtgt tgtgtcaagc ccacggtttg   720
acgcctgcac aagtggtcgc catcgccagc catgatggcg gtaagcaggc gctggaaaca   780
gtacagcgcc tgctgcctgt actgtgccag gatcatggac tgaccccaga ccaggtagtc   840
gcaatcgcgt cgaacattgg gggaaagcaa gccctggaaa ccgtgcaaag gttgttgccg   900
gtcctttgtc aagaccacgg ccttacaccg gagcaagtcg tggccattgc aaataataac   960
ggtggcaaac aggctcttga gacggttcag agacttctcc cagttctctg tcaagcccac  1020
gggctgactc ccgatcaagt tgtagcgatt gcgaataaca atggagggaa acaagcattg  1080
gagactgtcc aacggctcct tcccgtgttg tgtcaagccc acggtttgac gcctgcacaa  1140
gtggtcgcca tcgccagcca tgatggcggt aagcaggcgc tggaaacagt acagcgcctg  1200
ctgcctgtac tgtgccagga tcatggactg accccagacc aggtagtcgc aatcgcgtca  1260
aacggagggg gaaagcaagc cctggaaacc gtgcaaaggt tgttgccggt cctttgtcaa  1320
gaccacggcc ttacaccgga gcaagtcgtg gccattgcaa ataataacgg tggcaaacag  1380
gctcttgaga cggttcagag acttctccca gttctctgtc aagcccacgg gctgactccc  1440
gatcaagttg tagcgattgc gtcgcatgac ggagggaaac aagcattgga gactgtccaa  1500
cggctccttc ccgtgttgtg tcaagcccac ggtttgacgc ctgcacaagt ggtcgccatc  1560
gccagccatg atggcggtaa gcaggcgctg gaaacagtac agcgcctgct gcctgtactg  1620
tgccaggatc atggactgac cccagaccag gtagtcgcaa tcgcgaacaa taatggggga  1680
aagcaagccc tggaaaccgt gcaaaggttg ttgccggtcc tttgtcaaga ccacggcctt  1740
acaccggagc aagtcgtggc cattgcatcc cacgacggtg gcaaacaggc tcttgagacg  1800
gttcagagac ttctcccagt tctctgtcaa gcccacgggc tgactcccga tcaagttgta  1860
gcgattgcgt cgcatgacgg agggaaacaa gcattggaga ctgtccaacg gctccttccc  1920
gtgttgtgtc aagcccacgg tttgacgcct gcacaagtgg tcgccatcgc ctcgaatggc  1980
ggcggtaagc aggcgctgga aacagtacag cgcctgctgc ctgtactgtg ccaggatcat  2040
ggactgaccc cagaccaggt agtcgcaatc gcgtcacatg acgggggaaa gcaagccctg  2100
gaaaccgtgc aaaggttgtt gccggtcctt tgtcaagacc acggcctgac acccgaacag  2160
gtggtcgcca ttgcttctaa tgggggagga cggccagcct tggag                  2205
```

<210> SEQ ID NO 33
<211> LENGTH: 2205
<212> TYPE: DNA
<213> ORGANISM: Homo sapiens

<400> SEQUENCE: 33

```
atggtggact tgaggacact cggttattcg caacagcaac aggagaaaat caagcctaag    60
gtcaggagca ccgtcgcgca acaccacgag gcgcttgtgg ggcatggctt cactcatgcg   120
catattgtcg cgctttcaca gcaccctgcg gcgcttggga cggtggctgt caaataccaa   180
```

```
gatatgattg cggccctgcc cgaagccacg cacgaggcaa ttgtaggggt cggtaaacag     240
tggtcgggag cgcgagcact tgaggcgctg ctgactgtgg cgggtgagct tagggggcct     300
ccgctccagc tcgacaccgg gcagctgctg aagatcgcga agagaggggg agtaacagcg     360
gtagaggcag tgcacgcctg gcgcaatgcg ctcaccgggg ccccccttgaa cctgacccca     420
gaccaggtag tcgcaatcgc gtcacatgac gggggaaagc aagccctgga aaccgtgcaa     480
aggttgttgc cggtcctttg tcaagaccac ggccttacac cggagcaagt cgtggccatt     540
gcatcccacg acggtggcaa acaggctctt gagacggttc agagacttct cccagttctc     600
tgtcaagccc acgggctgac tcccgatcaa gttgtagcga ttgcgaataa caatggaggg     660
aaacaagcat tggagactgt ccaacggctc cttcccgtgt tgtgtcaagc ccacggtttg     720
acgcctgcac aagtggtcgc catcgccaac aacaacggcg gtaagcaggc gctggaaaca     780
gtacagcgcc tgctgcctgt actgtgccag gatcatggac tgaccccaga ccaggtagtc     840
gcaatcgcga acaataatgg gggaaagcaa gccctggaaa ccgtgcaaag gttgttgccg     900
gtcctttgtc aagaccacgg ccttacaccg gagcaagtcg tggccattgc aagcaatggg     960
ggtggcaaac aggctcttga gacggttcag agacttctcc cagttctctg tcaagcccac    1020
gggctgactc ccgatcaagt tgtagcgatt gcgtcgcatg acggagggaa acaagcattg    1080
gagactgtcc aacggctcct tcccgtgttg tgtcaagccc acggtttgac gcctgcacaa    1140
gtggtcgcca tcgccagcca tgatggcggt aagcaggcgc tggaaacagt acagcgcctg    1200
ctgcctgtac tgtgccagga tcatggactg accccagacc aggtagtcgc aatcgcgtca    1260
aacggagggg gaaagcaagc cctggaaacc gtgcaaaggt tgttgccggt cctttgtcaa    1320
gaccacggcc ttacaccgga gcaagtcgtg gccattgcat cccacgacgg tggcaaacag    1380
gctcttgaga cggttcagag acttctccca gttctctgtc aagcccacgg gctgactccc    1440
gatcaagttg tagcgattgc gtcgcatgac ggagggaaac aagcattgga gactgtccaa    1500
cggctccttc ccgtgttgtg tcaagcccac ggtttgacgc ctgcacaagt ggtcgccatc    1560
gcctccaata ttggcggtaa gcaggcgctg gaaacagtac agcgcctgct gcctgtactg    1620
tgccaggatc atggactgac cccagaccag gtagtcgcaa tcgcgtcaca tgacggggga    1680
aagcaagccc tggaaaccgt gcaaaggttg ttgccggtcc tttgtcaaga ccacggcctt    1740
acaccggagc aagtcgtggc cattgcatcc cacgacggtg gcaaacaggc tcttgagacg    1800
gttcagagac ttctcccagt tctctgtcaa gcccacgggc tgactcccga tcaagttgta    1860
gcgattgcgt cgaacattgg agggaaacaa gcattggaga ctgtccaacg gctccttccc    1920
gtgttgtgtc aagcccacgg tttgacgcct gcacaagtgg tcgccatcgc ctccaatatt    1980
ggcggtaagc aggcgctgga aacagtacag cgcctgctgc ctgtactgtg ccaggatcat    2040
ggactgaccc cagaccaggt agtcgcaatc gcgtcacatg acgggggaaa gcaagccctg    2100
gaaaccgtgc aaaggttgtt gccggtcctt tgtcaagacc acggcctgac acccgaacag    2160
gtggtcgcca ttgcttccca cgacggagga cggccagcct tggag                    2205
```

<210> SEQ ID NO 34
<211> LENGTH: 2205
<212> TYPE: DNA
<213> ORGANISM: Homo sapiens

<400> SEQUENCE: 34

```
atggtggact tgaggacact cggttattcg caacagcaac aggagaaaat caagcctaag      60
```

```
gtcaggagca ccgtcgcgca acaccacgag gcgcttgtgg ggcatggctt cactcatgcg    120

catattgtcg cgctttcaca gcaccctgcg gcgcttggga cggtggctgt caaataccaa    180

gatatgattg cggccctgcc cgaagccacg cacgaggcaa ttgtaggggt cggtaaacag    240

tggtcgggag cgcgagcact tgaggcgctg ctgactgtgg cgggtgagct taggggggcct    300

ccgctccagc tcgacaccgg gcagctgctg aagatcgcga agagaggggg agtaacagcg    360

gtagaggcag tgcacgcctg gcgcaatgcg ctcaccgggg ccccccttgaa cctgacccca    420

gaccaggtag tcgcaatcgc gaacaataat gggggaaagc aagccctgga aaccgtgcaa    480

aggttgttgc cggtcctttg tcaagaccac ggccttacac cggagcaagt cgtggccatt    540

gcatcccacg acggtggcaa acaggctctt gagacggttc agagacttct cccagttctc    600

tgtcaagccc acgggctgac tcccgatcaa gttgtagcga ttgcgtcgca tgacggaggg    660

aaacaagcat tggagactgt ccaacggctc cttcccgtgt tgtgtcaagc ccacggtttg    720

acgcctgcac aagtggtcgc catcgccagc catgatggcg gtaagcaggc gctggaaaca    780

gtacagcgcc tgctgcctgt actgtgccag gatcatggac tgaccccaga ccaggtagtc    840

gcaatcgcgt cgaacattgg gggaaagcaa gccctggaaa ccgtgcaaag gttgttgccg    900

gtcctttgtc aagaccacgg ccttacaccg gagcaagtcg tggccattgc atcccacgac    960

ggtggcaaac aggctcttga gacggttcag agacttctcc cagttctctg tcaagcccac   1020

gggctgactc ccgatcaagt tgtagcgatt gcgtcgcatg acggagggaa acaagcattg   1080

gagactgtcc aacggctcct tcccgtgttg tgtcaagccc acggtttgac gcctgcacaa   1140

gtggtcgcca tcgcctcgaa tggcggcggt aagcaggcgc tggaaacagt acagcgcctg   1200

ctgcctgtac tgtgccagga tcatggactg accccagacc aggtagtcgc aatcgcgtcg   1260

aacattgggg gaaagcaagc cctggaaacc gtgcaaaggt tgttgccggt cctttgtcaa   1320

gaccacggcc ttacaccgga gcaagtcgtg gccattgcaa ataataacgg tggcaaacag   1380

gctcttgaga cggttcagag acttctccca gttctctgtc aagcccacgg gctgactccc   1440

gatcaagttg tagcgattgc gtcgcatgac ggagggaaac aagcattgga gactgtccaa   1500

cggctccttc ccgtgttgtg tcaagcccac ggtttgacgc ctgcacaagt ggtcgccatc   1560

gccagccatg atggcggtaa gcaggcgctg gaaacagtac agcgcctgct gcctgtactg   1620

tgccaggatc atggactgac cccagaccag gtagtcgcaa tcgcgtcgaa cattgggggga   1680

aagcaagccc tggaaaccgt gcaaaggttg ttgccggtcc tttgtcaaga ccacggcctt   1740

acaccggagc aagtcgtggc cattgcaaat aataacggtg gcaaacaggc tcttgagacg   1800

gttcagagac ttctcccagt tctctgtcaa gcccacgggc tgactcccga tcaagttgta   1860

gcgattgcgt cgaacattgg agggaaacaa gcattggaga ctgtccaacg gctccttccc   1920

gtgttgtgtc aagcccacgg tttgacgcct gcacaagtgg tcgccatcgc caacaacaac   1980

ggcggtaagc aggcgctgga aacagtacag cgcctgctgc ctgtactgtg ccaggatcat   2040

ggactgaccc cagaccaggt agtcgcaatc gcgaacaata atgggggaaa gcaagccctg   2100

gaaaccgtgc aaaggttgtt gccggtcctt tgtcaagacc acggcctgac acccgaacag   2160

gtggtcgcca ttgctaataa taacggagga cggccagcct tggag                   2205
```

```
<210> SEQ ID NO 35
<211> LENGTH: 2205
<212> TYPE: DNA
<213> ORGANISM: Homo sapiens

<400> SEQUENCE: 35
```

```
atggtggact tgaggacact cggttattcg caacagcaac aggagaaaat caagcctaag     60
gtcaggagca ccgtcgcgca acaccacgag gcgcttgtgg ggcatggctt cactcatgcg    120
catattgtcg cgctttcaca gcaccctgcg gcgcttggga cggtggctgt caaataccaa    180
gatatgattg cggccctgcc cgaagccacg cacgaggcaa ttgtaggggt cggtaaacag    240
tggtcgggag cgcgagcact tgaggcgctg ctgactgtgg cgggtgagct tagggggcct    300
ccgctccagc tcgacaccgg gcagctgctg aagatcgcga agagaggggg agtaacagcg    360
gtagaggcag tgcacgcctg gcgcaatgcg ctcaccgggg ccccccttgaa cctgacccca    420
gaccaggtag tcgcaatcgc gaacaataat gggggaaagc aagccctgga aaccgtgcaa    480
aggttgttgc cggtcctttg tcaagaccac ggccttacac cggagcaagt cgtggccatt    540
gcaaataata acggtggcaa acaggctctt gagacggttc agagacttct cccagttctc    600
tgtcaagccc acgggctgac tcccgatcaa gttgtagcga ttgcgaataa caatggaggg    660
aaacaagcat tggagactgt ccaacggctc cttcccgtgt tgtgtcaagc ccacggtttg    720
acgcctgcac aagtggtcgc catcgccagc catgatggcg gtaagcaggc gctggaaaca    780
gtacagcgcc tgctgcctgt actgtgccag gatcatggac tgaccccaga ccaggtagtc    840
gcaatcgcgt cgaacattgg gggaaagcaa gccctggaaa ccgtgcaaag gttgttgccg    900
gtcctttgtc aagaccacgg ccttacaccg gagcaagtcg tggccattgc aaataataac    960
ggtggcaaac aggctcttga gacggttcag agacttctcc cagttctctg tcaagcccac   1020
gggctgactc ccgatcaagt tgtagcgatt gcgtcgcatg acggagggaa acaagcattg   1080
gagactgtcc aacggctcct tcccgtgttg tgtcaagccc acggtttgac gcctgcacaa   1140
gtggtcgcca tcgcctcgaa tggcggcggt aagcaggcgc tggaaacagt acagcgcctg   1200
ctgcctgtac tgtgccagga tcatggactg accccagacc aggtagtcgc aatcgcgtca   1260
catgacgggg gaaagcaagc cctggaaacc gtgcaaaggt tgttgccggt cctttgtcaa   1320
gaccacggcc ttacaccgga gcaagtcgtg gccattgcaa gcaacatcgg tggcaaacag   1380
gctcttgaga cggttcagag acttctccca gttctctgtc aagcccacgg gctgactccc   1440
gatcaagttg tagcgattgc gaataacaat ggagggaaac aagcattgga gactgtccaa   1500
cggctccttc ccgtgttgtg tcaagcccac ggtttgacgc ctgcacaagt ggtcgccatc   1560
gccagccatg atggcggtaa gcaggcgctg gaaacagtac agcgcctgct gcctgtactg   1620
tgccaggatc atggactgac cccagaccag gtagtcgcaa tcgcgtcaca tgacggggga   1680
aagcaagccc tggaaaccgt gcaaaggttg ttgccggtcc tttgtcaaga ccacggcctt   1740
acaccggagc aagtcgtggc cattgcaagc aatgggggtg gcaaacaggc tcttgagacg   1800
gttcagagac ttctcccagt tctctgtcaa gcccacgggc tgactcccga tcaagttgta   1860
gcgattgcga ataacaatgg agggaaacaa gcattggaga ctgtccaacg gctccttccc   1920
gtgttgtgtc aagcccacgg tttgacgcct gcacaagtgg tcgccatcgc ctcgaatggc   1980
ggcggtaagc aggcgctgga aacagtacag cgcctgctgc ctgtactgtg ccaggatcat   2040
ggactgaccc cagaccaggt agtcgcaatc gcgtcacatg acgggggaaa gcaagccctg   2100
gaaaccgtgc aaaggttgtt gccggtcctt tgtcaagacc acggcctgac acccgaacag   2160
gtggtcgcca ttgcttctaa catcggagga cggccagcct tggag                    2205
```

<210> SEQ ID NO 36
<211> LENGTH: 2205
<212> TYPE: DNA

<213> ORGANISM: Homo sapiens

<400> SEQUENCE: 36

```
atggtggact tgaggacact cggttattcg caacagcaac aggagaaaat caagcctaag      60
gtcaggagca ccgtcgcgca acaccacgag gcgcttgtgg ggcatggctt cactcatgcg     120
catattgtcg cgctttcaca gcaccctgcg gcgcttggga cggtggctgt caaataccaa     180
gatatgattg cggccctgcc cgaagccacg cacgaggcaa ttgtaggggt cggtaaacag     240
tggtcgggag cgcgagcact tgaggcgctg ctgactgtgg cgggtgagct tagggggcct     300
ccgctccagc tcgacaccgg gcagctgctg aagatcgcga agagaggggg agtaacagcg     360
gtagaggcag tgcacgcctg gcgcaatgcg ctcaccgggg ccccccttgaa cctgacccca    420
gaccaggtag tcgcaatcgc gaacaataat gggggaaagc aagccctgga aaccgtgcaa     480
aggttgttgc cggtcctttg tcaagaccac ggccttacac cggagcaagt cgtggccatt     540
gcatcccacg acggtggcaa acaggctctt gagacggttc agagacttct cccagttctc     600
tgtcaagccc acgggctgac tcccgatcaa gttgtagcga ttgcgtcgca tgacggaggg     660
aaacaagcat tggagactgt ccaacggctc cttcccgtgt tgtgtcaagc ccacggtttg     720
acgcctgcac aagtggtcgc catcgccagc catgatggcg gtaagcaggc gctggaaaca     780
gtacagcgcc tgctgcctgt actgtgccag gatcatggac tgaccccaga ccaggtagtc     840
gcaatcgcgt cgaacattgg gggaaagcaa gccctggaaa ccgtgcaaag gttgttgccg     900
gtcctttgtc aagaccacgg ccttacaccg gagcaagtcg tggccattgc aagcaacatc     960
ggtggcaaac aggctcttga gacggttcag agacttctcc cagttctctg tcaagcccac    1020
gggctgactc ccgatcaagt tgtagcgatt gcgaataaca atggagggaa acaagcattg    1080
gagactgtcc aacggctcct tcccgtgttg tgtcaagccc acggtttgac gcctgcacaa    1140
gtggtcgcca tcgccaacaa caacggcggt aagcaggcgc tggaaacagt acagcgcctg    1200
ctgcctgtac tgtgccagga tcatggactg accccagacc aggtagtcgc aatcgcgtca    1260
aacggagggg gaaagcaagc cctggaaacc gtgcaaaggt tgttgccggt cctttgtcaa    1320
gaccacggcc ttacaccgga gcaagtcgtg gccattgcat cccacgacgg tggcaaacag    1380
gctcttgaga cggttcagag acttctccca gttctctgtc aagcccacgg gctgactccc    1440
gatcaagttg tagcgattgc gtcgaacatt ggagggaaac aagcattgga gactgtccaa    1500
cggctccttc ccgtgttgtg tcaagcccac ggtttgacgc ctgcacaagt ggtcgccatc    1560
gcctcgaatg gcggcggtaa gcaggcgctg gaaacagtac agcgcctgct gcctgtactg    1620
tgccaggatc atggactgac cccagaccag gtagtcgcaa tcgcgtcaca tgacggggga    1680
aagcaagccc tggaaaccgt gcaaaggttg ttgccggtcc tttgtcaaga ccacggcctt    1740
acaccggagc aagtcgtggc cattgcatcc cacgacggtg gcaaacaggc tcttgagacg    1800
gttcagagac ttctcccagt tctctgtcaa gcccacgggc tgactcccga tcaagttgta    1860
gcgattgcgt cgaacattgg agggaaacaa gcattggaga ctgtccaacg gctccttccc    1920
gtgttgtgtc aagcccacgg tttgacgcct gcacaagtgg tcgccatcgc caacaacaac    1980
ggcggtaagc aggcgctgga aacagtacag cgcctgctgc ctgtactgtg ccaggatcat    2040
ggactgaccc cagaccaggt agtcgcaatc gcgaacaata atgggggaaa gcaagccctg    2100
gaaaccgtgc aaaggttgtt gccggtcctt tgtcaagacc acggcctgac acccgaacag    2160
gtggtcgcca ttgctaataa taacggagga cggccagcct tggag                   2205
```

<210> SEQ ID NO 37
<211> LENGTH: 2205
<212> TYPE: DNA
<213> ORGANISM: Homo sapiens

<400> SEQUENCE: 37

```
atggtggact tgaggacact cggttattcg caacagcaac aggagaaaat caagcctaag     60
gtcaggagca ccgtcgcgca acaccacgag gcgcttgtgg ggcatggctt cactcatgcg    120
catattgtcg cgctttcaca gcaccctgcg gcgcttggga cggtggctgt caaataccaa    180
gatatgattg cggccctgcc cgaagccacg cacgaggcaa ttgtaggggt cggtaaacag    240
tggtcgggag cgcgagcact tgaggcgctg ctgactgtgg cgggtgagct taggggggcct    300
ccgctccagc tcgacaccgg gcagctgctg aagatcgcga agagaggggg agtaacagcg    360
gtagaggcag tgcacgcctg gcgcaatgcg ctcaccgggg ccccccttgaa cctgacccca    420
gaccaggtag tcgcaatcgc gaacaataat gggggaaagc aagccctgga aaccgtgcaa    480
aggttgttgc cggtcctttg tcaagaccac ggccttacac cggagcaagt cgtggccatt    540
gcatcccacg acggtggcaa acaggctctt gagacggttc agagacttct cccagttctc    600
tgtcaagccc acgggctgac tcccgatcaa gttgtagcga ttgcgtcgca tgacggaggg    660
aaacaagcat tggagactgt ccaacggctc cttcccgtgt tgtgtcaagc ccacggtttg    720
acgcctgcac aagtggtcgc catcgccagc catgatggcg gtaagcaggc gctggaaaca    780
gtacagcgcc tgctgcctgt actgtgccag gatcatggac tgaccccaga ccaggtagtc    840
gcaatcgcgt cgaacattgg gggaaagcaa gccctggaaa ccgtgcaaag gttgttgccg    900
gtcctttgtc aagaccacgg ccttacaccg gagcaagtcg tggccattgc atcccacgac    960
ggtggcaaac aggctcttga gacggttcag agacttctcc cagttctctg tcaagcccac   1020
gggctgactc ccgatcaagt tgtagcgatt gcgtcgaaca ttggagggaa acaagcattg   1080
gagactgtcc aacggctcct tcccgtgttg tgtcaagccc acggtttgac gcctgcacaa   1140
gtggtcgcca tcgcctcgaa tggcggcggt aagcaggcgc tggaaacagt acagcgcctg   1200
ctgcctgtac tgtgccagga tcatggactg accccagacc aggtagtcgc aatcgcgtca   1260
aacggagggg gaaagcaagc cctggaaacc gtgcaaaggt tgttgccggt cctttgtcaa   1320
gaccacggcc ttacaccgga gcaagtcgtg gccattgcaa ataataacgg tggcaaacag   1380
gctcttgaga cggttcagag acttctccca gttctctgtc aagcccacgg gctgactccc   1440
gatcaagttg tagcgattgc gaataacaat ggagggaaac aagcattgga gactgtccaa   1500
cggctccttc ccgtgttgtg tcaagcccac ggtttgacgc ctgcacaagt ggtcgccatc   1560
gccaacaaca acggcggtaa gcaggcgctg gaaacagtac agcgcctgct gcctgtactg   1620
tgccaggatc atggactgac cccagaccag gtagtcgcaa tcgcgtcgaa cattggggga   1680
aagcaagccc tggaaaccgt gcaaaggttg ttgccggtcc tttgtcaaga ccacggcctt   1740
acaccggagc aagtcgtggc cattgcatcc cacgacggtg gcaaacaggc tcttgagacg   1800
gttcagagac ttctcccagt tctctgtcaa gcccacgggc tgactcccga tcaagttgta   1860
gcgattgcgt ccaacggtgg agggaaacaa gcattggaga ctgtccaacg gctccttccc   1920
gtgttgtgtc aagcccacgg tttgacgcct gcacaagtgg tcgccatcgc cagccatgat   1980
ggcggtaagc aggcgctgga aacagtacag cgcctgctgc ctgtactgtg ccaggatcat   2040
ggactgaccc cagaccaggt agtcgcaatc gcgtcaaacg gagggggaaa gcaagccctg   2100
gaaaccgtgc aaaggttgtt gccggtcctt tgtcaagacc acggcctgac acccgaacag   2160
```

gtggtcgcca ttgcttctaa tgggggagga cggccagcct tggag 2205

<210> SEQ ID NO 38
<211> LENGTH: 2715
<212> TYPE: DNA
<213> ORGANISM: Homo sapiens

<400> SEQUENCE: 38
atggtggact tgaggacact cggttattcg caacagcaac aggagaaaat caagcctaag 60
gtcaggagca ccgtcgcgca acaccacgag gcgcttgtgg ggcatggctt cactcatgcg 120
catattgtcg cgctttcaca gcaccctgcg gcgcttggga cggtggctgt caaataccaa 180
gatatgattg cggccctgcc cgaagccacg cacgaggcaa ttgtaggggt cggtaaacag 240
tggtcgggag cgcgagcact tgaggcgctg ctgactgtgg cgggtgagct tagggggcct 300
ccgctccagc tcgacaccgg gcagctgctg aagatcgcga agagaggggg agtaacagcg 360
gtagaggcag tgcacgcctg gcgcaatgcg ctcaccgggg ccccccttgaa cctgacccca 420 gaccaggtag tcgcaatcgc gaacaataat gggggaaagc aagccctgga aaccgtgcaa 480
aggttgttgc cggtcctttg tcaagaccac ggccttacac cggagcaagt cgtggccatt 540
gcatcccacg acggtggcaa acaggctctt gagacggttc agagacttct cccagttctc 600
tgtcaagccc acgggctgac tcccgatcaa gttgtagcga ttgcgtcgca tgacggaggg 660
aaacaagcat tggagactgt ccaacggctc cttcccgtgt tgtgtcaagc ccacggtttg 720
acgcctgcac aagtggtcgc catcgccaac aacaacggcg gtaagcaggc gctggaaaca 780
gtacagcgcc tgctgcctgt actgtgccag gatcatggac tgaccccaga ccaggtagtc 840
gcaatcgcgt cacatgacgg gggaaagcaa gccctggaaa ccgtgcaaag gttgttgccg 900
gtcctttgtc aagaccacgg ccttacaccg gagcaagtcg tggccattgc atcccacgac 960
ggtggcaaac aggctcttga gacggttcag agacttctcc cagttctctg tcaagcccac 1020
gggctgactc ccgatcaagt tgtagcgatt gcgtccaacg gtggagggaa acaagcattg 1080
gagactgtcc aacggctcct tcccgtgttg tgtcaagccc acggtttgac gcctgcacaa 1140
gtggtcgcca tcgccagcca tgatggcggt aagcaggcgc tggaaacagt acagcgcctg 1200
ctgcctgtac tgtgccagga tcatggactg accccagacc aggtagtcgc aatcgcgtca 1260
aacggagggg gaaagcaagc cctggaaacc gtgcaaaggt tgttgccggt cctttgtcaa 1320
gaccacggcc ttacaccgga gcaagtcgtg gccattgcaa gcaacatcgg tggcaaacag 1380
gctcttgaga cggttcagag acttctccca gttctctgtc aagcccacgg gctgactccc 1440
gatcaagttg tagcgattgc gtcgcatgac ggagggaaac aagcattgga gactgtccaa 1500
cggctccttc ccgtgttgtg tcaagcccac ggtttgacgc ctgcacaagt ggtcgccatc 1560
gccagccatg atggcggtaa gcaggcgctg gaaacagtac agcgcctgct gcctgtactg 1620
tgccaggatc atggactgac cccagaccag gtagtcgcaa tcgcgtcaca tgacggggga 1680
aagcaagccc tggaaaccgt gcaaaggttg ttgccggtcc tttgtcaaga ccacggcctt 1740
acaccggagc aagtcgtggc cattgcaagc aatgggggtg gcaaacaggc tcttgagacg 1800
gttcagagac ttctcccagt tctctgtcaa gcccacgggc tgactcccga tcaagttgta 1860
gcgattgcga ataacaatgg agggaaacaa gcattggaga ctgtccaacg gctccttccc 1920
gtgttgtgtc aagcccacgg tttgacgcct gcacaagtgg tcgccatcgc ctccaatatt 1980
ggcggtaagc aggcgctgga aacagtacag cgcctgctgc ctgtactgtg ccaggatcat 2040
ggactgaccc cagaccaggt agtcgcaatc gcgtcacatg acgggggaaa gcaagccctg 2100

```
gaaaccgtgc aaaggttgtt gccggtcctt tgtcaagacc acggccttac accggagcaa   2160
gtcgtggcca ttgcaagcaa catcggtggc aaacaggctc ttgagacggt tcagagactt   2220
ctcccagttc tctgtcaagc ccacgggctg actcccgatc aagttgtagc gattgcgtcg   2280
catgacggag ggaaacaagc attggagact gtccaacggc tccttcccgt gttgtgtcaa   2340
gcccacggtt tgacgcctgc acaagtggtc gccatcgcct ccaatattgg cggtaagcag   2400
gcgctggaaa cagtacagcg cctgctgcct gtactgtgcc aggatcatgg actgacccca   2460
gaccaggtag tcgcaatcgc gtcaaacgga gggggaaagc aagccctgga aaccgtgcaa   2520
aggttgttgc cggtcctttg tcaagaccac ggccttacac cggagcaagt cgtggccatt   2580
gcaagcaatg gggtggcaa acaggctctt gagacggttc agagacttct cccagttctc   2640
tgtcaagccc acgggctgac acccgaacag gtggtcgcca ttgctaataa taacggagga   2700
cggccagcct tggag                                                    2715
```

<210> SEQ ID NO 39
<211> LENGTH: 2817
<212> TYPE: DNA
<213> ORGANISM: Homo sapiens

<400> SEQUENCE: 39

```
atggtggact tgaggacact cggttattcg caacagcaac aggagaaaat caagcctaag     60
gtcaggagca ccgtcgcgca acaccacgag gcgcttgtgg ggcatggctt cactcatgcg    120
catattgtcg cgctttcaca gcaccctgcg gcgcttggga cggtggctgt caaataccaa    180
gatatgattg cggccctgcc cgaagccacg cacgaggcaa ttgtaggggt cggtaaacag    240
tggtcgggag cgcgagcact tgaggcgctg ctgactgtgg cgggtgagct tagggggcct    300
ccgctccagc tcgacaccgg gcagctgctg aagatcgcga agagaggggg agtaacagcg    360
gtagaggcag tgcacgcctg gcgcaatgcg ctcaccgggg ccccccttgaa cctgacccca   420
gaccaggtag tcgcaatcgc gtcacatgac gggggaaagc aagccctgga aaccgtgcaa    480
aggttgttgc cggtcctttg tcaagaccac ggccttacac cggagcaagt cgtggccatt    540
gcatcccacg acggtggcaa acaggctctt gagacggttc agagacttct cccagttctc    600
tgtcaagccc acgggctgac tcccgatcaa gttgtagcga ttgcgtcgca tgacggaggg    660
aaacaagcat tggagactgt ccaacggctc cttcccgtgt tgtgtcaagc ccacggtttg    720
acgcctgcac aagtggtcgc catcgccaac aacaacggcg gtaagcaggc gctggaaaca    780
gtacagcgcc tgctgcctgt actgtgccag gatcatggac tgaccccaga ccaggtagtc    840
gcaatcgcgt cacatgacgg gggaaagcaa gccctggaaa ccgtgcaaag gttgttgccg    900
gtcctttgtc aagaccacgg ccttacaccg gagcaagtcg tggccattgc atcccacgac    960
ggtggcaaac aggctcttga gacggttcag agacttctcc cagttctctg tcaagcccac   1020
gggctgactc ccgatcaagt tgtagcgatt gcgtcgaaca ttggagggaa acaagcattg   1080
gagactgtcc aacggctcct tcccgtgttg tgtcaagccc acggtttgac gcctgcacaa   1140
gtggtcgcca tcgccaacaa caacggcggt aagcaggcgc tggaaacagt acagcgcctg   1200
ctgcctgtac tgtgccagga tcatggactg accccagacc aggtagtcgc aatcgcgtca   1260
aacggagggg gaaagcaagc cctggaaacc gtgcaaaggt tgttgccggt cctttgtcaa   1320
gaccacggcc ttacaccgga gcaagtcgtg gccattgcat cccacgacgg tggcaaacag   1380
gctcttgaga cggttcagag acttctccca gttctctgtc aagcccacgg gctgactccc   1440
```

```
gatcaagttg tagcgattgc gtcgcatgac ggagggaaac aagcattgga gactgtccaa   1500
cggctccttc ccgtgttgtg tcaagcccac ggtttgacgc ctgcacaagt ggtcgccatc   1560
gccaacaaca acggcggtaa gcaggcgctg gaaacagtac agcgcctgct gcctgtactg   1620
tgccaggatc atggactgac cccagaccag gtagtcgcaa tcgcgtcaca tgacggggga   1680
aagcaagccc tggaaaccgt gcaaaggttg ttgccggtcc tttgtcaaga ccacggcctt   1740
acaccggagc aagtcgtggc cattgcatcc cacgacggtg gcaaacaggc tcttgagacg   1800
gttcagagac ttctcccagt tctctgtcaa gcccacgggc tgactcccga tcaagttgta   1860
gcgattgcgt cgcatgacgg agggaaacaa gcattggaga ctgtccaacg gctccttccc   1920
gtgttgtgtc aagcccacgg tttgacgcct gcacaagtgg tcgccatcgc ctccaatatt   1980
ggcggtaagc aggcgctgga aacagtacag cgcctgctgc ctgtactgtg ccaggatcat   2040
ggactgaccc cagaccaggt agtcgcaatc gcgtcacatg acgggggaaa gcaagccctg   2100
gaaaccgtgc aaaggttgtt gccggtcctt tgtcaagacc acggccttac accggagcaa   2160
gtcgtggcca ttgcaagcaa tgggggtggc aaacaggctc ttgagacggt tcagagactt   2220
ctcccagttc tctgtcaagc ccacgggctg actcccgatc aagttgtagc gattgcgaat   2280
aacaatggag ggaaacaagc attggagact gtccaacggc tccttcccgt gttgtgtcaa   2340
gcccacggtt tgacgcctgc acaagtggtc gccatcgcca acaacaacgg cggtaagcag   2400
gcgctggaaa cagtacagcg cctgctgcct gtactgtgcc aggatcatgg actgacccca   2460
gaccaggtag tcgcaatcgc gtcgaacatt gggggaaagc aagccctgga aaccgtgcaa   2520
aggttgttgc cggtcctttg tcaagaccac ggccttacac cggagcaagt cgtggccatt   2580
gcaagcaaca tcggtggcaa acaggctctt gagacggttc agagacttct cccagttctc   2640
tgtcaagccc acgggctgac tcccgatcaa gttgtagcga ttgcgtcgca tgacggaggg   2700
aaacaagcat tggagactgt ccaacggctc cttcccgtgt tgtgtcaagc ccacggtctg   2760
acacccgaac aggtggtcgc cattgcttct aacatcggag gacggccagc cttggag      2817
```

<210> SEQ ID NO 40
<211> LENGTH: 2817
<212> TYPE: DNA
<213> ORGANISM: Homo sapiens

<400> SEQUENCE: 40

```
atggtggact tgaggacact cggttattcg caacagcaac aggagaaaat caagcctaag     60
gtcaggagca ccgtcgcgca acaccacgag gcgcttgtgg ggcatggctt cactcatgcg    120
catattgtcg cgctttcaca gcaccctgcg gcgcttggga cggtggctgt caaataccaa    180
gatatgattg cggccctgcc cgaagccacg cacgaggcaa ttgtaggggt cggtaaacag    240
tggtcgggag cgcgagcact tgaggcgctg ctgactgtgg cgggtgagct tagggggcct    300
ccgctccagc tcgacaccgg gcagctgctg aagatcgcga agagaggggg agtaacagcg    360
gtagaggcag tgcacgcctg gcgcaatgcg ctcaccgggg ccccccttgaa cctgacccca    420
gaccaggtag tcgcaatcgc gtcacatgac gggggaaagc aagccctgga aaccgtgcaa    480
aggttgttgc cggtcctttg tcaagaccac ggccttacac cggagcaagt cgtggccatt    540
gcatcccacg acggtggcaa acaggctctt gagacggttc agagacttct cccagttctc    600
tgtcaagccc acgggctgac tcccgatcaa gttgtagcga ttgcgaataa caatggaggg    660
aaacaagcat tggagactgt ccaacggctc cttcccgtgt tgtgtcaagc ccacggtttg    720
acgcctgcac aagtggtcgc catcgccagc catgatggcg gtaagcaggc gctggaaaca    780
```

```
gtacagcgcc tgctgcctgt actgtgccag gatcatggac tgaccccaga ccaggtagtc    840
gcaatcgcgt cacatgacgg gggaaagcaa gccctggaaa ccgtgcaaag gttgttgccg    900
gtcctttgtc aagaccacgg ccttacaccg gagcaagtcg tggccattgc atcccacgac    960
ggtggcaaac aggctcttga gacggttcag agacttctcc cagttctctg tcaagcccac   1020
gggctgactc ccgatcaagt tgtagcgatt gcgtcgaaca ttggagggaa acaagcattg   1080
gagactgtcc aacggctcct tcccgtgttg tgtcaagccc acggtttgac gcctgcacaa   1140
gtggtcgcca tcgccagcca tgatggcggt aagcaggcgc tggaaacagt acagcgcctg   1200
ctgcctgtac tgtgccagga tcatggactg accccagacc aggtagtcgc aatcgcgtca   1260
aacggagggg gaaagcaagc cctggaaacc gtgcaaaggt tgttgccggt cctttgtcaa   1320
gaccacggcc ttacaccgga gcaagtcgtg gccattgcaa ataataacgg tggcaaacag   1380
gctcttgaga cggttcagag acttctccca gttctctgtc aagcccacgg gctgactccc   1440
gatcaagttg tagcgattgc gaataacaat ggagggaaac aagcattgga gactgtccaa   1500
cggctccttc ccgtgttgtg tcaagcccac ggtttgacgc ctgcacaagt ggtcgccatc   1560
gcctccaata ttggcggtaa gcaggcgctg gaaacagtac agcgcctgct gcctgtactg   1620
tgccaggatc atggactgac cccagaccag gtagtcgcaa tcgcgtcgaa cattggggga   1680
aagcaagccc tggaaaccgt gcaaaggttg ttgccggtcc tttgtcaaga ccacggcctt   1740
acaccggagc aagtcgtggc cattgcatcc cacgacggtg gcaaacaggc tcttgagacg   1800
gttcagagac ttctcccagt tctctgtcaa gcccacgggc tgactcccga tcaagttgta   1860
gcgattgcgt cgaacattgg agggaaacaa gcattggaga ctgtccaacg gctccttccc   1920
gtgttgtgtc aagcccacgg tttgacgcct gcacaagtgg tcgccatcgc cagccatgat   1980
ggcggtaagc aggcgctgga aacagtacag cgcctgctgc ctgtactgtg ccaggatcat   2040
ggactgaccc cagaccaggt agtcgcaatc gcgaacaata atgggggaaa gcaagccctg   2100
gaaaccgtgc aaaggttgtt gccggtcctt tgtcaagacc acggccttac accggagcaa   2160
gtcgtggcca ttgcaaataa taacggtggc aaacaggctc ttgagacggt tcagagactt   2220
ctcccagttc tctgtcaagc ccacgggctg actcccgatc aagttgtagc gattgcgaat   2280
aacaatggag ggaaacaagc attggagact gtccaacggc tccttcccgt gttgtgtcaa   2340
gcccacggtt tgacgcctgc acaagtggtc gccatcgcct cgaatggcgg cggtaagcag   2400
gcgctggaaa cagtacagcg cctgctgcct gtactgtgcc aggatcatgg actgacccca   2460
gaccaggtag tcgcaatcgc gtcaaacgga gggggaaagc aagccctgga aaccgtgcaa   2520
aggttgttgc cggtcctttg tcaagaccac ggccttacac cggagcaagt cgtggccatt   2580
gcatcccacg acggtggcaa acaggctctt gagacggttc agagacttct cccagttctc   2640
tgtcaagccc acgggctgac tcccgatcaa gttgtagcga ttgcgtcgca tgacggaggg   2700
aaacaagcat tggagactgt ccaacggctc cttcccgtgt tgtgtcaagc ccacggtctg   2760
acacccgaac aggtggtcgc cattgcttct aacatcggag gacggccagc cttggag      2817
```

<210> SEQ ID NO 41
<211> LENGTH: 2817
<212> TYPE: DNA
<213> ORGANISM: Homo sapiens

<400> SEQUENCE: 41

```
atggtggact tgaggacact cggttattcg caacagcaac aggagaaaat caagcctaag     60
```

-continued

```
gtcaggagca ccgtcgcgca acaccacgag gcgcttgtgg ggcatggctt cactcatgcg    120
catattgtcg cgctttcaca gcaccctgcg gcgcttggga cggtggctgt caaataccaa    180
gatatgattg cggccctgcc cgaagccacg cacgaggcaa ttgtaggggt cggtaaacag    240
tggtcgggag cgcgagcact tgaggcgctg ctgactgtgg cgggtgagct taggggggcct   300
ccgctccagc tcgacaccgg gcagctgctg aagatcgcga agagaggggg agtaacagcg    360
gtagaggcag tgcacgcctg gcgcaatgcg ctcaccgggg ccccccttgaa cctgacccca   420
gaccaggtag tcgcaatcgc gaacaataat gggggaaagc aagccctgga aaccgtgcaa    480
aggttgttgc cggtcctttg tcaagaccac ggccttacac cggagcaagt cgtggccatt    540
gcaaataata acggtggcaa acaggctctt gagacggttc agagacttct cccagttctc    600
tgtcaagccc acgggctgac tcccgatcaa gttgtagcga ttgcgtcgca tgacggaggg    660
aaacaagcat tggagactgt ccaacggctc cttcccgtgt tgtgtcaagc ccacggtttg    720
acgcctgcac aagtggtcgc catcgccagc catgatggcg gtaagcaggc gctggaaaca    780
gtacagcgcc tgctgcctgt actgtgccag gatcatggac tgaccccaga ccaggtagtc    840
gcaatcgcgt cgaacattgg gggaaagcaa gccctggaaa ccgtgcaaag gttgttgccg    900
gtcctttgtc aagaccacgg ccttacaccg gagcaagtcg tggccattgc aaataataac    960
ggtggcaaac aggctcttga gacggttcag agacttctcc cagttctctg tcaagcccac   1020
gggctgactc ccgatcaagt tgtagcgatt gcgaataaca atggagggaa acaagcattg   1080
gagactgtcc aacggctcct tcccgtgttg tgtcaagccc acggtttgac gcctgcacaa   1140
gtggtcgcca tcgccagcca tgatggcggt aagcaggcgc tggaaacagt acagcgcctg   1200
ctgcctgtac tgtgccagga tcatggactg accccagacc aggtagtcgc aatcgcgtca   1260
aacggagggg gaaagcaagc cctggaaacc gtgcaaaggt tgttgccggt cctttgtcaa   1320
gaccacggcc ttacaccgga gcaagtcgtg gccattgcaa ataataacgg tggcaaacag   1380
gctcttgaga cggttcagag acttctccca gttctctgtc aagcccacgg gctgactccc   1440
gatcaagttg tagcgattgc gtcgcatgac ggagggaaac aagcattgga gactgtccaa   1500
cggctccttc ccgtgttgtg tcaagcccac ggtttgacgc ctgcacaagt ggtcgccatc   1560
gccagccatg atggcggtaa gcaggcgctg gaaacagtac agcgcctgct gcctgtactg   1620
tgccaggatc atggactgac cccagaccag gtagtcgcaa tcgcgaacaa taatggggga   1680
aagcaagccc tggaaaccgt gcaaaggttg ttgccggtcc tttgtcaaga ccacggcctt   1740
acaccggagc aagtcgtggc cattgcatcc cacgacggtg gcaaacaggc tcttgagacg   1800
gttcagagac ttctcccagt tctctgtcaa gcccacgggc tgactcccga tcaagttgta   1860
gcgattgcgt cgcatgacgg agggaaacaa gcattggaga ctgtccaacg gctccttccc   1920
gtgttgtgtc aagcccacgg tttgacgcct gcacaagtgg tcgccatcgc ctcgaatggc   1980
ggcggtaagc aggcgctgga aacagtacag cgcctgctgc ctgtactgtg ccaggatcat   2040
ggactgaccc cagaccaggt agtcgcaatc gcgtcacatg acgggggaaa gcaagccctg   2100
gaaaccgtgc aaaggttgtt gccggtcctt tgtcaagacc acggccttac accggagcaa   2160
gtcgtggcca ttgcaagcaa tgggggtggc aaacaggctc ttgagacggt tcagagactt   2220
ctcccagttc tctgtcaagc ccacgggctg actcccgatc aagttgtagc gattgcgtcg   2280
catgacggag ggaaacaagc attggagact gtccaacggc tccttcccgt gttgtgtcaa   2340
gcccacggtt tgacgcctgc acaagtggtc gccatcgcct ccaatattgg cggtaagcag   2400
gcgctggaaa cagtacagcg cctgctgcct gtactgtgcc aggatcatgg actgacccca   2460
```

```
gaccaggtag tcgcaatcgc gtcacatgac gggggaaagc aagccctgga aaccgtgcaa   2520
aggttgttgc cggtcctttg tcaagaccac ggccttacac cggagcaagt cgtggccatt   2580
gcatcccacg acggtggcaa acaggctctt gagacggttc agagacttct cccagttctc   2640
tgtcaagccc acgggctgac tcccgatcaa gttgtagcga ttgcgtcgca tgacggaggg   2700
aaacaagcat tggagactgt ccaacggctc cttcccgtgt tgtgtcaagc ccacggtctg   2760
acacccgaac aggtggtcgc cattgcttct aatgggggag gacggccagc cttggag      2817
```

<210> SEQ ID NO 42
<211> LENGTH: 2817
<212> TYPE: DNA
<213> ORGANISM: Homo sapiens

<400> SEQUENCE: 42

```
atggtggact tgaggacact cggttattcg caacagcaac aggagaaaat caagcctaag     60
gtcaggagca ccgtcgcgca acaccacgag gcgcttgtgg ggcatggctt cactcatgcg    120
catattgtcg cgctttcaca gcaccctgcg gcgcttggga cggtggctgt caaataccaa    180
gatatgattg cggccctgcc cgaagccacg cacgaggcaa ttgtaggggt cggtaaacag    240
tggtcgggag cgcgagcact tgaggcgctg ctgactgtgg cgggtgagct tagggggcct    300
ccgctccagc tcgacaccgg gcagctgctg aagatcgcga agagaggggg agtaacagcg    360
gtagaggcag tgcacgcctg gcgcaatgcg ctcaccgggg ccccccttgaa cctgacccca    420
gaccaggtag tcgcaatcgc gtcacatgac gggggaaagc aagccctgga aaccgtgcaa    480
aggttgttgc cggtcctttg tcaagaccac ggccttacac cggagcaagt cgtggccatt    540
gcatcccacg acggtggcaa acaggctctt gagacggttc agagacttct cccagttctc    600
tgtcaagccc acgggctgac tcccgatcaa gttgtagcga ttgcgaataa caatggaggg    660
aaacaagcat tggagactgt ccaacggctc cttcccgtgt tgtgtcaagc ccacggtttg    720
acgcctgcac aagtggtcgc catcgccaac aacaacggcg gtaagcaggc gctggaaaca    780
gtacagcgcc tgctgcctgt actgtgccag gatcatggac tgaccccaga ccaggtagtc    840
gcaatcgcga acaataatgg gggaaagcaa gccctggaaa ccgtgcaaag gttgttgccg    900
gtcctttgtc aagaccacgg ccttacaccg gagcaagtcg tggccattgc aagcaatggg    960
ggtggcaaac aggctcttga gacggttcag agacttctcc cagttctctg tcaagcccac   1020
gggctgactc ccgatcaagt tgtagcgatt gcgtcgcatg acggagggaa acaagcattg   1080
gagactgtcc aacggctcct tcccgtgttg tgtcaagccc acggtttgac gcctgcacaa   1140
gtggtcgcca tcgccagcca tgatggcggt aagcaggcgc tggaaacagt acagcgcctg   1200
ctgcctgtac tgtgccagga tcatggactg accccagacc aggtagtcgc aatcgcgtca   1260
aacggagggg gaaagcaagc cctggaaacc gtgcaaaggt tgttgccggt cctttgtcaa   1320
gaccacggcc ttacaccgga gcaagtcgtg gccattgcat cccacgacgg tggcaaacag   1380
gctcttgaga cggttcagag acttctccca gttctctgtc aagcccacgg gctgactccc   1440
gatcaagttg tagcgattgc gtcgcatgac ggagggaaac aagcattgga gactgtccaa   1500
cggctccttc ccgtgttgtg tcaagcccac ggtttgacgc ctgcacaagt ggtcgccatc   1560
gcctccaata ttggcggtaa gcaggcgctg gaaacagtac agcgcctgct gcctgtactg   1620
tgccaggatc atggactgac cccagaccag gtagtcgcaa tcgcgtcaca tgacggggga   1680
aagcaagccc tggaaaccgt gcaaaggttg ttgccggtcc tttgtcaaga ccacggcctt   1740
```

```
acaccggagc aagtcgtggc cattgcatcc cacgacggtg gcaaacaggc tcttgagacg   1800

gttcagagac ttctcccagt tctctgtcaa gcccacgggc tgactcccga tcaagttgta   1860

gcgattgcgt cgaacattgg agggaaacaa gcattggaga ctgtccaacg gctccttccc   1920

gtgttgtgtc aagcccacgg tttgacgcct gcacaagtgg tcgccatcgc ctccaatatt   1980

ggcggtaagc aggcgctgga aacagtacag cgcctgctgc ctgtactgtg ccaggatcat   2040

ggactgaccc cagaccaggt agtcgcaatc gcgtcacatg acgggggaaa gcaagccctg   2100

gaaaccgtgc aaaggttgtt gccggtcctt tgtcaagacc acggccttac accggagcaa   2160

gtcgtggcca ttgcatccca cgacggtggc aaacaggctc ttgagacggt tcagagactt   2220

ctcccagttc tctgtcaagc ccacgggctg actcccgatc aagttgtagc gattgcgtcg   2280

catgacggag ggaaacaagc attggagact gtccaacggc tccttcccgt gttgtgtcaa   2340

gcccacggtt tgacgcctgc acaagtggtc gccatcgcct ccaatattgg cggtaagcag   2400

gcgctggaaa cagtacagcg cctgctgcct gtactgtgcc aggatcatgg actgacccca   2460

gaccaggtag tcgcaatcgc gaacaataat gggggaaagc aagccctgga aaccgtgcaa   2520

aggttgttgc cggtcctttg tcaagaccac ggccttacac cggagcaagt cgtggccatt   2580

gcaagcaaca tcggtggcaa acaggctctt gagacggttc agagacttct cccagttctc   2640

tgtcaagccc acgggctgac tcccgatcaa gttgtagcga ttgcgtcgca tgacggaggg   2700

aaacaagcat tggagactgt ccaacggctc cttcccgtgt tgtgtcaagc ccacggtctg   2760

acacccgaac aggtggtcgc cattgcttct aacatcggag gacggccagc cttggag      2817
```

<210> SEQ ID NO 43
<211> LENGTH: 2817
<212> TYPE: DNA
<213> ORGANISM: Homo sapiens

<400> SEQUENCE: 43

```
atggtggact tgaggacact cggttattcg caacagcaac aggagaaaat caagcctaag     60

gtcaggagca ccgtcgcgca acaccacgag gcgcttgtgg ggcatggctt cactcatgcg    120

catattgtcg cgctttcaca gcaccctgcg gcgcttggga cggtggctgt caaataccaa    180

gatatgattg cggccctgcc cgaagccacg cacgaggcaa ttgtaggggt cggtaaacag    240

tggtcgggag cgcgagcact tgaggcgctg ctgactgtgg cgggtgagct tagggggcct    300

ccgctccagc tcgacaccgg gcagctgctg aagatcgcga agagaggggg agtaacagcg    360

gtagaggcag tgcacgcctg gcgcaatgcg ctcaccgggg ccccccttgaa cctgacccca    420

gaccaggtag tcgcaatcgc gaacaataat gggggaaagc aagccctgga aaccgtgcaa    480

aggttgttgc cggtcctttg tcaagaccac ggccttacac cggagcaagt cgtggccatt    540

gcatcccacg acggtggcaa acaggctctt gagacggttc agagacttct cccagttctc    600

tgtcaagccc acgggctgac tcccgatcaa gttgtagcga ttgcgtcgca tgacggaggg    660

aaacaagcat tggagactgt ccaacggctc cttcccgtgt tgtgtcaagc ccacggtttg    720

acgcctgcac aagtggtcgc catcgccagc catgatggcg gtaagcaggc gctggaaaca    780

gtacagcgcc tgctgcctgt actgtgccag gatcatggac tgaccccaga ccaggtagtc    840

gcaatcgcgt cgaacattgg gggaaagcaa gccctggaaa ccgtgcaaag gttgttgccg    900

gtcctttgtc aagaccacgg ccttacaccg gagcaagtcg tggccattgc atcccacgac    960

ggtggcaaac aggctcttga gacggttcag agacttctcc cagttctctg tcaagcccac   1020

gggctgactc ccgatcaagt tgtagcgatt gcgtcgcatg acggagggaa acaagcattg   1080
```

gagactgtcc aacggctcct tcccgtgttg tgtcaagccc acggtttgac gcctgcacaa 1140
gtggtcgcca tcgcctcgaa tggcggcggt aagcaggcgc tggaaacagt acagcgcctg 1200
ctgcctgtac tgtgccagga tcatggactg accccagacc aggtagtcgc aatcgcgtcg 1260
aacattgggg gaaagcaagc cctggaaacc gtgcaaaggt tgttgccggt cctttgtcaa 1320
gaccacggcc ttacaccgga gcaagtcgtg gccattgcaa ataataacgg tggcaaacag 1380
gctcttgaga cggttcagag acttctccca gttctctgtc aagcccacgg gctgactccc 1440
gatcaagttg tagcgattgc gtcgcatgac ggagggaaac aagcattgga gactgtccaa 1500
cggctccttc ccgtgttgtg tcaagcccac ggtttgacgc ctgcacaagt ggtcgccatc 1560
gccagccatg atggcggtaa gcaggcgctg gaaacagtac agcgcctgct gcctgtactg 1620
tgccaggatc atggactgac cccagaccag gtagtcgcaa tcgcgtcgaa cattgggga 1680 aagcaagccc tggaaaccgt gcaaaggttg ttgccggtcc tttgtcaaga ccacggcctt 1740
acaccggagc aagtcgtggc cattgcaaat aataacggtg gcaaacaggc tcttgagacg 1800
gttcagagac ttctcccagt tctctgtcaa gcccacgggc tgactcccga tcaagttgta 1860
gcgattgcgt cgaacattgg agggaaacaa gcattggaga ctgtccaacg gctccttccc 1920
gtgttgtgtc aagcccacgg tttgacgcct gcacaagtgg tcgccatcgc caacaacaac 1980
ggcggtaagc aggcgctgga aacagtacag cgcctgctgc ctgtactgtg ccaggatcat 2040
ggactgaccc cagaccaggt agtcgcaatc gcgaacaata atgggggaaa gcaagccctg 2100
gaaaccgtgc aaaggttgtt gccggtcctt tgtcaagacc acggccttac accggagcaa 2160
gtcgtggcca ttgcaaataa taacggtggc aaacaggctc ttgagacggt tcagagactt 2220
ctcccagttc tctgtcaagc ccacgggctg actcccgatc aagttgtagc gattgcgtcg 2280
aacattggag ggaaacaagc attggagact gtccaacggc tccttcccgt gttgtgtcaa 2340
gcccacggtt tgacgcctgc acaagtggtc gccatcgcct cgaatggcgg cggtaagcag 2400
gcgctggaaa cagtacagcg cctgctgcct gtactgtgcc aggatcatgg actgacccca 2460
gaccaggtag tcgcaatcgc gtcacatgac gggggaaagc aagccctgga aaccgtgcaa 2520
aggttgttgc cggtcctttg tcaagaccac ggccttacac cggagcaagt cgtggccatt 2580
gcaagcaaca tcggtggcaa acaggctctt gagacggttc agagacttct cccagttctc 2640
tgtcaagccc acgggctgac tcccgatcaa gttgtagcga ttgcgaataa caatggaggg 2700
aaacaagcat tggagactgt ccaacggctc cttcccgtgt tgtgtcaagc ccacggtctg 2760
acacccgaac aggtggtcgc cattgcttcc cacgacggag gacggccagc cttggag 2817

<210> SEQ ID NO 44
<211> LENGTH: 2817
<212> TYPE: DNA
<213> ORGANISM: Homo sapiens

<400> SEQUENCE: 44
atggtggact tgaggacact cggttattcg caacagcaac aggagaaaat caagcctaag 60
gtcaggagca ccgtcgcgca acaccacgag gcgcttgtgg ggcatggctt cactcatgcg 120
catattgtcg cgctttcaca gcaccctgcg gcgcttggga cggtggctgt caaataccaa 180
gatatgattg cggccctgcc cgaagccacg cacgaggcaa ttgtaggggt cggtaaacag 240
tggtcgggag cgcgagcact tgaggcgctg ctgactgtgg cgggtgagct tagggggcct 300
ccgctccagc tcgacaccgg gcagctgctg aagatcgcga agagaggggg agtaacagcg 360

```
gtagaggcag tgcacgcctg gcgcaatgcg ctcaccgggg ccccccttgaa cctgacccca    420
gaccaggtag tcgcaatcgc gaacaataat gggggaaagc aagccctgga aaccgtgcaa    480
aggttgttgc cggtcctttg tcaagaccac ggccttacac cggagcaagt cgtggccatt    540
gcatcccacg acggtggcaa acaggctctt gagacggttc agagacttct cccagttctc    600
tgtcaagccc acgggctgac tcccgatcaa gttgtagcga ttgcgtcgca tgacggaggg    660
aaacaagcat tggagactgt ccaacggctc cttcccgtgt tgtgtcaagc ccacggtttg    720
acgcctgcac aagtggtcgc catcgccagc catgatggcg gtaagcaggc gctggaaaca    780
gtacagcgcc tgctgcctgt actgtgccag gatcatggac tgaccccaga ccaggtagtc    840
gcaatcgcgt cgaacattgg gggaaagcaa gccctggaaa ccgtgcaaag gttgttgccg    900
gtcctttgtc aagaccacgg ccttacaccg gagcaagtcg tggccattgc aagcaacatc    960
ggtggcaaac aggctcttga gacggttcag agacttctcc cagttctctg tcaagcccac   1020
gggctgactc ccgatcaagt tgtagcgatt gcgaataaca atggagggaa acaagcattg   1080
gagactgtcc aacggctcct tcccgtgttg tgtcaagccc acggtttgac gcctgcacaa   1140
gtggtcgcca tcgccaacaa caacggcggt aagcaggcgc tggaaacagt acagcgcctg   1200
ctgcctgtac tgtgccagga tcatggactg accccagacc aggtagtcgc aatcgcgtca   1260
aacggagggg gaaagcaagc cctggaaacc gtgcaaaggt tgttgccggt cctttgtcaa   1320
gaccacggcc ttacaccgga gcaagtcgtg gccattgcat cccacgacgg tggcaaacag   1380
gctcttgaga cggttcagag acttctccca gttctctgtc aagcccacgg gctgactccc   1440
gatcaagttg tagcgattgc gtcgaacatt ggagggaaac aagcattgga gactgtccaa   1500
cggctccttc ccgtgttgtg tcaagcccac ggtttgacgc ctgcacaagt ggtcgccatc   1560
gcctcgaatg gcggcggtaa gcaggcgctg gaaacagtac agcgcctgct gcctgtactg   1620
tgccaggatc atggactgac cccagaccag gtagtcgcaa tcgcgtcaca tgacggggga   1680
aagcaagccc tggaaaccgt gcaaaggttg ttgccggtcc tttgtcaaga ccacggcctt   1740
acaccggagc aagtcgtggc cattgcatcc cacgacggtg gcaaacaggc tcttgagacg   1800
gttcagagac ttctcccagt tctctgtcaa gcccacgggc tgactcccga tcaagttgta   1860
gcgattgcgt cgaacattgg agggaaacaa gcattggaga ctgtccaacg gctccttccc   1920
gtgttgtgtc aagcccacgg tttgacgcct gcacaagtgg tcgccatcgc caacaacaac   1980
ggcggtaagc aggcgctgga aacagtacag cgcctgctgc ctgtactgtg ccaggatcat   2040
ggactgaccc cagaccaggt agtcgcaatc gcgaacaata atgggggaaa gcaagccctg   2100
gaaaccgtgc aaaggttgtt gccggtcctt tgtcaagacc acggccttac accggagcaa   2160
gtcgtggcca ttgcaaataa taacggtggc aaacaggctc ttgagacggt tcagagactt   2220
ctcccagttc tctgtcaagc ccacgggctg actcccgatc aagttgtagc gattgcgtcg   2280
catgacggag ggaaacaagc attggagact gtccaacggc tccttcccgt gttgtgtcaa   2340
gcccacggtt tgacgcctgc acaagtggtc gccatcgcca gccatgatgg cggtaagcag   2400
gcgctggaaa cagtacagcg cctgctgcct gtactgtgcc aggatcatgg actgacccca   2460
gaccaggtag tcgcaatcgc gtcgaacatt gggggaaagc aagccctgga aaccgtgcaa   2520
aggttgttgc cggtcctttg tcaagaccac ggccttacac cggagcaagt cgtggccatt   2580
gcaaataata acggtggcaa acaggctctt gagacggttc agagacttct cccagttctc   2640
tgtcaagccc acgggctgac tcccgatcaa gttgtagcga ttgcgaataa caatggaggg   2700
aaacaagcat tggagactgt ccaacggctc cttcccgtgt tgtgtcaagc ccacggtctg   2760
```

acacccgaac aggtggtcgc cattgcttcc cacgacggag gacggccagc cttggag 2817

<210> SEQ ID NO 45
<211> LENGTH: 2817
<212> TYPE: DNA
<213> ORGANISM: Homo sapiens

<400> SEQUENCE: 45
atggtggact tgaggacact cggttattcg caacagcaac aggagaaaat caagcctaag 60
gtcaggagca ccgtcgcgca acaccacgag gcgcttgtgg ggcatggctt cactcatgcg 120
catattgtcg cgctttcaca gcaccctgcg gcgcttggga cggtggctgt caaataccaa 180
gatatgattg cggccctgcc cgaagccacg cacgaggcaa ttgtaggggt cggtaaacag 240
tggtcgggag cgcgagcact tgaggcgctg ctgactgtgg cgggtgagct tagggggcct 300
ccgctccagc tcgacaccgg gcagctgctg aagatcgcga agagaggggg agtaacagcg 360
gtagaggcag tgcacgcctg gcgcaatgcg ctcaccgggg ccccccttgaa cctgacccca 420 gaccaggtag tcgcaatcgc gaacaataat gggggaaagc aagccctgga aaccgtgcaa 480
aggttgttgc cggtcctttg tcaagaccac ggccttacac cggagcaagt cgtggccatt 540
gcaaataata acggtggcaa acaggctctt gagacggttc agagacttct cccagttctc 600
tgtcaagccc acgggctgac tcccgatcaa gttgtagcga ttgcgtcgca tgacggaggg 660
aaacaagcat tggagactgt ccaacggctc cttcccgtgt tgtgtcaagc ccacggtttg 720
acgcctgcac aagtggtcgc catcgcctcc aatattggcg gtaagcaggc gctggaaaca 780
gtacagcgcc tgctgcctgt actgtgccag gatcatggac tgaccccaga ccaggtagtc 840
gcaatcgcga acaataatgg gggaaagcaa gccctggaaa ccgtgcaaag gttgttgccg 900
gtcctttgtc aagaccacgg ccttacaccg gagcaagtcg tggccattgc atcccacgac 960
ggtggcaaac aggctcttga gacggttcag agacttctcc cagttctctg tcaagcccac 1020
gggctgactc ccgatcaagt tgtagcgatt gcgtcgaaca ttggagggaa acaagcattg 1080
gagactgtcc aacggctcct tcccgtgttg tgtcaagccc acggtttgac gcctgcacaa 1140
gtggtcgcca tcgccaacaa caacggcggt aagcaggcgc tggaaacagt acagcgcctg 1200
ctgcctgtac tgtgccagga tcatggactg accccagacc aggtagtcgc aatcgcgtca 1260
catgacgggg gaaagcaagc cctggaaacc gtgcaaaggt tgttgccggt cctttgtcaa 1320
gaccacggcc ttacaccgga gcaagtcgtg gccattgcat cccacgacgg tggcaaacag 1380
gctcttgaga cggttcagag acttctccca gttctctgtc aagcccacgg gctgactccc 1440
gatcaagttg tagcgattgc gtcgcatgac ggagggaaac aagcattgga gactgtccaa 1500
cggctccttc ccgtgttgtg tcaagcccac ggtttgacgc ctgcacaagt ggtcgccatc 1560
gcctcgaatg gcggcggtaa gcaggcgctg gaaacagtac agcgcctgct gcctgtactg 1620
tgccaggatc atggactgac cccagaccag gtagtcgcaa tcgcgtcaaa cggaggggga 1680
aagcaagccc tggaaaccgt gcaaaggttg ttgccggtcc tttgtcaaga ccacggcctt 1740
acaccggagc aagtcgtggc cattgcatcc cacgacggtg gcaaacaggc tcttgagacg 1800
gttcagagac ttctcccagt tctctgtcaa gcccacgggc tgactcccga tcaagttgta 1860
gcgattgcgt cgaacattgg agggaaacaa gcattggaga ctgtccaacg gctccttccc 1920
gtgttgtgtc aagcccacgg tttgacgcct gcacaagtgg tcgccatcgc caacaacaac 1980
ggcggtaagc aggcgctgga aacagtacag cgcctgctgc ctgtactgtg ccaggatcat 2040

```
ggactgaccc cagaccaggt agtcgcaatc gcgtcaaacg gagggggaaa gcaagccctg   2100
gaaaccgtgc aaaggttgtt gccggtcctt tgtcaagacc acggccttac accggagcaa   2160
gtcgtggcca ttgcaaataa taacggtggc aaacaggctc ttgagacggt tcagagactt   2220
ctcccagttc tctgtcaagc ccacgggctg actcccgatc aagttgtagc gattgcgaat   2280
aacaatggag ggaaacaagc attggagact gtccaacggc tccttcccgt gttgtgtcaa   2340
gcccacggtt tgacgcctgc acaagtggtc gccatcgcct ccaatattgg cggtaagcag   2400
gcgctggaaa cagtacagcg cctgctgcct gtactgtgcc aggatcatgg actgacccca   2460
gaccaggtag tcgcaatcgc gtcaaacgga gggggaaagc aagccctgga aaccgtgcaa   2520
aggttgttgc cggtcctttg tcaagaccac ggccttacac cggagcaagt cgtggccatt   2580
gcaaataata acggtggcaa acaggctctt gagacggttc agagacttct cccagttctc   2640
tgtcaagccc acgggctgac tcccgatcaa gttgtagcga ttgcgtcgaa cattggaggg   2700
aaacaagcat tggagactgt ccaacggctc cttcccgtgt tgtgtcaagc ccacggtctg   2760
acacccgaac aggtggtcgc cattgctaat aataacggag gacggccagc cttggag      2817
```

```
<210> SEQ ID NO 46
<211> LENGTH: 2817
<212> TYPE: DNA
<213> ORGANISM: Homo sapiens

<400> SEQUENCE: 46
```

```
atggtggact tgaggacact cggttattcg caacagcaac aggagaaaat caagcctaag     60
gtcaggagca ccgtcgcgca acaccacgag gcgcttgtgg ggcatggctt cactcatgcg    120
catattgtcg cgctttcaca gcaccctgcg gcgcttggga cggtggctgt caaataccaa    180
gatatgattg cggccctgcc cgaagccacg cacgaggcaa ttgtaggggt cggtaaacag    240
tggtcgggag cgcgagcact tgaggcgctg ctgactgtgg cgggtgagct tagggggcct    300
ccgctccagc tcgacaccgg gcagctgctg aagatcgcga agagaggggg agtaacagcg    360
gtagaggcag tgcacgcctg gcgcaatgcg ctcaccgggg ccccccttgaa cctgacccca    420
gaccaggtag tcgcaatcgc gtcacatgac gggggaaagc aagccctgga aaccgtgcaa    480
aggttgttgc cggtcctttg tcaagaccac ggccttacac cggagcaagt cgtggccatt    540
gcatcccacg acggtggcaa acaggctctt gagacggttc agagacttct cccagttctc    600
tgtcaagccc acgggctgac tcccgatcaa gttgtagcga ttgcgtcgca tgacggaggg    660
aaacaagcat tggagactgt ccaacggctc cttcccgtgt tgtgtcaagc ccacggtttg    720
acgcctgcac aagtggtcgc catcgcctcc aatattggcg gtaagcaggc gctggaaaca    780
gtacagcgcc tgctgcctgt actgtgccag gatcatggac tgaccccaga ccaggtagtc    840
gcaatcgcga acaataatgg gggaaagcaa gccctggaaa ccgtgcaaag gttgttgccg    900
gtcctttgtc aagaccacgg ccttacaccg gagcaagtcg tggccattgc aaataataac    960
ggtggcaaac aggctcttga gacggttcag agacttctcc cagttctctg tcaagcccac   1020
gggctgactc ccgatcaagt tgtagcgatt gcgaataaca atggagggaa acaagcattg   1080
gagactgtcc aacggctcct tcccgtgttg tgtcaagccc acggtttgac gcctgcacaa   1140
gtggtcgcca tcgcctcgaa tggcggcggt aagcaggcgc tggaaacagt acagcgcctg   1200
ctgcctgtac tgtgccagga tcatggactg accccagacc aggtagtcgc aatcgcgaac   1260
aataatgggg gaaagcaagc cctggaaacc gtgcaaaggt tgttgccggt cctttgtcaa   1320
gaccacggcc ttacaccgga gcaagtcgtg gccattgcaa gcaacatcgg tggcaaacag   1380
```

```
gctcttgaga cggttcagag acttctccca gttctctgtc aagcccacgg gctgactccc   1440
gatcaagttg tagcgattgc gtcgcatgac ggagggaaac aagcattgga gactgtccaa   1500
cggctccttc ccgtgttgtg tcaagcccac ggtttgacgc ctgcacaagt ggtcgccatc   1560
gcctcgaatg gcggcggtaa gcaggcgctg gaaacagtac agcgcctgct gcctgtactg   1620
tgccaggatc atggactgac cccagaccag gtagtcgcaa tcgcgaacaa taatgggga    1680
aagcaagccc tggaaaccgt gcaaaggttg ttgccggtcc tttgtcaaga ccacggcctt   1740
acaccggagc aagtcgtggc cattgcaaat aataacggtg gcaaacaggc tcttgagacg   1800
gttcagagac ttctcccagt tctctgtcaa gcccacgggc tgactcccga tcaagttgta   1860
gcgattgcga ataacaatgg agggaaacaa gcattggaga ctgtccaacg gctccttccc   1920
gtgttgtgtc aagcccacgg tttgacgcct gcacaagtgg tcgccatcgc ctcgaatggc   1980
ggcggtaagc aggcgctgga aacagtacag cgcctgctgc ctgtactgtg ccaggatcat   2040
ggactgaccc cagaccaggt agtcgcaatc gcgaacaata atgggggaaa gcaagccctg   2100
gaaaccgtgc aaaggttgtt gccggtcctt tgtcaagacc acggccttac accggagcaa   2160
gtcgtggcca ttgcaaataa taacggtggc aaacaggctc ttgagacggt tcagagactt   2220
ctcccagttc tctgtcaagc ccacgggctg actcccgatc aagttgtagc gattgcgaat   2280
aacaatggag ggaaacaagc attggagact gtccaacggc tccttcccgt gttgtgtcaa   2340
gcccacggtt tgacgcctgc acaagtggtc gccatcgcct cgaatggcgg cggtaagcag   2400
gcgctggaaa cagtacagcg cctgctgcct gtactgtgcc aggatcatgg actgacccca   2460
gaccaggtag tcgcaatcgc gaacaataat gggggaaagc aagccctgga aaccgtgcaa   2520
aggttgttgc cggtcctttg tcaagaccac ggccttacac cggagcaagt cgtggccatt   2580
gcaagcaaca tcggtggcaa acaggctctt gagacggttc agagacttct cccagttctc   2640
tgtcaagccc acgggctgac tcccgatcaa gttgtagcga ttgcgtcgaa cattggaggg   2700
aaacaagcat tggagactgt ccaacggctc cttcccgtgt tgtgtcaagc ccacggtctg   2760
acacccgaac aggtggtcgc cattgctaat aataacggag gacggccagc cttggag      2817
```

<210> SEQ ID NO 47
<211> LENGTH: 2817
<212> TYPE: DNA
<213> ORGANISM: Homo sapiens

<400> SEQUENCE: 47

```
atggtggact tgaggacact cggttattcg caacagcaac aggagaaaat caagcctaag     60
gtcaggagca ccgtcgcgca acaccacgag gcgcttgtgg ggcatggctt cactcatgcg    120
catattgtcg cgctttcaca gcaccctgcg gcgcttggga cggtggctgt caaataccaa    180
gatatgattg cggccctgcc cgaagccacg cacgaggcaa ttgtaggggt cggtaaacag    240
tggtcgggag cgcgagcact tgaggcgctg ctgactgtgg cgggtgagct tagggggcct    300
ccgctccagc tcgacaccgg gcagctgctg aagatcgcga agagaggggg agtaacagcg    360
gtagaggcag tgcacgcctg gcgcaatgcg ctcaccgggg ccccccttgaa cctgacccca    420
gaccaggtag tcgcaatcgc gaacaataat gggggaaagc aagccctgga aaccgtgcaa    480
aggttgttgc cggtcctttg tcaagaccac ggccttacac cggagcaagt cgtggccatt    540
gcaaataata acggtggcaa acaggctctt gagacggttc agagacttct cccagttctc    600
tgtcaagccc acgggctgac tcccgatcaa gttgtagcga ttgcgaataa caatggaggg    660
```

```
aaacaagcat tggagactgt ccaacggctc cttcccgtgt tgtgtcaagc ccacggtttg     720

acgcctgcac aagtggtcgc catcgcctcg aatggcggcg gtaagcaggc gctggaaaca     780

gtacagcgcc tgctgcctgt actgtgccag gatcatggac tgaccccaga ccaggtagtc     840

gcaatcgcga acaataatgg gggaaagcaa gccctggaaa ccgtgcaaag gttgttgccg     900

gtcctttgtc aagaccacgg ccttacaccg gagcaagtcg tggccattgc aaataataac     960

ggtggcaaac aggctcttga gacggttcag agacttctcc cagttctctg tcaagcccac    1020

gggctgactc ccgatcaagt tgtagcgatt gcgaataaca atggagggaa acaagcattg    1080

gagactgtcc aacggctcct tcccgtgttg tgtcaagccc acggtttgac gcctgcacaa    1140

gtggtcgcca tcgcctcgaa tggcggcggt aagcaggcgc tggaaacagt acagcgcctg    1200

ctgcctgtac tgtgccagga tcatggactg accccagacc aggtagtcgc aatcgcgaac    1260

aataatgggg gaaagcaagc cctggaaacc gtgcaaaggt tgttgccggt cctttgtcaa    1320

gaccacggcc ttacaccgga gcaagtcgtg gccattgcaa gcaacatcgg tggcaaacag    1380

gctcttgaga cggttcagag acttctccca gttctctgtc aagcccacgg gctgactccc    1440

gatcaagttg tagcgattgc gtcgaacatt ggagggaaac aagcattgga gactgtccaa    1500

cggctccttc ccgtgttgtg tcaagcccac ggtttgacgc ctgcacaagt ggtcgccatc    1560

gccaacaaca acggcggtaa gcaggcgctg gaaacagtac agcgcctgct gcctgtactg    1620

tgccaggatc atggactgac cccagaccag gtagtcgcaa tcgcgaacaa taatgggga    1680

aagcaagccc tggaaaccgt gcaaaggttg ttgccggtcc tttgtcaaga ccacggcctt    1740

acaccggagc aagtcgtggc cattgcaagc aacatcggtg gcaaacaggc tcttgagacg    1800

gttcagagac ttctcccagt tctctgtcaa gcccacgggc tgactcccga tcaagttgta    1860

gcgattgcgt cgaacattgg agggaaacaa gcattggaga ctgtccaacg gctccttccc    1920

gtgttgtgtc aagcccacgg tttgacgcct gcacaagtgg tcgccatcgc ctcgaatggc    1980

ggcggtaagc aggcgctgga aacagtacag cgcctgctgc ctgtactgtg ccaggatcat    2040

ggactgaccc cagaccaggt agtcgcaatc gcgtcaaacg gagggggaaa gcaagccctg    2100

gaaaccgtgc aaaggttgtt gccggtcctt tgtcaagacc acggccttac accggagcaa    2160

gtcgtggcca ttgcaaataa taacggtggc aaacaggctc ttgagacggt tcagagactt    2220

ctcccagttc tctgtcaagc ccacgggctg actcccgatc aagttgtagc gattgcgtcg    2280

aacattggag ggaaacaagc attggagact gtccaacggc tccttcccgt gttgtgtcaa    2340

gcccacggtt tgacgcctgc acaagtggtc gccatcgcca acaacaacgg cggtaagcag    2400

gcgctggaaa cagtacagcg cctgctgcct gtactgtgcc aggatcatgg actgacccca    2460

gaccaggtag tcgcaatcgc gtcacatgac gggggaaagc aagccctgga aaccgtgcaa    2520

aggttgttgc cggtcctttg tcaagaccac ggccttacac cggagcaagt cgtggccatt    2580

gcaagcaaca tcggtggcaa acaggctctt gagacggttc agagacttct cccagttctc    2640

tgtcaagccc acgggctgac tcccgatcaa gttgtagcga ttgcgtcgaa cattggaggg    2700

aaacaagcat tggagactgt ccaacggctc cttcccgtgt tgtgtcaagc ccacggtctg    2760

acacccgaac aggtggtcgc cattgcttcc cacgacggag gacggccagc cttggag       2817
```

<210> SEQ ID NO 48
<211> LENGTH: 20
<212> TYPE: DNA
<213> ORGANISM: Homo sapiens

<400> SEQUENCE: 48
ggtggtggtg gttctggggs 20

<210> SEQ ID NO 49
<211> LENGTH: 44
<212> TYPE: PRT
<213> ORGANISM: Homo sapiens

<400> SEQUENCE: 49

```
Gly Ala Cys Gly Cys Thr Thr Thr Gly Gly Ala Cys Gly Ala Cys Thr
1               5                   10                  15

Thr Cys Gly Ala Cys Thr Thr Gly Gly Ala Cys Ala Thr Gly Thr Thr
            20                  25                  30

Gly Asp Ala Leu Asp Asp Phe Asp Leu Asp Met Leu
        35                  40
```

<210> SEQ ID NO 50
<211> LENGTH: 200
<212> TYPE: PRT
<213> ORGANISM: Homo sapiens

<400> SEQUENCE: 50

```
Gly Ala Cys Gly Cys Thr Thr Thr Gly Gly Ala Cys Gly Ala Cys Thr
1               5                   10                  15

Thr Cys Gly Ala Cys Thr Thr Gly Gly Ala Cys Ala Thr Gly Thr Thr
            20                  25                  30

Gly Gly Gly Thr Thr Cys Thr Gly Ala Cys Gly Cys Thr Thr Thr Gly
        35                  40                  45

Gly Ala Cys Gly Ala Cys Thr Thr Cys Gly Ala Cys Thr Thr Gly Gly
    50                  55                  60

Ala Cys Ala Thr Gly Thr Thr Gly Gly Gly Thr Thr Cys Thr Gly Ala
65                  70                  75                  80

Cys Gly Cys Thr Thr Thr Gly Gly Ala Cys Gly Ala Cys Thr Thr Cys
                85                  90                  95

Gly Ala Cys Thr Thr Gly Gly Ala Cys Ala Thr Gly Thr Thr Gly Gly
            100                 105                 110

Gly Thr Thr Cys Thr Gly Ala Cys Gly Cys Thr Thr Thr Gly Gly Ala
        115                 120                 125

Cys Gly Ala Cys Thr Thr Cys Gly Ala Cys Thr Thr Gly Gly Ala Cys
    130                 135                 140

Ala Thr Gly Thr Thr Gly Asp Ala Leu Asp Asp Phe Asp Leu Asp Met
145                 150                 155                 160

Leu Gly Ser Asp Ala Leu Asp Asp Phe Asp Leu Asp Met Leu Gly Ser
                165                 170                 175

Asp Ala Leu Asp Asp Phe Asp Leu Asp Met Leu Gly Ser Asp Ala Leu
            180                 185                 190

Asp Asp Phe Asp Leu Asp Met Leu
        195                 200
```

<210> SEQ ID NO 51
<211> LENGTH: 20
<212> TYPE: DNA
<213> ORGANISM: Homo sapiens

<400> SEQUENCE: 51
cccaaaagaa gaggaaggtg 20

<210> SEQ ID NO 52

<211> LENGTH: 51
<212> TYPE: DNA
<213> ORGANISM: Homo sapiens

<400> SEQUENCE: 52
atggccccca agaagaagag gaaggtgggc attcaccgcg gggtacctat g 51

<210> SEQ ID NO 53
<211> LENGTH: 2418
<212> TYPE: DNA
<213> ORGANISM: Homo sapiens

<400> SEQUENCE: 53
atggccccca agaagaagag gaaggtgggc attcaccgcg gggtacctat ggtggacttg 60
aggacactcg gttattcgca acagcaacag gagaaaatca agcctaaggt caggagcacc 120
gtcgcgcaac accacgaggc gcttgtgggg catggcttca ctcatgcgca tattgtcgcg 180
ctttcacagc accctgcggc gcttgggacg gtggctgtca aataccaaga tatgattgcg 240
gccctgcccg aagccacgca cgaggcaatt gtaggggtcg gtaaacagtg gtcgggagcg 300
cgagcacttg aggcgctgct gactgtggcg ggtgagctta gggggcctcc gctccagctc 360
gacaccgggc agctgctgaa gatcgcgaag agagggggag taacagcggt agaggcagtg 420
cacgcctggc gcaatgcgct caccggggcc ccccttgaacc tgaccccaga ccaggtagtc 480
gcaatcgcgt cacatgacgg gggaaagcaa gccctggaaa ccgtgcaaag gttgttgccg 540
gtcctttgtc aagaccacgg ccttacaccg gagcaagtcg tggccattgc atcccacgac 600
ggtggcaaac aggctcttga gacggttcag agacttctcc cagttctctg tcaagcccac 660
gggctgactc ccgatcaagt tgtagcgatt gcgtcgcatg acggagggaa acaagcattg 720
gagactgtcc aacggctcct tcccgtgttg tgtcaagccc acggtttgac gcctgcacaa 780
gtggtcgcca tcgccaacaa caacggcggt aagcaggcgc tggaaacagt acagcgcctg 840
ctgcctgtac tgtgccagga tcatggactg accccagacc aggtagtcgc aatcgcgtca 900
catgacgggg gaaagcaagc cctggaaacc gtgcaaaggt tgttgccggt cctttgtcaa 960
gaccacggcc ttacaccgga gcaagtcgtg gccattgcat cccacgacgg tggcaaacag 1020
gctcttgaga cggttcagag acttctccca gttctctgtc aagcccacgg gctgactccc 1080
gatcaagttg tagcgattgc gtcgaacatt ggagggaaac aagcattgga gactgtccaa 1140
cggctccttc ccgtgttgtg tcaagcccac ggtttgacgc ctgcacaagt ggtcgccatc 1200
gccaacaaca acggcggtaa gcaggcgctg gaaacagtac agcgcctgct gcctgtactg 1260
tgccaggatc atggactgac cccagaccag gtagtcgcaa tcgcgtcaaa cggaggggga 1320
aagcaagccc tggaaaccgt gcaaaggttg ttgccggtcc tttgtcaaga ccacggcctt 1380
acaccggagc aagtcgtggc cattgcatcc cacgacggtg gcaaacaggc tcttgagacg 1440
gttcagagac ttctcccagt tctctgtcaa gcccacgggc tgactcccga tcaagttgta 1500
gcgattgcgt cgcatgacgg agggaaacaa gcattggaga ctgtccaacg gctccttccc 1560
gtgttgtgtc aagcccacgg tttgacgcct gcacaagtgg tcgccatcgc caacaacaac 1620
ggcggtaagc aggcgctgga aacagtacag cgcctgctgc ctgtactgtg ccaggatcat 1680
ggactgaccc cagaccaggt agtcgcaatc gcgtcacatg acgggggaaa gcaagccctg 1740
gaaaccgtgc aaaggttgtt gccggtcctt tgtcaagacc acggccttac accggagcaa 1800
gtcgtggcca ttgcatccca cgacggtggc aaacaggctc ttgagacggt tcagagactt 1860
ctcccagttc tctgtcaagc ccacgggctg actcccgatc aagttgtagc gattgcgtcg 1920

```
catgacggag ggaaacaagc attggagact gtccaacggc tccttcccgt gttgtgtcaa   1980

gcccacggtt tgacgcctgc acaagtggtc gccatcgcct ccaatattgg cggtaagcag   2040

gcgctggaaa cagtacagcg cctgctgcct gtactgtgcc aggatcatgg actgacccca   2100

gaccaggtag tcgcaatcgc gtcacatgac gggggaaagc aagccctgga aaccgtgcaa   2160

aggttgttgc cggtcctttg tcaagaccac ggcctgacac ccgaacaggt ggtcgccatt   2220

gcttctaatg gggaggacg gccagccttg gagggtggtg gtggttctga cgctttggac   2280

gacttcgact tggacatgtt gggttctgac gctttggacg acttcgactt ggacatgttg   2340

ggttctgacg ctttggacga cttcgacttg gacatgttgg gttctgacgc tttggacgac   2400

ttcgacttgg acatgttg                                                 2418
```

<210> SEQ ID NO 54
<211> LENGTH: 806
<212> TYPE: PRT
<213> ORGANISM: Homo sapiens

<400> SEQUENCE: 54

```
Met Ala Pro Lys Lys Lys Arg Lys Val Gly Ile His Arg Gly Val Pro
1               5                   10                  15

Met Val Asp Leu Arg Thr Leu Gly Tyr Ser Gln Gln Gln Gln Glu Lys
            20                  25                  30

Ile Lys Pro Lys Val Arg Ser Thr Val Ala Gln His His Glu Ala Leu
        35                  40                  45

Val Gly His Gly Phe Thr His Ala His Ile Val Ala Leu Ser Gln His
    50                  55                  60

Pro Ala Ala Leu Gly Thr Val Ala Val Lys Tyr Gln Asp Met Ile Ala
65                  70                  75                  80

Ala Leu Pro Glu Ala Thr His Glu Ala Ile Val Gly Val Gly Lys Gln
                85                  90                  95

Trp Ser Gly Ala Arg Ala Leu Glu Ala Leu Leu Thr Val Ala Gly Glu
            100                 105                 110

Leu Arg Gly Pro Pro Leu Gln Leu Asp Thr Gly Gln Leu Leu Lys Ile
        115                 120                 125

Ala Lys Arg Gly Gly Val Thr Ala Val Glu Ala Val His Ala Trp Arg
    130                 135                 140

Asn Ala Leu Thr Gly Ala Pro Leu Asn Leu Thr Pro Asp Gln Val Val
145                 150                 155                 160

Ala Ile Ala Ser His Asp Gly Gly Lys Gln Ala Leu Glu Thr Val Gln
                165                 170                 175

Arg Leu Leu Pro Val Leu Cys Gln Asp His Gly Leu Thr Pro Glu Gln
            180                 185                 190

Val Val Ala Ile Ala Ser His Asp Gly Gly Lys Gln Ala Leu Glu Thr
        195                 200                 205

Val Gln Arg Leu Leu Pro Val Leu Cys Gln Ala His Gly Leu Thr Pro
    210                 215                 220

Asp Gln Val Val Ala Ile Ala Ser His Asp Gly Gly Lys Gln Ala Leu
225                 230                 235                 240

Glu Thr Val Gln Arg Leu Leu Pro Val Leu Cys Gln Ala His Gly Leu
                245                 250                 255

Thr Pro Ala Gln Val Val Ala Ile Ala Asn Asn Asn Gly Gly Lys Gln
            260                 265                 270

Ala Leu Glu Thr Val Gln Arg Leu Leu Pro Val Leu Cys Gln Asp His
```

```
        275                 280                 285

Gly Leu Thr Pro Asp Gln Val Val Ala Ile Ala Ser His Asp Gly Gly
    290                 295                 300

Lys Gln Ala Leu Glu Thr Val Gln Arg Leu Leu Pro Val Leu Cys Gln
305                 310                 315                 320

Asp His Gly Leu Thr Pro Glu Gln Val Val Ala Ile Ala Ser His Asp
                325                 330                 335

Gly Gly Lys Gln Ala Leu Glu Thr Val Gln Arg Leu Leu Pro Val Leu
            340                 345                 350

Cys Gln Ala His Gly Leu Thr Pro Asp Gln Val Val Ala Ile Ala Ser
        355                 360                 365

Asn Ile Gly Gly Lys Gln Ala Leu Glu Thr Val Gln Arg Leu Leu Pro
    370                 375                 380

Val Leu Cys Gln Ala His Gly Leu Thr Pro Ala Gln Val Val Ala Ile
385                 390                 395                 400

Ala Asn Asn Asn Gly Gly Lys Gln Ala Leu Glu Thr Val Gln Arg Leu
                405                 410                 415

Leu Pro Val Leu Cys Gln Asp His Gly Leu Thr Pro Asp Gln Val Val
            420                 425                 430

Ala Ile Ala Ser Asn Gly Gly Gly Lys Gln Ala Leu Glu Thr Val Gln
        435                 440                 445

Arg Leu Leu Pro Val Leu Cys Gln Asp His Gly Leu Thr Pro Glu Gln
    450                 455                 460

Val Val Ala Ile Ala Ser His Asp Gly Gly Lys Gln Ala Leu Glu Thr
465                 470                 475                 480

Val Gln Arg Leu Leu Pro Val Leu Cys Gln Ala His Gly Leu Thr Pro
                485                 490                 495

Asp Gln Val Val Ala Ile Ala Ser His Asp Gly Gly Lys Gln Ala Leu
            500                 505                 510

Glu Thr Val Gln Arg Leu Leu Pro Val Leu Cys Gln Ala His Gly Leu
        515                 520                 525

Thr Pro Ala Gln Val Val Ala Ile Ala Asn Asn Asn Gly Gly Lys Gln
    530                 535                 540

Ala Leu Glu Thr Val Gln Arg Leu Leu Pro Val Leu Cys Gln Asp His
545                 550                 555                 560

Gly Leu Thr Pro Asp Gln Val Val Ala Ile Ala Ser His Asp Gly Gly
                565                 570                 575

Lys Gln Ala Leu Glu Thr Val Gln Arg Leu Leu Pro Val Leu Cys Gln
            580                 585                 590

Asp His Gly Leu Thr Pro Glu Gln Val Val Ala Ile Ala Ser His Asp
        595                 600                 605

Gly Gly Lys Gln Ala Leu Glu Thr Val Gln Arg Leu Leu Pro Val Leu
    610                 615                 620

Cys Gln Ala His Gly Leu Thr Pro Asp Gln Val Val Ala Ile Ala Ser
625                 630                 635                 640

His Asp Gly Gly Lys Gln Ala Leu Glu Thr Val Gln Arg Leu Leu Pro
                645                 650                 655

Val Leu Cys Gln Ala His Gly Leu Thr Pro Ala Gln Val Val Ala Ile
            660                 665                 670

Ala Ser Asn Ile Gly Gly Lys Gln Ala Leu Glu Thr Val Gln Arg Leu
        675                 680                 685

Leu Pro Val Leu Cys Gln Asp His Gly Leu Thr Pro Asp Gln Val Val
    690                 695                 700
```

```
Ala Ile Ala Ser His Asp Gly Gly Lys Gln Ala Leu Glu Thr Val Gln
705                 710                 715                 720

Arg Leu Leu Pro Val Leu Cys Gln Asp His Gly Leu Thr Pro Glu Gln
                725                 730                 735

Val Val Ala Ile Ala Ser Asn Gly Gly Gly Arg Pro Ala Leu Glu Gly
            740                 745                 750

Gly Gly Gly Ser Asp Ala Leu Asp Asp Phe Asp Leu Asp Met Leu Gly
        755                 760                 765

Ser Asp Ala Leu Asp Asp Phe Asp Leu Asp Met Leu Gly Ser Asp Ala
    770                 775                 780

Leu Asp Asp Phe Asp Leu Asp Met Leu Gly Ser Asp Ala Leu Asp Asp
785                 790                 795                 800

Phe Asp Leu Asp Met Leu
                805


<210> SEQ ID NO 55
<211> LENGTH: 2403
<212> TYPE: DNA
<213> ORGANISM: Homo sapiens

<400> SEQUENCE: 55

atggccccca agaagaagag gaaggtgggc attcaccgcg gggtacctat ggtggacttg     60

aggacactcg gttattcgca acagcaacag gagaaaatca agcctaaggt caggagcacc    120

gtcgcgcaac accacgaggc gcttgtgggg catggcttca ctcatgcgca tattgtcgcg    180

ctttcacagc accctgcggc gcttgggacg gtggctgtca aataccaaga tatgattgcg    240

gccctgcccg aagccacgca cgaggcaatt gtaggggtcg gtaaacagtg gtcgggagcg    300

cgagcacttg aggcgctgct gactgtggcg ggtgagctta gggggcctcc gctccagctc    360

gacaccgggc agctgctgaa gatcgcgaag agagggggag taacagcggt agaggcagtg    420

cacgcctggc gcaatgcgct caccggggcc ccccttgaacc tgaccccaga ccaggtagtc    480

gcaatcgcgt cacatgacgg gggaaagcaa gccctggaaa ccgtgcaaag gttgttgccg    540

gtcctttgtc aagaccacgg ccttacaccg gagcaagtcg tggccattgc atcccacgac    600

ggtggcaaac aggctcttga gacggttcag agacttctcc cagttctctg tcaagcccac    660

gggctgactc ccgatcaagt tgtagcgatt gcgtcgcatg acggagggaa acaagcattg    720

gagactgtcc aacggctcct tcccgtgttg tgtcaagccc acggtttgac gcctgcacaa    780

gtggtcgcca tcgccaacaa caacggcggt aagcaggcgc tggaaacagt acagcgcctg    840

ctgcctgtac tgtgccagga tcatggactg accccagacc aggtagtcgc aatcgcgtca    900

catgacgggg gaaagcaagc cctggaaacc gtgcaaaggt tgttgccggt cctttgtcaa    960

gaccacggcc ttacaccgga gcaagtcgtg gccattgcat cccacgacgg tggcaaacag   1020

gctcttgaga cggttcagag acttctccca gttctctgtc aagcccacgg gctgactccc   1080

gatcaagttg tagcgattgc gtcgaacatt ggagggaaac aagcattgga gactgtccaa   1140

cggctccttc ccgtgttgtg tcaagcccac ggtttgacgc ctgcacaagt ggtcgccatc   1200

gccaacaaca acggcggtaa gcaggcgctg gaaacagtac agcgcctgct gcctgtactg   1260

tgccaggatc atggactgac cccagaccag gtagtcgcaa tcgcgtcaaa cggaggggga   1320

aagcaagccc tggaaaccgt gcaaaggttg ttgccggtcc tttgtcaaga ccacggcctt   1380

acaccggagc aagtcgtggc cattgcatcc cacgacggtg gcaaacaggc tcttgagacg   1440

gttcagagac ttctcccagt tctctgtcaa gcccacgggc tgactcccga tcaagttgta   1500
```

```
gcgattgcgt cgcatgacgg agggaaacaa gcattggaga ctgtccaacg gctccttccc   1560
gtgttgtgtc aagcccacgg tttgacgcct gcacaagtgg tcgccatcgc caacaacaac   1620
ggcggtaagc aggcgctgga aacagtacag cgcctgctgc ctgtactgtg ccaggatcat   1680
ggactgaccc cagaccaggt agtcgcaatc gcgtcacatg acgggggaaa gcaagccctg   1740
gaaaccgtgc aaaggttgtt gccggtcctt tgtcaagacc acggccttac accggagcaa   1800
gtcgtggcca ttgcatccca cgacggtggc aaacaggctc ttgagacggt tcagagactt   1860
ctcccagttc tctgtcaagc ccacgggctg actcccgatc aagttgtagc gattgcgtcg   1920
catgacggag ggaaacaagc attggagact gtccaacggc tccttcccgt gttgtgtcaa   1980
gcccacggtt tgacgcctgc acaagtggtc gccatcgcct ccaatattgg cggtaagcag   2040
gcgctggaaa cagtacagcg cctgctgcct gtactgtgcc aggatcatgg actgacccca   2100
gaccaggtag tcgcaatcgc gtcacatgac gggggaaagc aagccctgga aaccgtgcaa   2160
aggttgttgc cggtcctttg tcaagaccac ggcctgacac ccgaacaggt ggtcgccatt   2220
gcttctaatg gggaggacg gccagccttg gaggacgctt tggacgactt cgacttggac    2280
atgttgggtt ctgacgcttt ggacgacttc gacttggaca tgttgggttc tgacgctttg   2340
gacgacttcg acttggacat gttgggttct gacgctttgg acgacttcga cttggacatg   2400
ttg                                                                 2403
```

```
<210> SEQ ID NO 56
<211> LENGTH: 802
<212> TYPE: PRT
<213> ORGANISM: Homo sapiens

<400> SEQUENCE: 56

Met Ala Pro Lys Lys Lys Arg Lys Val Gly Ile His Arg Gly Val Pro
1               5                   10                  15

Met Val Asp Leu Arg Thr Leu Gly Tyr Ser Gln Gln Gln Gln Glu Lys
            20                  25                  30

Ile Lys Pro Lys Val Arg Ser Thr Val Ala Gln His His Glu Ala Leu
        35                  40                  45

Val Gly His Gly Phe Thr His Ala His Ile Val Ala Leu Ser Gln His
    50                  55                  60

Pro Ala Ala Leu Gly Thr Val Ala Val Lys Tyr Gln Asp Met Ile Ala
65                  70                  75                  80

Ala Leu Pro Glu Ala Thr His Glu Ala Ile Val Gly Val Gly Lys Gln
                85                  90                  95

Trp Ser Gly Ala Arg Ala Leu Glu Ala Leu Leu Thr Val Ala Gly Glu
            100                 105                 110

Leu Arg Gly Pro Pro Leu Gln Leu Asp Thr Gly Gln Leu Leu Lys Ile
        115                 120                 125

Ala Lys Arg Gly Gly Val Thr Ala Val Glu Ala Val His Ala Trp Arg
    130                 135                 140

Asn Ala Leu Thr Gly Ala Pro Leu Asn Leu Thr Pro Asp Gln Val Val
145                 150                 155                 160

Ala Ile Ala Ser His Asp Gly Gly Lys Gln Ala Leu Glu Thr Val Gln
                165                 170                 175

Arg Leu Leu Pro Val Leu Cys Gln Asp His Gly Leu Thr Pro Glu Gln
            180                 185                 190

Val Val Ala Ile Ala Ser His Asp Gly Gly Lys Gln Ala Leu Glu Thr
        195                 200                 205
```

```
Val Gln Arg Leu Leu Pro Val Leu Cys Gln Ala His Gly Leu Thr Pro
    210                 215                 220

Asp Gln Val Val Ala Ile Ala Ser His Asp Gly Gly Lys Gln Ala Leu
225                 230                 235                 240

Glu Thr Val Gln Arg Leu Leu Pro Val Leu Cys Gln Ala His Gly Leu
                245                 250                 255

Thr Pro Ala Gln Val Val Ala Ile Ala Asn Asn Asn Gly Gly Lys Gln
            260                 265                 270

Ala Leu Glu Thr Val Gln Arg Leu Leu Pro Val Leu Cys Gln Asp His
        275                 280                 285

Gly Leu Thr Pro Asp Gln Val Val Ala Ile Ala Ser His Asp Gly Gly
    290                 295                 300

Lys Gln Ala Leu Glu Thr Val Gln Arg Leu Leu Pro Val Leu Cys Gln
305                 310                 315                 320

Asp His Gly Leu Thr Pro Glu Gln Val Val Ala Ile Ala Ser His Asp
                325                 330                 335

Gly Gly Lys Gln Ala Leu Glu Thr Val Gln Arg Leu Leu Pro Val Leu
            340                 345                 350

Cys Gln Ala His Gly Leu Thr Pro Asp Gln Val Val Ala Ile Ala Ser
        355                 360                 365

Asn Ile Gly Gly Lys Gln Ala Leu Glu Thr Val Gln Arg Leu Leu Pro
    370                 375                 380

Val Leu Cys Gln Ala His Gly Leu Thr Pro Ala Gln Val Val Ala Ile
385                 390                 395                 400

Ala Asn Asn Asn Gly Gly Lys Gln Ala Leu Glu Thr Val Gln Arg Leu
                405                 410                 415

Leu Pro Val Leu Cys Gln Asp His Gly Leu Thr Pro Asp Gln Val Val
            420                 425                 430

Ala Ile Ala Ser Asn Gly Gly Gly Lys Gln Ala Leu Glu Thr Val Gln
        435                 440                 445

Arg Leu Leu Pro Val Leu Cys Gln Asp His Gly Leu Thr Pro Glu Gln
    450                 455                 460

Val Val Ala Ile Ala Ser His Asp Gly Gly Lys Gln Ala Leu Glu Thr
465                 470                 475                 480

Val Gln Arg Leu Leu Pro Val Leu Cys Gln Ala His Gly Leu Thr Pro
                485                 490                 495

Asp Gln Val Val Ala Ile Ala Ser His Asp Gly Gly Lys Gln Ala Leu
            500                 505                 510

Glu Thr Val Gln Arg Leu Leu Pro Val Leu Cys Gln Ala His Gly Leu
        515                 520                 525

Thr Pro Ala Gln Val Val Ala Ile Ala Asn Asn Asn Gly Gly Lys Gln
    530                 535                 540

Ala Leu Glu Thr Val Gln Arg Leu Leu Pro Val Leu Cys Gln Asp His
545                 550                 555                 560

Gly Leu Thr Pro Asp Gln Val Val Ala Ile Ala Ser His Asp Gly Gly
                565                 570                 575

Lys Gln Ala Leu Glu Thr Val Gln Arg Leu Leu Pro Val Leu Cys Gln
            580                 585                 590

Asp His Gly Leu Thr Pro Glu Gln Val Val Ala Ile Ala Ser His Asp
        595                 600                 605

Gly Gly Lys Gln Ala Leu Glu Thr Val Gln Arg Leu Leu Pro Val Leu
    610                 615                 620
```

```
Cys Gln Ala His Gly Leu Thr Pro Asp Gln Val Val Ala Ile Ala Ser
625                 630                 635                 640

His Asp Gly Gly Lys Gln Ala Leu Glu Thr Val Gln Arg Leu Leu Pro
                645                 650                 655

Val Leu Cys Gln Ala His Gly Leu Thr Pro Ala Gln Val Val Ala Ile
            660                 665                 670

Ala Ser Asn Ile Gly Gly Lys Gln Ala Leu Glu Thr Val Gln Arg Leu
        675                 680                 685

Leu Pro Val Leu Cys Gln Asp His Gly Leu Thr Pro Asp Gln Val Val
    690                 695                 700

Ala Ile Ala Ser His Asp Gly Gly Lys Gln Ala Leu Glu Thr Val Gln
705                 710                 715                 720

Arg Leu Leu Pro Val Leu Cys Gln Asp His Gly Leu Thr Pro Glu Gln
                725                 730                 735

Val Val Ala Ile Ala Ser Asn Pro Ala Leu Glu Gly Gly Gly Gly Ser
            740                 745                 750

Asp Ala Leu Asp Asp Phe Asp Leu Asp Met Leu Gly Ser Asp Ala Leu
        755                 760                 765

Asp Asp Phe Asp Leu Asp Met Leu Gly Ser Asp Ala Leu Asp Asp Phe
    770                 775                 780

Asp Leu Asp Met Leu Gly Ser Asp Ala Leu Asp Asp Phe Asp Leu Asp
785                 790                 795                 800

Met Leu


<210> SEQ ID NO 57
<211> LENGTH: 2286
<212> TYPE: DNA
<213> ORGANISM: Homo sapiens

<400> SEQUENCE: 57

gccgcgatcg ccatggggct gaggacagcg aagaagaggg ggcttggggg aggggggaaa     60

tggaagagag aggagggagg aggtacaaga ggaaggagag aagtgcggcc agcttgcttt    120

ctccagtcgg gtggccgcgg ggacccgggc gacgtcggag gccctgccgg gaacccaggc    180

tgcagccccc acccccgcgc tgcgacacgc cccccacccc ttccggctca cacccccgcc    240

cacactcctg agtggtgcgg tgcagcgtcg gccgaggcag cagagccgag gagagcaggt    300

ccacacctct gcatccctgc accaggactc accaagacgc ccatcctgga aaaggtcccc    360

cgtaagatgg cagcaaaaac tcccagcagt gaggagtctg ggctgcccaa actgcccgtg    420

cccccgctgc agcagaccct ggccacgtac ctgcagtgca tgcgacactt ggtgtctgag    480

gagcagttca ggaagagcca ggccattgtg cagcagtttg ggcccctgg tggcctcggc     540

gagaccctgc agcagaaact cctggagcgg caggagaaga cagccaactg ggtgtctgag    600

tactggctga atgacatgta tctcaacaac cgcctggccc tgcctgtcaa ctccagccct    660

gccgtgatct ttgctcggca gcacttccct ggcaccgatg accagctgag gtttgcagcc    720

agcctcatct ctggtgtact cagctacaag gccctgctgg acagccactc cattcccact    780

gactgtgcca aaggccagct gtcagggcag cccctttgca tgaagcaata ctatgggctc    840

ttctcctcct accggctccc cggccatacc caggacacgc tggtggctca gaacagcagc    900

atcatgccgg agcctgagca cgtcatcgta gcctgctgca atcagttctt tgtcttggat    960

gttgtcatta atttccgccg tctcagtgag gggatctgt tcactcagtt gagaaagata    1020

gtcaaaatgg cttccaacga ggacgagcgt ttgcctccaa ttggcctgct gacgtctgac   1080
```

```
gggaggagcg agtgggccga ggccaggacg gtcctcgtga aagactccac caaccgggac   1140

tcgctggaca tgattgagcg ctgcatctgc cttgtatgcc tggacgcgcc aggaggcgtg   1200

gagctcagcg acacccacag ggcactccag ctccttcacg gcggaggcta cagcaagaac   1260

ggggccaatc gctggtacga caagtccctg cagtttgtgg tgggccgaga cggcacctgc   1320

ggtgtggtgt gcgaacactc cccattcgat ggcatcgtcc tggtgcagtg cactgagcat   1380

ctgctcaagc acatgacgca gagcagcagg aagctgatcc gagcagactc cgtcagcgag   1440

ctccccgccc cccggaggct gcggtggaaa tgctccccgg aaattcaagg ccacttagcc   1500

tcctcggcag aaaaacttca acgaatagta aagaaccttg acttcattgt ctataagttt   1560

gacaactatg ggaaaacatt cattaagaag cagaaatgca gccctgatgc cttcatccag   1620

gtggccctcc agctggcctt ctacaggctc catcgaagac tggtgcccac ctacgagagc   1680

gcgtccatcc gccgattcca ggagggacgc gtggacaaca tcagatcggc cactccagag   1740

gcactggctt ttgtgagagc cgtgactgac cacaaggctg ctgtgccagc ttctgagaag   1800

cttctgctcc tgaaggatgc catccgtgcc cagactgcat acacagtcat ggccataaca   1860

gggatggcca ttgacaacca cctgctggca ctgcgggagc tggcccgggc catgtgcaag   1920

gagctgcccg agatgttcat ggatgaaacc tacctgatga gcaaccggtt tgtcctctcc   1980

actagccagg tgcccacaac cacggagatg ttctgctgct atggtcctgt ggtcccaaat   2040

gggtatggtg cctgctacaa cccccagcca gagaccatcc ttttctgcat ctctagcttt   2100

cacagctgca aagagacttc ttctagcaag tttgcaaaag ctgtggaaga aagcctcatt   2160

gacatgagag acctctgcag tctgctgccg cctactgaga gcaagccatt ggcaacaaag   2220

gaaaaagcca cgaggcccag ccagggacac caacctagcg gaccgacgcg tacgcggccg   2280

ctctaa                                                              2286
```

<210> SEQ ID NO 58
<211> LENGTH: 1461
<212> TYPE: PRT
<213> ORGANISM: Homo sapiens

<400> SEQUENCE: 58

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160
```

```
Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575
```

```
Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
```

-continued

```
        995                 1000                1005

Val Tyr  Gly Asp Tyr Lys Val  Tyr Asp Val Arg Lys  Met Ile Ala
    1010                 1015                 1020

Lys Ser  Glu Gln Glu Ile Gly  Lys Ala Thr Ala Lys  Tyr Phe Phe
    1025                 1030                 1035

Tyr Ser  Asn Ile Met Asn Phe  Phe Lys Thr Glu Ile  Thr Leu Ala
    1040                 1045                 1050

Asn Gly  Glu Ile Arg Lys Arg  Pro Leu Ile Glu Thr  Asn Gly Glu
    1055                 1060                 1065

Thr Gly  Glu Ile Val Trp Asp  Lys Gly Arg Asp Phe  Ala Thr Val
    1070                 1075                 1080

Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365

Gly Ser  Pro Lys Lys Lys Arg  Lys Val Ser Ser Asp  Tyr Lys Asp
    1370                 1375                 1380

His Asp  Gly Asp Tyr Lys Asp  His Asp Ile Asp Tyr  Lys Asp Asp
    1385                 1390                 1395
```

```
Asp Asp  Lys Ala Ala Gly Gly  Gly Gly Ser Gly Arg  Ala Asp Ala
    1400                 1405                 1410

Leu Asp  Asp Phe Asp Leu Asp  Met Leu Gly Ser Asp  Ala Leu Asp
    1415                 1420                 1425

Asp Phe  Asp Leu Asp Met Leu  Gly Ser Asp Ala Leu  Asp Asp Phe
    1430                 1435                 1440

Asp Leu  Asp Met Leu Gly Ser  Asp Ala Leu Asp Asp  Phe Asp Leu
    1445                 1450                 1455

Asp Met  Leu
    1460


<210> SEQ ID NO 59
<211> LENGTH: 23
<212> TYPE: DNA
<213> ORGANISM: Homo sapiens

<400> SEQUENCE: 59

tctttgcact gcatcgcggc act                                           23


<210> SEQ ID NO 60
<211> LENGTH: 24
<212> TYPE: DNA
<213> ORGANISM: Homo sapiens

<400> SEQUENCE: 60

tctttgcact gcatcgcggc actt                                          24


<210> SEQ ID NO 61
<211> LENGTH: 27
<212> TYPE: DNA
<213> ORGANISM: Homo sapiens

<400> SEQUENCE: 61

tctttgcact gcatcgcggc acttcct                                       27


<210> SEQ ID NO 62
<211> LENGTH: 23
<212> TYPE: DNA
<213> ORGANISM: Homo sapiens

<400> SEQUENCE: 62

tgcactgcat cgcggcactt cct                                           23


<210> SEQ ID NO 63
<211> LENGTH: 30
<212> TYPE: DNA
<213> ORGANISM: Homo sapiens

<400> SEQUENCE: 63

tgttcttcac aagacccaca agtgaaaaat                                    30


<210> SEQ ID NO 64
<211> LENGTH: 27
<212> TYPE: DNA
<213> ORGANISM: Homo sapiens

<400> SEQUENCE: 64

tcttcacaag acccacaagt gaaaaat                                       27


<210> SEQ ID NO 65
<211> LENGTH: 28
```

<212> TYPE: DNA
<213> ORGANISM: Homo sapiens

<400> SEQUENCE: 65
tgcccacatt gggactcttt tcctccct 28

<210> SEQ ID NO 66
<211> LENGTH: 26
<212> TYPE: DNA
<213> ORGANISM: Homo sapiens

<400> SEQUENCE: 66
tccccatccc ctcatcctac agccat 26

<210> SEQ ID NO 67
<211> LENGTH: 28
<212> TYPE: DNA
<213> ORGANISM: Homo sapiens

<400> SEQUENCE: 67
tccccatccc ctcatcctac agccatct 28

<210> SEQ ID NO 68
<211> LENGTH: 29
<212> TYPE: DNA
<213> ORGANISM: Homo sapiens

<400> SEQUENCE: 68
tggagacatt ccaatgccct ccgggtcct 29

<210> SEQ ID NO 69
<211> LENGTH: 29
<212> TYPE: DNA
<213> ORGANISM: Homo sapiens

<400> SEQUENCE: 69
tgctgcttta cttttgaggc cagaaaaat 29

<210> SEQ ID NO 70
<211> LENGTH: 25
<212> TYPE: DNA
<213> ORGANISM: Homo sapiens

<400> SEQUENCE: 70
tggccaggct gccgcctctc accct 25

<210> SEQ ID NO 71
<211> LENGTH: 29
<212> TYPE: DNA
<213> ORGANISM: Homo sapiens

<400> SEQUENCE: 71
tccatgtgcc atccagggtc aacgccgct 29

<210> SEQ ID NO 72
<211> LENGTH: 31
<212> TYPE: DNA
<213> ORGANISM: Homo sapiens

<400> SEQUENCE: 72
tccatgtgcc atccagggtc aacgccgctc t 31

<210> SEQ ID NO 73

<211> LENGTH: 26
<212> TYPE: DNA
<213> ORGANISM: Homo sapiens

<400> SEQUENCE: 73
tgctcttact gtgtgcccgg cccccct 26

<210> SEQ ID NO 74
<211> LENGTH: 27
<212> TYPE: DNA
<213> ORGANISM: Homo sapiens

<400> SEQUENCE: 74
tgctcttact gtgtgcccgg cccccctt 27

<210> SEQ ID NO 75
<211> LENGTH: 25
<212> TYPE: DNA
<213> ORGANISM: Homo sapiens

<400> SEQUENCE: 75
tccaacctca gccgccctgg agcct 25

<210> SEQ ID NO 76
<211> LENGTH: 27
<212> TYPE: DNA
<213> ORGANISM: Homo sapiens

<400> SEQUENCE: 76
tccaacctca gccgccctgg agcctct 27

<210> SEQ ID NO 77
<211> LENGTH: 29
<212> TYPE: DNA
<213> ORGANISM: Homo sapiens

<400> SEQUENCE: 77
tccaacctca gccgccctgg agcctctct 29

<210> SEQ ID NO 78
<211> LENGTH: 31
<212> TYPE: DNA
<213> ORGANISM: Homo sapiens

<400> SEQUENCE: 78
tccgggtcct ccaccaaccc agacagagcc t 31

<210> SEQ ID NO 79
<211> LENGTH: 29
<212> TYPE: DNA
<213> ORGANISM: Homo sapiens

<400> SEQUENCE: 79
tgcccggccc ccttagcagt aggtactat 29

<210> SEQ ID NO 80
<211> LENGTH: 30
<212> TYPE: DNA
<213> ORGANISM: Homo sapiens

<400> SEQUENCE: 80
tgcccggccc ccttagcagt aggtactatt 30

<210> SEQ ID NO 81
<211> LENGTH: 25
<212> TYPE: DNA
<213> ORGANISM: Homo sapiens

<400> SEQUENCE: 81
tgccatccag ggtcaacgcc gctct 25

<210> SEQ ID NO 82
<211> LENGTH: 25
<212> TYPE: DNA
<213> ORGANISM: Homo sapiens

<400> SEQUENCE: 82
tcctccacca acccagacag agcct 25

<210> SEQ ID NO 83
<211> LENGTH: 30
<212> TYPE: DNA
<213> ORGANISM: Homo sapiens

<400> SEQUENCE: 83
tcctccacca acccagacag agcctggagt 30

<210> SEQ ID NO 84
<211> LENGTH: 27
<212> TYPE: DNA
<213> ORGANISM: Homo sapiens

<400> SEQUENCE: 84
tccaccaacc cagacagagc ctggagt 27

<210> SEQ ID NO 85
<211> LENGTH: 30
<212> TYPE: DNA
<213> ORGANISM: Homo sapiens

<400> SEQUENCE: 85
tggagcctct ctcccgccag tccgcccact 30

<210> SEQ ID NO 86
<211> LENGTH: 27
<212> TYPE: DNA
<213> ORGANISM: Homo sapiens

<400> SEQUENCE: 86
tctacacacg ataacaacat agcaagt 27

<210> SEQ ID NO 87
<211> LENGTH: 30
<212> TYPE: DNA
<213> ORGANISM: Homo sapiens

<400> SEQUENCE: 87
tctacacacg ataacaacat agcaagtcct 30

<210> SEQ ID NO 88
<211> LENGTH: 31
<212> TYPE: DNA
<213> ORGANISM: Homo sapiens

<400> SEQUENCE: 88
tctacacacg ataacaacat agcaagtcct t 31

<210> SEQ ID NO 89
<211> LENGTH: 27
<212> TYPE: DNA
<213> ORGANISM: Homo sapiens

<400> SEQUENCE: 89
tccctgcagg tactctaatg agtacgt 27

<210> SEQ ID NO 90
<211> LENGTH: 23
<212> TYPE: DNA
<213> ORGANISM: Homo sapiens

<400> SEQUENCE: 90
tctgcgtcta atgctgcttt act 23

<210> SEQ ID NO 91
<211> LENGTH: 26
<212> TYPE: DNA
<213> ORGANISM: Homo sapiens

<400> SEQUENCE: 91
tgtgcccaca ttgggactct tttcct 26

<210> SEQ ID NO 92
<211> LENGTH: 30
<212> TYPE: DNA
<213> ORGANISM: Homo sapiens

<400> SEQUENCE: 92
tgtgcccaca ttgggactct tttcctccct 30

<210> SEQ ID NO 93
<211> LENGTH: 29
<212> TYPE: DNA
<213> ORGANISM: Homo sapiens

<400> SEQUENCE: 93
tactgctctt actgtgtgcc cggcccccct 29

<210> SEQ ID NO 94
<211> LENGTH: 30
<212> TYPE: DNA
<213> ORGANISM: Homo sapiens

<400> SEQUENCE: 94
tactgctctt actgtgtgcc cggcccccctt 30

<210> SEQ ID NO 95
<211> LENGTH: 26
<212> TYPE: DNA
<213> ORGANISM: Homo sapiens

<400> SEQUENCE: 95
tgctttactt ttgaggccag aaaaat 26

<210> SEQ ID NO 96
<211> LENGTH: 26
<212> TYPE: DNA
<213> ORGANISM: Homo sapiens

<400> SEQUENCE: 96
tccgcccact ggaacacggg ttccat 26

<210> SEQ ID NO 97
<211> LENGTH: 28
<212> TYPE: DNA
<213> ORGANISM: Homo sapiens

<400> SEQUENCE: 97
tagcaagtcc ttatactgct cttactgt 28

<210> SEQ ID NO 98
<211> LENGTH: 30
<212> TYPE: DNA
<213> ORGANISM: Homo sapiens

<400> SEQUENCE: 98
tagcaagtcc ttatactgct cttactgtgt 30

<210> SEQ ID NO 99
<211> LENGTH: 30
<212> TYPE: DNA
<213> ORGANISM: Homo sapiens

<400> SEQUENCE: 99
tctcaacaac acaatcccca cctccaacct 30

<210> SEQ ID NO 100
<211> LENGTH: 28
<212> TYPE: DNA
<213> ORGANISM: Homo sapiens

<400> SEQUENCE: 100
tcttttcctc cctcagacag agggcact 28

<210> SEQ ID NO 101
<211> LENGTH: 29
<212> TYPE: DNA
<213> ORGANISM: Homo sapiens

<400> SEQUENCE: 101
tcttttcctc cctcagacag agggcactt 29

<210> SEQ ID NO 102
<211> LENGTH: 24
<212> TYPE: DNA
<213> ORGANISM: Homo sapiens

<400> SEQUENCE: 102
tgccgcctct caccctgaca catt 24

<210> SEQ ID NO 103
<211> LENGTH: 27
<212> TYPE: DNA
<213> ORGANISM: Homo sapiens

<400> SEQUENCE: 103
tgccgcctct caccctgaca cattggt 27

<210> SEQ ID NO 104
<211> LENGTH: 31
<212> TYPE: DNA
<213> ORGANISM: Homo sapiens

<400> SEQUENCE: 104
tatactgctc ttactgtgtg cccggccccc t 31

<210> SEQ ID NO 105
<211> LENGTH: 23
<212> TYPE: DNA
<213> ORGANISM: Homo sapiens

<400> SEQUENCE: 105
tcctccctca gacagagggc act 23

<210> SEQ ID NO 106
<211> LENGTH: 24
<212> TYPE: DNA
<213> ORGANISM: Homo sapiens

<400> SEQUENCE: 106
tcctccctca gacagagggc actt 24

<210> SEQ ID NO 107
<211> LENGTH: 28
<212> TYPE: DNA
<213> ORGANISM: Homo sapiens

<400> SEQUENCE: 107
tcctccctca gacagagggc acttcagt 28

<210> SEQ ID NO 108
<211> LENGTH: 25
<212> TYPE: DNA
<213> ORGANISM: Homo sapiens

<400> SEQUENCE: 108
tacacacgat aacaacatag caagt 25

<210> SEQ ID NO 109
<211> LENGTH: 28
<212> TYPE: DNA
<213> ORGANISM: Homo sapiens

<400> SEQUENCE: 109
tacacacgat aacaacatag caagtcct 28

<210> SEQ ID NO 110
<211> LENGTH: 29
<212> TYPE: DNA
<213> ORGANISM: Homo sapiens

<400> SEQUENCE: 110
tacacacgat aacaacatag caagtcctt 29

<210> SEQ ID NO 111
<211> LENGTH: 31
<212> TYPE: DNA
<213> ORGANISM: Homo sapiens

<400> SEQUENCE: 111
tacacacgat aacaacatag caagtcctta t 31

<210> SEQ ID NO 112
<211> LENGTH: 25
<212> TYPE: DNA
<213> ORGANISM: Homo sapiens

<400> SEQUENCE: 112
tccctcagac agagggcact tcagt 25

<210> SEQ ID NO 113
<211> LENGTH: 29
<212> TYPE: DNA
<213> ORGANISM: Homo sapiens

<400> SEQUENCE: 113
tccctcagac agagggcact tcagtcact 29

<210> SEQ ID NO 114
<211> LENGTH: 26
<212> TYPE: DNA
<213> ORGANISM: Homo sapiens

<400> SEQUENCE: 114
tctcaccctg acacattggt ccccat 26

<210> SEQ ID NO 115
<211> LENGTH: 31
<212> TYPE: DNA
<213> ORGANISM: Homo sapiens

<400> SEQUENCE: 115
tctcaccctg acacattggt ccccatcccc t 31

<210> SEQ ID NO 116
<211> LENGTH: 30
<212> TYPE: DNA
<213> ORGANISM: Homo sapiens

<400> SEQUENCE: 116
tcttactgtg tgcccggccc ccttagcagt 30

<210> SEQ ID NO 117
<211> LENGTH: 23
<212> TYPE: DNA
<213> ORGANISM: Homo sapiens

<400> SEQUENCE: 117
tctctcccgc cagtccgccc act 23

<210> SEQ ID NO 118
<211> LENGTH: 30
<212> TYPE: DNA
<213> ORGANISM: Homo sapiens

<400> SEQUENCE: 118
tcctggttgt ctgcctcgaa agaccacact 30

<210> SEQ ID NO 119
<211> LENGTH: 27
<212> TYPE: DNA
<213> ORGANISM: Homo sapiens

<400> SEQUENCE: 119
tggttgtctg cctcgaaaga ccacact 27

<210> SEQ ID NO 120
<211> LENGTH: 29
<212> TYPE: DNA
<213> ORGANISM: Homo sapiens

<400> SEQUENCE: 120
tggttgtctg cctcgaaaga ccacactct 29

<210> SEQ ID NO 121
<211> LENGTH: 30
<212> TYPE: DNA
<213> ORGANISM: Homo sapiens

<400> SEQUENCE: 121
tggttgtctg cctcgaaaga ccacactctt 30

<210> SEQ ID NO 122
<211> LENGTH: 31
<212> TYPE: DNA
<213> ORGANISM: Homo sapiens

<400> SEQUENCE: 122
tggttgtctg cctcgaaaga ccacactctt t 31

<210> SEQ ID NO 123
<211> LENGTH: 29
<212> TYPE: DNA
<213> ORGANISM: Homo sapiens

<400> SEQUENCE: 123
tggtccccat cccctcatcc tacagccat 29

<210> SEQ ID NO 124
<211> LENGTH: 31
<212> TYPE: DNA
<213> ORGANISM: Homo sapiens

<400> SEQUENCE: 124
tggtccccat cccctcatcc tacagccatc t 31

<210> SEQ ID NO 125
<211> LENGTH: 22
<212> TYPE: DNA
<213> ORGANISM: Homo sapiens

<400> SEQUENCE: 125
tagccaagtg ccccctgtgt ct 22

<210> SEQ ID NO 126
<211> LENGTH: 23
<212> TYPE: DNA
<213> ORGANISM: Homo sapiens

<400> SEQUENCE: 126
tagccaagtg ccccctgtgt ctt 23

<210> SEQ ID NO 127
<211> LENGTH: 24
<212> TYPE: DNA
<213> ORGANISM: Homo sapiens

<400> SEQUENCE: 127
tagccaagtg ccccctgtgt cttt 24

<210> SEQ ID NO 128
<211> LENGTH: 27
<212> TYPE: DNA
<213> ORGANISM: Homo sapiens -continued

```
<400> SEQUENCE: 128

tagccaagtg ccccctgtgt ctttcat                                          27


<210> SEQ ID NO 129
<211> LENGTH: 29
<212> TYPE: DNA
<213> ORGANISM: Homo sapiens

<400> SEQUENCE: 129

tagccaagtg ccccctgtgt ctttcatct                                        29


<210> SEQ ID NO 130
<211> LENGTH: 31
<212> TYPE: DNA
<213> ORGANISM: Homo sapiens

<400> SEQUENCE: 130

tagccaagtg ccccctgtgt ctttcatctg t                                     31


<210> SEQ ID NO 131
<211> LENGTH: 30
<212> TYPE: DNA
<213> ORGANISM: Homo sapiens

<400> SEQUENCE: 131

tctgcctcga aagaccacac tctttgcact                                       30


<210> SEQ ID NO 132
<211> LENGTH: 28
<212> TYPE: DNA
<213> ORGANISM: Homo sapiens

<400> SEQUENCE: 132

tgcctcgaaa gaccacactc tttgcact                                         28


<210> SEQ ID NO 133
<211> LENGTH: 25
<212> TYPE: DNA
<213> ORGANISM: Homo sapiens

<400> SEQUENCE: 133

tcctacagcc atctcaggga cagat                                            25


<210> SEQ ID NO 134
<211> LENGTH: 11
<212> TYPE: PRT
<213> ORGANISM: Homo sapiens

<400> SEQUENCE: 134

Asp Ala Leu Asp Asp Phe Asp Leu Asp Met Leu
1               5                   10
```